United States Patent
Modlin et al.

(10) Patent No.: US 12,305,240 B2
(45) Date of Patent: May 20, 2025

(54) METHODS FOR COLON CANCER DETECTION AND TREATMENT

(71) Applicant: Liquid Biopsy Research LLC, Charlestown (KN)

(72) Inventors: Irvin Mark Modlin, Woodbridge, CT (US); Mark Kidd, New Haven, CT (US); Ignat Drozdov, Stratford Upon Avon (GB)

(73) Assignee: Liquid Biopsy Research LLC, Charlestown (KN)

( * ) Notice: Subject to any disclaimer, the term of this patent is extended or adjusted under 35 U.S.C. 154(b) by 42 days.

(21) Appl. No.: 17/815,008

(22) Filed: Jul. 26, 2022

(65) Prior Publication Data

US 2023/0220482 A1 Jul. 13, 2023

Related U.S. Application Data

(62) Division of application No. 16/253,697, filed on Jan. 22, 2019, now Pat. No. 11,414,707.

(60) Provisional application No. 62/620,015, filed on Jan. 22, 2018.

(51) Int. Cl.
| | | |
|---|---|---|
| C12Q 1/68 | (2018.01) |
| A61K 31/496 | (2006.01) |
| A61K 31/513 | (2006.01) |
| A61K 31/7072 | (2006.01) |
| A61P 35/00 | (2006.01) |
| C07K 16/28 | (2006.01) |
| C12Q 1/6827 | (2018.01) |
| C12Q 1/686 | (2018.01) |
| C12Q 1/6886 | (2018.01) |
| G16B 20/20 | (2019.01) |
| G16B 40/00 | (2019.01) |

(52) U.S. Cl.
CPC .......... *C12Q 1/6886* (2013.01); *A61K 31/496* (2013.01); *A61K 31/513* (2013.01); *A61K 31/7072* (2013.01); *A61P 35/00* (2018.01); *C07K 16/2803* (2013.01); *C12Q 1/6827* (2013.01); *C12Q 1/686* (2013.01); *G16B 20/20* (2019.02); *G16B 40/00* (2019.02); *C12Q 2600/106* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | |
|---|---|---|
| 11,414,707 B2 | 8/2022 | Modlin et al. |
| 2017/0233495 A1* | 8/2017 | Missotten ............... A61P 27/02 424/139.1 |
| 2019/0226030 A1 | 7/2019 | Modlin et al. |

FOREIGN PATENT DOCUMENTS

| | | |
|---|---|---|
| CN | 102232115 A | 11/2011 |
| CN | 105821125 A | 8/2016 |
| EP | 2169078 A1 | 3/2010 |
| EP | 2309002 A1 | 4/2011 |
| EP | 2426216 A1 | 3/2012 |
| JP | 2014503222 A | 2/2014 |
| JP | 2016104014 A | 6/2016 |
| WO | WO-2010047448 A1 | 4/2010 |
| WO | WO-2010061996 A1 | 6/2010 |
| WO | WO-2010127322 A1 | 11/2010 |
| WO | WO-2012099872 A1 | 7/2012 |
| WO | WO-2012103250 A2 | 8/2012 |
| WO | WO-2014041185 A2 | 3/2014 |
| WO | WO-2014085826 A2 | 6/2014 |
| WO | WO-2019144099 A1 | 7/2019 |

OTHER PUBLICATIONS

Amri, R. et al. (2013) "Preoperative Carcinoembryonic Antigen as an Outcome Predictor in Colon Cancer" J Surg Oncol, 108:14-18.
Chen, V.W. et al. (Dec. 1, 2014) "Analysis of Stage and Clinical/Prognostic Factors for Colon and Rectal Cancer From SEER Registries: AJCC and Collaborative Stage Data Collection System" Cancer, 120(23 Suppl):3793-3806.
Chen, W. et al. (2009) "Knockdown of the novel proteasome subunit Adrml located on the 20q13 amplicon inhibits colorectal cancer cell migration, survival and tumorigenicity" Oncology Reports, 21:531-537.
Ferlay, J. et al. (2013) "Cancer incidence and mortality patterns in Europe: Estimates for 40 countries in 2012" Eur J Cancer, 49:1374-1403.
Fritzmann, J. et al. (2009) "A Colorectal Cancer Expression Profile That Includes Transforming Growth Factor ß Inhibitor BAMBI Predicts Metastatic Potential" Gastroenterology, 137:165-175.
Garcia-Bilbao, A. et al. (2012) "Identification of a biomarker panel for colorectal cancer diagnosis" BMC Cancer, 12:43, 13 pages.
GENBANK Accession No. NM_000075.3 (Nov. 4, 2018) "*Homo sapiens* cyclin dependent kinase 4 (CDK4), mRNA" National Center for Biotechnology Information, U.S. National Library of Medicine [online]. Retrieved from: www.ncbi.nlm.nih.gov/nuccore/NM_000075.3; retrieved on Apr. 24, 2019, 5 pages.
GENBANK Accession No. NM_000181.3 (Jul. 8, 2018) "*Homo sapiens* glucuronidase beta (GUSB), transcript variant 1, mRNA" National Center for Biotechnology Information, U.S. National Library of Medicine [online]. Retrieved from: www.ncbi.nlm.nih.gov/nuccore/NM_000181.3; retrieved on Apr. 24, 2019, 5 pages.
GENBANK Accession No. NM_000194.2 (Sep. 16, 2018) "*Homo sapiens* hypoxanthine phosphoribosyltransferase 1 (HPRT1), mRNA" National Center for Biotechnology Information, U.S. National Library of Medicine [online]. Retrieved from: www.ncbi.nlm.nih.gov/nuccore/NM_000194.2; retrieved on Apr. 24, 2019, 4 pages.

(Continued)

*Primary Examiner* — Jehanne S Sitton
(74) *Attorney, Agent, or Firm* — COOLEY LLP

(57) ABSTRACT

The present invention is directed to methods for detecting a colon cancer, methods for determining whether a colon cancer is stable or progressive, methods for determining a risk for disease relapse, and methods for determining a response by a subject having a colon cancer to a therapy.

12 Claims, 8 Drawing Sheets

Specification includes a Sequence Listing.

(56) References Cited

OTHER PUBLICATIONS

GENBANK Accession No. NM_000291.3 (Oct. 20, 2018) "*Homo sapiens* phosphoglycerate kinase 1 (PGK1), mRNA" National Center for Biotechnology Information, U.S. National Library of Medicine [online]. Retrieved from: www.ncbi.nlm.nih.gov/nuccore/NM_000291.3; retrieved on Apr. 24, 2019, 7 pages.

GENBANK Accession No. NM_000373.3 (Nov. 11, 2018) "*Homo sapiens* uridine monophosphate synthetase (UMPS), transcript variant 1, mRNA" National Center for Biotechnology Information, U.S. National Library of Medicine [online]. Retrieved from: www.ncbi.nlm.nih.gov/nuccore/NM_000373.3; retrieved on Apr. 24, 2019, 6 pages.

GENBANK Accession No. NM_000754.3 (Apr. 23, 2019) "*Homo sapiens* catechol-O-methyltransferase (COMT), transcript variant 1, mRNA" National Center for Biotechnology Information, U.S. National Library of Medicine [online]. Retrieved from: www.ncbi.nlm.nih.gov/nuccore/NM_000754.3; retrieved on Apr. 24, 2019, 4 pages.

GENBANK Accession No. NM_001002.3 (Oct. 20, 2018) "*Homo sapiens* ribosomal protein lateral stalk subunit P0 (PLP0), transcript variant 1, mRNA" National Center for Biotechnology Information, U.S. National Library of Medicine [online]. Retrieved from: www.ncbi.nlm.nih.gov/nuccore/NM_001002.3; retrieved on Apr. 24, 2019, 5 pages.

GENBANK Accession No. NM_001020658.1 (Apr. 13, 2019) "*Homo sapiens* pumilio RNA binding family member 1 (PUM1), transcript variant 1, mRNA" National Center for Biotechnology Information, U.S. National Library of Medicine [online]. Retrieved from: www.ncbi.nlm.nih.gov/nuccore/NM_001020658.1; retrieved on Apr. 24, 2019, 9 pages.

GENBANK Accession No. NM_001101.4 (Oct. 21, 2018) "*Homo sapiens* actin beta (ACTB), mRNA" National Center for Biotechnology Information, U.S. National Library of Medicine [online]. Retrieved from: www.ncbi.nlm.nih.gov/nuccore/NM_001101.4; retrieved on Apr. 24, 2019, 4 pages.

GENBANK Accession No. NM_001127204.1 (Feb. 21, 2019) "*Homo sapiens* oxygenase 2 (HMOX2), transcript variant 1, mRNA" National Center for Biotechnology Information, U.S. National Library of Medicine [online]. Retrieved from: www.ncbi.nlm.nih.gov/nuccore/NM_001127204.1; retrieved on Apr. 24, 2019, 4 pages.

GENBANK Accession No. NM_001163817.1 (Feb. 23, 2019) "*Homo sapiens* 7-dehydrocholesterol reductase (DHCR7), transcript variant 2, mRNA" National Center for Biotechnology Information, U.S. National Library of Medicine [online]. Retrieved from: www.ncbi.nlm.nih.gov/nuccore/NM_001163817.1; retrieved on Apr. 24, 2019, 5 pages.

GENBANK Accession No. NM_001265603.1 (Jun. 11, 2018) "*Homo sapiens* mortality factor 4 like 1 (MORF4L1), transcript variant 3, mRNA" National Center for Biotechnology Information, U.S. National Library of Medicine [online]. Retrieved from: www.ncbi.nlm.nih.gov/nuccore/NM_001265603.1; retrieved on Apr. 24, 2019, 4 pages.

GENBANK Accession No. NM_001287031.1 (Feb. 10, 2019) "*Homo sapiens* stomatin like 2 (STOML2), transcript variant 2, mRNA" National Center for Biotechnology Information, U.S. National Library of Medicine [online]. Retrieved from: www.ncbi.nlm.nih.gov/nuccore/NM_001287031.1; retrieved on Apr. 24, 2019, 4 pages.

GENBANK Accession No. NM_002046.6 (Oct. 21, 2018) "*Homo sapiens* glyceraldehyde-3-phosphate dehydrogenase (GAPDH), transcript variant 1, mRNA" National Center for Biotechnology Information, U.S. National Library of Medicine [online]. Retrieved from: www.ncbi.nlm.nih.gov/nuccore/NM_002046.6; retrieved on Apr. 24, 2019, 9 pages.

GENBANK Accession No. NM_003104.5 (Jun. 24, 2018) "*Homo sapiens* sorbitol dehydrogenase (SORD), transcript variant 1, mRNA" National Center for Biotechnology Information, U.S. National Library of Medicine [online]. Retrieved from: www.ncbi.nlm.nih.gov/nuccore/NM_003104.5; retrieved on Apr. 24, 2019, 4 pages.

GENBANK Accession No. NM_003234.3 (Apr. 20, 2019) "*Homo sapiens* transferrin receptor (TFRC), transcript variant 1, mRNA" National Center for Biotechnology Information, U.S. National Library of Medicine [online]. Retrieved from: www.ncbi.nlm.nih.gov/nuccore/NM_003234.3; retrieved on Apr. 24, 2019, 7 pages.

GENBANK Accession No. NM_003406.3 (Mar. 25, 2019) "*Homo sapiens* tyrosine 3-monooxygenase/tryptophan 5-monooxygenase activation protein zeta (YWHAZ), transcript variant 1, mRNA" National Center for Biotechnology Information, U.S. National Library of Medicine [online]. Retrieved from: www.ncbi.nlm.nih.gov/nuccore/NM_003406.3; retrieved on Apr. 24, 2019, 6 pages.

GENBANK Accession No. NM_003681.4 (Oct. 20, 2018) "*Homo sapiens* pyridoxal kinase (PDXK), transcript variant 1, mRNA" National Center for Biotechnology Information, U.S. National Library of Medicine [online]. Retrieved from: www.ncbi.nlm.nih.gov/nuccore/NM_003681.4; retrieved on Apr. 24, 2019, 6 pages.

GENBANK Accession No. NM_004048.2 (Mar. 29, 2018) "*Homo sapiens* beta-2-microglobulin (B2M), mRNA" National Center for Biotechnology Information, U.S. National Library of Medicine [online]. Retrieved from: www.ncbi.nlm.nih.gov/nuccore/NM_004048.2; retrieved on Apr. 24, 2019, 4 pages.

GENBANK Accession No. NM_004168.3 (Oct. 21, 2018) "*Homo sapiens* succinate dehydrogenase complex flavoprotein subunit A (SDHA), transcript variant 1, mRNA" National Center for Biotechnology Information, U.S. National Library of Medicine [online]. Retrieved from: www.ncbi.nlm.nih.gov/nuccore/NM_004168.3; retrieved on Apr. 24, 2019, 8 pages.

GENBANK Accession No. NM_004526.3 (Nov. 4, 2018) "*Homo sapiens* minichromosome maintenance complex component 2 (MCM2), transcript variant 1, mRNA" National Center for Biotechnology Information, U.S. National Library of Medicine [online]. Retrieved from: www.ncbi.nlm.nih.gov/nuccore/NM_004526.3; retrieved on Apr. 24, 2019, 8 pages.

GENBANK Accession No. NM_004596.4 (Oct. 21, 2018) "*Homo sapiens* small nuclear ribonucleoprotein polypeptide A (SNRPA), mRNA" National Center for Biotechnology Information, U.S. National Library of Medicine [online]. Retrieved from: www.ncbi.nlm.nih.gov/nuccore/NM_004596.4; retrieved on Apr. 24, 2019, 4 pages.

GENBANK Accession No. NM_005837.2 (Jun. 24, 2018) "*Homo sapiens* POP7 homolog, ribonuclease P/MRP subunit (POP7), mRNA" National Center for Biotechnology Information, U.S. National Library of Medicine [online]. Retrieved from: www.ncbi.nlm.nih.gov/nuccore/NM_005837.2; retrieved on Apr. 24, 2019, 3 pages.

GENBANK Accession No. NM_005877.5 (Jun. 3, 2018) "*Homo sapiens* splicing factor 3a subunit 1 (SF3A1), mRNA" National Center for Biotechnology Information, U.S. National Library of Medicine [online]. Retrieved from: www.ncbi.nlm.nih.gov/nuccore/NM_005877.5; retrieved on Apr. 24, 2019, 6 pages.

GENBANK Accession No. NM_005980.2 (Jun. 17, 2018) "*Homo sapiens* S100 calcium binding protein P (S100P), mRNA" National Center for Biotechnology Information, U.S. National Library of Medicine [online]. Retrieved from: www.ncbi.nlm.nih.gov/nuccore/NM_005980.2; retrieved on Apr. 24, 2019, 3 pages.

GENBANK Accession No. NM_007002.3 (Oct. 21, 2018) "*Homo sapiens* adhesion regulating molecule 1 (ADRM1), transcript variant 1, mRNA" National Center for Biotechnology Information, U.S. National Library of Medicine [online]. Retrieved from: www.ncbi.nlm.nih.gov/nuccore/NM_007002.3; retrieved on Apr. 24, 2019, 5 pages.

GENBANK Accession No. NM_012423.3 (Oct. 20, 2018) "*Homo sapiens* ribosomal protein L13a (RPL13A), transcript variant 1, mRNA" National Center for Biotechnology Information, U.S. National Library of Medicine [online]. Retrieved from: www.ncbi.nlm.nih.gov/nuccore/NM_012423.3; retrieved on Apr. 24, 2019, 7 pages.

GENBANK Accession No. NM_014763.3 (Nov. 11, 2018) "*Homo sapiens* mitochondrial ribosomal protein L19 (MRPL19), mRNA" National Center for Biotechnology Information, U.S. National Library of Medicine [online]. Retrieved from: www.ncbi.nlm.nih.gov/nuccore/NM_014763.3; retrieved on Apr. 24, 2019, 6 pages.

GENBANK Accession No. NM_021130.4 (Nov. 18, 2018) "*Homo sapiens* peptidylprolyl isomerase A (PPIA), transcript variant 1, mRNA" National Center for Biotechnology Information, U.S. National Library of Medicine [online]. Retrieved from: www.ncbi.nlm.nih.gov/nuccore/NM_021130.4; retrieved on Apr. 24, 2019, 5 pages.

(56) References Cited

OTHER PUBLICATIONS

GENBANK Accession No. NM_153001.2 (Apr. 14, 2019) "*Homo sapiens* proteasome 26S subunit, ATPase 4 (PSMC4), transcript variant 2, mRNA" National Center for Biotechnology Information, U.S. National Library of Medicine [online]. Retrieved from: www.ncbi.nlm.nih.gov/nuccore/NM_153001.2; retrieved on Apr. 24, 2019, 4 pages.

GENBANK Accession No. X03205.1 (Dec. 16, 1994) "Human 18S ribosomal RNA" National Center for Biotechnology Information, U.S. National Library of Medicine [online]. Retrieved from: www.ncbi.nlm.nih.gov/nuccore/X03205.1; retrieved on Apr. 24, 2019, 3 pages.

Heald, R.J. and Lockhart-Mummery, H.E. (Jan. 1972) "The Lesion of the Second Cancer of the Large Bowel" Brit J Surg, 59(1):16-19.

Jansen, N. and Coy, J.F. (2013) "Diagnostic use of epitope detection in monocytes blood test for early detection of colon cancer metastasis" Future Oncol, 9(4):605-609.

Kalinin, A.A. et al. (2018) "Deep learning in pharmacogenomics: from gene regulation to patient stratification" Pharmacogenomics, 19(7):629-650.

Kanth P., et al., "Gene Signature in Sessile Serrated Polyps Identifies Colon Cancer Subtype," Cancer Prevention Research, 2016, vol. 9, No. 6, pp. 456-465.

Liu, R. et al. (Aug. 2015) "Comparison of Nine Statistical Model Based Warfarin Pharmacogenetic Dosing Algorithms Using the Racially Diverse International Warfarin Pharmacogenetic Consortium Database" PLoS One, 10(8):e0135784; doi:10.1371/journal.pone.0135784, 11 pages.

Locker, G.Y. et al. "ASCO 2006 Update of Recommendations for the Use of Tumor Markers in Gastrointestinal Cancer" J Clin Oncol, 24(33):5313-5327.

Mead, R. et al. (2011) "Circulating tumour markers can define patients with normal colons, benign polyps, and cancers" Br J Cancer, 105:239-245.

Mishaeli, M. et al. (1998) "Initial TPS Serum Level as an Indicator of Relapse and Survival in Colorectal Cancer" Anticancer Res, 18:2101-2106.

Mokhles, S. et al. (2016) "Meta-analysis of colorectal cancer follow-up after potentially curative resection" BJS, 103:1259-1268.

Molnar, B. et al. (2008) "Elevation in peripheral blood circulating tumor cell number correlates with macroscopic progression in UICC stage IV colorectal cancer patients" Disease Markers, 24:141-150.

Parkkila, S. et al. (2008) "The calcium-binding protein S100P in normal and malignant human tissues" BMC Clin Pathol, 8:2, 9 pages.

Piepoli, A. et al. (Mar. 3, 2009) "Promoter methylation correlates with reduced NDRG2 expression in advanced colon tumour" BMC Medical Genomics, 2:11, 12 pages.

Siegel, R.L. et al. (2017) "Cancer Statistics, 2017" CA Cancer J Clin, 67:7-30.

Tempestini A., et al., "Molecular Characterization of Established Human Colon Carcinoma Cell Lines (HCT-8) Made Resistant to 5-Fluorouracil by Different Selection Schedules," Oncology Research, 2006, vol. 16, pp. 143-156.

Thomas, S.N. et al. (Jun. 6, 2008) "Carcinoembryonic Antigen and CD44 Variant Isoforms Cooperate to Mediate Colon Carcinoma Cell Adhesion to E- and L-selectin in Shear Flow" J Biol Chem, 283(23):15647-15655.

Uzozie, A. et al. (2014) "Sorbitol Dehydrogenase Overexpression and Other Aspects of Dysregulated Protein Expression in Human Precancerous Colorectal Neoplasms: A Quantitative Proteomics Study" Mol Cell Proteomics, 13:1198-1218.

Warren, J.D. et al. (2011) "Septin 9 methylated DNA is a sensitive and specific blood test for colorectal cancer" BMC Medicine, 9:133, 9 pages.

Lech, G., et al., "Colorectal cancer tumour markers and biomarkers: Recent therapeutic advances," World J Gastroenterol. (2016); 22(5):1745-1755.

Lu, Y., et al., "Research progress on the application of next-generation sequencing technology in colorectal cancer genome sequencing. Progress research on application of next-generation sequencing techniques in colorectal cancer genome," Journal of Jilin University (Medical Edition) (2016); 42(6): 1263-1266, doi: 10.13481/j.1671-587x.20160642, with English Abstract, 8 pages.

Uzozie, A.C., et al., "Targeted Proteomics for Multiplexed Verification of Markers of Colorectal Tumorigenesis," Mol Cell Proteomics (2017); 16(3):407-427.

\* cited by examiner

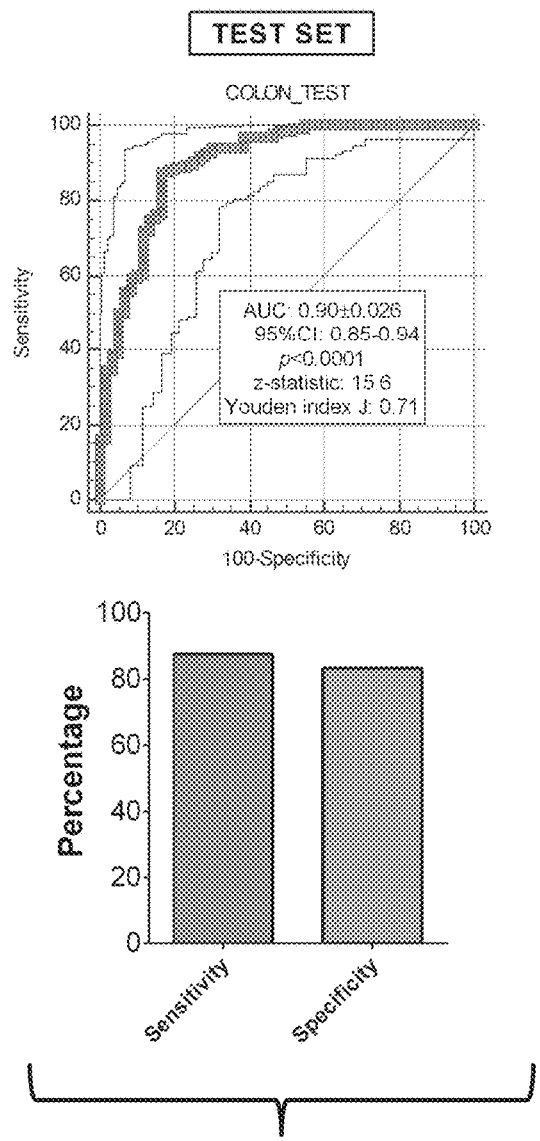
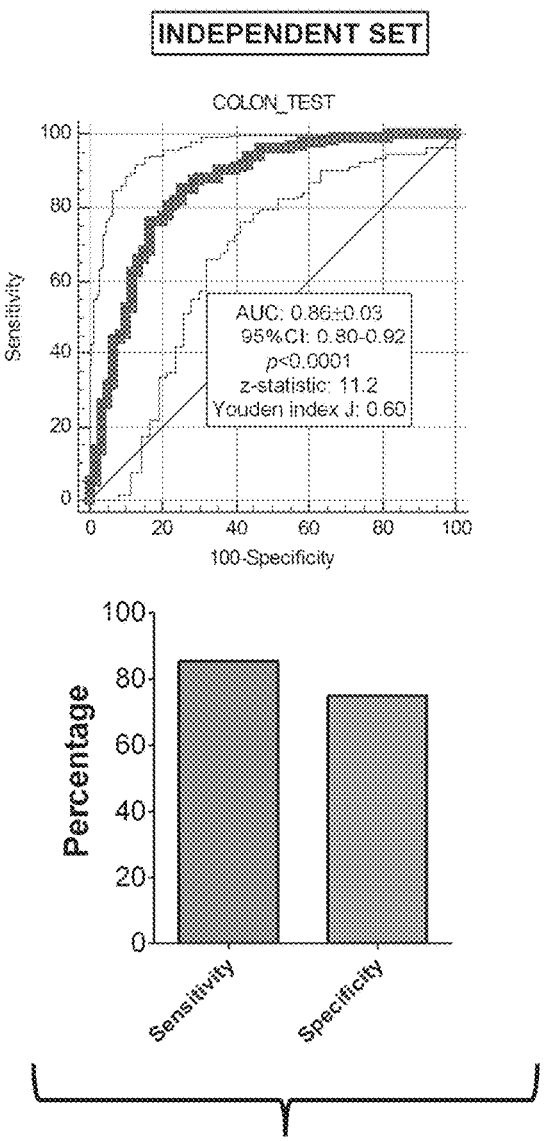
FIG. 2A
FIG. 2B

METHODS FOR COLON CANCER DETECTION AND TREATMENT

CROSS-REFERENCE TO RELATED APPLICATIONS

This application is a divisional of U.S. patent application Ser. No. 16/253,697, filed Jan. 22, 2019, now U.S. Pat. No. 11,414,707, which claims priority to, and the benefit of, U.S. Provisional Application No. 62/620,015, filed Jan. 22, 2018. The contents of each of the aforementioned patent applications are incorporated herein by reference in their entireties.

SEQUENCE LISTING

The Sequence Listing XML associated with this application is provided electronically in XML file format and is hereby incorporated by reference into the specification. The name of the XML file containing the Sequence Listing XML is "LBIO-004_C01US_SeqList.xml". The XML filed is 112,806 bytes in size, and was created on Jul. 25, 2022, and is being submitted elelctronically via USPTO Patent Center.

FIELD OF THE INVENTION

The present invention relates to colon cancer detection.

BACKGROUND OF THE INVENTION

Colorectal cancer (CRC) is one of the most commonly diagnosed cancers worldwide. In the US, CRC is the second leading cause of death as it is in Europe, after lung cancer. Worldwide, it is the fourth most common cause of cancer death. Although surgical resection followed by chemotherapy is the leading treatment option, approximately half eventually die due to distant metastases. Currently, the 5-year overall survival rate of patients with primary CRC can be up to 90%, but it will be reduced to ~50% in patients with advanced non-metastatic tumors, and can be further decreased to <10% in patients in whom the disease is resected at its earliest stages, owing to an incomplete understanding of the molecular mechanisms underpinning its pathogenesis.

Overall survival is associated with the disease stage at the time of diagnosis, suggesting that early detection of disseminated disease is of considerable significance. Consequently, the development of new diagnostic methods that better define disease stage and can better monitor disease progression is critical.

Surveillance remains a cornerstone approach to detect recurrence at an early stage and plan further therapeutic strategies. After potentially curative resection, monitoring can be undertaken through measurement of blood biomarkers and/or imaging like CT to detect asymptomatic metastatic disease earlier. Pooled data from randomized trials published from 1995 to 2016, however, identifies that a benefit from surgical treatment resulting from earlier detection of metastases, does not occur. This likely reflects the poor sensitivity of current biomarkers.

The current biomarker is carcinoembryonic antigen (CEA), a glycoprotein involved in cell adhesion that is not generally expressed in adult tissues except in heavy smokers. Its specialized sialofucosylated glycoforms serve as functional colon carcinoma L-selectin and E-selectin ligands, which may play a role in metastatic dissemination of colon carcinoma cells. CEA is principally used to monitor colorectal carcinoma treatment, to identify recurrences after surgical resection, for staging or to localize cancer spread through measurement of biological fluids. There are, however, significant limitations. While preoperative CEA levels have shown an association with (disease-free) survival, this was chiefly because it was a surrogate for metastatic presentation. Extrapolating the predictive value of preoperative CEA has, however, been shown to be of limited significance for predictions of long-term outcomes in individual cases. This has been independently supported by a prospective analysis, which identified that levels of CEA, and other biomarkers like CA19-9, does not indicate metastasis even at a time-point where clinical signs and imaging techniques has already demonstrated metastasis.

While the molecular basis for the colorectal cancer disease has been well-characterized e.g., microsatellite instability, K-RAS mutations etc., the development of diagnostic and prognostic markers e.g., in urine or stool or as circulating-free DNA that captures this information, remains nascent but have begun to be developed. Examples include measurements of methylation of septin 9, a tumor suppressor involved in cytokinesis during cellular division. This has been used to detect colon cancer; the metrics range between 60-70%. Assessment of circulating free DNA (Line 1 and Alu-based PCR) has a predictive value of 81% with a ROC of 0.86 as a diagnostic, while measurements of circulating tumor cells are also considered useful. TPS (tissue polypeptide specific antigen) can be used as a monitor of colon cancer as can TAG-72 (tumor-associated glycoprotein) but measurements of other single analytes, like CEA or CA19-9, are non-specific.

SUMMARY OF THE INVENTION

Among other things, disclosed herein is a 14-gene expression tool for colon cancer detection.

In one aspect, the present disclosure provides a method for detecting a colon cancer in a subject in need thereof, comprising: (a) determining the expression level of at least 14 biomarkers from a test sample from the subject by contacting the test sample with a plurality of agents specific to detect the expression of the at least 14 biomarkers, wherein the 14 biomarkers comprise ADM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a predetermined cutoff value; and (e) identifying the presence of a colon cancer in the subject when the score is equal to or greater than the predetermined cutoff value or identifying the absence of a colon cancer in the subject when the score is less than the predetermined cutoff value.

In one aspect, the present disclosure provides a method for detecting a colon cancer in a subject in need thereof, the method comprising: (a) determining the expression level of at least 14 biomarkers from a test sample from the subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM41, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a first predetermined cutoff value; and (e) producing a report, wherein the report identifies the presence of a colon cancer in the subject when the score is equal to or greater than the first predetermined cutoff value or identifies the absence of a colon cancer in the subject when the score is less than the first predetermined cutoff value, wherein the first predetermined cutoff value is 50% on a scale of 0-100%.

In one aspect, the present disclosure provides a method for determining whether a colon cancer in a subject is stable or progressive, the method comprising: (a) determining the expression level of at least 14 biomarkers from a test sample from the subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a predetermined cutoff value; and (e) identifying that the colon cancer in the subject is progressive when the score is equal to or greater than the predetermined cutoff value or identifying that the colon cancer in the subject is stable when the score is less than the predetermined cutoff value.

In one aspect, the present disclosure provides a method for determining whether a colon cancer in a subject is stable or progressive, the method comprising: (a) determining the expression level of at least 14 biomarkers from a test sample from the subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a second predetermined cutoff value; and (e) producing a report, wherein the report identifies that the colon cancer is progressive when the score is equal to or greater than the second predetermined cutoff value or identifies that the colon cancer is stable when the score is less than the second predetermined cutoff value, wherein the second predetermined cutoff value is 60% on a scale of 0 to 100%.

In one aspect, a method for determining the completeness of surgery in a subject having a colon cancer, the method comprising: (a) determining the expression level of at least 14 biomarkers from a test sample from the subject after the surgery by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a predetermined cutoff value; and (e) identifying that the colon cancer in the subject is not completely removed when the score is equal to or greater than the predetermined cutoff value or identifying that the colon cancer in the subject is completely removed when the score is less than the predetermined cutoff value.

In one aspect, the present disclosure provides a method for determining the completeness of surgery in a subject having a colon cancer, the method comprising: (a) determining the expression level of at least 14 biomarkers from a test sample from the subject after the surgery by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a first predetermined cutoff value; and (e) producing a report, wherein the report identifies that the colon cancer is not completely removed when the score is equal to or greater than the first predetermined cutoff value or identifies that the colon cancer is completely removed when the score is less than the first predetermined cutoff value, wherein the first predetermined cutoff value is 50% on a scale of 0-100%.

In one aspect, the present disclosure provides a method comprising: (a) determining the expression level of at least 14 biomarkers from a test sample from a subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a predetermined cutoff value; and (e) administering a first therapy to the subject when the score is equal to or greater than the predetermined cutoff value.

In one aspect, the present disclosure provides a method for evaluating the response of a subject having a colon cancer to a first therapy, the method comprising: (1) at a first time point: (a) determining the expression level of at least 14 biomarkers from a first test sample from the subject by contacting the first test sample with a plurality of agents specific to detect the expression of the at least 14 biomarkers, wherein the 14 biomarkers comprise ADM1, CDK4, COMT, DHCR7, HMOX2, MCM2, PDXK, POP7, S100P, SNRPA, SORD, STOML2, UMPS, and a housekeeping gene; (b) normalizing the expression level of each of ADM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a first score; (2) at a second time point, wherein the second time point is after the first time point and after the administration of the therapy to the subject: (a) determining the expression level of at least 14 biomarkers from a second test sample from the subject by contacting the second test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and the housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADM1, CDK4, COMT, DHCR7, HMOX2, MCM2, PDXK, POP7, S100P, SNRPA, SORD, STOML2, and UMPS; (c) inputting each normalized expression level into the algorithm to generate a second score; (3) comparing the first score with the second score; and (4) identifying that the subject is responsive to the first therapy when the second score is significantly decreased as compared to the first score or identifying that the subject is not responsive to the first therapy when the second score is not significantly decreased as compared to the first score.

In one aspect, the present disclosure provides a method for evaluating the response of a subject having a colon cancer to a therapy, the method comprising: (1) at a first time point, performing the following steps that include (a) determining the expression level of at least 14 biomarkers from a first test sample from the subject by contacting the first test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADM1, CDK4, COMT, DHCR7, HMOX2, MCM2, PDXK, POP7, S100P, SNRPA, SORD, STOML2, and UMPS; (c) inputting each normalized expression level into an algorithm to generate a first score; and (2) at a second time point, performing the following steps that include (d) determining the expression level of at least 14 biomarkers from a second test sample from the subject by contacting the second test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and the housekeeping gene; (e) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADM1, CDK4, COMT, DHCR7, HMOX2, MCM2, PDXK, POP7, S100P, SNRPA, SORD, STOML2, and UMPS; (f) inputting each normalized expression level into the algorithm to generate a second score, wherein the second time point is after the first time point and after the administration of the therapy to the subject; (3) comparing the first score with the second score; and (4) producing a report, wherein the report identifies that the subject is responsive to the therapy when the second score is significantly decreased as compared to the first score or identifies that the subject is not responsive to the therapy when the second score is not significantly decreased as compared to the first score.

In some aspects, a method of the present disclosure can further comprise continuing to administer a first therapy to a subject when a second score is significantly decreased as compared to a first score.

In some aspects, a method of the present disclosure can further comprise discontinuing administration of a first therapy to a subject when a second score is not significantly decreased as compared to a first score.

In some aspects, a method of the present disclosure can further comprise administering a second therapy to a subject when a second score is not significantly decreased as compared to a first score.

In some aspects, a second score is significantly decreased as compared to a first score when the second score is at least 25% less than the first score.

In some aspects, a predetermined cutoff value can be 50% on a scale of 0-100%. A predetermined cutoff value can be 60% on a scale of 0-100%.

In some aspects of any one of the methods disclosed herein, a housekeeping gene can be selected from the group consisting of MRPL19, PSMC4, SF3A1, PUM1, ACTB, GAPD, GUSB, RPLP0, TFRC, MORF4L1, 18S, PPIA, PGK1, RPL13A, B2M, YWHAZ, SDHA, and HPRT1. For example, the housekeeping gene can be MORF4L1.

In some aspects, a method of the present disclosure can have a sensitivity greater than 85%. In some aspects, a method of the present disclosure can have a specificity of greater than 85%.

In some aspects, a biomarker can comprise RNA, cDNA, protein or any combination thereof.

In some aspects, wherein when the biomarker is RNA, the RNA can be reverse transcribed to produce cDNA, and the produced cDNA expression level can be detected.

In some aspects, a biomarker or the expression of a biomarker can be detected by forming a complex between the biomarker and a labeled probe or primer.

In some aspects, when a biomarker is protein, the protein can be detected by forming a complex between the protein and a labeled antibody.

In some aspects, when a biomarker is RNA or cDNA, the RNA or cDNA can be detected by forming a complex between the RNA or cDNA and a labeled nucleic acid probe or primer. A complex between the RNA or cDNA and the labeled nucleic acid probe or primer can be a hybridization complex.

In some aspects, a predetermined cutoff value can be derived from a plurality of reference samples obtained from subjects not having or not diagnosed with a neoplastic disease. The neoplastic disease can be colon cancer.

In some aspects, an algorithm can be XGBoost (XGB), Random Forest (RF), glmnet, cforest, Classification and Regression Trees for Machine Learning (CART), treebag, K-Nearest Neighbors (kNN), neural network (nnet), Support Vector Machine radial (SVM-radial), Support Vector Machine linear (SVM-linear), Naïve Bayes (NB), multilayer perceptron (mlp) or any combination thereof.

In some aspects, the methods of the present disclosure can further comprise administering to a subject a first therapy when a score is equal to or greater than a predetermined cutoff.

In some aspects, a first time point can be prior to the administration of a first therapy to the subject. A first time point can be after the administration of the first therapy to the subject.

In some aspects, a therapy can comprise anti-cancer therapy, surgery, chemotherapy, targeted drug therapy, radiation therapy, immunotherapy or any combination thereof.

In some aspects, surgery can comprise removing a polyp during a colonoscopy, endoscopic mucosal resection, a partial colectomy, an ostomy, removing at least one cancerous lesion from the liver, or any combination thereof.

In some aspects, chemotherapy can comprise FOLFOX, FOLFIRI, a combination of 5-FU and leucovorin, capecitabine, irinotecan, CapeOx or any combination thereof.

In some aspects, targeted drug therapy can comprise bevacizumab, cetuximab, panitumumab, regorafenib, a combination of trifluridine and tipiracil, a EGFR TKI inhibitor or any combination thereof.

In some aspects, anti-cancer therapy can comprise anti-colon cancer therapy.

In some aspects, immunotherapy can comprise pembrolizumab, nivolumab or a combination of pembrolizumab and nivolumab.

In some aspects, a test sample can be blood, serum, plasma, neoplastic tissue or any combination thereof. A reference sample can be blood, serum, plasma, non-neoplastic tissue or any combination thereof.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

FIGS. 2A-2B are graphs showing receiver operator curve analysis of the test set (FIG. 2A) and independent set (FIG. 2B). Each cohort included 136 cancers and 60 controls. The AUROC in the test set was 0.9 and the Youden J index was 0.71. In the independent set the AUROC was 0.86 with a Youden index of 0.6. Z-statistics ranged 11.2-15.6 and were highly significant (p<0.0001). The sensitivity and specificity of the test ranged 85-87.5% and 75-83%, respectively.

DETAILED DESCRIPTION OF THE INVENTION

Figure 1A:
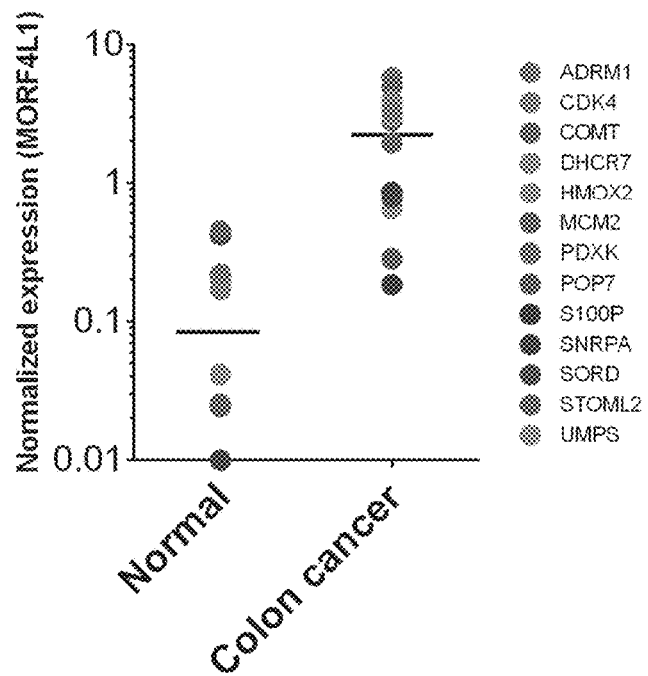
FIGS. 1A-1B are graphs showing normalized gene expression of the 13 gene signature in colon mucosa (FIG. 1A) and cell lines (FIG. 1B). Gene expression was significantly (p<0.0001) elevated in colon cancer samples (n=7) compared to matched normal mucosa (n=7). Levels were ~20-fold elevated in colon cancer tumor tissue than in normal mucosa. All genes were expressed in three different colon cancer cell lines. Levels were ~1000× elevated compared to normal mucosa. Horizontal lines identify median normalized expression of the 13 genes.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Colon cancer is cancer of the large intestine (colon). Symptoms of colon cancer include, but are not limited to: (a) a change in bowel habits, (b) rectal bleeding or blood in the stool, (c) persistent abdominal discomfort, such as cramps, gas or pain, (d) a feeling that the bowel doesn't empty completely, (e) weakness or fatigue, and (f) unexplained weight loss.

Described herein are methods to quantitate (score) the circulating colon cancer molecular signature with high sensitivity and specificity for purposes including, but not limited to, detecting a colon cancer, determining whether a colon cancer is stable or progressive, determining the completeness of surgery, and evaluating the response to a colon cancer therapy. Specifically, the present invention is based on the discovery that the expression levels of ADRM1, CDK4, COMT, DHCR7, HMOX2, MCM2, PDXK, POP7, S100P, SNRPA, SORD, STOML2, and UMPS, normalized by the expression level of a housekeeping gene such as MORF4L1, are elevated in subjects having colon cancers as compared to healthy subjects.

Accordingly, the present disclosure provides a method for detecting a colon cancer in a subject in need thereof, the method comprising: (a) determining the expression level of at least 14 biomarkers from a test sample from the subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a first predetermined cutoff value; and (e) identifying the presence of a colon cancer in the subject when the score is equal to or greater than the predetermined cutoff value or identifying the absence of a colon cancer in the subject when the score is less than the predetermined cutoff value.

In some aspects of the preceding method, step (e) can comprise producing a report, wherein the report identifies the presence of a colon cancer in the subject when the score is equal to or greater than the first predetermined cutoff value or identifies the absence of a colon cancer in the subject when the score is less than the first predetermined cutoff value.

In some aspects, the preceding method can further comprise administering to the subject a first therapy. The preceding method can further comprise administering to the subject a first therapy when the score is equal to or greater than the predetermined cutoff.

The present disclosure also provides a method for determining whether a colon cancer in a subject is stable or progressive, the method comprising: (a) determining the expression level of at least 14 biomarkers from a test sample from the subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a second predetermined cutoff value; and (e) identifying that the colon cancer in the subject is progressive when the score is equal to or greater than the predetermined cutoff value or identifying that the colon cancer in the subject is stable when the score is less than the predetermined cutoff value.

In some aspects of the preceding method, step (e) can comprise producing a report, wherein the report identifies that the colon cancer is progressive when the score is equal to or greater than the second predetermined cutoff value or identifies that the colon cancer is stable when the score is less than the second predetermined cutoff value.

In some aspects, the preceding method can further comprise administering to the subject a first therapy. The preceding method can further comprise administering to the subject a first therapy when the score is equal to or greater than the predetermined cutoff.

In some aspects, the method further comprises treating the subject with a progressive colon cancer with surgery, chemotherapy, targeted drug therapy, radiation therapy, immunotherapy, or a combination thereof.

The present disclosure also provides a method for determining the completeness of surgery in a subject having a colon cancer, the method comprising: (a) determining the expression level of at least 14 biomarkers from a test sample from the subject after the surgery by contacting the test sample with a plurality of agents specific to detect the expression of the at least 14 biomarkers, wherein the 14 biomarkers comprise ADM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a first predetermined cutoff value; and (e) identifying that the colon cancer in the subject is not completely removed when the score is equal to or greater than the predetermined cutoff value or identifying that the colon cancer in the subject is completely removed when the score is less than the predetermined cutoff value.

In some aspects of the preceding method, step (e) can comprise producing a report, wherein the report identifies that the colon cancer is not completely removed when the score is equal to or greater than the first predetermined cutoff value or identifies that the colon cancer is completely removed when the score is less than the first predetermined cutoff value.

In some aspects, the preceding method can further comprise administering to the subject a first therapy. The preceding method can further comprise administering to the subject a first therapy when the score is equal to or greater than the predetermined cutoff.

The present disclosure also provides a method comprising: (a) determining the expression level of at least 14 biomarkers from a test sample from a subject by contacting the test sample with a plurality of agents specific to detect the expression of the at least 14 biomarkers, wherein the 14 biomarkers comprise ADM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a score; (d) comparing the score with a predetermined cutoff value; and (e) administering a first therapy to the subject when the score is equal to or greater than the predetermined cutoff value.

The response of a subject having a colon cancer to a therapy can also be evaluated by comparing the scores determined by the same algorithm at different time points of the therapy. For example, the first time point can be prior to or after the administration of the therapy to the subject; the second time point is after the first time point and after the administration of the therapy to the subject. A first score is generated at the first time point, and a second score is generated at the second time point. When the second score is significantly decreased as compared to the first score, the subject is considered to be responsive to the therapy.

Accordingly, the present disclosure provides a method for evaluating the response of a subject having a colon cancer to a first therapy, the method comprising: (1) at a first time point: (a) determining the expression level of at least 14 biomarkers from a first test sample from the subject by contacting the first test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into an algorithm to generate a first score; (2) at a second time point, wherein the second time point is after the first time point and after the administration of the therapy to the subject: (a) determining the expression level of at least 14 biomarkers from a second test sample from the subject by contacting the second test sample with a plurality of agents specific to detect the expression of the at least 14 biomarkers, wherein the 14 biomarkers comprise ADM1, CDK4, COMT, DHCR7, HMOX2, MCM2, PDXK, POP7, S100P, SNRPA, SORD, STOML2, UMPS, and the housekeeping gene; (b) normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS; (c) inputting each normalized expression level into the algorithm to generate a second score; (3) comparing the first score with the second score; and (4) identifying that the subject is responsive to the first therapy when the second score is significantly decreased as compared to the first score or identifying that the subject is not responsive to the first therapy when the second score is not significantly decreased as compared to the first score.

In some aspects of the preceding method, step (4) can comprise producing a report, wherein the report identifies that the subject is responsive to the first therapy when the second score is significantly decreased as compared to the first score or identifies that the subject is not responsive to the first therapy when the second score is not significantly decreased as compared to the first score.

In some aspects of the preceding method, the second score is significantly decreased as compared to the first score when the second score is at least about 10% less than the first score, or at least about 20% less than the first score, or at least about 25% less than the first score, at least about 40% less than the first score, at least about 50% less than the first score, or at least about 60% less than the first score, or at least about 70% less than the first score, or at least about 75% less than the first score, or at least about 80% less than the first score, or at least about 90% less than the first score, or at least about 95% less than the first score or at least about 95% less than the first score. In some aspects, when the second score is not significantly decreased as compared to the first score, the subject is considered to be not responsive to the therapy.

In some aspects of the preceding method, a first time point can be prior to the administration of a first therapy to the subject. A first time point can be after the administration of a first therapy to the subject.

In some aspects, the preceding method can further comprise continuing to administer the first therapy to the subject when the second score is significantly decreased as compared to the first score.

In some aspects, the preceding method can further comprise discontinuing administration of the first therapy to the subject when the second score is not significantly decreased as compared to the first score.

In some aspects, the preceding method can further comprise administering a second therapy to the subject when the second score is not significantly decreased as compared to the first score.

In some aspects of the methods of the present disclosure, a predetermined cutoff value can be about 50% on a scale of 0-100%. A predetermined cutoff value can be about 60% on a scale of 0-100%. A predetermine cutoff value can be about 10%, or about 20%, or about 30%, or about 40%, or about 70%, or about 80%, or about 90% on a scale of 0-100%.

In some aspects of the methods of the present disclosure, a test sample can be any biological fluid obtained from the subject. A test sample can be blood, serum, plasma, neoplastic tissue or any combination thereof. In some aspects, the test sample is blood. In some aspects, the test sample is serum. In some aspects, the test sample is plasma.

In some aspects of the methods of the present disclosure, a housekeeping gene can comprise, but is not limited to, MRPL19, PSMC4, SF3A1, PUM1, ACTB, GAPD, GUSB, RPLP0, TFRC, MORF4L1, 18S, PPIA, PGK1, RPL13A, B2M, YWHAZ, SDHA, and HPRT1. In some aspects, the housekeeping gene is MORF4L1.

The methods of the present disclosure can have a sensitivity of at least about 50%, or at least about 60%, or at least about 70%, or at least about 75%, or at least about 80%, or at least about 85%, or at least about 90%, or at least about 95%, or at least about 99%. The methods of the present disclosure can have a sensitivity of greater than about 50%, or greater than about 60%, or greater than about 70%, or greater than about 75%, or greater than about 80%, or greater than about 85%, or greater than about 90%, or greater than about 95%, or greater than about 99%.

The methods of the present disclosure can have a specificity of at least about 50%, or at least about 60%, or at least about 70%, or at least about 75%, or at least about 80%, or at least about 85%, or at least about 90%, or at least about 95%, or at least about 99%. The methods of the present disclosure can have a specificity of greater than about 50%, or greater than about 60%, or greater than about 70%, or greater than about 75%, or greater than about 80%, or greater than about 85%, or greater than about 90%, or greater than about 95%, or greater than about 99%.

The methods of the present disclosure can have an accuracy of at least about 50%, or at least about 60%, or at least about 70%, or at least about 75%, or at least about 80%, or at least about 85%, or at least about 90%, or at least about 95%, or at least about 99%. The methods of the present disclosure can have an accuracy of greater than about 50%, or greater than about 60%, or greater than about 70%, or greater than about 75%, or greater than about 80%, or greater than about 85%, or greater than about 90%, or greater than about 95%, or greater than about 99%.

In some aspects of the methods of the present disclosure, a predetermined cutoff value can be derived from a plurality of reference samples obtained from subjects not having or not diagnosed with a neoplastic disease. In some aspects, the neoplastic disease can be colon cancer.

The plurality of reference samples can comprise about 2-500, 2-200, 10-100, or 20-80 reference samples. Each reference sample produces a score using the algorithm, and the first predetermined cutoff value can be an arithmetic mean of these scores. Each reference sample can be blood, serum, plasma, or non-neoplastic tissue. In some aspects, each reference sample is blood. In some aspects, each reference sample is of the same type as the test sample.

Each of the biomarkers disclosed herein may have one or more transcript variants. The methods disclosed herein can measure the expression level of any one of the transcript variants for each biomarker.

The expression level can be measured in a number of ways, including, but not limited to: measuring the mRNA encoded by the selected genes; measuring the amount of protein encoded by the selected genes; and measuring the activity of the protein encoded by the selected genes.

In some aspects of the methods of the present disclosure, a biomarker can be RNA, cDNA, protein or any combination thereof. When the biomarker is RNA, the RNA can be reverse transcribed to produce cDNA (such as by RT-PCR), and the produced cDNA expression level can be detected. The expression level of a biomarker can be detected by forming a complex between the biomarker and a labeled probe or primer. When the biomarker is RNA or cDNA, the RNA or cDNA can be detected by forming a complex between the RNA or cDNA and a labeled nucleic acid probe or primer. The complex between the RNA or cDNA and the labeled nucleic acid probe or primer can be a hybridization complex.

In some aspects of the methods of the present disclosure, gene expression can be detected by microarray analysis. Differential gene expression can also be identified, or confirmed using the microarray technique. Thus, the expression profile biomarkers can be measured in either fresh or fixed tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. The source of mRNA typically is total RNA isolated from a biological sample, and corresponding normal tissues or cell lines may be used to determine differential expression.

In some aspects of microarray techniques, PCR amplified inserts of cDNA clones are applied to a substrate in a dense array. In some aspects, at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the microarray chip is scanned by a device such as, confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. Microarray analysis can be performed by commercially available equipment, following manufacturer's protocols.

In some aspects of the methods of the present disclosure, the biomarkers can be detected in a biological sample using qRT-PCR. The first step in gene expression profiling by RT-PCR is extracting RNA from a biological sample followed by the reverse transcription of the RNA template into cDNA and amplification by a PCR reaction. The reverse transcription reaction step is generally primed using specific primers, random hexamers, or oligo-dT primers, depending on the goal of expression profiling. The two commonly used reverse transcriptases are avilo myeloblastosis virus reverse transcriptase (AMV-RT) and Moloney murine leukemia virus reverse transcriptase (MLV-RT).

In some aspects of the methods of the present disclosure, when the biomarker is a protein, the protein can be detected by forming a complex between the protein and a labeled antibody. The label can be any label for example a fluorescent label, chemiluminescence label, radioactive label, etc. Exemplary methods for protein detection include, but are not limited to, enzyme immunoassay (EIA), radioimmunoassay (MA), Western blot analysis and enzyme linked immunoabsorbant assay (ELISA). For example, the biomarker can be detected in an ELISA, in which the biomarker antibody is bound to a solid phase and an enzyme-antibody conjugate is employed to detect and/or quantify biomarker present in a sample. Alternatively, a western blot assay can be used in which solubilized and separated biomarker is bound to nitrocellulose paper. The combination of a highly specific, stable liquid conjugate with a sensitive chromogenic substrate allows rapid and accurate identification of samples.

In some aspects of the methods of the present disclosure, the methods described herein can have a specificity, sensitivity, and/or accuracy of at least 75%, 80%, 85%, 90%, 91%, 92%, 93%, 94%, 95%, 96%, 97%, 98%, or 99%.

In some aspects of the methods of the present disclosure, a labeled probe, a labeled primer, a labeled antibody or a labeled nucleic acid can comprise a fluorescent label.

Any algorithm that can generate a score for a sample by assessing where that sample value falls onto a prediction model generated using different techniques, e.g., decision trees, can be used in the methods disclosed herein. The algorithm analyzes the data (i.e., expression levels) and then assigns a score. In some aspects, the algorithm can be a machine-learning algorithm. Exemplary algorithms that can be used in the methods disclosed herein can include, but are not limited to, XGBoost (XGB), Random Forest (RF), glmnet, cforest, Classification and Regression Trees for Machine Learning (CART), treebag, K-Nearest Neighbors (kNN), neural network (nnet), Support Vector Machine radial (SVM-radial), Support Vector Machine linear (SVM-linear), Naïve Bayes (NB), multilayer perceptron (mlp) or any combination thereof.

In some aspects of the methods of the present disclosure, the algorithm can be XGB (also called XGBoost). XGB is an implementation of gradient boosted decision trees designed for speed and performance.

In some aspects of the methods of the present disclosure, a therapy can comprise anti-cancer therapy, surgery, chemotherapy, targeted drug therapy, radiation therapy, immunotherapy, or any combination thereof.

In some aspects of the methods of the present disclosure, surgery can comprise removing a polyp during a colonoscopy, endoscopic mucosal resection, a partial colectomy, an ostomy, removing at least one cancerous lesion from the liver, or any combination thereof.

In some aspects of the methods of the present disclosure, anti-cancer therapy can comprise anti-colon cancer therapy.

In some aspects of the methods of the present disclosure, chemotherapy can comprise FOLFOX, FOLFIRI, a combination of 5-FU and leucovorin, capecitabine, irinotecan, CapeOx or any combination thereof.

In some aspects of the methods of the present disclosure, targeted drug therapy can comprise bevacizumab, cetuximab, panitumumab, regorafenib, a combination of trifluridine and tipiracil, an EGFR TKI inhibitor or any combination thereof.

In some aspects of the methods of the present disclosure, immunotherapy can comprise pembrolizumab, nivolumab or a combination of pembrolizumab and nivolumab.

For early-stage colon cancer, a minimally invasive approach to surgery can be used to remove the cancer. For example, if the cancer is completely contained within a polyp, the polyp can be removed during a colonoscopy. Endoscopic mucosal resection can be performed to remove larger polyps. Polyps that cannot be removed during a colonoscopy may be removed using laparoscopic surgery.

If the cancer has grown into or through the colon, partial colectomy can be performed to remove the part of the colon that contains the cancer, along with a margin of normal tissue on either side of the cancer. When it's not possible to reconnect the healthy portions of the colon or rectum, an ostomy can be performed to create an opening in the wall of the abdomen from a portion of the remaining bowel for the elimination of stool into a bag that fits securely over the opening. Lymph node removal can also be performed.

For advanced colon cancer, an operation to relieve a blockage of the colon or other conditions can also be performed. In specific cases where the cancer has spread only to the liver, surgery to remove the cancerous lesion from the liver can be performed.

For chemotherapies, either the FOLFOX (5-FU, leucovorin, and oxaliplatin) or CapeOx (capecitabine and oxaliplatin) regimens are used most often, but some patients may get 5-FU with leucovorin or capecitabine alone based on their age and health needs. Irinotecan can also be used as a chemotherapeutic agent for treating a colon cancer.

Targeted drug therapies target specific malfunctions that allow cancer cells to grow. These therapies include, but are not limited to, bevacizumab, cetuximab, panitumumab, ramucirumab, regorafenib, ziv-aflibercept, a combination of trifluridine and tipiracil, and an EGFR TKI inhibitor.

Immunotherapies for colon cancer include, but are not limited to, pembrolizumab (Keytruda®) and nivolumab (Opdivo®).

The sequence information of the colon cancer biomarkers and housekeepers is shown in Table 1.

TABLE 1

Colon Cancer Biomarker/Housekeeper Sequence Information

| Gene Name | RefSeq Accession | Sequence | SEQ ID NO: |
|---|---|---|---|
| ADRM1 | NM_007002.3 | gttagagccggctgcgcggcttacggggctcaatcggcgg cgagagcggcaggcggggcgggccgaacgcgggtttccgg cggggcccggcaggcgccgaggaggaagagcgagcccgga cggcgcctctcgaacgagtgtgggcgcgaggcaggatgac gacctcaggcgcgctcttctcaagcctggtgccaggctct cggggcgcctccaacaagtacttggtggagtttcgggcgg gaaagatgtccctgaaggggaccaccgtgactccggataa gcggaaagggctggtgtacattcagcagacggacgactcg cttattcacttctgctggaaggacaggacgtccgggaacg tggaagacgacttgatcatcttccctgacgactgtgagtt caagcgggtgccgcagtgccccagcgggagggtctacgtg ctgaagttcaaggcagggtccaagcggcttttcttctgga | 1 |

TABLE 1-continued

Colon Cancer Biomarker/Housekeeper Sequence Information

| Gene Name | RefSeq Accession | Sequence | SEQ ID NO: |
|---|---|---|---|
| | | tgcaggaacccaagacagaccaggatgaggagcattgccg gaaagtcaacgagtatctgaacaaccccccgatgcctggg gcgctgggggccagcggaagcagcggccacgaactctctg cgctaggcggtgagggtggcctgcagagcctgctgggaaa catgagccacagccagctcatgcagctcatcggaccagcc ggcctcggaggactgggtgggctgggggccctgactggac ctggcctggccagcttactggggagcagtgggcctccagg gagcagctcctcctccagctcccggagccagtcggcagcg gtcaccccgtcatccaccacctcttccacccgtgccaccc cagccccttctgctccagcagctgcctcagcaactagccc gagccccgcgcccagttccgggaatggagccagcacagca gccagcccgacccagcccatccagctgagcgacctccaga gcatcctggccacgatgaacgtaccagccgggccagcagg cggccagcaagtggacctggccagtgtgctgacgccggag ataatggctcccatcctcgccaacgcggatgtccaggagc gcctgcttccctacttgccatctggggagtcgctgccgca gaccgcggatgagatccagaatacccctgacctcgcccag ttccagcaggccctgggcatgttcagcgcagccttggcct cggggcagctgggcccctcatgtgccagttcggtctgcc tgcagaggctgtggaggccgccaacaagggcgatgtggaa gcgtttgccaaagccatgcagaacaacgccaagcccgagc agaaagagggcgacacgaaggacaagaaggacgaagagga ggacatgagcctggactgagccacgcgccgtcctccgagg aactgggcgcttgcagtgcgttgcacaccctcacctccca cccactgattattaataaagtcttttcttttacctgccaa aaaaaaaaaaaaaaaa | |
| CDK4 | NM_000075.3 | cacctcctgtccgcccctcagcgcatgggtggcggtcacg tgcccagaacgtccggcgttcgccccgccctcccagtttc cgcgcgcctctttggcagctggtcacatggtgagggtggg ggtgaggggcctctctagcttgcggcctgtgtctatggt cgggccctctgcgtccagctgctccggaccgagctcgggt gtatggggccgtaggaaccggctccggggccccgataacg ggccgccccacagcaccccgggctggcgtgagggtctcc cttgatctgagaatggctacctctcgatatgagccagtgg ctgaaattggtgtcggtgcctatgggacagtgtacaaggc ccgtgatccccacagtggccactttgtggccctcaagagt gtgagagtccccaatggaggaggaggtggaggaggccttc ccatcagcacagttcgtgaggtggctttactgaggcgact ggaggcttttgagcatcccaatgttgtccggctgatggac gtctgtgccacatcccgaactgaccgggagatcaaggtaa ccctggtgtttgagcatgtagaccaggacctaaggacata tctggacaaggcaccccaccaggcttgccagccgaaacg atcaaggatctgatgcgccagtttctaagaggcctagatt tccttcatgccaattgcatcgttcaccgagatctgaagcc agagaacattctggtgacaagtggtggaacagtcaagctg gctgactttggcctggccagaatctacagctaccagatgg cacttacacccgtggttgttacactctggtaccgagctcc cgaagttcttctgcagtccacatatgcaacacctgtggac atgtggagtgttggctgtatctttgcagagatgtttcgtc gaaagcctctcttctgtggaaactctgaagccgaccagtt gggcaaaatctttgacctgattggctgcctccagaggat gactggcctcgagatgtatccctgccccgtggagcctttc cccccagagggcccgcccagtgcagtcggtggtacctga gatggaggagtcgggagcacagctgctgctggaaatgctg acttttaacccacacaagcgaatctctgcctttcgagctc tgcagcactcttatctacataaggatgaaggtaatccgga gtgagcaatggagtggctgccatggaaggaagaaaagctg ccatttcccttctggacactgagagggcaatctttgcctt tatctctgaggctatggagggtcctcctccatctttctac agagattactttgctgccttaatgacattcccctcccacc tctccttttgaggcttctccttctccttcccatttctcta cactaagggatgttccctcttgtccctttccctacctt tatatttggggtccttttttatacaggaaaaacaaaacaa agaaataatggtctttttttttttttttaatgttttcttcct ctgtttggctttgccattgtgcgatttggaaaaaccactt ggaagaagggactttcctgcaaaaccttaaagactggtta aattacagggcctaggaagtcagtggagcccttgactga caaagcttagaaaggaactgaaattgcttctttgaatatg gattttaggcggggcgtggtggctcacgcctataatccca gcacgtgggaggccaacgcgggtggatcacctgaggtca ggagttcgagaccagcctgactaacatggtgaaaccctgt ctctactaaaaatacaaaattagtcaggcgtggtggtgca cacctgtaatcccagctacttgggagactgaggcaggagg | 2 |

TABLE 1-continued

Colon Cancer Biomarker/Housekeeper Sequence Information

| Gene Name | RefSeq Accession | Sequence | SEQ ID NO: |
|---|---|---|---|
| | | atcgcttgaacccgggaggcagaggttgcggtgagccgag atcatgccattgcactccagcctgggcaacagagcaagac tctgtgtcaaaaaaaaaaaaagaatatagatttttaaatg gcaaaaaaaaaaaaaaaaa | |
| COMT | NM_000754.3 | cggcctgcgtccgccaccggaagcgccctcctaatccccg cagcgccaccgccattgccgccatcgtcgtggggcttctg gggcagctagggctgcccgccgcgctgcctgcgccggacc ggggcgggtccagtcccgggcgggccgtcgcgggagagaa ataacatctgctttgctgccgagctcagaggagaccccag accccctcccgcagccagagggctggagcctgctcagaggt gctttgaagatgccggaggccccgcctctgctgttggcag ctgtgttgctgggcctggtgctgctggtggtgctgctgct gcttctgaggcactggggctggggcctgtgccttatcggc tggaacgagttcatcctgcagcccatccacaacctgctca tgggtgacaccaaggagcagcgcatcctgaaccacgtgct gcagcatgcggagcccgggaacgcacagagcgtgctggag gccattgacacctactgcgagcagaaggagtgggccatga acgtgggcgacaagaaaggcaagatcgtggacgccgtgat tcaggagcaccagccctccgtgctgctggagctggggggcc tactgtggctactcagctgtgcgcatggcccgcctgctgt caccaggggcgaggctcatcaccatcgagatcaaccccga ctgtgccgccatcacccagcggatggtggatttcgctggc gtgaaggacaaggtcacccttgtggttgggagcgtcccagg acatcatccccagctgaagaagaagtatgatgtggacac actggacatggtcttcctcgaccactggaaggaccggtac ctgccggacacgcttctcttggaggaatgtggcctgctgc ggaaggggacagtgctactggctgacaacgtgatctgccc aggtgcgccagacttcctagcacacgtgcgcgggagcagc tgctttgagtgcacacactaccaatcgttcctggaataca gggaggtggtggacggcctggagaaggccatctacaaggg cccaggcagcgaagcagggccctgactgccccccggccc ccctctcgggctctctcacccagcctggtactgaaggtgc cagacgtgctcctgctgaccttctgcggctccgggctgtg tcctaaatgcaaagcacacctcggccgaggcctgcgccct gacatgctaacctctctgaactgcaacactggattgttct tttttaagactcaatcatgacttctttactaacactggct agctatattatcttatatactaatatcatgttttaaaaat ataaaatagaaattaagaatctaaatatttagatataact cgacttagtacatccttctcaactgccattcccctgctgc ccttgacttgggcaccaaacattcaaagctccccttgacg gacgctaacgctaagggcggggcccctagctggctgggtt ctgggtggcacgcctggcccactggcctccagccacagt ggtgcagaggtcagccctcctgcagctaggcagggggcac ctgttagccccatggggacgactgccggcctgggaaacga agaggagtcagccagcattcacacctttctgaccaagcag gcgctggggacaggtggaccccgcagcagcaccagcccct ctgggccccatgtggcacagagtggaagcatctccttccc tactccccactgggccttgcttacagaagaggcaatggct cagaccagctcccgcatccctgtagttgcctccctggccc atgagtgaggatgcagtgctggtttctgcccacctacacc tagagctgtccccatctcctccaaggggtcagactgctag ccacctcagaggctccaagggcccagttcccaggcccagg acaggaatcaaccctgtgctagctgagttcacctgcaccg agaccagcccctagccaagattctactcctgggctcaagg cctggctagccccagccagcccactcctatggatagaca gaccagtgagcccaagtggacaagtttggggccacccagg gaccagaaacagagcctctgcaggacacagcagatgggca cctgggaccacctccacccagggccctgcccagacgcgc agagcccgacacaagggagaagccagccacttgtgccag acctgagtggcagaaagcaaaaagttcctttgctgcttta atttttaaattttcttacaaaaatttaggtgtttaccaat agtcttattttggcttatttttaa | 3 |
| DHCR7 | NM_001163817.1 | aatcgctgacatcatccgggggcgggcgcccctgccctgc gggtgactccgaccctggctagagggtaggcggcgtgga gcagcgcgcgcaagcgaggccaggggaaggtgggcgcagg actttagccggttgagaaggatcaagcaggcatttggagc acaggtgtctagaaactttttaaggggccggttcaagaagg aaaagttcccttctgctgtgaaactatttggcaagaggct ggagggcccaatggctgcaaaatcgcaacccaacattccc aaagccaagagtctagatggcgtcaccaatgacagaaccg catctcaagggcagtggggccgtgcctgggaggtggactg gttttcactggcgagcgtcatcttcctactgctgttcgcc | 4 |

TABLE 1-continued

Colon Cancer Biomarker/Housekeeper Sequence Information

| Gene Name | RefSeq Accession | Sequence | SEQ ID NO: |
|---|---|---|---|
| | | cccttcatcgtctactacttcatcatggcttgtgaccagt acagctgcgccctgactggccctgtggtggacatcgtcac cggacatgctcggctctcggacatctgggccaagactcca cctataacgaggaaagccgcccagctctataccttgtggg tcaccttccaggtgcttctgtacacgtctctccctgactt ctgccataagtttctaccggctacgtaggaggcatccag gaggggccgtgactcctgcaggggttgtgaacaagtatc agatcaatggcctgcaagcctggctcctcacgcacctgct ctggtttgcaaacgctcatctcctgtcctggttctcgccc accatcatcttcgacaactggatcccactgctgtggtgcg ccaacatccttggctatgccgtctccaccttcgccatggt caagggctacttcttcccaccagcgccagagactgcaaa ttcacaggcaatttctttacaactacatgatgggcatcg agtttaaccctcggatcgggaagtggtttgacttcaagct gttcttcaatgggcgccccgggatcgtcgcctggaccctc atcaacctgtccttcgcagcgaagcagcgggagctccaca gccatgtgaccaatgccatggtcctggtcaacgtcctgca ggccatctacgtgattgacttcttctggaacgaaacctgg tacctgaagaccattgacatctgccatgaccacttcgggt ggtacctgggctggggcgactgtgtctggctgccttatct ttacacgctgcagggtctgtacttggtgtaccaccccgtg cagctgtccaccccgcacgccgtgggcgtcctgctgctgg gcctggtgggctactacatcttccgggtggccaaccacca gaaggacctgttccgccgcacggatgggcgctgcctcatc tgggggcaggaagcccaaggtcatcgagtgctcctacacat ccgccgatgggcagaggcaccacagcaagctgctggtgtc gggcttctgggcgtggcccgccacttcaactacgtcggc gacctgatgggcagcctggcctactgcctggcctgtggcg gcggccacctgctgccctacttctacatcatctacatggc catcctgctgacccaccgctgcctccgggacgagcaccgc tgcgccagcaagtacggccgggactgggagcgctacaccg ccgcagtgccttaccgcctgctgcctggaatcttctaagg gcacgccctagggagaagccctgtggggctgtcaagagcg tgttctgccaggtccatgggggctggcatcccagctccaa ctcgaggagcctcagtttcctcatctgtaaactggagaga gcccagcacttggcaggtgtccagtacctaatcacgctct gttccttgcttttgccttcaagggaattccgagtgtccag cactgccgtattgccagcacagacggattttctctaatca gtgtccctggggcaggaggatgacccagtcaccttacta gtcctttggagacaatttacctgtattaggagcccaggcc acgctacactctgcccacactggtgagcaggaggtcttcc cacgccctgtcattaggctgcatttactcttgctaaataa aagtgggagtggggcgtgcgcgttatccatgtattgcctt tcagctctagatccccctcccctgcctgctctgcagtcgt gggtggggcccgtgcgccgtttctccttggtagcgtgcac ggtgttgaactgggacactggggagaaaggggctttcatg tcgttttccttcctgctcctgctgcacagctgccaggagtg ctctgcctggagtctgcagacctcagagaggtcccagcac cggctgtggcctttcaggtgtaggcaggtgggctctgctt cccgattccctgtgagcgcccaccctctcgaaagaattt ctgcttgccctatgactgtgcagactctggctcgagcaac ccggggaacttcaccctcaggggcctccacaccttctcc agcgaggaggtctcagtcccagcctcgggagggcacctcc ttttctgtgctttcttccctgaggcattcttcctcatccc tagggtgttgtgtagaactcttttaaactctatgctccg agtagagttcatctttatattaaacttcccctgttcaaat aa | |
| HMOX2 | NM_001127204.1 | catctctaggccccgccccgcgctgcgtgcccacgttgcg ccggcctcgcgccagtccgctgggctgcagggactgcggc gcctgagggagtcgctgacgggcacgctgactggaggctg gcggacaggcgacagcgacctgcggcagagtcttgctgcg acacccaggctggagtgcaatggcgctatctcggctcact gcaacctccgcttcccggattcaagcgattctcctgcctc agcctcccgagtaggtgggactacaggaccagaggagcga gagcagcaagaaccacacccagcagcaatgtcagcggaag tggaaacctcagagggggtagacgagtcagaaaaaagaa ctctggggcctagaaaaggagaaccaaatgagaatggct gacctctcggagctcctgaaggaagggaccaaggaagcac acgaccgggcagaaaacacccagtttgtcaaggacttctt gaaaggcaacattaagaaggagctgtttaagctggccacc acggcactttacttcacatactcagccctcgaggaggaaa tggagcgcaacaaggaccatccagcctttgccccttgta cttccccatggagctgcaccggaaggaggcgctgaccaag | 5 |

TABLE 1-continued

Colon Cancer Biomarker/Housekeeper Sequence Information

| Gene Name | RefSeq Accession | Sequence | SEQ ID NO: |
|---|---|---|---|
| | | gacatggagtatttctttggtgaaaactgggaggagcagg<br>tgcagtgccccaaggctgcccagaagtacgtggagcggat<br>ccactacatagggcagaacgagccggagctactggtggcc<br>catgcatacacccgctacatgggggatctctcgggggggcc<br>aggtgctgaagaaggtggcccagcgagcactgaaactccc<br>cagcacaggggaagggacccagttctacctgtttgagaat<br>gtggacaatgcccagcagttcaagcagctctaccgggcca<br>ggatgaacgccctggacctgaacatgaagaccaaagagag<br>gatcgtggaggaggccaacaaggcttttgagtataacatg<br>cagatattcaatgaactggaccaggccggctccacactgg<br>ccagagagaccttggaggatgggttccctgtacacgatgg<br>gaaaggagacatgcgtaaatgcccttctacgctgctgaa<br>caagacaaaggtgccctggagggcagcagctgtcccttcc<br>gaacagctatggctgtgctgaggaagcccagcctccagtt<br>catcctggccgctggtgtggccctagctgctggactcttg<br>gcctggtactacatgtgaagcacccatcatgccacaccgg<br>taccctcctcccgactgaccactggcctaccccttctcc<br>agccctgactaaactaccacctcaggtgactttttaaaaa<br>atgctgggtttaagaaaggcaaccaataaaagccagatgc<br>tagagcctctgcctgacagcatcctctctatgggccatat<br>tccgcactgggcacaggccgtcaccctgggagcagtcggc<br>acagtgcagcaagcctggcccccgacccagctctactcca<br>ggcttccacacttctgggccctaggctgcttccggtagtc<br>cctgtttttgcagtacatgggtgactatctcccctgttgg<br>aggtgagtggcctgtaagtccaagctgtgcgagggggcct<br>tgctggatgctgctgtacaacttctgggcctctcttggac<br>cctgggagtgagggtgggtgtgggtggaagcctcagaggc<br>cttgggagctcatccctctcacccagaatccctctaaccc<br>cttgggtgcggtttgctcagccccagcttatctcctcctc<br>cgcgctgtgtaaatgctccagcactcaataaagtgggctt<br>tgcaagctaaaaaaaaaaaaaaaaaaaaaaa | |
| MCM2 | NM_004526.3 | atgacgtcgcgttccgtagggctcttcccgggctttggtg<br>ggtcacgtgaaccacttttcgcgcgaaacctggttgttgc<br>tgtagtggcggagaggatcgtggtactgctatggcggaat<br>catcggaatccttcaccatggcatccagcccggcccagcg<br>tcggcgaggcaatgatcctctcacctccagccctggccga<br>agctcccggcgtactgatgccctcacctccagccctggcc<br>gtgaccttccaccatttgaggatgagtccgaggggctcct<br>aggcacagaggggcccctggaggaagaagaggatggagag<br>gagctcattggagatggcatggaaagggactaccgcgcca<br>tcccagagctggacgcctatgaggccgagggactggctct<br>ggatgatgaggacgtagaggagctgacggccagtcagagg<br>gaggcagcagagcgggccatgcggcagcgtgaccgggagg<br>ctggccggggcctgggccgcatgcgccgtgggctcctgta<br>tgacagcgatgaggaggacgaggagcgccctgcccgcaag<br>cgccgccaggtggagcgggccacggaggacggcgaggagg<br>acgaggagatgatcgagagcatcgagaacctggaggatct<br>caaaggccactctgtgcgcgagtgggtgagcatggcgggc<br>ccccggctggagatccaccaccgcttcaagaacttcctgc<br>gcactcacgtcgacagccacggccacaacgtcttcaagga<br>gcgcatcagcgacatgtgcaaagagaaccgtgagagcctg<br>gtggtgaactatgaggacttggcagccagggagcacgtgc<br>tggcctacttcctgcctgaggcaccggcggagctgctgca<br>gatctttgatgaggctgccctggaggtggtactggccatg<br>tacccaagtacgaccgcatcaccaaccacatccatgtcc<br>gcatctcccacctgcctctggtggaggagctgcgctcgct<br>gaggcagctgcatctgaaccagctgatccgcaccagtggg<br>gtggtgaccagctgcactggcgtcctgccccagctcagca<br>tggtcaagtacaactgcaacaagtgcaatttcgtcctggg<br>tccttctgccagtcccagaaccaggaggtgaaaccaggc<br>tcctgtcctgagtgccagtcggccggccccttgaggtca<br>acatggaggagaccatctatcagaactaccagcgtatccg<br>aatccaggagagtccaggcaaagtggcggctggccggctg<br>ccccgctccaaggacgccattctcctcgcagatctggtgg<br>acagctgcaagccaggagacgagatagagctgactggcat<br>ctatcacaacaactatgatggctccctcaacactgccaat<br>ggcttccctgtctttgccactgtcatcctagccaaccacg<br>tggccaagaaggacaacaaggttgctgtaggggaactgac<br>cgatgaagatgtgaagatgatcactagcctctccaaggat<br>cagcagatcggagagaagatctttgccagcattgctcctt<br>ccatctatggtcatgaagacatcaagagaggcctggctct<br>ggccctgttcggaggggagcccaaaaacccaggtggcaag<br>cacaaggtacgtggtgatatcaacgtgctcttgtgcggag | 6 |

TABLE 1-continued

Colon Cancer Biomarker/Housekeeper Sequence Information

| Gene Name | RefSeq Accession | Sequence | SEQ ID NO: |
|---|---|---|---|
| | | accctggcacagcgaagtcgcagtttctcaagtatattga gaaagtgtccagccgagccatcttcaccactggccagggg gcgtcggctgtgggcctcacggcgtatgtccagcggcacc ctgtcagcagggagtggaccttggaggctggggccctggt tctggctgaccgaggagtgtgtctcattgatgaatttgac aagatgaatgaccaggacagaaccagcatccatgaggcca tggagcaacagagcatctccatctcgaaggctggcatcgt cacctccctgcaggctcgctgcacggtcattgctgccgcc aaccccataggagggcgctacgacccctcgctgactttct ctgagaacgtggacctcacagagcccatcatctcacgctt tgacatcctgtgtgtggtgagggacaccgtggacccagtc caggacgagatgctggcccgcttcgtggtgggcagccacg tcagacaccacccagcaacaaggaggaggaggggctggc caatggcagcgctgctgagcccgccatgcccaacacgtat ggcgtggagcccctgccccaggaggtcctgaagaagtaca tcatctacgccaaggagagggtccacccgaagctcaacca gatggaccaggacaaggtggccaagatgtacagtgacctg aggaaagaatctatggcgacaggcagcatccccattacgg tgcggcacatcgagtccatgatccgcatggcggaggccca cgcgcgcatccatctgcgggactatgtgatcgaagacgac gtcaacatggccatccgcgtgatgctggagagcttcatag acacacagaagttcagcgtcatgcgcagcatgcgcaagac ttttgcccgctaccttttcattccggcgtgacaacaatgag ctgttgctcttcatactgaagcagttagtggcagagcagg tgacatatcagcgcaaccgctttggggcccagcaggacac tattgaggtccctgagaaggacttggtggataaggctcgt cagatcaacatccacaacctctctgcatttttatgacagtg agctcttcaggatgaacaagttcagccacgacctgaaaag gaaaatgatcctgcagcagttctgaggccctatgccatcc ataaggattccttgggattctggtttggggtggtcagtgc cctctgtgctttatggacacaaaaccagagcacttgatga actcggggtactagggtcagggcttatagcaggatgtctg gctgcacctggcatgactgtttgtttctccaagcctgctt tgtgcttctcacctttgggtgggatgccttgccagtgtgt cttacttggttgctgaacatcttgccacctccgagtgctt tgtctccactcagtaccttggatcagagctgctgagttca ggatgcctgcgtgtggtttaggtgttagccttcttacatg gatgtcaggagagctgctgccctcttggcgtgagttgcgt attcaggctgcttttgctgccttttggccagagagctggtt gaagatgtttgtaatcgttttcagtctcctgcaggtttct gtgcccctgtggtggaagagggcacgacagtgccagcgca gcgttctgggctcctcagtcgcaggggtgggatgtgagtc atgcggattatccactcgccacagttatcagctgccattg ctccctgtctgtttcccactctcttatttgtgcattcgg tttggtttctgtagttttaattttaataaagttgaataa aatataaaaaaaaaaaaaaaaaa | |
| PDXK | NM_003681.4 | cggaactcgcgggttcggagccgcccgctgaggtcagaag gaggcgtctgcgctgatcgggtccgccgcgcgccagagcc agagtcgcagccgaggggagccggggccggagcccgagcc cgagccgagccggagcccgagcgagcggcggagaccgtgc ccccgcctcggccccgcgccgccgcggccaggcccggcat ggaggaggagtgccgggtgctctccatacagagccacgtc atccgcggctacgtgggcaaccgggcggccacgttcccgc tgcaggttttgggatttgagattgacgcggtgaactctgt ccagttttcaaaccacacaggctatgcccactggaagggc caagtgctgaattcagatgagctccaggagttgtacgaag gcctgaggctgaacaacatgaataaatatgactacgtgct cacaggttatacgagggacaagtcgttcctggccatggtg gtggacattgtgcaggagctgaagcagcagaaccccaggc tggtgtacgtgtgtgatccagtcttgggtgacaagtggga cggcgaaggctcgatgtacgtcccggaggacctccttccc gtctacaaagaaaagtggtgccgcttgcagacattatca cgcccaaccagtttgaggccgagttactgagtggccggaa gatccacagccaggaggaagccttgcgggtgatggacatg ctgcactctatggccccgacaccgtggtcatcaccagct ccgacctgccctccccgcagggcagcaactacctgattgt gctggggagtcagaggaggaggaatcccgctggctccgtg gtgatggaacgcatccggatggacattcgcaaagtggacg ccgtctttgtgggcactggggacctgtttgctgccatgct cctggcgtggacacacaagcaccccaataacctcaaggtg gcctgtgagaagaccgtgtctaccttgcaccacgttctgc agaggaccatccagtgtgcaaaagcccaggccggggaagg agtgaggcccagccccatgcagctggagctgcggatggtg | 7 |

TABLE 1-continued

Colon Cancer Biomarker/Housekeeper Sequence Information

| Gene Name | RefSeq Accession | Sequence | SEQ ID NO: |
|---|---|---|---|
| | | cagagcaaaagggacatcgaggacccagagatcgtcgtcc aggccacggtgctgtgagggccccgccgcttgcccgtgac acgcagcgcgttggtgtctccgtgtttgtccctgtgaaaa catgtaacgtctgccttagagccatgaccgaaacttgata ttttttctttcatgagtgtccggcatctgctggtcttca ttgtgaaacgtgccagtcgtgctttgtgaaaaataacaaa gtggtcacagaaatttgtgatctgaaaaccggctcccctt ccccacaaggctcctgggcctccgggaagacgggcccctg tttgccatctcggggtgttccctgtgggagggtgagtgg gtgaggccgagcctgctgcgtgtggagcctcgagtgggcc ctggctgccactaccgtacagaggccgtgtcgcgctgggc tgggcctgggtggcctctgtctttgcatctctgagaagga gtcgggtggtaacggttggggtcaggaagaattctgccaa gtatctttactgtcattctgaccatagcctctttgttccc gcattcgaacttttggttcttactttgctgctcgtttagt ccctgggatttcagatcttaggctgttgtttcaccgtat gggagggttgatgtgagcttgcttggagacacacggtgca gcatcagggaccttcccaggccccagcaaattcaagtcgg tctgcagacctctcagctacccgcgggacctcttgtaacc catcggcatcttccaggaatccgccgagtgacttgaggaa gatgctaacgcagtaaggtctgtgctgggccaagagcagc tttgaagctccagagaaccaccccgtcaggttccttgtgg aagctcccctcatccgtggtgcagcaggctgagcactgcg cgtttgccacgtgctgcccgtgacagcacattgagccaca gcatttgtagacaggacagaggggtgcctgcccctgccc ctgctggcacatttaacccttgtcccctgacctcagttct gtgccccaccaaatgcccaggggcaagaggccaccctgga agctgccaatcttccaaggtgggtgtggggcacggtgggg gcgggcagctcccaggcccttgggcaggctggggtgacgg cagaggccacagcaccagctctgacaagtcctatcatcct ctgctcagcagtgacctccctggccccactttgcccagag tttggggtcccccaggtatagctataggcggcagtgcct gtccctggcctgccttgatttcagccacacccctgcagcc ctgcatcccagctctggggtgtgcagaggtttgtgtctcc agggaacccacggctggagagaaatagggagatgcaggaa gtggggcccatggggcccccaagaagcggactctccaag gggtaccccccaccccgctaccttccccacggacgggcccc tcctggagcccatacccctcctgtgaggcattccagtgtc ttctagaaagactcgcttgccaggagtgcgttctttgttg aaaaatgccctgaagcgaaaagatgcaggtttatatggaa ccccaccccctcccccactctcccactctgttcgttctg aatgtcttcacgagcgtgcatcagggcgcctggctccccc acctcagccagtgagtcagacacgggtttcgcagccatgt ttcctggctccgaggacacgggtggcaggcccgttgcagc ccagagccactggtccctacagggcgccgccacaccagca ggaaggaggatggctgtgtccggagcctggcggggaggcg gcctccccagtatgtgagtgcagggatctgccagaaccac ctggccctctgtagggcgtttaactggaaatacccctcact gccaagtgggagactggggcgtgtgccacattgccagccac caggaaagcttttcttttctttttttttttttaaac accaagagcacgtatagcatgggggaaagaacctaaatgt ctctctgtcctgtgagctggtgaaaaacccagcatgagaa cgcagtgtcaggtgtgggactccttctgcccctgcagtgg gtgttacgggcggtgtgccctggcgagcaagctttgattc ttggttctttgagctcgtttcagaggctgagtccccacat cagctttagttcttggacttccctgtattaagcaagaatt aggagaatggctgtccctgcaggcgcctcccgtaaatcct gagctctctgbgcgcaatctgaaacttctcttctgttttct ttggctgtatcagccgaaccaggagaggcctgggctgcga ctaaggagaaagaaatcggggggtttctgagagcagatggt gcctttgtgggtgcagggcttttgtggaaattgtcagcct ctacgggcagagtccggcatcccctccccagactgcctgc tgtcaaaccacggagcagctggagcctgccctgtccacgg cccgtttccacccgggcatgttcgtctctcatgacttcgg cagaggcccctggtggccttcagtttcagtttctcatcca ggaaggtaaccttgggcattggcagtgggtttccctatgg cttggatccagattagaattgatctttgttttcactttcc atagttaataacatgcaaaataatgagaagaatttatttt aaggtgacagctatactggtccaacatcgcctgcttattg tcagggtacagaagtttaatactttcttaatccagttttt caaacttctccctgtagaccgtaaggatgaattccacaat aggatccttttttaaaatcgattttaaattgttgcctagtc ctgccaaggttattatgtgcatctgttatttttccaatac atgtaaacagttgcagcatgatgctttgtttaatgtcctg | |

TABLE 1-continued

Colon Cancer Biomarker/Housekeeper Sequence Information

| Gene Name | RefSeq Accession | Sequence | SEQ ID NO: |
|---|---|---|---|
| | | ttcttaagctcgttagagccagttttgaaacgtttggtct<br>taccgtgaacggaggctggcttggcttagccacgctgatg<br>agtaagtgagggatgtctccatcttgagatcaccaggcaa<br>gagagttgcctgcaccaggtaagaggccaaagcccctggg<br>gtaacagtccccaccgctacccgaggtaaaacaataaaag<br>ctatgtggttgagctcaggcctctcgtgcctggtgtcaga<br>gaaggcagagcccacagtaggtgcacggtgcaaggccctg<br>ggagggcactggccagggaaggtggtatagatggccctca<br>gattgcggggccccgagcagctcccactctgcccgtcca<br>ccttccctggctccagcctcattctctctttagtttaact<br>atgcaaagagaggaggttgagagtgttctggcagctggag<br>ctcttttccttgtccttcctgccctccgatggggccacct<br>gtgtcggggcagcagtgtccatgtttatggagatcagagg<br>tgtccccactgtgtggctggactgtactctgctgcccggg<br>tagccaggagtctctccctctctcccctgccgcctgcctg<br>gtctcatgggcctccttcacacaccccctccctgtggatcg<br>cctgcctgggcccagagcaggggaactggagtttgtgagt<br>gagcagagcaggttatgtgcagacagggaaacgagaactt<br>tggacctggctttctgagtccaggtgagagctgtgtggcc<br>ccccgatgccactctgcccgccggagggatgtgcctgctg<br>agccttttccttccacgccgcctctcactgccaggccagc<br>ggcttccgctgagactcgctggagaggcggctcccgtgtc<br>cgtccaccgagcactcagatggatgctgatcaccagggcc<br>gagggggctcccagaaggaccccaggccctggggagggtg<br>gctgtgggaggccaagtccactgcccggaagtcttgtcag<br>ccctaagccagggaagcctggagcgtggcctggcgggtct<br>gggtggacaccgtccccactccggactcccagcacagggg<br>aggatacctgagcctgtatggccctgtagccctgggcaga<br>gctgggcctgtcgtgtgttcctgcctggcaggtgcaggtg<br>ctggccatctgcaggtggaaggaggtgggaatcttggatt<br>ttttgtttttttttgttttttttttttgagatgaagtct<br>cgctctgacacccaggctggcgtgcagtggtgtgatctcg<br>gctcactgcaaactccgcttcctgggttcaagtggttctc<br>ctgccccagcctcccaagtagctgggattacaggcatgcg<br>ccaccacgctcagctgattttgtattttagtagagatg<br>gggtttcaccatgttggccaagctggtctcaaactcctga<br>cctcaagtgatctgcccgcctcggcctcccagagtgctgg<br>gattacaggcatgagccagtgcaccggcggaatcttgga<br>attttatagacagcacctcagtttctgactccagccgca<br>cacctcctgcctctgccagcaggggttgccgccagaccag<br>agccagggccaggtccctgcgtccatccccccccggtagga<br>tggacgtgagccatccttctaggggactttttttcagtgtg<br>cgactcgtctctgttaggtggtaggagccagtttgtgtgg<br>cctgtgccacgctccacagtgcgtggctgggctctgtgtg<br>tggcctgtgtccctgtccctgcaggacccagcaggcatc<br>gtggcgtgacagctgtgtccaagccactgcccgggcatcc<br>catcacccaccagggtgcacggtctctcctgctgggggct<br>ttctgtcgcatgtgtgtctcctgtcgactctgcagtttgt<br>tctcagagcagaatgtttcctgttctcagtgcacaaagac<br>actggttttcaatcggcgtctaaaaccacgttcctgcctt<br>tcattgcaacacggtgtgttcatttgtttaaaacagttta<br>atgagtaagtttagatgactggtcaatatcttaaaaatgt<br>atattagtaagaagttcttcctggaattttttcttcgatt<br>ctggcagaataaacaggtgttttagttttcccactgtct<br>gagccaagcaggaccctgtcccagagcaagagatgtcccc<br>ttccatctctgaccccttgcctgggacaagctttgatgggg<br>ggcccagcttcaaggctgtggtgggaacagcacccccaa<br>atgccagcctctccttcttcccatccaccagtatactgc<br>ggggccatttctggtctttgtccaacaggaaacccatttc<br>tggtgggatatgccttccagtgccacagggccactcaccc<br>catgcatctctgtcctgcccgtcagtgctgggacggacag<br>caagggcaagcccagtgtctggcggataggtgggtgggaa<br>cagagagggagaatgccgtcctaagcttctgcttgggga<br>tcccccacacgacctgggtactgcctgggaaacctgtcct<br>aagtaaaactatggacctcgcctcgcccaccggcctgcga<br>agccagcatctccgtgaaggtggatggaagcgcctttgtc<br>ctcattttgagctgcaagctgggtcagcggctctgaagcc<br>ctcgagtgactttctaacccaagacccagcccctggcagg<br>aggagggtgggtgcagggctggtgggacaaaaagaggcct<br>cagcaggcctggaagaccctttccagtacatcccacagcgt<br>gtcgagcagctgggagaacctgtgtcaagctcgagccgtc<br>ataggtccccatgaggtgtctgaagcccttcttggtgat<br>gggaggcagaggtgctgacgttctggagcatggacgtgag<br>tcctcagctggctccgcgtgggcccttggagggtgccagg | |

TABLE 1-continued

Colon Cancer Biomarker/Housekeeper Sequence Information

| Gene Name | RefSeq Accession | Sequence | SEQ ID NO: |
|---|---|---|---|
| | | tgtgtggtgaccttctggatgcctttaacttcatggctgc gtcattcctgatttagaactttaaccggagcttcatctag tgattgcaaaactggaccaatgggaggacggcggcgcagc ccgctccctccgtggaatggagctcagctcttcggaggca tcaaagcacctgtcgcctccgtggtcccctgctgaggga gtgcggcctctgcaaggttcgggggtggcttcgtttgcct ggagtggccggccctgcttgtgccatgtggatgtttgtga gcctcggtcctacagcactgtgtaggctgcatctgtttcg tgctggtcctgttgacttgtatgatatccacaaataaata ttttcatggcggtcgtgttgaaaaaaaaaa | |
| POP7 | NM_005837.2 | ggaaggggcggggcgaacggaagccgggaaggcgattcat agctcgcggggtacgggcgcgcgtgcgcactccgcagccc gttcaggaccccggcgcgggcagggcgcccacgagctggc tggctgcttgcacccacatccttctttctctgggacctgg ggtcgcggttacttgggctggccggcgaacccttgagtgg cctggcggggagcgggcctcgcgcgcctggagggccctgt ggaacgaagagaggcacacagcatggcagaaaaccgagag ccccgcggtgctgtggaggctgaactggatccagtggaat acacccttaggaaaaggcttcccagccgcctgccccggag acccaatgacatttatgtcaacatgaagacggactttaag gcccagctggcccgctgccagaagctgctggacggagggg cccggggtcagaacgcgtgctctgagatctacattcacgg cttgggcctggccatcaaccgcgccatcaacatcgcgctg cagctgcaggcgggcagcttcgggtccttgcaggtggctg ccaatacctccaccgtggagcttgttgatgagctggagcc agagaccgacacacgggagccactgactcggatccgcaac aactcagccatccacatccgagtcttcagggtcacaccca agtaattgaaaagacactcctccacttatcccctccgtga tatggctcttcgcatgctgagtactggacctcggaccaga gccatgtaagaaaaggcctgttccctggaagcccaagga ctctgcattgagggtgggggtaattgtctcttggtgggcc cagttagtgggccttcctgagtgtgtgtatgcggtctgta actattgccatataaataaaaaatcctgttgcactagtgt cctgccatcccaaaaaaaaaaaaaaaaaa | 8 |
| S100P | NM_005980.2 | tgaggctgccttataaagcaccaagaggctgccagtggga cattttctcggccctgccagcccccaggaggaaggtgggt ctgaatctagcaccatgacggaactagagacagccatggg catgatcatagacgtctttcccgatattcgggcagcgag ggcagcacgcagaccctgaccaagggggagctcaaggtgc tgatggagaaggagctaccaggcttcctgcagagtggaaa agacaaggatgccgtggataaattgctcaaggacctggac gccaatggagatgcccaggtggacttcagtgagttcatcg tgttcgtggctgcaatcacgtctgcctgtcacaagtactt tgagaaggcaggactcaaatgatgccctggagatgtcaca gattcctggcagagccatggtcccaggcttcccaaaagtg tttgttggcaattattcccctaggctgagcctgctcatgt acctctgattaataaatgcttatgaaatga | 9 |
| SNRPA | NM_004596.4 | ggcggggccaggagagaaagctttgtggtttggtctcagg gaagtagcaggcgccggttgagagaactacggccctgtcg gaaggtaacctccggtgcaaacgaccatcggcggcaggcg agcggtacgcttggcgtccgggccttcctgggcccgtctg aggaaacttgctgctcgaggccaggctgcctaggacctgt ccctttttctatactggctcccacatccgggttttttct ccgggacggcccttcggatgcttgggcaatgggaatcgc catttagggtgctccgcccaccgggtcgcgtagagcatcc tggaagtcgtagtaaatctctcgagagttctctccgcacg cgggctggagaagcgggtcctacgcacgctttgttgtcgc gctttgcctccgtccttgcccctactcccgccttacctga cttccttttcggaggaagatccttgagcagccgacgttgg gacaaaggatttggagaaacccagggctaaagtcacgttt ttcctccttttaagacttacctcaacacttcactccatggc agttcccgagacccgccctaaccacactatttatatcaac aacctcaatgagaagatcaagaaggatgagctaaaaaagt ccctgtacgccatcttctcccagtttggccagatcctgga tatcctggtatcacggagcctgaagatgaggggccaggcc tttgtcatcttcaaggaggtcagcagcgccaccaacgccc tgcgctccatgcagggtttccctttctatgacaaacctat gcgtatccagtatgccaagaccgactcagatatcattgcc aagatgaaaggcaccttcgtggacgggaccgcaagcggg agaagaggaagcccaagagccaggagaccccggccaccaa gaaggctgtgcaaggcggggagccaccccgtggtgggg | 10 |

TABLE 1-continued

Colon Cancer Biomarker/Housekeeper Sequence Information

| Gene Name | RefSeq Accession | Sequence | SEQ ID NO: |
|---|---|---|---|
| | | gctgtccaggggcctgtcccgggcatgccgccgatgactc aggcgccccgcattatgcaccacatgccgggccagccgcc ctacatgccgcccctggtatgatcccccccgccaggcctt gcacctggccagatcccaccaggggccatgcccccgcagc agcttatgccaggacagatgcccctgcccagcctctttc tgagaatccaccgaatcacatcttgttcctcaccaacctg ccagaggagaccaacgagctcatgctgtccatgcttttca atcagttccctggcttcaaggaggtccgtctggtacccgg gcggcatgacatcgccttcgtggagtttgacaatgaggta caggcaggggcagctcgcgatgccctgcagggctttaaga tcacgcagaacaacgccatgaagatctcctttgccaagaa gtagcaccttttcccccatgcctgccccttccctgttc tggggccacccctttccccttggctcagcccctgaagg taagtccccccttgggggccttcttggagccgtgtgtgag tgagtggtcgccacacagcattgtacccagagtctgtccc cagacattgcacctggcgctgttaggccggaattaaagtg gcttttgaggtttggttttcacaatcaaaaaaaaaa aaaaaa | |
| SORD | NM_003104.5 | ctccacgctagcgccgcccaggctggcacaaaggaggaag cctagtcccgcccctgcgtgcggcgcttctcccaggcccc accttccatccagtgccctggaccctcggctgggtagcgc caccagagcgaccaaacgtcccgcgccttccaggccgcac tccagagccaaaagagctccatggcggcggcggccaagcc caacaacctttccctggtggtgcacggaccggggacttg cgcctggagaactatcctatccctgaaccaggcccaaatg aggtcttgctgaggatgcattctgttggaatctgtggctc agatgtccactactgggagtatggtcgaattgggaatttt attgtgaaaaagcccatggtgctgggacatgaagcttcgg gaacagtcgaaaaagtgggatcatcggtaaagcacctaaa accaggtgatcgtgttgccatcgagcctggtgctcccga gaaaatgatgaattctgcaagatgggccgatacaatctgt caccttccatcttcttctgtgccacgcccccgatgacgg gaacctctgccggttctataagcacaatgcagccttttgt tacaagcttcctgacaatgtcacctttgaggaaggcgccc tgatcgagccactttctgtggggatccatgcctgcaggag aggcggagttaccctgggacacaaggtccttgtgtgtgga gctgggccaatcgggatggtcactttgctcgtgccaaag caatgggagcagctcaagtagtggtgactgatctgtctgc tacccgattgtccaaagccaaggagattggggctgattta gtcctccagatctccaaggagagccctcaggaaatcgcca ggaaagtagaaggtcagctggggtgcaagccggaagtcac catcgagtgcacggggcagaggcctccatccaggcgggc atctacgccactcgctctggtggaacctcgtgcttgtgg ggctgggctctgagatgaccaccgtaccctactgcatgc agccatcgggaggtggatatcaagggcgtgtttcgatac tgcaacacgtggccagtggcgatttcgatgcttgcgtcca agtctgtgaatgtaaaacccctcgtcacccataggtttcc tctggagaaagctctggaggcctttgaaacatttaaaaag ggattgggttgaaaatcatgctcaagtgtgaccccagtg accagaatccctgatgttaatgggctctgccctcatcccc acagtcttgggatctcagggcacaatggctggacatgggt gggctctgatgcagaacttctctttgaatgttaagaat aactaatacaattcattgtgaacagaagtccttaagcaga ggaattggtgtgccttaaagatacaatctgggatagtttg ggggaacttgtagccagaatgccctgttcatgctgagcaa agttcagcaagtagagcagagtttggcaggcaggtgccag gaactccccttcttcctggagtgccttcattgaggaagga aatctggcccttgggtttcctggttccactgctactgacc cagaggggaatgagggctgagttatgaaaagataacttca tgaagacttaactgggcagaagctgattttcatgaaaat ctgccactcagggtctgggatgaaggcttgtcagcacttc cagtttagaacgcaatgtttctagagacatattggctgtt tgttttgatgataaaaggagaataagaaaaggcatcactt tcctggatccaggataattttaaaccaatcaaatgaaaa aaacaaacaaacaaaaaaggaaatgtcatgtgaggttaaa ccagtttgcattcccctaatgtgaaaaagtaagaggact actcagcactgtttgaagattgcctcttctacagcttctg agaattgtgttatttcacttgccaagtgaaggacccctc cccaacatgccccagcccaccccctaagcatggtcccttgt caccaggcaaccaggaaactgctacttgtggacctcacca gagaccaggagggtttggttagctcacaggacttcccca ccccagaagattagcatcccatactagactcatactcaac tcaactaggctcatactcaattgatggttattagacaatt | 11 |

TABLE 1-continued

Colon Cancer Biomarker/Housekeeper Sequence Information

| Gene Name | RefSeq Accession | Sequence | SEQ ID NO: |
|---|---|---|---|
| | | ccatttctttctggttattataaacagaaaatctttcctc ttctcattaccagtaaaggctcttggtatctttctgttgg aatgatttctatgaacttgtcttattttaatggtgggttt tttttctggtaagatttagacctaaatcgcatcatgccaa cttgtgactttgagactattcatcaagaatgaggatatag tagccatgacatagcttgagctatagcctttaattcctta cttggctatgggtggagggtgagtttgaagaggttctga ttttcttgtaacctgggaaagccatgaccttgtgcccgat tctttcagattgctttgggtaataaatattggtggtggta tctgactcatgctgctgtttatggtcctgtttagtgggga atggactcaggttacccatttcccagagggaaggatccca ggattttttgaaggttacatattttctgtaccaaatataat ttcattgacatgaattatctctaatcctcatgacaagcca catacacaatcattttgtagataaagaagatataaatgcc agaggagaccttaagattgtcttacaacacaacccttcag ttaacgagagagg | |
| STOML2 | NM_001287031.1 | tccgggggagcggaactgcaagaggaaaggctcgggtagg cttctgggagcgaccgctccgctcgtctcgttggttccgg aggtcgctgcggcggtgggaaatgctggcgcgcgcggcgc ggggcactgggcccttttgctgaggggctctctactggc ttctggccgcgctccgcgccgcgcctcctctggattgccc cgaaacaccgtggtactgttcgtgccgcagcaggaggct gggtggtgggagcgaatgggccgattccaccggatcctgga gcctggtttgaacatcctcatccctgtgttagaccggatc cgatatgtgcagagtctcaaggaaattgtcatcaacgtgc ctgagcagtcggctgtgactctcgacaatgtaactctgca aatcgatggagtcctttacctgcgcatcatggacccttac aaggcaagctacggtgtggaggaccctgagtatgccgtca cccagctagctcaaacaaccatgagatcagagctcggcaa actctctctggacaaagtcttccgggtggaggcagagcgg cggaaacgggccacagttctagagtctgaggggacccgag agtcggccatcaatgtggcagaagggaagaaacaggccca gatcctggcctccgaagcagaaaaggctgaacagataaat caggcagcaggagaggccagtgcagttctggcgaaggcca aggctaaagctgaagctattcgaatcctggctgcagctct gacacaacataatggagatgcagcagcttcactgactgtg gccgagcagtatgtcagcgcgttctccaaactggccaagg actccaacactatcctactgccctccaaccctggcgatgt caccagcatggtggctcaggccatgggtgtatatgagcc ctcaccaaagcccagtgccagggactccagactcactct ccagtgggagcagcagagatgtccagggtacagatgcaag tcttgatgaggaacttgatcgagtcaagatgagttagtgg agctgggcttggccagggagtctgggaacaaggaagcaga ttttcctgattctggctctagcttccctgccaagattttg gttttattttttttatttgaactttagtcgtgtaataaac tcaccagtggcaaaccagaaactgtcctcctttgattgggg aatgaagttgggaaagtcactagcattttccttggatcca gtcctgtcagcatgatgcctccatgaataagagtgaactt cttgtaaagtgaaact | 12 |
| UMPS | NM_000373.3 | ctgcagacgaggcaggcggaagaggcgggacttcgcgggt gacgtcatcgggcgccggaggcccggggcgcctgggaat ttgaagcaaacaggcagcgcgcgacaatggcggtcgctcg tgcagctttggggccattggtgacgggtctgtacgacgtg caggcttcaagtttggggacttcgtgctgaagagcggc tttcctcccccatctacatcgatctgcggggcatcgtgtc tcgaccgcgtcttctgagtcaggttgcagatatttttattc caaactgcccaaaatgcaggcatcagttttgacaccgtgt gtggagtgccttatacagctttgccattggctacagttat ctgttcaaccaatcaaattccaatgcttattagaaggaaa gaaacaaaggattatggaactaagcgtcttgtagaaggaa ctattaatccaggagaaacctgtttaatcattgaagatgt tgtcaccagtggatctagtgttttggaaactgttgaggtt cttcagaaggaggggcttgaaggtcactgatgccatagtgc tgttggacagagagcaggggaggcaaggacaagttgcaggc gcacgggatccgcctccactcagtgtgtacattgtcccaaa atgctggagattctcgagcagcagaaaaaagttgatgctg agacagttgggagagtgaagaggtttattcaggagaatgt ctttgtggcgcgaatcataatggttctccccttttctata aaggaagcacccaaagaactcagcttcggtgcacgtgcag agctgcccaggatccaccccagttgcatcgaagcttctcag gcttatgcaaaagaaggagaccaatctgtgtctatctgct gatgtttcactggccagagagctgttgcagctagcagatg | 13 |

TABLE 1-continued

Colon Cancer Biomarker/Housekeeper Sequence Information

| Gene Name | RefSeq Accession | Sequence | SEQ ID NO: |
|---|---|---|---|
| | | ctttaggacctagtatctgcatgctgaagactcatgtaga tattttgaatgattttactctggatgtgatgaaggagttg ataactctggcaaaatgccatgagttcttgatatttgaag accggaagtttgcagatataggaaacacagtgaaaaagca gtatgaaggaggtatctttaaaatagcttcctgggcagat ctagtaaatgctcacgtggtgccaggctcaggagttgtga aaggcctgcaagaagtgggcctgcctttgcatcggggtg cctccttattgcggaaatgagctccaccggctccctggcc actggggactacactagagcagcggttagaatggctgagg agcactctgaatttgttgttggttttattctggctcccg agtaagcatgaaaccagaatttcttcacttgactccagga gttcagttggaagcaggaggagataatcttggccaacagt acaatagcccacaagaagttattggcaaacgaggttccga tatcatcattgtaggtcgtggcataatctcagcagctgat cgtctggaagcagcagagatgtacagaaaagctgcttggg aagcgtatttgagtagacttggtgtttgagtgcttcagat acattttttcagatacaatgtgaagacattgaagatatgtg gtcctcctgaaagtcactggctggaaataatccaattatt cctgcttggattcttccacagggcctgtgtaagaatgggt tctggagttctcatggtctttaggaaatattgagtaattt gtaatcaccgcattgatactataataagttcattcttaag cttgctttttttgagactggtgtttgttagacagccacag tcctgtctgggttagggtcttccacatttgaggatccttc ctatctctccatgggactagactgctttgttattctattt attttttaattttttttcgagacaggatctcactctgttgc ccaggatggagtgcagtggtgagatcacggctcattgcag cctcgacctcccaggtgatcctcccacctcagcttccaga ttagctggtgctataggcatgcaccaccacgtccatctaa atttctttattatttgtagagatgaggtcttgccatgtta cccaggctggtctcaactcctgggctcaagcgatcctcct gcctcagtctctcaaagtgctgggattacaggtgtgagcc actgtgcccagcctaattgcagtaagacaaaaattctagg gcaccaagaggctaaagtcagcacagcttttcttgtgtcc tgtattctctgtctaatgtgttgcccaaataataacctaat tgttagccattcccctccatctctggcctaaaagtgatag tccaggtatccacatgggctggttcccagaactgccattg ctcactctccaaagagggggaaggtggggaaggggaaggtg actatagctcagctcctgagctagtatctggctgttattt caacaaccggagttgggtttgggctcattttttcccta gccagcaattatggaccagtagtaacacaagtgacagctt cctgtgactgacttcacaattaggaggtctaagattccat ttgggtatttgcttaaggatcccacataattgtcccaacg gtcattagtagagggggaggtaagccttcattaataataaa gagaaagcccacattcaaggtggtgtttgagcaggggcag ggtgagggctgtcccggtgctcattgcaccagcacactca cattccttctcatttggggcccacctgcaggaagtggcac aggatcagccatttccccacccttgtcagctgatggccca ctgttctttaatgactcagaggaatgcctaggatttttt ttttttttgagacagaatctcactgtcgcccaggctggag ttcagtggcacgatctcggctcactgcaacttctgcctct ctggttcaagcagttctcctgcctcagcctcccgagtagc tgggactacaagcctaggattttttaactcaggtttttatt atattccctcctgaagttttacttcaagagcttctgctc taaagtccaatttgggcttcatgtccccagtgctgcatct ccagggaaatgctgtctgtgggagagaccaactctcaagg aagaagtggccacagaaggagcaggaagggagttggccct cagggctactctgggggaagccaaaagtcatgaagggggaga agaattttctgacaaaaacttgcaggaatctcttaggtgt cttcagtgttggagtgatatgttgagaggcctttggagtg atgtgctgaggtctcaggcgcccacctccctggctgtcac ttccatgtgtcagtggttctcccactttagcaggtatcag agtcacctggagtcttgtcaaaacaggtaccagccccacc cgcagcgtttctgactctgggtagctctgggatggggctt gagaatttgcgtttccaaaaaggtcccaggtgatgctgcg gttgcctgcgcagggactggactttgagaaccacttcact ggttattcacatttctgcctctgcagtgagacagccttga ggtctgcctcctgctaagagtcacatgctcctgtccttta gaaatgtgggctcctgccatctccaggacgcaggcactgt tcctgttgatgaaccctatttcacaggaccctgctaagg tgatttgaggggaaatgagaggaggctcaaataatcaccc agcccctgccacttactgaaagtgtaggtccttgtgcccc acaccatcagagtttctgcgttagcagatttgtggtttgc ccagcagcctgggcgtgtgcatttctaatgggtgcctcaa gtgatctgtttctgatttgtatttctattgtgaagagtca | |

TABLE 1-continued

Colon Cancer Biomarker/Housekeeper Sequence Information

| Gene Name | RefSeq Accession | Sequence | SEQ ID NO: |
|---|---|---|---|
| | | gcccagtactgcaggcctcttacctaagcagaatcccagt ctggcatcaaagctttagaggacaagttgattcaggcaga gaagaacttgggctatacaagcgctgttcttcagcattga agtattttggaggcattagatagtttaacccttctcagt caaggaatatttacagaacatgatctctgggcattgtaac tcctggtcttagtggggaatataggggaccccatgtctcca tggggtgcacagaatgtctgtgagactgatggagtggaga acgccatcccccagcctctccagctactcgaggcattctg tagaacataagcccatagattgtgtgtgtgtgtgtgtgtg tgtgtgtgtgtgtgtgtgtgcatgcgcgcgcgtgcgca ctggaggaacctaagaaactatttggtgcacttcctctta ttttagagctcccaaagtgtagctccagaatcgtaaaggg atatgctcagtctcacagccagcctgtggatctcagtccc aacactcacccttgtgctactgagtcagctctaagaaaat ctgccaaaagtaggccgagggctggttttttgttttgttt tgtttgtttgatacagggtcttcactctgttgcccaggct ggagtatatcatggctcactgcaaccttgacttgggctca agcgatccgctcaagtagctggaactactctcaagtagct ctcaagagcctctcgagtggctggaactacaggcgtgcac caccacagctggttaatttttaaaattttttgtagagacg gtggaggaggttctcactgtgactcagtgtgtgcccgaca gcagagcccacaccactccagttgcagtggttgccatctg ggtcatcagacctggctgtcaggggtgcagccacaggaga gccaacagcagagggtgctggccgctgagctagctgctaa tgctggcctgggtgcagttctcatccaaagtacccggtgg gtgggagtcactcagtaccagttccgagcctgaacccaaa ctctcgtgtttctgctcacccctctctggcttctgccacc acatgggaagaatatgccctggttagcccatggcttctga agagcaagagaaagtagagcagagcctactccagcctccc ccgtccaatgtatgaaagccccagctgatctgtaagcctg ggagcgtgataaatgcttagtagtgcatgccatggagttc cagggtggtttattacacggcaatatctagctaaatacat ttaacttgctgcagctctctggatccagcctggttaccag gaagacaaaaactgggctccaccaggaaccagtcttctgc cttcccaaccatcacctctggctgcatcagcgatctctcc cagcgaaatagctgcttggtcttgtgtgaatcctgtactt taacacagtggaccaagtgtcagtcattgaaaatgaccat gagtaaccctgtggactctctgcagcttggttcctttgcc ccttaacaggtgggtatgaatcgtgtcttcagtgccaggg ctgaatgagaaagggcattccttttttgaaggaatctgata ctaaacacaaagcatgagaaaaatcaggacttgttggagt tatatttttaaaatatatattttaacagttatatatatta gatataatatataagtatatataaataatactatattg cccaggctggtctcgaactccttagctcaagtgatcctcc tgccttggcttcccaaagtgctaggattacaggtgtgagc cactgctcccggcctgttggagttctttacatttattta taatcaatgctgttttattaaatgcggatttattttgga ttacaggatgtagaatgccatattttctagatcatagg gcctttcacatttgtaatttggccttgtatgagttaccct gcaatccctttgttttccccataaccctttccaaaggaagg ccgcaatagaaatacaaagagaaacaaaataattagaata ttttttaacttctaaagttcaaggttttggcataagtctg gtttagaagcacatttgcctagcccttttccttcccaccaa gggggaaagtcttcctctagacaagaggcagagggctcct cagagtcagatcctggtgtgggctctcacgtgctgctgct gaatcccagggaaggagggaggaagggcagttgacaccca aaataagggtggggaactgtcagcagaggaggtctgtgtc atgttttttcagcgctgggttggggggagcccaggagagc aggaagatccagagatccctcgccccagctcggccatgtg tgtctgggacagagcctgaggtggcctgagcttcctgtgg ctccagagtaacattatagagaagctgaattctcctgttt ttctgaaaagggcatgggagttagctgagaagcagacctg gtgggcctgagagtctcaatcgtcaggtaaggacagtcag tgggaagtggacgggccgcacaaccaaggttctcatgagg acaaccatgtcttcgggggtgcccttgtgcacagacagct ccatagtcctgcctccaatgtcccaacactgcattgtctc cctgcacttagcagccctgcagggtgagacttggggagga tcctgaaatgattgtatttaacaagacatgctgtccttgt ttacctggaacctagcaatgttgttttctgccacaacttg aatagatacttgaagcagagatgatgttgagttaaaaaaa atatatacataaaaatatgggttcttttcaacctgaatag atggcctaaaaattcaaa | |

TABLE 1-continued

Colon Cancer Biomarker/Housekeeper Sequence Information

| Gene Name | RefSeq Accession | Sequence | SEQ ID NO: |
|---|---|---|---|
| MORF4L1 | NM_001265603.1 | cggcgtgccctggggcggcgcgggcgcaggggcgcgtgcg cggcgggctgtcgttggctggagcagcggctgcgcgggtc gcggtgctgtgaggtctgcgggcgctggcaaatccggccc aggatgtagagctggcagtgcctgacggcgcgtctgacgc ggagttgggtggggtagagagtaggggggcggtagtcgggg gtggtgggagaaggaggaggcggcgaatcacttataaatg gcgccgaagcaggacccgaagcctaaattccaggaggttg ggatgaatgggttccggagagcagagtactcaaatacgtg gacaccaatttgcagaaacagcgagaacttcaaaaagcca atcaggagcagtatgcagaggggaagatgagaggggctgc cccaggaaagaagacatctggtctgcaacagaaaaatgtt gaagtgaaaacgaaaaagaacaaacagaaaacacctggaa atggagatggtggcagtaccagtgagacccctcagcctcc tcggaagaaaagggcccgggtagatcctactgttgaaaat gaggaaacattcatgaacagagttgaagttaaagtaaaga ttcctgaagagctaaaaccgtggcttgttgatgactggga cttaattaccaggcaaaaacagctcttttatcttcctgcc aagaagaatgtggattccattcttgaggattatgcaaatt acaagaaatctcgtggaaacacagataataaggagtatgc ggttaatgaagttgtggcagggataaaagaatacttcaac gtaatgttgggtacccagctactctataaatttgagagac cacagtatgctgaaattcttgcagatcatcccgatgcacc catgtcccaggtgtatggagcgccacatctcctgagatta tttgtacgaattggagcaatgttggcttatacacctctgg atgagaagagccttgctttattactcaattatcttcacga tttcctaaagtacctggcaaagaattctgcaactttgttc agtgccagcgattatgaagtggctcctcctgagtaccatc ggaaagctgtgtgagaggcactctcactcacttatgtttg gatctccgtaaacacattttgttcttagtctatctcttg tacaaacgatgtgctttgaagatgttagtgtataacaatt gatgtttgttttctgtttgattttaaacagagaaaaaata aaggggtaatagctcctttttttcttctttctttttttt tttcatttcaaaattgctgccagtgttttcaatgatggac aacagagggatatgctgtagagtgttttattgcctagttg acaaagctgcttttgaatgctggtggttctattcctttga cactacgcacttttataatacatgttaatgctatatgaca aaatgctctgattcctagtgccaaaggttcaattcagtgt atataactgaacacactcatccatttgtgcttttgtttt ttttatggtgcttaaagtaaagagcccatccttgcaagt catccatgttgttacttaggcattttatcttggctcaaat tgttgaagaatggtggcttgtttcatggtttttgtatttg tgtctaatgcacgttttaacatgatagacgcaatgcattg tgtagctagttttctggaaaagtcaatcttttaggaattg tttttcagatcttcaataaatttttcttaaatttcaaa gaacaaaaaaaaaaaaaa | 14 |
| MRPL19 | NM_014763.3 | gtagtcttgacgtgagctagctggcatggcggcctgcatt gcagcggggcactgggctgcaatgggcctaggccggagtt tccaagccgccaggactctgctccccccgccggcctctat cgcctgcagggtccacgcggggcctgtccggcagcagagc actgggccttccgagcccggtgcgttccaaccgccgccga aaccggtcatcgtggacaagcaccgccccgtggaaccgga acgcaggttcttgagtcctgaattcattcctcgaagggga agaacagatcctctgaaatttcaaatagaaagaaaagata tgttagaaaggagaaaagtactccacattccagagttcta tgttggaagtattcttcgtgttactacagctgacccatat gccagtggaaaaatcagccagtttctggggatttgcattc agagatcaggaagaggacttggagctactttcatccttag gaatgttatcgaaggacaaggtgtcgagatttgctttgaa ctttataatcctcgggtccaggagattcaggtggtcaaat tagagaaacggctggatgatagcttgctatacttacgaga tgcccttcctgaatatagcacttttgatgtgaatatgaag ccagtagtacaagagcctaaccaaaaagttcctgttaatg agctgaaagtaaaaatgaagcctaagccctggtctaaacg ctgggaacgtccaaattttaatattaaaggaatcagattt gatctttgtttaactgaacagcaaatgaaagaagctcaga agtggaatcagccatggcttgaatttgatatgatgaggga atatgatacttcaaaaattgaagctgcaatatggaaggaa attgaagcgtcgaaaaggtcttgattctgagaatgaattt ggttagttgcagaagatacattggctctaagaggatatat tttgagaccaatttaatttcatttataagaacatagtaat taagtgaactaagcattcattgttttattaatactttttt tctaaaataaaacttgtacaccagtttattactctaaaaa gagaattacacatgccaaatggaccaatgtccatttgctt | 15 |

TABLE 1-continued

Colon Cancer Biomarker/Housekeeper Sequence Information

| Gene Name | RefSeq Accession | Sequence | SEQ ID NO: |
|---|---|---|---|
| | | attggaggcaaagctacaatagaagtcagagcatcaccag<br>aatggtctttaatgagcatggaacctgagcaaagggaata<br>ggtgggatgaattttttttttaattgtgaaacaattcata<br>agcacaatatgatttacagaataataaacattcatgtacc<br>cactatcaggttaagaaatagaacatttattaatatgtag<br>gaatgttaagaaataaaacatttaataagatctcagaaga<br>ctccagtaaatctgcaattgtatctctctcctttttaaat<br>gtaaatatcatcttgacttgttaattattcccttgcattt<br>cttttagtttactgccaacacatatattcttcaacaatat<br>atttaattttgaaaaacctgaaaaaaaaacctgttagca<br>agtataaaggggcagtattactattattgcatgaaggctt<br>caagggaaacgttacagtctttgggtcatagtctggcttc<br>agcttcctctgagagtttacagaggccaattttgagcaaa<br>ttcatggctaaggttatgagtgagttctgctaaacagaag<br>gctcaccacaaggtatctggcaggattatactgggtagct<br>ggatgttgcagaaatgtggttagaggaagtaaactgtttt<br>ttgatgctcacagcatgatgaatcaaactctgtatcttag<br>gattaggttaaaacaatacctttggtatgatatgagtgtt<br>gttgctgatccatgcagcatggattggaaagctggggtat<br>aagcacacatgctaaagaaaaacatgtaatttggtccata<br>ctcacctggatatactgttcctcaggttaaaaaatacagt<br>actatcctaaatcttgaaggcaactctcagcctatccatt<br>gagttaccttcagatctgccctctggttcctagctgtctt<br>gggactaacttctttcctgcgctcagctgttttctggatt<br>ccatgttttccattttattgagtactaacttgttttgctg<br>cagcacatcctttggtagcttctagaggaagtttgtgtgg<br>aggtaaaattttgagaccttgcatgtctcatgtttgatt<br>gatactttatacgtttaggtaggaggtaattttccttcag<br>gactttaaaaatattgttgctccattttctttgtttctat<br>tgttgtattgagaaatccaatgccattttgatttcccccat<br>cataaatttcatgatgatgtgtcttggtgtgggtctatat<br>ttatccattgtattgggttttaggtgaacccttccagata<br>gtaactcatttctgtcagttctgggaaacacttagcattg<br>gttgatgatttattctctgctgctttgttctcccaactat<br>tatttggatgttggatatccagcactgggtatctattttc<br>ttacctccctcccttgacccagtctctgttttttagctc<br>tttagctcaatcttccaactctttgctattgtattttaaa<br>atcttaagacccccttcttgatttgtagaagttccttttct<br>tacaaccaaaaagcctttatctatggatttgttcacagat<br>aaggggtattcaatatagtgtattttttttttcatttaaaa<br>ttgtttgcgcatctatttcctccaaatttctttctgtatt<br>tattttttgttgtctatatttcagacttttccaggatatc<br>tgataatctttggctgtcttcttatggttgaaagagggac<br>taaaaagcttggaaagcctttgggttgtgggaaggggctg<br>tctttaggattatctgaatgggcttttttgggagtcccct<br>cctccacatgaatattttggttttgtcagattccctagaa<br>tagaggcttccaatctccttcctggaggggtctgtccagg<br>aaggagattgtctaggggtctgtcagacagcagctttcag<br>ctacttccttgatcttttcactaatgattatatagtcat<br>ctaactactgtcaacaagtaatagatatcctatccttcac<br>ttgtttagattatttgctgagataacctctcaaaagaacc<br>tctcaaaataaaaggttaacaagagcctatatcttatatt<br>tttcttctcttttatcttgttagaagatagctattaaaacc<br>tgttctttttctgtcttgataaacacacttcaatcttggt<br>agaatggtagatgggacagtatattttaggacctaaagct<br>ctgcaaatgtatgatcagcttgtaagtacaggtgctcaaa<br>aacatgtaaacaatcatgctttttactctgtaggaatatc<br>tttaaaattcttgtgaattttccccagaagtaaagcaaa<br>tcttcccccagaaataaaattaaatgtgcataatctaaag<br>ctttttttttttattgtggtaggatatatatataaaacat<br>aatttgccattgtaaacattttaaatttacaagtcagagg<br>cattaattacatcacaatgttgtgaaattattactactat<br>ttccaaaattttctcatcaccccaaactgaaactctgtaa<br>ctgttgagcaataacctcattcctgtatctctcccaaccc<br>caggtaacctcaaatctttcttttttatctttgagacaagg<br>tctcattctatcactcaggtaggagtgcagtggtgtgatc<br>atagctcattgcagcctcaaaatcctgggctcaagcaatc<br>ctccttgagtagctaagactataggcacacattaactgcg<br>cctggctgattttgtttttttgtagagatgtggtcttgcta<br>tgtttcccatgctggtcttgagttcctggcctcaagcagt<br>cctaagattcatccatgttgtggcatgtgtcagaatttc<br>atttgtttttatgactaaataatattccattgtatgtata<br>tacattttgttcatccatcttctgatgaacactgggatat<br>gtctaccttttggctattgtgaataatgctgcagtaaaca | |

TABLE 1-continued

Colon Cancer Biomarker/Housekeeper Sequence Information

| Gene Name | RefSeq Accession | Sequence | SEQ ID NO: |
|---|---|---|---|
| | | ttgacataacaagtatgtatttgattgcctgtttctaagt<br>tcttttgggtatacatcttgagtagaattgctagataatg<br>tcatgttttatttctcttgtgatttcttcttcgatcccct<br>ggttgagtgtgttaatttctacatgtttatgaatttccca<br>ctgttttttgttattgatttccaagttcattccattgtg<br>attagagaagatacttagtatgattttaatgtttttgaga<br>attggtgtgtggcctgatagatggtctgtcctggagaatg<br>ttcctcatacacttgagcaaaatatttatcatgctattgt<br>tgactgtagttttctatatgtctcttaggtcaaggtggtt<br>tacaatgtgttaaggttctcttttttaaaaaaattttg<br>cacagagtatcttttctatgtgttccatgtatttgtgtc<br>tttggagctatagtctcttgtagacagcatatcactatct<br>tgttttgttttgtttttctgtccattctgccaatttctg<br>ccttttgattggaaaatttaatccatttgcatttaaagta<br>attaaggaaggactttcttctaccatttaacacttcttct<br>atatgtcatatacttttttggcccctcatttcctctttat<br>ggccttcttttctgtttttttgtagtgaactagtctgatt<br>ctcttccactccctttgtgtatatttgttagatgtttt<br>atttgtggttgctatggggattatagttaacatcctacac<br>ttaaaacaatctaatttaaactgataccaatttaccttca<br>atagcatacaaaatctctactcctgtaaagctctgcccct<br>gccccccttatgttattgatggcacaaattgcctaataaa<br>taatttatagttatttgtatgagtttgtcttttaaatcat<br>ttaggaaataaaaagtggagttagaaaacagtatgatagt<br>aatactgactttatatttgtcaatatatttatcttattt<br>tggatccttatttcattatatagatttgagttactgtcta<br>gtgcccttccatttcggcccaaaggattcccttatgcatt<br>tcttgcagggcaagtctaattgtaataaaactccctcagct<br>tttgtttatctgagaatgtcttgatttctcccttatttt<br>tgatggataatttttgccagatacatgaatttttggtaaca<br>gtattttctttcagcactttaaatatgtcatcccactac<br>cttctgacttcatggtttctcatgagatattagatgttat<br>aaaatttgaggattcctcattcttgatgagtcagttctgt<br>cttattgcttttcggatttgctcagcttttgtcttttgac<br>agtttgattataacgcggctcagtgtgggtctctgagttt<br>atcccacttagagtttgttgagtttcttggagtcatagat<br>ttatgtcttttatcaaattttggacatatttggctattat<br>ttcttcaattttttttcactgcttctttcttttccttctga<br>aatattcttaatgtatatgttggtctgtttgatgctgtct<br>caccagtttcttaggctgtgttctcttttgttcctcagac<br>ttgattattgcagttgccctttcttttttattttttcaagt<br>ttgttgattcttctccctgttcagatcaactgttgaactc<br>ctctagtgaatttatttcagttactgtacttttcagctcc<br>aagatttatctttggttcctttttataacgtctgtgtctt<br>tattgatattctcatttgttcatatgtctcttcttcct<br>ttagttctttgtccatgttttccttagctctttgggctt<br>atttaagacaattgtttaaagtctttgcatagtaagtcca<br>atgtctgtttcttcagggatggttttcattattttgtt<br>ttcaatgagccatactttcctgtgtctttgtatgctgtct<br>ttttgttgttgaaaactgtatgtttgaacatcataacgtg<br>gtggccctgaaaatcagatattcccccttcctgagagtt<br>agttttatttttattattgaagattgtagcagtctattgc<br>tacatgtgcagtcatttccaaactattttgcaaagactg<br>tattccttctgtgtgtcatcactgaagtctctgttcctta<br>gtttgtgtttaatagtttgacatagatttccttgaaagga<br>gttaaaactagcagaaaaatctctctcccagtctttccag<br>tctttgtagattggttctgtgctgggcttttccattaata<br>cttagccaggcttgtactgagcctaacaatcaggcccaaa<br>agcgtagggtctttgcagatcttgtctgagcatgcttctt<br>gctgtgtatgcacgtagttttctaaatctccctgtatgtg<br>ctgttgaatattctaatttcccaaagaaactcctttgcag<br>ctttttctcacagaacatagatggttttttggatatcttg<br>accatagtctttcgacccaggtgtttgcggttgttagttc<br>accttacactttttcaagcattgcctactgcttacgatg<br>agtgctctgtcaatcctttaagtagcccagacaggctac<br>cagagacttaaacaagaatttgtaagttctgctcagcttc<br>ctctagaaatggggatcagggtccaagacagaatgcagtt<br>gctgatttcaagactgctgcaacaccagggagcttgtggg<br>ggaagggcaagcagaaatgtcacaaagctttcttgccatt<br>ttaaagttgcctgttcttgactcagcatttgcttcattgc<br>tataaacttttttactgtttttcagagttctgataaaattg<br>gctatgcctgttcctgcttaaaaaatatatatatatttt<br>ttagggattggggtctcactatactgaccaggctggtctt<br>gaacttctggcctcaagccatcctctcatttcagcttccc | |

TABLE 1-continued

Colon Cancer Biomarker/Housekeeper Sequence Information

| Gene Name | RefSeq Accession | Sequence | SEQ ID NO: |
|---|---|---|---|
| | | aaagtgctgcaattacacgcgtgaaccaccacacccagcc cctgcttgtttttcaatgtgcctactccaccatgttgctc aagtatgtatattttctaaactaccttgtagtgttgtgat gggaaataaatccctgagccttttgaataactcagagaga tcaaaaacttagtttatcctattcgaaggattagaaaaat gatatatctttcactttttcagggataggctcctcattag aaggctcctatgtgccgatgctgtacaagacatttcattt ctcttaatgtttacaacaagcttgttgccaaggctgatct tgaactcctggcctcaaacgatcctcccagctcagtctca caaagtgttgggatgtctggccaactaatgactatcttaa ctcttgtgtttcaatgtttatgccttcttttatcttgact gattgtatgactatgtcttctagaacaatgttgaacagaa atggtgagagcagacatccttgctttaatatttcaccatt atatatgatgttaggtatagattttctcacagatgcctt ttatcagattgaggaatttatattcctactttgccgaaag gttttttgtagtatgagggggtgctgaatttttgtcaaacac tttttcggtaataattgagatgattggttctgcagtcatc gagatgtggattttctcctttattctgttcgtgagtgatt acactggttgactaatgttaaaacaaccttactttccagg aataaaccctattatctttttataca | |
| PSMC4 | NM_153001.2 | tgcgggtacggacagcgcatgagcttatgttgagggcgga gcccagaccagcccttcgtcctatcctgccctccagcac ctctcagccgtaacttaaactacacttcccagaagcctcc tcagccagggacttccgttgtcgtcagcggaagcggtgac agatcatcccaggccacacagaggccggcttggtcactat ggaggagataggcatcttggtggagaaggctcaggatgag atcccagcactgtccgtgtcccggcccagaccggcctgt ccttcctgggccctgagcctgaggacctggaggacctgta cagccgctacaaggaggaggtgaagcgaatccaaagcatc ccgctggtcatcggacaatttctggaggctgtggatcaga atacagccatcgtgggctctaccacaggctccaactatta tgtgcgcatcctgagcaccatcgatcgggagctgctcaag cccaacgcctcagtggccctccacaagcacagcaatgcac tggtggacgtgctgccccccgaagccgacagcagcatcat gatgctcacctcagaccagaagccagatgtgatgtacgcg gacatcggaggcatggacatccagaagcaggaggtgcggg aggccgtggagctcccgctcacgcatttcgagctctacaa gcagatcggcatcgatccccccgaggcgtcctcatgtat ggcccacctggctgtgggaagaccatgttggcaaaggcg tggcacatcacacaacagctgcattcatccgggtcgtggg ctcggagtttgtacagaagtatctgggtgagggcccccgc atggtccgggatgtgttccgcctggccaaggagaatgcac ctgccatcatcttcatagacgagattgatgccatcgccac caagagattcgatgctcagacaggggccgacagggaggtt cagaggatcctgctggagctgctgaatcagatggatggat ttgatcagaatgtcaatgtcaaggtaatcatggccacaaa cagagcagacaccctggatccggccctgctacggccagga cggctggaccgtaaaattgaatttccacttcctgaccgcc gccagaagagattgatttctccactatcactagcaagat gaacctctctgaggaggttgacttggaagactatgtggcc cggccagataagatttcaggagctgatattaactccatct gtcaggagagtggaatgttggctgtccgtgaaaaccgcta cattgtcctggccaaggacttcgagaaagcatacaagact gtcatcaagaaggacgagcaggagcatgagttttacaagt gaccctccccttccctccaccacaccactcaggggctggg gcttctctcgcaccccagcacctctgtcccaaaacctca ttccctttttctttacccaggattggtttcttcaataaa tagataagatcgaatccatttaatttcttcttagaagttt aactcctttggagaatgtgggccttgaataggatcctctg ggtccctcttaatctgacagatgagcagacgaggtgcatg gcctgggttgcagcttgagagaaccaaaatattcaaacca gatgacttccaaaatgtggggaaagggatggaaaatgaac ctgagatggagtccttaatcacgggataaagccctgtgca tctccctcatttcctacaggtaaaagacagtaaagaaatt caggtcacaggccttgggagttcataggaaggagatgtcc agtgctgtccagtagaactttt | 16 |
| SF3A1 | NM_005877.5 | ggtcccggaagtgcgccagtcgtaccttcgcggccgcaac tcgctcggccgccgccatcttgcgagctcgtcgtactgac cgagcggggaggctgtcttgaggcggcaccgctcaccgac accgaggcggactggcagccctgagcgtcgcagtcatgcc ggccggaccgtgcaggcggtgccccgcgccgcccgtg cccacggagcccaaacagcccacagaagaagaagcatctt | 17 |

TABLE 1-continued

Colon Cancer Biomarker/Housekeeper Sequence Information

| Gene Name | RefSeq Accession | Sequence | SEQ ID NO: |
|---|---|---|---|
| | | caaaggaggattctgcaccttctaagccagttgtggggat<br>tatttaccctcctccagaggtcagaaatattgttgacaag<br>actgccagctttgtggccagaaacgggcctgaatttgaag<br>ctaggatccgacagaacgagatcaacaaccccaagttcaa<br>ctttctgaaccccaatgacccttaccatgcctactaccgc<br>cacaaggtcagcgagttcaaggaagggaaggctcaggagc<br>cgtccgccgccatccccaaggtcatgcagcagcagcagca<br>gaccacccagcagcagctgccccagaaggtccaagcccaa<br>gtaatccaagagaccatcgtgcccaaagagcctcctcctg<br>agtttgagttcattgctgatcctccctctatctcagcctt<br>cgacttggatgtggtgaagctgacggctcagtttgtggcc<br>aggaatgggcgccagtttctgacccagctgatgcagaaag<br>agcagcgcaactaccagtttgactttctccgcccacagca<br>cagcctcttcaactacttcacgaagctagtggaacagtac<br>accaagatcttgattccacccaaaggtttattttcaaagc<br>tcaagaaagaggctgaaaaccccgagaagttttggatca<br>ggtgtgttaccgagtggaatgggccaaattccaggaacgt<br>gagaggaagaaggaagaagaggagaaggagaaggagcggg<br>tggcctatgctcagatcgactggcatgattttgtggtggt<br>ggaaacagtggacttccaacccaatgagcaagggaacttc<br>cctcccccaccacgccagaggagctgggggcccgaatcc<br>tcattcaggagcgctatgaaaagtttggggagagtgagga<br>agttgagatggaggtcgagtctgatgaggaggatgacaaa<br>caggagaaggcggaggagcctccttcccagctggaccagg<br>acacccaagtacaagatatggatgagggttcagatgatga<br>agaagaagggcagaaagtgcccccacccccagagacaccc<br>atgcctccacctctgcccccaactccagaccaagtcattg<br>tccgcaaggattatgatcccaaagcctccaagcccttgcc<br>tccagcccctgctccagatgagtatcttgtgtcccccatt<br>actggggagaagatccccgccagcaaaatgcaggaacaca<br>tgcgcattggacttcttgaccctcgctggctggagcagcg<br>ggatcgctccatccgtgagaagcagagcgatgatgaggtg<br>tacgcaccaggtctggatattgagagcagcttgaagcagt<br>tggctgagcggcgtactgacatcttcggtgtagaggaaac<br>agccattggtaagaagatcggtgaggaggagatccagaag<br>ccagaggaaaaggtgacctgggatggccactcaggcagca<br>tggcccggacccagcaggctgcccaggccaacatcaccct<br>ccaggagcagattgaggccattcacaaggccaaaggcctg<br>gtgccagaggatgacactaaagagaagattggccccagca<br>agcccaatgaaatccctcaacagccaccgccaccatcttc<br>agccaccaacatccccagctcggctccacccatcacttca<br>gtgccccgaccacccacaatgccacctccagttcgtacta<br>cagttgtctccgcagtacccgtcatgccccggcccccaat<br>ggcatctgtggtccggctgcccccaggctcagtgatcgcc<br>cccatgccgcccatcatccacgcgcccagaatcaacgtgg<br>tgcccatgcctccctcggcccctcctattatggccccccg<br>cccaccccccatgattgtgccaacagcctttgtgcctgct<br>ccacctgtggcacctgtcccagctccagccccaatgcccc<br>ctgtgcatcccccacctcccatggaagatgagcccacctc<br>caaaaaactgaagacagaggacagcctcatgccagaggag<br>gagttcctgcgcagaaacaagggtccagtgtccatcaaag<br>tccaggtgcccaacatgcaggataagacggaatggaaact<br>gaatgggcaggtgctggtcttcaccctccactcacggac<br>caggtctctgtcattaaggtgaagattcatgaagccacag<br>gcatgcctgcagggaaacagaagctacagtatgagggtat<br>cttcatcaaagattccaactcactggcttactacaacatg<br>gccaatggcgcagtcatccacctggccctcaaggagagag<br>gcgggaggaagaagtagacaagaggaacctgctgtcaagt<br>ccctgccattttgcctctcctgtctccaccccctgcccc<br>agacccaggagccccctgaggctttgccttgcctgcata<br>tttgtttcgctcttactcagtttgggaattcaaattgtcc<br>tgcagaggttcattcccctgacccttccccacattggta<br>agagtagctgggttttctaagccactctctggaatctctt<br>tgtgttagggtctcgatttgaggacattcatttcttcagc<br>agcccattagcaactgagagcccagggatgtcctacagga<br>tagtttcatagtgacaggtggcacttggctaatagaatat<br>ggctgatattgtcattaatcattttgtaccttgacatggg<br>ttgtctaataaaactcggaccccttcttgtgaaatcagtta<br>aataagacttgtctcggtcacctgtgccctgtccagactc<br>gaggcagtggtaacactgcacagtgctatgtggcttctct<br>ttgaggattttttgggttttgtaactaaattcttgctgccc<br>tcatacttttttatgtattagaatcatattcgtattgccct<br>tttaaaacattgggatcctccaaaggcctgccccatgtat<br>ttaacagtaatacaggaagcatggcaggcaccatgcaaac | |

TABLE 1-continued

Colon Cancer Biomarker/Housekeeper Sequence Information

| Gene Name | RefSeq Accession | Sequence | SEQ ID NO: |
|---|---|---|---|
| | | caaggatggatggtgcagtccctgtgtcagtgggcggtgg<br>tttcctgctggcctggaatcactcatcacctgattgattg<br>gctctgtggtcctgggcaggtgcctcataggtgtgtggat<br>atgatgacgtttctttaaaatgtatgtatttaacaaatac<br>ttaattgtattaaggtcatgtaccaaggatttgataaagt<br>ttaaataatttactctctacttttatccattttatccatt<br>ttaactcatgtaatcctcatgtgagtattcctgtttaaca<br>cttgagtaaactgaggcacagagaacataagttgcatgcc<br>atagtcacacactgtgaaagtgaaaagagaatgtgtgcaa<br>aacacgtcacagtcctggtttctgagtaaaggcaggctgt<br>tatctttagaatcaagctatcacagggagataggcaatgc<br>tgtgggtgttggaggaaggtgagagcctgttgctaacaat<br>ttcctggttttaaagctaaggctgattttattgggaagat<br>ctcacatgtgtgtggccctgagagttcccagtgccttt<br>atttgcagtccttccatttggacctcctagctgccccatc<br>aggtcatctccagggctcagaggggtgagaccatttccca<br>aggtcacagaaccagctctctagtcaccaccctgcctctc<br>cctctcacccagagtcagtaccagttttatggctttatta<br>caaactgctgggtccctcccatttcaacttgattgatgg<br>gatgtcatcccttatcctgtctgacattttgcctctggcct<br>ggttgctagaagtttgccccaggggcaagagttgaaattt<br>ggcttcctgaggtgggctttgtggtttgcgtccctaaagt<br>gagcccactactggttgcttgtccatggccaacaccagaa<br>atcccctgagcactacctgggtctcattccaagaaggaag<br>agggtcaggagacctggggagtctcatattccaagttctt<br>ctttctttctgggagcagtgggcagttcatggtgttaggg<br>cactcaccccacagactggcaaaccctgcaggacttccg<br>tggctgaggctgtgaccggaggccaggaatgccgttgggt<br>ggattgtgagtgaatgggccctttgagctgccctctagag<br>agcaaatccagtttcctggagctcctgaatgaatatctgt<br>actggctcgctcagatgcagaagctccattgaccatgagg<br>ccttgtgaacatcagtggccacaggcccagtgtgctgctt<br>ggcactgcactagtttaggacctgcagcatgtaggtagcg<br>tcctagtgtttataatacaaagctgctctgcacagctttt<br>ctgattcttcttgcaatctcctgaggattatctgccccat<br>ttttaaaacgaggtggaatacccaaggtcatgtagccagt<br>gagtgctctggaaagccaaagcagctcatcccttcctggg<br>gaccacactgctctgctccaccagaccacactatgaaata<br>ggaataagtgctcctgttgcaggactgctgggaaaacagg<br>tggtgtgggacttaagtcaccataattttgaagacttgca<br>tgcagagggctccaggaattgtagacattaaggaatttca<br>ctttcagttctacccactacttaagtacttgtcatgtact<br>cttagaggaggccagtaatgatcagaaccatttactta<br>aaattaataatattgtattagagaatatattaaatggtta<br>tattgggttatgttaggatatacttgaatggaaataca<br>tgtactattagcaatcatatttcatttatccctgtaatta<br>gacaagaaagcataatatagctctactcatgggtacacat<br>accagtgtataagatttttagaagtttacttttaaaaat<br>aaaagcaaaatgtaagatcttaaaaaaaaaaaaaaaa | |
| PUM1 | NM_001020658.1 | agtgggccgccatgttgtcggagtgaaaggtaaggggag<br>cgagagcgccagagagagaagatcgggggggctgaaatcca<br>tcttcatcctaccgctccgcccgtgttggtggaatgagcg<br>ttgcatgtgtcttgaagagaaaagcagtgctttggcagga<br>ctctttcagccccacctgaaacatcaccctcaagaacca<br>gctaatcccaacatgcctgttgtttttgacatctggaacag<br>ggtcgcaagcgcagccacaaccagctgcaaatcaggctct<br>tgcagctgggactcactccagccctgtcccaggatctata<br>ggagttgcaggccgttccaggacgacgctatggtggact<br>acttctttcagaggcagcatggtgagcagcttggggagg<br>aggaagtggaggaggcggctataataatagcaaacatcga<br>tggcctactggggataacattcatgcagaacatcaggtgc<br>gttccatggatgaactgaatcatgattttcaagcacttgc<br>tctggagggaagagcgatgggagagcagctcttgccaggt<br>aaaaagttttgggaaacagatgaatccagcaaagatggac<br>caaaaggaatattcctgggtgatcaatggcgagacagtgc<br>ctggggaacatcagatcattcagtttcccagccaatcatg<br>gtgcagagaagacctggtcagagtttccatgtgaacagtg<br>aggtcaattctgtactgtcccacgatcggagagtggggg<br>actaggcgttagcatggtggagtatgtgttgagctcatcc<br>ccggggcgattcctgtctaagaaaaggaggatttggcccaa<br>gggatgcagacagtgatgaaaacgacaaaggtgaaaagaa<br>gaacaagggtacgtttgatggagataagctaggagatttg<br>aaggaggagggtgatgtgatggacaagaccaatggtttac | 18 |

TABLE 1-continued

Colon Cancer Biomarker/Housekeeper Sequence Information

| Gene Name | RefSeq Accession | Sequence | SEQ ID NO: |
|---|---|---|---|
| | | cagtgcagaatgggattgatgcagacgtcaaagattttag<br>ccgtacccctggtaattgccagaactctgctaatgaagtg<br>gatcttctgggtccaaaccagaatggttctgagggcttag<br>cccagctgaccagcaccaatggtgccaagcctgtggagga<br>tttctccaacatggagtcccagagtgtccccttggacccc<br>atggaacatgtgggcatggagcctcttcagtttgattatt<br>caggcacgcaggtacctgtggactcagcagcagcaactgt<br>gggacttttttgactacaattctcaacaacagctgttccaa<br>agacctaatgcgcttgctgtccagcagttgacagctgctc<br>agcagcagcagtatgcactggcagctgctcatcagccgca<br>catcggtttagctcccgctgcgtttgtcccaatccatac<br>atcatcagcgctgctcccccagggacggacccctacacag<br>ctggattggctgcagcagcgacactaggcccagctgtggt<br>ccctcaccagtattatggagttactccctggggagtctac<br>cctgccagtcttttccagcagcaagctgccgctgccgctg<br>cagcaactaattcagctaatcaacagaccaccccacaggc<br>tcagcaaggacagcagcaggttctccgtggaggagccagc<br>caacgtcctttgaccccaaaccagaaccagcagggacagc<br>aaacggatccccttgtggcagctgcagcagtgaattctgc<br>ccttgcatttggacaaggtctggcagcaggcatgccaggt<br>tatccggtgttggctcctgctgcttactatgaccaaactg<br>gtgcccttgtagtgaatgcaggcgcgagaaatggtcttgg<br>agctcctgttcgacttgtagctcctgccccagtcatcatt<br>agttcctcagctgcacaagcagctgttgcagcagccgcag<br>cttcagcaaatggagcagctggtggtcttgctggaacaac<br>aaatggaccatttcgcccttaggaacacagcagcctcag<br>ccccagccccagcagcagcccaataacaacctggcatcca<br>gttctttctacggcaacaactctctgaacagcaattcaca<br>gagcagctccctcttctcccagggctctgcccagcctgcc<br>aacacatccttgggattcggaagtagcagttctctcggcg<br>ccaccctgggatccgcccttggagggtttggaacagcagt<br>tgcaaactccaacactggcagtggctcccgccgtgactcc<br>ctgactggcagcagtgacctttataagaggacatcgagca<br>gcttgacccccattggacacagttttataacggccttag<br>cttttcctcctctcctggacccgtgggcatgcctctccct<br>agtcagggaccaggacattcacagacaccacctccttccc<br>tctcttcacatggatcctcttcaagcttaaacctgggagg<br>actcacgaatggcagtggaagatacatctctgctgctcca<br>ggcgctgaagccaagtaccgcagtgcaagcagcgcctcca<br>gcctcttcagcccgagcagcactcttttctcttcctctcg<br>tttgcgatatggaatgtctgatgtcatgccttctggcagg<br>agcaggcttttggaagattttcgaaacaaccggtacccca<br>atttacaactgcgggagattgctggacatataatggaatt<br>ttcccaagaccagcatgggtccagattcattcagctgaaa<br>ctggagcgtgccacaccagctgagcgccagcttgtcttca<br>atgaaatcctccaggctgcctaccaactcatggtggatgt<br>gtttggtaattacgtcattcagaagttctttgaatttggc<br>agtcttgaacagaagctggctttggcagaacggattcgag<br>gccacgtcctgtcattggcactacagatgtatggctgccg<br>tgttatccagaaagctcttgagtttattccttcagaccag<br>caggtaattaatgagatggttcgggaactagatggccatg<br>tcttgaagtgtgtgaaagatcagaatggcaatcacgtggt<br>tcagaaatgcattgaatgtgtacagccccagtctttgcaa<br>tttatcatcgatgcgtttaagggacaggtatttgccttat<br>ccacacatccttatggctgccgagtgattcagagaatcct<br>ggagcactgtctccctgaccagacactccctattttagag<br>gagcttcaccagcacacagagcagcttgtacaggatcaat<br>atggaaattatgtaatccaacatgtactggagcacggtcg<br>tcctgaggataaaagcaaaattgtagcagaaatccgaggc<br>aatgtacttgtattgagtcagcacaaatttgcaagcaatg<br>ttgtggagaagtgtgttactcacgcctcacgtacggagcg<br>cgctgtgctcatcgatgaggtgtgcaccatgaacgacggt<br>ccccacagtgccttatacaccatgatgaaggaccagtatg<br>ccaactacgtggtccagaagatgattgacgtggcggagcc<br>aggccagcggaagatcgtcatgcataagatccggccccac<br>atcgcaactcttcgtaagtacacctatggcaagcacattc<br>tggccaagctggagaagtactacatgaagaacggtgttga<br>cttagggcccatctgtggcccccctaatggtatcatctga<br>ggcagtgtcacccgctgttccctcattcccgctgacctca<br>ctggcccactggcaaatccaaccagcaaccagaaatgttc<br>tagtgtagagtctgagacgggcaagtggttgctccaggat<br>tactcccctcctccaaaaaaggaatcaaatccacgagtgga<br>aaagcctttgtaaatttaattttattacacataacatgta<br>ctatttttttaattgactaattgccctgctgttttactg | |

TABLE 1-continued

Colon Cancer Biomarker/Housekeeper Sequence Information

| Gene Name | RefSeq Accession | Sequence | SEQ ID NO: |
|---|---|---|---|
| | | gtgtataggatacttgtacataggtaaccaatgtacatgg gaggccacatattttgttcactgttgtatctatatttcac atgtggaaactttcagggtggttggtttaacaaaaaaaaa aagctttaaaaaaaaaagaaaaaaaggaaaaggtttttag ctcatttgcctggccggcaagttttgcaaatagctcttcc ccacctcctcattttagtaaaaaacaaacaaaaacaaaaa aacctgagaagtttgaattgtagttaaatgaccccaaact ggcatttaacactgtttataaaaaatatatatatatatat atatatataatgaaaaaggtttcagagttgctaaagct tcagtttgtgacattaagtttatgaaattctaaaaaatgc ctttttttggagactatattatgctgaagaaggctgttcgt gaggaggagatgcgagcacccagaacgtcttttgaggctg ggcgggtgtgattgtttactgcctactggatttttttcta ttaacattgaaaggtaaaatctgattatttagcatgagaa aaaaaaatccaactctgcttttggtcttgcttctataaat atatagtgtatacttggtgtagactttgcatatatacaaa tttgtagtattttcttgttttgatgtctaatctgtatcta taatgtaccctagtagtcgaacatacttttgattgtacaa ttgtacatttgtatacctgtaatgtaaatgtggagaagtt tgaatcaacatataaacacgttttttggtaagaaaagagaat tagccagccctgtgcattcagtgtatattctcaccttta tggtcgtagcatatagtgttgtatattgtaaattgtaatt tcaaccagaagtaaattttttctttttgaaggaataaatg ttcttatacagcctagttaatgtttaaaaagaaaaaaat agcttggttttatttgtcatctagtctcaagtatagcgag attctttctaaatgttattcaagattgagttctcactagt gtttttttaatcctaaaaaagtaatgttttgattttgtga cagtcaaaaggacgtgcaaaagtctagccttgcccgagct ttccttacaatcagagcccctctcaccttgtaaagtgtga atcgcccttcccttttgtacagaagatgaactgtattttg cattttgtctacttgtaagtgaatgtaacatactgtcaat tttccttgtttgaatatagaattgtaacactacacggtgt acatttccagagccttgtgtatatttccaatgaactttt tgcaagcacacttgtaaccatatgtgtataattaacaaac ctgtgtatgcttatgcctgggcaactatttttgtaactc ttgtgtagattgtctctaaacaatgtgtgatctttatttt gaaaaatacagaactttggaatctgaaaaaaaaaaaaaaa aaaaaaaaaaaaaaa | |
| ACTB | NM_001101.4 | gagtgagcggcgcggggccaatcagcgtgcgccgttccga aagttgcctttttatggctcgagcggccgcggcggcgccct ataaaacccagcggcgcgacgcgccaccaccgccgagacc gcgtccgccccgcgagcacagagcctcgcctttgccgatc cgccgcccgtccacaccgccgccagctcaccatggatga tgatatcgccgcgctcgtcgtcgacaacggctccggcatg tgcaaggccggcttcgcggggacgatgcccccgggccg tcttcccctccatcgtggggcgccccaggcaccagggcgt gatggtgggcatgggtcagaaggattcctatgtgggcgac gagcccagagcaagagaggcatcctcaccctgaagtacc ccatcgagcacggcatcgtcaccaactgggacgacatgga gaaaatctggcaccacaccttctacaatgagctgcgtgtg gctcccgaggagcaccccgtgctgctgaccgaggccccc tgaacccaaggccaaccgcgagaagatgacccagatcat gtttgagaccttcaacacccccagccatgtacgttgctatc caggctgtgctatccctgtacgcctctggccgtaccactg gcatcgtgatggactccggtgacggggtcacccacactgt gcccatctacgaggggtatgcccctcccccatgccatcctg cgtctggacctggctggccgggacctgactgactacctca tgaagatcctcaccgagcgcggctacagcttcaccaccac ggccgagcgggaaatcgtgcgtgacattaaggagaagctg tgctacgtcgccctggacttcgagcaagagatggccacgg ctgcttccagctcctcccctggagaagagctacgagctgcc tgacggccaggtcatcaccattggcaatgagcggttccgc tgccctgaggcactcttccagccttcttcctgggcatgg agtcctgtggcatccacgaaactaccttcaactccatcat gaagtgtgacgtggacatccgcaaagacctgtacgccaac acagtgctgtctggcggcaccaccatgtaccctggcattg ccgacaggatgcagaaggagatcactgccctggcacccag cacaatgaagatcaagatcattgctcctcctgagcgcaag tactccgtgtggatcggcggctccatcctggcctcgctgt ccaccttccagcagatgtggatcagcaagcaggagtatga cgagtccgcccctccatcgtccaccgcaaatgcttctag gcggactatgacttagttgcgttacacccttctcttgacaa aacctaacttgcgcagaaaacaagatgagattggcatggc | 19 |

TABLE 1-continued

Colon Cancer Biomarker/Housekeeper Sequence Information

| Gene Name | RefSeq Accession | Sequence | SEQ ID NO: |
|---|---|---|---|
| | | tttatttgttttttttgttttgttttggttttttttttttt ttttggcttgactcaggatttaaaaactggaacggtgaag gtgacagcagtcggttggagcgagcatcccccaaagttca caatgtggccgaggactttgattgcacattgttgttttt taatagtcattccaaatatgagatgcgttgttacaggaag tcccttgccatcctaaaagccaccccacttctctctaagg agaatggcccagtcctctcccaagtccacacaggggaggt gatagcattgctttcgtgtaaattatgtaatgcaaaattt ttttaatcttcgccttaatactttttattttgttttatt ttgaatgatgagccttcgtgcccccccttcccccttttt gtccccccaacttgagatgtatgaaggcttttggtctccct gggagtgggtggaggcagccagggcttacctgtacactga cttgagaccagttgaataaaagtgcacaccttaaaaatga ggaaaaaaaaaaaaaaaaa | |
| GAPD | NM_002046.6 | gctctctgctcctcctgttcgacagtcagccgcatcttct tttgcgtcgccagccgagccacatcgctcagacaccatgg ggaaggtgaaggtcggagtcaacggatttggtcgtattgg gcgcctggtcaccagggctgcttttaactctggtaaagtg gatattgttgccatcaatgacccttcattgacctcaact acatggtttacatgttccaatatgattccacccatggcaa attccatggcaccgtcaaggctgagaacgggaagcttgtc atcaatggaaatcccatcaccatcttccaggagcgagatc cctccaaaatcaagtggggcgatgctggcgctgagtacgt cgtggagtccactggcgtcttcaccaccatggagaaggct ggggctcatttgcaggggggagccaaaagggtcatcatct ctgcccctctgctgatgcccccatgttcgtcatgggtgt gaaccatgagaagtatgacaacagcctcaagatcatcagc aatgcctcctgcaccaccaactgcttagcacccctggcca aggtcatccatgacaactttggtatcgtggaaggactcat gaccacagtccatgccatcactgccacccagaagactgtg gatggcccctccgggaaactggccgtgatggccgcgggg ctctccagaacatcatccctgcctctactggcgctgccaa ggctgtgggcaaggtcatccctgagctgaacgggaagctc actggcatggccttccgtgtccccactgccaacgtgtcag tggtggacctgacctgccgtctagaaaaacctgccaaata tgatgacatcaagaaggtggtgaagcaggcgtcggagggc cccctcaagggcatcctgggctacactgagcaccaggtgg tctcctctgacttcaacagcgacaccccactcctccacctt tgacgctggggctggcattgccctcaacgaccactttgtc aagctcatttcctggtatgacaacgaatttggctacagca acagggtggtggacctcatggcccacatggcctccaagga gtaagacccctggaccaccagccccagcaagagcacaaga ggaagagagagaccctcactgctggggagtccctgccaca ctcagtcccccaccacactgaatctcccctcctcacagtt gccatgtagacccttgaagaggggaggggcctagggagc cgcaccttgtcatgtaccatcaataaagtaccctgtgctc aaccagttaaaaaaaaaaaaaaaaaaaaa | 20 |
| GUSB | NM_000181.3 | gtcctcaaccaagatggcgcggatggcttcaggcgcatca cgacaccggcgcgtcacgcgacccgccctacgggcacctc ccgcgcttttcttagcgccgcagacggtggccgagcgggg gaccgggaagcatggcccgggggtcggcggttgcctgggc ggcgctcgggccgttgttgtgggctgcgcgctggggctg cagggcgggatgctgtaccccaggagagcccgtcgcggg agtgcaaggagctggacggcctctggagcttccgcgccga cttctctgacaaccgacgccggggcttcgaggagcagtgg taccggcggccgctgtgggagtcaggccccaccgtggaca tgccagttccctccagcttcaatgacatcagccaggactg gcgtctgcggcattttgtcggctgggtgtggtacgaacgg gaggtgatcctgccggagcgatgacccaggacctgcgca caagagtggtgctgaggattggcagtgcccattcctatgc catcgtgtgggtgaatgggtcgacacgctagagcatgag ggggctacctccccttcgaggccgacatcagcaacctgg tccaggtgggggccctgccctcccggctccgaatcactat cgccatcaacaacacactcccccaccaccctgccacca gggaccatccaatacctgactgacacctccaagtatccca agggttactttgtccagaacacatattttgacttttcaa ctacgctggactgcagcggtctgtacttctgtacgacaca cccaccacctacatcgatgacatcaccgtcaccaccagcg tggagcaagacagtgggctggtgaattaccagatctctgt caagggcagtaacctgttcaagttggaagtgcgtctttgg gatgcagaaaacaaagtcgtggcgaatgggactgggaccc agggccaacttaaggtgccaggtgtcagcctctggtggcc | 21 |

TABLE 1-continued

Colon Cancer Biomarker/Housekeeper Sequence Information

| Gene Name | RefSeq Accession | Sequence | SEQ ID NO: |
|---|---|---|---|
| | | gtacctgatgcacgaacgccctgcctatctgtattcattg gaggtgcagctgactgcacagacgtcactggggcctgtgt ctgacttctacacactccctgtggggatccgcactgtggc tgtcaccaagagccagttcctcatcaatgggaaacctttc tatttccacggtgtcaacaagcatgaggatgcggacatcc gagggaagggcttcgactggccgctgctggtgaaggactt caacctgcttcgctggcttggtgccaacgctttccgtacc agccactacccctatgcagaggaagtgatgcagatgtgtg accgctatgggattgtggtcatcgatgagtgtcccggcgt gggcctggcgctgccgcagttcttcaacaacgtttctctg catcaccacatgcaggtgatggaagaagtggtgcgtaggg acaagaaccaccccgcggtcgtgatgtggtctgtggccaa cgagcctgcgtcccacctagaatctgctggctactacttg aagatggtgatcgctcacaccaaatccttggacccctccc ggcctgtgacctttgtgagcaactctaactatgcagcaga caaggggctccgtatgtggatgtgatctgtttgaacagc tactactcttggtatcacgactacgggcacctggagttga ttcagctgcagctggccacccagtttgagaactggtataa gaagtatcagaagcccattattcagagcgagtatggagca gaaacgattgcagggtttcaccaggatccacctctgatgt tcactgaagagtaccagaaaagtctgctagagcagtacca tctgggtctggatcaaaaacgcagaaaatacgtggttgga gagctcatttggaattttgccgatttcatgactgaacagt caccgacgagagtgctggggaataaaaagggggatcttcac tcggcagagacaaccaaaaagtgcagcgttccttttgcga gagagatactggaagattgccaatgaaaccaggtatcccc actcagtagccaagtcacaatgtttggaaaaacagcctgtt tacttgagcaagactgataccacctgcgtgtccccttcctc cccgagtcagggcgacttccacagcagcagaacaagtgcc tcctggactgttcacggcagaccagaacgtttctggcctg ggttttgtggtcatctattctagcagggaacactaaaggt ggaaataaaagattttctattatggaaataaagagttggc atgaaagtggctactgaaaaaaaaaaaaaaaaaaaaaaaa a | |
| RPLP0 | NM_001002.3 | gtctgacgggcgatggcgcagccaatagacaggagcgcta tccgcggtttctgattggctactttgttcgcattataaaa ggcacgcgcgggcgcgaggccccttctctcgccaggcgtcc tcgtggaagtgacatcgtctttaaaccctgcgtggcaatc cctgacgcaccgccgtgatgcccagggaagacagggcgac ctggaagtccaactacttccttaagatcatccaactattg gatgattatccgaaatgtttcattgtgggagcagacaatg tgggctccaagcagatgcagcagatccgcatgtcccttcg cgggaaggctgtggtgctgatgggcaagaacaccatgatg cgcaaggccatccgagggcacctggaaaacaacccagctc tggagaaactgctgcctcatatccggggggaatgtgggctt tgtgttcaccaaggaggacctcactgagatcagggacatg ttgctggccaataaggtgccagctgctgccccgtgctggtg ccattgccccatgtgaagtcactgtgccagcccagaacac tggtctcgggcccgagaagacctcctttttccaggctta ggtatcaccactaaaatctccagggggcaccattgaaatcc tgagtgatgtgcagctgatcaagactggagacaaagtggg agccagcgaagccacgctgctgaacatgctcaacatctcc ccccttctcctttgggctggtcatccagcaggtgttcgaca atggcagcatctacaaccctgaagtgcttgatatcacaga ggaaactctgcattctcgcttcctggagggtgtccgcaat gttgccagtgtctgtctgcagattggctacccaactgttg catcagtaccccattctatcatcaacgggtacaaacgagt cctggccttgtctgtggagacggattacaccttcccactt gctgaaaaggtcaaggccttcttggctgatcatctgcct ttgtggctgctgcccctgtggctgctgccaccacagctgc tcctgctgctgctgcagcccagctaaggttgaagccaag gaagagtcggaggagtcggacgaggatatgggatttggtc tcttttgactaatcaccaaaaagcaaccaacttagccagtt ttatttgcaaaacaaggaaataaaggcttacttctttaaa aagtaaaaaaaaaaaaaaaaaaaaaaaaa | 22 |
| TFRC | NM_003234.3 | agagcgtcgggatatcgggtggcggctcgggacggaggac gcgctagtgtgagtgcgggcttctagaactacaccgaccc tcgtgtcctcccttcatcctgcggggctggctgagcggc cgctccggtgctgtccagcagccatagggagccgcacggg gagcgggaaagcggtcgcggccccaggcggggcggccggg atggagcggggccgcgagcctgtggggaaggggctgtggc ggcgcctcgagcggctgcaggttcttctgtgtggcagttc | 23 |

TABLE 1-continued

Colon Cancer Biomarker/Housekeeper Sequence Information

| Gene Name | RefSeq Accession | Sequence | SEQ ID NO: |
|---|---|---|---|
| | | agaatgatggatcaagctagatcagcattctctaacttgt<br>ttggtggagaaccattgtcatatacccggttcagcctggc<br>tcggcaagtagatggcgataacagtcatgtggagatgaaa<br>cttgctgtagatgaagaagaaatgctgacaataacacaa<br>aggccaatgtcacaaaaccaaaaaggtgtagtggaagtat<br>ctgctatgggactattgctgtgatcgtcttttcttgatt<br>ggatttatgattggctacttgggctattgtaaaggggtag<br>aaccaaaaactgagtgtgagagactggcaggaaccgagtc<br>tccagtgagggaggagccaggagaggacttccctgcagca<br>cgtcgcttatattgggatgacctgaagagaaagttgtcgg<br>agaaactggacagcacagacttcaccggcaccatcaagct<br>gctgaatgaaaattcatatgtccctcgtgaggctggatct<br>caaaaagatgaaaatcttgcgttgtatgttgaaaatcaat<br>ttcgtgaatttaaactcagcaaagtctggcgtgatcaaca<br>ttttgttaagattcaggtcaaagacagcgctcaaaactcg<br>gtgatcatagttgataagaacggtagacttgtttacctgg<br>tggagaatcctgggggttatgtggcgtatagtaaggctgc<br>aacagttactggtaaactggtccatgctaattttggtact<br>aaaaaagattttgaggatttatacactcctgtgaatggat<br>ctatagtgattgtcagagcagggaaaatcacctttgcaga<br>aaaggttgcaaatgctgaaagcttaaatgcaattggtgtg<br>ttgatatacatggaccagactaaatttcccattgttaacg<br>cagaactttcattctttggacatgctcatctggggacagg<br>tgacccttacacacctggattcccttccttcaatcacact<br>cagtttccaccatctcggtcatcaggattgcctaatatac<br>ctgtccagacaatctccagagctgctgcagaaaagctgtt<br>tgggaatatggaaggagactgtccctctgactggaaaaca<br>gactctacatgtaggatggtaacctcagaaagcaagaatg<br>tgaagctcactgtgagcaatgtgctgaaagagataaaaat<br>tcttaacatctttggagttattaaaggctttgtagaacca<br>gatcactatgttgtagttggggcccagagagatgcatggg<br>gccctggagctgcaaaatccggtgtaggcacagctctcct<br>attgaaacttgcccagatgttctcagatatggtcttaaaa<br>gatgggtttcagcccagcagaagcattatctttgccagtt<br>ggagtgctggagactttggatcggttggtgccactgaatg<br>gctagagggatacctttcgtccctgcatttaaaggctttc<br>acttatattaatctggataaagcggttcttggtaccagca<br>acttcaaggtttctgccagcccactgttgtatacgcttat<br>tgagaaaacaatgcaaaatgtgaagcatccggttactggg<br>caatttctatatcaggacagcaactgggccagcaaagttg<br>agaaactcactttagacaatgctgctttcccttttccttgc<br>atattctggaatcccagcagtttctttctgtttttgcgag<br>gacacagattatccttatttgggtaccaccatggacacct<br>ataaggaactgattgagaggattcctgagttgaacaaagt<br>ggcacgagcagctgcagaggtcgctggtcagttcgtgatt<br>aaactaacccatgatgttgaattgaacctggactatgaga<br>ggtacaacagccaactgctttcatttgtgagggatctgaa<br>ccaatacagagcagacataaaggaaatgggcctgagttta<br>cagtggctgtattctgctcgtggagacttcttccgtgcta<br>cttccagactaacaacagatttcgggaatgctgagaaaac<br>agacagatttgtcatgaagaaactcaatgatcgtgtcatg<br>agagtggagtatcacttcctctctccctacgtatctccaa<br>aagagtctcctttccgacatgtcttctggggctccggctc<br>tcacacgctgccagctttactggagaacttgaaactgcgt<br>aaacaaaataacggtgcttttaatgaaacgctgttcagaa<br>accagttggctctagctacttggactattcagggagctgc<br>aaatgccctctctggtgacgtttgggacattgacaatgag<br>ttttaaatgtgatacccatagcttccatgagaacagcagg<br>gtagtctggtttctagacttgtgctgatcgtgctaaattt<br>tcagtagggctacaaaacctgatgttaaaattccatccca<br>tcatcttggtactactagatgtctttaggcagcagctttt<br>aatacagggtagataacctgtacttcaagttaaagtgaat<br>aaccacttaaaaaatgtccatgatggaatattcccctatc<br>tctagaattttaagtgctttgtaatgggaactgcctcttt<br>cctgttgttgttaatgaaaatgtcagaaaccagttatgtg<br>aatgatctctctgaatcctaagggctggtctctgctgaag<br>gttgtaagtggtcgcttactttgagtgatcctccaacttc<br>atttgatgctaaataggagataccaggttgaaagaccttc<br>tccaaatgagatctaagcctttccataaggaatgtagctg<br>gtttcctcattcctgaaagaaacagttaactttcagaaga<br>gatgggcttgttttcttgccaatgaggtctgaaatggagg<br>tccttctgctggataaaatgaggttcaactgttgattgca<br>ggaataaggccttaatatgttaacctcagtgtcatttatg<br>aaaagaggggaccagaagccaaagacttagtatattttct | |

TABLE 1-continued

Colon Cancer Biomarker/Housekeeper Sequence Information

| Gene Name | RefSeq Accession | Sequence | SEQ ID NO: |
|---|---|---|---|
| | | tttcctctgtcccttcccccataagcctccatttagttct ttgttattttgtttcttccaaagcacattgaaagagaac cagtttcaggtgtttagttgcagactcagtttgtcagact ttaaagaataatatgctgccaaattttggccaaagtgtta atcttaggggagagctttctgtccttttggcactgagata tttattgttatttatcagtgacagagttcactataaatg gtgttttttaatagaatataattatcggaagcagtgcct tccataattatgacagttatactgtcggttttttttaaat aaaagcagcatctgctaataaaacccaacagatactggaa gttttgcatttatggtcaacacttaagggttttagaaaac agccgtcagccaaatgtaattgaataaagttgaagctaag atttagagatgaattaaatttaattaggggttgctaagaa gcgagcactgaccagataagaatgctggttttcctaaatg cagtgaattgtgaccaagttataaatcaatgtcacttaaa ggctgtggtagtactcctgcaaaattttatagctcagttt atccaaggtgtaactctaattcccattttgcaaaatttcc agtacctttgtcacaatcctaacacattatcgggagcagt gtcttccataatgtataaagaacaaggtagttttttaccta ccacagtgtctgtatcggagacagtgatctccatatgtta cactaagggtgtaagtaattatcgggaacagtgtttccca taattttcttcatgcaatgacatcttcaaagcttgaagat cgttagtatctaacatgtatcccaactcctataattccct atcttttagttttagttgcagaaacattttgtggtcatta agcattgggtgggtaaattcaaccactgtaaaatgaaatt actacaaaatttgaaatttagcttgggttttgttaccttt tatggtttctccaggtcctctacttaatgagatagtagca tacatttataatgtttgctattgacaagtcatttttaactt tatcacattatttgcatgttacctcctataaacttagtgc ggacaagttttaatccagaattgacctttgacttaaagc agagggactttgtatagaaggtttgggggctgtgggaag gagagtcccctgaaggtctgacacgtctgcctacccattc gtggtgatcaattaaatgtaggtatgaataagttcgaagc tccgtgagtgaaccatcattataaacgtgatgatcagctg tttgtcatagggcagttggaaacggcctcctagggaaaag ttcatagggtctcttcaggttcttagtgtcacttacctag atttacagcctcacttgaatgtgtcactactcacagtctc tttaatcttcagttttatctttaatctcctcttttatctt ggactgacatttagcgtagctaagtgaaaaggtcatagct gagattcctggttcgggtgttacgcacacgtacttaaatg aaagcatgtggcatgttcatcgtataacacaatatgaata cagggcatgcattttgcagcagtgagtctcttcagaaaac ccttttctacagttaggggttgagttacttcctatcaagcc agtacgtgctaacaggctcaatattcctgaatgaaatatc agactagtgacaagctcctggtcttgagatgtcttctcgt taaggagatgggccttttggaggtaaaggataaaatgaat gagttctgtcatgattcactattctagaacttgcatgacc tttactgtgttagctctttgaatgttcttgaaattttaga cttctttgtaaacaaatgatatgtccttatcattgtata aaagctgttatgtgcaacagtgtggagattccttgtctga tttaataaaatacttaaacactgaaaaaaaaaaa | |
| 18S | X03205.1 | tacctggttgatcctgccagtagcatatgcttgtctcaaa gattaagccatgcatgtctaagtacgcacggccggtacag tgaaactgcgaatggctcattaaatcagttatggttcctt tggtcgctcgctcctctcccacttggataactgtggtaat tctagagctaatacatgccgacgggcgctgacccccttcg cgggggggatgcgtgcatttatcagatcaaaaccaacccg gtcagcccctctccggccccggccgggggcgggcgccgg cggctttggtgactctagataacctcgggccgatcgcacg cccccgtggcggcgacgacccattcgaacgtctgcccta tcaactttcgatggtagtcgccgtgcctaccatggtgacc acgggtgacgggaatcagggttcgattccggagagggag cctgagaaacggctaccacatccaaggaaggcagcaggcg cgcaaattacccactcccgacccggggaggtagtgacgaa aaataacaatacaggactctttcgaggccctgtaattgga atgagtccactttaaatcctttaacgaggatccattggag ggcaagtctggtgccagcagccgcggtaattccagctcca atagcgtatattaaagttgctgcagttaaaaagctcgtag ttggatcttgggagcgggcgggcggtccgccgcgaggcga gccaccgcccgtccccgcccttgcctctcggcgccccct cgatgctcttagctgagtgtcccgcggggcccgaagcgtt tactttgaaaaaattagagtgttcaaagcaggcccgagcc gcctggataccgcagctaggaataatggaataggaccgcg gttctattttgttggttttcggaactgaggccatgattaa | 24 |

TABLE 1-continued

Colon Cancer Biomarker/Housekeeper Sequence Information

| Gene Name | RefSeq Accession | Sequence | SEQ ID NO: |
|---|---|---|---|
| | | gagggacggccggggcattcgtattgcgccgctagaggt<br>gaaattcttggaccggcgcaagacggaccagagcgaaagc<br>atttgccaagaatgttttcattaatcaagaacgaaagtcg<br>gaggttcgaagacgatcagataccgtcgtagttccgacca<br>taaacgatgccgaccggcgatgcggcggcgttattcccat<br>gaccegccgggcagcttccgggaaaccaaagtctttgggt<br>tccgggggagtatggttgcaaagctgaaacttaaaggaa<br>ttgacggaagggcaccaccaggagtggagcctgcggctta<br>atttgactcaacacgggaaacctcaccggcccggacacg<br>gacaggattgacagattgatagctctttctcgattccgtg<br>ggtggtggtgcatggccgttcttagttggtggagcgattt<br>gtctggttaattccgataacgaacgagactctggcatgct<br>aactagttacgcgaccccgagcggtcggcgtcccccaac<br>ttcttagagggacaagtggcgttcagccacccgagattga<br>gcaataacaggtctgtgatgcccttagatgtccggggctg<br>cacgcgcgctacactgactggctcagcgtgtgcctaccct<br>acgccggcaggcgcgggtaacccgttgaaccccattcgtg<br>atggggatcggggattgcaattattccccatgaacgagga<br>attcccagtaagtgcgggtcataagcttgcgttgattaag<br>tccctgccctttgtacacaccgcccgtcgctactaccgat<br>tggatggtttagtgaggcccctcggatcggccccgccgggg<br>tcggcccacggccctggcggagcgctgagaagacggtcga<br>acttgactatctagaggaagtaaaagtcgtaacaaggttt<br>ccgtaggtgaacctgcggaaggatcatta | |
| PPIA | NM_021130.4 | ggggccgaacgtggtataaaaggggcgggaggccaggctc<br>gtgccgttttgcagacgccaccgccgaggaaaaccgtgta<br>ctattagccatggtcaaccccaccgtgttcttcgacattg<br>ccgtcgacggcgagccccttgggccgcgtctcctttgagct<br>gtttgcagacaaggtcccaaagacagcagaaaattttcgt<br>gctctgagcactggagagaaaggatttggttataagggtt<br>cctgctttcacagaattattccagggtttatgtgtcaggg<br>tggtgacttcacacgccataatggcactggtggcaagtcc<br>atcatggggagaaatttgaagatgagaacttcatcctaa<br>agcatacgggtcctggcatcttgtccatggcaaatgctgg<br>acccaacacaaatggttcccagtttttcatctgcactgcc<br>aagactgagtggttggatggcaagcatgtggtgtttggca<br>aagtgaaagaaggcatgaatattgtggaggccatggagcg<br>ctttgggtccaggaatggcaagaccagcaagaagatcacc<br>attgctgactgtggacaactcgaataagtttgacttgtgt<br>tttatcttaaccaccagatcattccttctgtagctcagga<br>gagcacccctccaccccatttgctcgcagtatcctagaat<br>ctttgtgctctcgctgcagttccctttgggttccatgttt<br>tccttgttccctcccatgcctagctggattgcagagttaa<br>gtttatgattatgaaataaaaactaaataacaattgtcct<br>cgtttgagttaagagtgttgatgtaggctttatttaagc<br>agtaatgggttacttctgaaacatcacttgtttgcttaat<br>tctacacagtacttagattttttttactttccagtcccag<br>gaagtgtcaatgtttgttgagtggaatattgaaaatgtag<br>gcagcaactgggcatggtggctcactgtctgtaatgtatt<br>acctgaggcagaagaccacctgagggtaggagtcaagatc<br>agcctgggcaacatagtgagacgctgtctctacaaaaaat<br>aattagcctggcctggtggtgcatgcctagtcctagctga<br>tctggaggctgacgtggaggattgcttgagcctagagtg<br>agctattatcatgccactgtacagcctgggtgttcacaga<br>tcttgtgtctcaaaggtaggcagaggcaggaaaagcaagg<br>agccagaattaagaggttgggtcagtctgcagtgagttca<br>tgcatttagaggtgttcttcaagatgactaatgtcaaaaa<br>ttgagacatctgttgcggttttttttttttttttccc<br>tggaatgcagtggcgtgatctcagctcactgcagcctccg<br>cctcctgggttcaagtgattctagtgcctcagcctcctga<br>gtagctgggataatgggcgtgtgccaccatgcccagctaa<br>ttttgtattttagtatagatggggtttcatcatttga<br>ccaggctggtctcaaactcttgacctcagctgatgcgcct<br>gccttggcctcccaaactgctgagattacagatgtgagcc<br>accgcaccctacctcattttctgtaacaaagctaagcttg<br>aacactgttgatgttcttgagggaagcatattgggctta<br>ggctgtaggtcaagtttatacatcttaattatggtggaat<br>tcctatgtagagtctaaaaagccaggtacttggtgctaca<br>gtcagtctccctgcagaggggttaaggcgcagactacctgc<br>agtgaggaggtactgcttgtagcatatagagcctctccct<br>agctttggttatggaggctttgaggttttgcaaacctgac<br>caatttaagccataagatctggtcaaagggatacccttcc<br>cactaaggacttggtttctcaggaaattatatgtacagtg | 25 |

TABLE 1-continued

Colon Cancer Biomarker/Housekeeper Sequence Information

| Gene Name | RefSeq Accession | Sequence | SEQ ID NO: |
|---|---|---|---|
| | | cttgctggcagttagatgtcaggacaatctaagctgagaa aaccccttctctgcccaccttaacagacctctagggttct taacccagcaatcaagtttgcctatcctagaggtggcgga tttgatcatttggtgtgttgggcaattttttgttttactgt ctggttccttctgcgtgaattaccaccaccaccacttgtg catctcagtcttgtgtgttgtctggttacgtattccctgg gtgataccattcaatgtcttaatgtacttgtggctcagac ctgagtgcaaggtggaaataaacatcaaacatcttttcat tatcccta | |
| PGK1 | NM_000291.3 | gagagcagcggccgggaaggggcggtgcgggaggcgggt gtggggcggtagtgtgggccctgttcctgcccgcgcggtg ttccgcattctgcaagcctccggagcgcacgtcggcagtc ggctccctcgttgaccgaatcaccgacctctctcccagc tgtatttccaaaatgtcgctttctaacaagctgacgctgg acaagctggacgttaaagggaagcgggtcgttatgagagt cgacttcaatgttcctatgaagaacaaccagataacaaac aaccagaggattaaggctgctgtcccaagcatcaaattct gcttggacaatggagccaagtcggtagtccttatgagcca cctaggccggcctgatggtgtgcccatgcctgacaagtac tccttagagccagttgctgtagaactcaaatctctgctgg gcaaggatgttctgttcttgaaggactgtgtaggcccaga agtggagaaagcctgtgccaacccagctgctgggtctgtc atcctgctggagaacctccgctttcatgtggaggaagaag ggaagggaaaagatgcttctgggaacaaggttaaagccga gccagccaaaatagaagctttccgagcttcacttttccaag ctaggggatgtctatgtcaatgatgcttttggcactgctc acagagcccacagctccatggtaggagtcaatctgccaca gaaggctggtgggttttttgatgaagaaggagctgaactac tttgcaaaggccttggagagcccagagcgaccttcctgg ccatcctgggcggagctaaagttgcagacaagatccagct catcaataatatgctggacaaagtcaatgagatgattatt ggtggtggaatggcttttaccttccttaaggtgctcaaca acatggagattggcacttctctgtttgatgaagagggagc caagattgtcaaagacctaatgtccaaagctgagaagaat ggtgtgaagattaccttgcctgttgactttgtcactgctg acaagtttgatgagaatgccaagactggccaagccactgt ggcttctggcatacctgctggctggatgggcttggactgt ggtcctgaaagcagcaagaagtatgctgaggctgtcactc gggctaagcagattgtgtggaatggtcctgtgggggtatt tgaatgggaagcttttgcccgggggaaccaaagctctcatg gatgaggtggtgaaagccacttctaggggctgcatcacca tcataggtggtggagacactgccacttgctgtgccaaatg gaacacggaggataaagtcagccatgtgagcactggggt ggtgccagtttggagctcctggaaggtaaagtccttcctg gggtggatgctctcagcaatatttagtactttcctgcctt ttagttcctgtgcacagcccctaagtcaacttagcatttt ctgcatctccacttggcattagctaaaaccttccatgtca agattcagctagtggccaagagatgcagtgccaggaaccc ttaaacagttgcacagcatctcagctcatcttcactgcac cctggatttgcatacattcttcaagatcccatttgaattt tttagtgactaaaccattgtgcattctagagtgcatatat ttatattttgcctgttaaaaagaaagtgagcagtgttagc ttagttctcttttgatgtaggttattatgattagctttgt cactgtttcactactcagcatggaaacaagatgaaattcc atttgtaggtagtgagacaaaattgatgatccattaagta aacaataaaagtgtccattgaaaccgtgattttttttttt ttcctgtcatactttgttaggaagggtgagaatagaatct tgaggaacggatcagatgtctatattgctgaatgcaagaa gtggggcagcagcagtggagagatgggacaattagataaa tgtccattctttatcaagggcctactttatggcagacatt gtgctagtgcttttattctaacttttatttttatcagtta cacatgatcataatttaaaaagtcaaggcttataacaaaa aagccccagcccattcctcccattcaagattcccactccc cagaggtgaccactttcaactcttgagttttttcaggtata tacctccatgtttctaagtaatatgcttatattgttcact tctttttttttttatttttttaaagaaatctatttcatacca tggaggaaggctctgttccacatatatttccacttcttca ttctctcggtatagttttgtcacaattatagattagatca aaagtctacataactaatacagctgagctatgtagtatgc tatgattaaatttacttatgtaaaaaaaaaaaaaaaaaaa | 26 |

TABLE 1-continued

Colon Cancer Biomarker/Housekeeper Sequence Information

| Gene Name | RefSeq Accession | Sequence | SEQ ID NO: |
|---|---|---|---|
| RPL13A | NM_012423.3 | cacttctgccgcccctgtttcaagggataagaaaccctgc gacaaaacctcctcctttccaagcggctgccgaagatgg cggaggtgcaggtcctggtgcttgatggtcgaggccatct cctgggccgcctggcggccatcgtggctaaacaggtactg ctgggccgaaggtggtggtcgtacgctgtgaaggcatca acatttctggcaatttctacagaaacaagttgaagtacct ggctttcctccgcaagcggatgaacaccaacccttcccga ggcccctaccacttccggggccccagccgcatcttctggc ggaccgtgcgaggtatgctgccccacaaaaccaagcgagg ccaggccgctctggaccgtctcaaggtgtttgacggcatc ccaccgccctacgacaagaaaaagcggatggtggttcctg ctgccctcaaggtcgtgcgtctgaagcctacaagaaagtt tgcctatctggggcgcctggctcacgaggttggctggaag taccaggcagtgacagccaccctggaggagaagaggaaag agaaagccaagatccactaccggaagaagaaacagctcat gaggctacggaaacaggccgagaagaacgtggagaagaaa attgacaaatacacagaggtcctcaagacccacggactcc tggtctgagcccaataaagactgttaattcctcatgcgtt gcctgcccttcctccattgttgccctggaatgtacgggac ccaggggcagcagcagtccaggtgccacaggcagccctgg gacataggaagctgggagcaaggaaagggtcttagtcact gcctcccgaagttgcttgaaagcactcggagaattgtgca ggtgtcatttatctatgaccaataggaagagcaaccagtt actatgagtgaaagggagccagaagactgattggagggcc ctatcttgtgagtggggcatctgttggacttccacctgg tcatatactctgcagctgttagaatgtgcaagcacttggg gacagcatgagcttgctgttgtacacagggtatttctaga agcagaaatagactgggaagatgcacaaccaaggggttac aggcatcgcccatgctcctcacctgtattttgtaatcaga aataaattgcttttaaagaaaaaaaaaaaaaaaaaaa | 27 |
| B2M | NM_004048.2 | aatataagtggaggcgtcgcgctggcgggcattcctgaag ctgacagcattcgggccgagatgtctcgctccgtggcctt agctgtgctcgcgctactctctcttctggcctggaggct atccagcgtactccaaagattcaggtttactcacgtcatc cagcagagaatggaaagtcaaatttcctgaattgctatgt gtctgggtttcatccatccgacattgaagttgacttactg aagaatggagagagaattgaaaaagtggagcattcagact tgtctttcagcaaggactggtcttctatctcttgtacta cactgaattcaccccccactgaaaaagatgagtatgcctgc cgtgtgaaccatgtgactttgtcacagcccaagatagtta agtgggatcgagacatgtaagcagcatcatggaggtttga agatgccgcatttggattggatgaattccaaattctgctt gcttgctttttaatattgatatgcttatacacttacactt tatgcacaaaatgtagggttataataatgttaacatggac atgatcttctttataattctactttgagtgctgtctccat gtttgatgtatctgagcaggttgctccacaggtagctcta ggagggctggcaacttagaggtggggagcagagaattctc ttatccaacatcaacatcttggtcagatttgaactcttca atctcttgcactcaaagcttgttaagatagttaagcgtgc ataagttaacttccaatttacatactctgcttagaatttg ggggaaaatttagaaataattgacaggattattggaaa tttgttataatgaatgaaacattttgtcatataagattca tatttacttcttatacatttgataaagtaaggcatggttg tggttaatctggtttattttgttccacaagttaaataaa tcataaaacttgatgtgttatctctta | 28 |
| YWHAZ | NM_003406.3 | ctttctccttcccttcttccgggctcccgtcccggctca tcacccggcctgtggcccactccaccgccagctggaacc ctggggactacgacgtccctcaaaccttgcttctaggaga taaaaagaacatccagtcatggataaaaatgagctggttc agaaggccaaactggccgagcaggctgagcgatatgatga catggcagcctgcatgaagtctgtaactgagcaaggagct gaattatccaatgaggagaggaatcttctctcagttgctt ataaaaatgttgtaggagcccgtaggtcatcttggagggt cgtctcaagtattgaacaaaagacggaaggtgctgagaaa aaacagcagatggctcgagaatacagagagaaaattgaga cggagctaagagatatctgcaatgatgtactgtctctttt ggaaaagttcttgatcccaatgcttcacaagcagagagc aaagtcttctatttgaaaatgaaaggagattactaccgtt acttggctgaggttgccgctggtgatgacaagaaagggat tgtcgatcagtcacaacaagcataccaagaagcttttgaa atcagcaaaaaggaaatgcaaccaacacatcctatcagac tgggtctggcccttaacttctctgtgttctattatgagat | 29 |

TABLE 1-continued

Colon Cancer Biomarker/Housekeeper Sequence Information

| Gene Name | RefSeq Accession | Sequence | SEQ ID NO: |
|---|---|---|---|
| | | tctgaactccccagagaaagcctgctctcttgcaaagaca gcttttgatgaagccattgctgaacttgatacattaagtg aagagtcatacaaagacagcacgctaataatgcaattact gagagacaacttgacattgtggacatcggatacccaagga gacgaagctgaagcaggagaaggaggggaaaattaaccgg ccttccaacttttgtctgcctcattctaaaatttacacag tagaccatttgtcatccatgctgtcccacaaatagttttt tgtttacgatttatgacaggtttatgttacttctatttga atttctatatttcccatgtggttttatgtttaatattag gggagtagagccagttaacatttagggagttatctgtttt catcttgaggtggccaatatggggatgtggaattttata caagttataagtgtttggcatagtacttttggtacattgt ggcttcaaaagggccagtgtaaaactgcttccatgtctaa gcaaagaaaactgcctacatactggtttgtcctggcgggg aataaaagggatcattggttccagtcacaggtgtagtaat tgtgggtacttaaggtttggagcacttacaaggctgtgg tagaatcatacccatggataccacatattaaaccatgta tatctgtggaatactcaatgtgtacacctttgactacagc tgcagaagtgttcctttagacaaagttgtgacccatttta ctctggataagggcagaaacggttcacattccattatttg taaagttacctgctgttagctttcattattttgctacac tcattttatttgtatttaaatgttttaggcaacctaagaa caaatgtaaaagtaaagatgcaggaaaaatgaattgcttg gtattcattacttcatgtatatcaagcacagcagtaaaac aaaaacccatgtatttaacttttttttaggattttgctt ttgtgatttttttttttttgatacttgcctaacatgcatg tgctgtaaaaatagttaacagggaaataacttgagatgat ggctagctttgtttaatgtcttatgaaattttcatgaaca atccaagcataattgttaagaacacgtgtattaaattcat gtaagtggaataaaagttttatgaatggacttttcaacta ctttctctacagcttttcatgtaaattagtcttggttctg aaacttctctaaaggaaattgtacattttttgaaatttat tccttattccctcttggcagctaatgggctcttaccaagt ttaaacacaaaatttatcataacaaaaatactactaatat aactactgtttccatgtcccatgatccctctcttcctcc ccaccctgaaaaaatgagttcctattttttctgggagag gggggattgattagaaaaaaatgtagtgtgttccattta aaattttggcatatggcatttttctaacttaggaagccaca atgttcttggcccatcatgacattgggtagcattaactgt aagttttgtgcttccaaatcactttttggttttaagaat ttcttgatactcttatagcctgccttcaattttgatcctt tattctttctatttgtcaggtgcacaagattaccttcctg ttttagccttctgtcttgtcaccaaccattcttacttggt ggccatgtacttggaaaaaggccgcatgatctttctggct ccactcagtgtctaaggcaccctgcttcctttgcttgcat cccacagactatttccctcatcctatttactgcagcaaat ctctccttagttgatgagactgtgtttatctcccttaaa accctacctatcctgaatggtctgtcattgtctgccttta aaatccttcctctttcttcctcctctattctctaaataat gatggggctaagttatacccaaagctcactttacaaaata ttcctcagtactttgcagaaaacaccaaacaaaatgcc attttaaaaaggtgtattttttcttttagaatgtaagct cctcaagagcagggacaatgttttctgtatgttctattgt gcctagtacactgtaaatgctcaataaatattgatgatgg gaggcagtgagtcttgatgataagggtgagaaactgaaat cccaaacactgttttgttgcttgttttattatgacctcag attaaattgggaaatattggcccttttgaataattgtccc aaatattacattcaaataaaagtgcaatggagaaaaaaaa aaa | |
| SDHA | NM_004168.3 | actgcagccccgctcgactccggcgtggtgcgcaggcgcg gtatcccccctcccccgccagctcgaccccggtgtggtgc gcaggcgcagtctgcgcagggactggcgggactgcgcggc ggcaacagcagacatgtcgggggtccggggcctgtcgcgg ctgctgagcgctcggcgcctggcgctggccaaggcgtggc caacagtgttgcaaacaggaacccgaggttttcacttcac tgttgatgggaacaagagggcatctgctaaagtttcagat tccatttctgctcagtatccagtagtggatcatgaatttg atgcagtggtggtaggcgctggaggggcaggcttgcgagc tgcatttggcctttctgaggcagggtttaatacagcatgt gttaccaagctgtttcctaccaggtcacacactgttgcag cacaggaggaatcaatgctgctctggggaacatggagga ggacaactggaggtggcatttctacgacaccgtgaagggc tcgactggctgggggaccaggatgccatccactacatga | 30 |

TABLE 1-continued

Colon Cancer Biomarker/Housekeeper Sequence Information

| Gene Name | RefSeq Accession | Sequence | SEQ ID NO: |
|---|---|---|---|
| | | cggagcaggccccgccgccgtggtcgagctagaaaatta tggcatgccgtttagcagaactgaagatgggaagatttat cagcgtgcatttggtggacagagcctcaagtttggaaagg gcgggcaggcccatcggtgctgctgtgtggctgatcggac tggccactcgctattgcacaccttatatggaaggtctctg cgatatgataccagctattttgtggagtattttgccttgg atctcctgatggagaatggggagtgccgtggtgtcatcgc actgtgcatagaggacgggtccatccatcgcataagagca aagaacactgttgttgccacaggaggctacgggcgcacct acttcagctgcacgtctgcccacaccagcactggcgacgg cacggccatgatcaccagggcaggccttccttgccaggac ctagagtttgttcagttccaccctacaggcatatatggtg ctggttgtctcattacggaaggatgtcgtggagagggagg cattctcattaacagtcaaggcgaaaggtttatggagcga tacgcccctgtcgcgaaggacctggcgtctagagatgtg tgtctcggtccatgactctggagatccgagaaggaagagg ctgtggccctgagaaagatcacgtctacctgcagctgcac cacctacctccagagcagctggccacgcgcctgcctggca tttcagagacagccatgatcttcgctggcgtggacgtcac gaaggagccgatccctgtcctcccaccgtgcattataac atgggcggcattcccaccaactacaaggggcaggtcctga ggcacgtgaatggccaggatcagattgtgcccggcctgta cgcctgtggggaggccgcctgtgcctcggtacatggtgcc aaccgcctcgggcaaactcgctcttggacctggttgtct ttggtcgggcatgtgccctgagcatcgaagagtcatgcag gcctggagataaagtccctccaattaaaccaaacgctggg gaagaatctgtcatgaatcttgacaaattgagatttgctg atggaagcataagaacatcggaactgcgactcagcatgca gaagtcaatgcaaaatcatgctgccgtgttccgtgtggga agcgtgttgcaagaaggttgtgggaaaatcagcaagctct atggagacctaaagcacctgaagacgttcgaccggggaat ggtctggaacacggacctggtggagaccctggagctgcag aacctgatgctgtgtgcgctgcagaccatctacggagcag aggcacggaaggagtcacggggcgcgcatgccagggaaga ctacaaggtgcggattgatgagtacgattactccaagccc atccaggggcaacagaagaagcccttgaggagcactgga ggaagcacaccctgtcctatgtggacgttggcactgggaa ggtcactctggaatatagacccgtgatcgacaaaactttg aacgaggctgactgtgccaccgtcccgccagccattcgct cctactgatgagacaagatgtggtgatgacagaatcagct tttgtaattatgtataatagctcatgcatgtgtccatgtc ataactgtcttcatacgcttctgcactctggggaagaagg agtacattgaagggagattggcacctagtggctgggagct tgccaggaacccagtggccagggagcgtggcacttacctt tgtcccttgcttcattcttgtgagatgataaaactgggca cagctcttaaataaaatataaatgaacaaactttctttta tttccaaatccatttgaaatattttactgttgtgacttta gtcatatttgttgacctaaaaatcaaatgtaatctttgta ttgtgttacatcaaaatccagatattttgtatagtttctt ttttctttttctttctttttttttttgagacaggatcg gtgcagtagtacaatcacagctcactgcagcctcaaactc ctgggcagctcaggtgatcttcctgactcagccttctgag tagttggggctacaggtgtgcaccaccatgcccagctcat ttattttgtaattgtagggacagggtctcactgtgttgcc taggctggtctcaagtgatcctcctccttggcctcccaa ggtgctggaattataggtgtgaacaaaccaaaaaaaaaaa aaa | |
| HPRT1 | NM_000194.2 | ggcggggcctgcttctcctcagcttcaggcggctgcgacg agccctcaggcgaacctctcggctttcccgcgcggcgccg cctcttgctgcgcctccgcctcctcctctgctccgccacc ggcttcctcctcctgagcagtcagcccgcgcgccggccgg ctccgttatggcgacccgcagccctggcgtcgtgattagt gatgatgaaccaggttatgaccttgatttattttgcatac ctaatcattatgctgaggatttggaaagggtgtttattcc tcatggactaattatggacaggactgaacgtcttgctcga gatgtgatgaaggagatgggaggccatacattgtagccc tctgtgtgctcaaggggggctataaattctttgctgacct gctggattacatcaaagcactgaatagaaatagtgataga tccattcctatgactgtagattttatcagactgaagagct attgtaatgaccagtcaacaggggacataaaagtaattgg tggagatgatctctcaactttaactggaaagaatgtcttg attgtggaagatataattgacactggcaaaacaatgcaga cttttgctttccttggtcaggcagtataatccaaagatggt | 31 |

TABLE 1-continued

Colon Cancer Biomarker/Housekeeper Sequence Information

| Gene Name | RefSeq Accession | Sequence | SEQ ID NO: |
|---|---|---|---|
| | | caaggtcgcaagcttgctggtgaaaaggacccacgaagt<br>gttggatataagccagactttgttggatttgaaattccag<br>acaagtttgttgtaggatatgcccttgactataatgaata<br>cttcagggatttgaatcatgtttgtgtcattagtgaaact<br>ggaaaagcaaaatacaaagcctaagatgagagttcaagtt<br>gagtttggaaacatctggagtcctattgacatcgccagta<br>aaattatcaatgttctagttctgtggccatctgcttagta<br>gagcttttgcatgtatcttctaagaattttatctgtttt<br>gtactttagaaatgtcagttgctgcattcctaaactgttt<br>atttgcactatgagcctatagactatcagttccctttggg<br>cggattgttgtttaacttgtaaatgaaaaaattctcttaa<br>accacagcactattgagtgaaacattgaactcatatctgt<br>aagaaataaagagaagatatattagtttttaattggtat<br>tttaatttttatatatgcaggaaagaatagaagtgattga<br>atattgttaattataccaccgtgtgttagaaaagtaagaa<br>gcagtcaattttcacatcaaagacagcatctaagaagttt<br>tgttctgtcctggaattattttagtagtgtttcagtaatg<br>ttgactgtattttccaacttgttcaaattattaccagtga<br>atctttgtcagcagttccctttaaatgcaaatcaataaa<br>ttcccaaaaatttaaaaaaaaaaaaaaaaaaaaa | |

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

As used herein, the terms "polynucleotide" and "nucleic acid molecule" are used interchangeably to mean a polymeric form of nucleotides of at least 10 bases or base pairs in length, either ribonucleotides or deoxynucleotides or a modified form of either type of nucleotide, and is meant to include single and double stranded forms of DNA. As used herein, a nucleic acid molecule or nucleic acid sequence that serves as a probe in a microarray analysis preferably comprises a chain of nucleotides, more preferably DNA and/or RNA. In other aspects, a nucleic acid molecule or nucleic acid sequence comprises other kinds of nucleic acid structures such a for instance a DNA/RNA helix, peptide nucleic acid (PNA), locked nucleic acid (LNA) and/or a ribozyme. Hence, as used herein the term "nucleic acid molecule" also encompasses a chain comprising non-natural nucleotides, modified nucleotides and/or non-nucleotide building blocks which exhibit the same function as natural nucleotides.

As used herein, the terms "hybridize," "hybridizing", "hybridizes," and the like, used in the context of polynucleotides, are meant to refer to conventional hybridization conditions, such as hybridization in 50% formamide/6×SSC/ 0.1% SDS/100 µg/ml ssDNA, in which temperatures for hybridization are above 37 degrees centigrade and temperatures for washing in 0.1×SSC/0.1% SDS are above 55 degrees C., and preferably to stringent hybridization conditions.

As used herein, the term "normalization" or "normalizer" refers to the expression of a differential value in terms of a standard value to adjust for effects which arise from technical variation due to sample handling, sample preparation, and measurement methods rather than biological variation of biomarker concentration in a sample. For example, when measuring the expression of a differentially expressed protein, the absolute value for the expression of the protein can be expressed in terms of an absolute value for the expression of a standard protein that is substantially constant in expression.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore, the term diagnosis includes: a. prediction (determining if a patient will likely develop aggressive disease (hyperproliferative/invasive)), b. prognosis (predicting whether a patient will likely have a better or worse outcome at a pre-selected time in the future), c. therapy selection, d. therapeutic drug monitoring, and e. relapse monitoring.

"Accuracy" refers to the degree of conformity of a measured or calculated quantity (a test reported value) to its actual (or true) value. Clinical accuracy relates to the proportion of true outcomes (true positives (TP) or true negatives (TN)) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarkers. Examples of biological samples include tissue, organs, or bodily fluids such as whole blood, plasma, serum, tissue, lavage or any other specimen used for detection of disease.

The term "subject" as used herein refers to a mammal, preferably a human. In some aspects, a subject can have at least one colon cancer symptom. In some aspects, a subject can have a predisposition or familial history for developing a colon cancer. A subject can also have been previously diagnosed with a colon cancer and is tested for cancer recurrence.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Biomarker levels may change due to treatment of the disease. The changes in biomarker levels may be measured by the present disclosure. Changes in biomarker levels may be used to monitor the progression of disease or therapy.

"Altered", "changed" or "significantly different" refer to a detectable change or difference from a reasonably comparable state, profile, measurement, or the like. Such changes may be all or none. They may be incremental and need not be linear. They may be by orders of magnitude. A change may be an increase or decrease by 5%, 10%, 20%, 30%, 40%, 50%, 60%, 70%, 80%, 90%, 95%, 99%, 100%, or more, or any value in between 0% and 100%. Alternatively, the change may be 1-fold, 1.5-fold, 2-fold, 3-fold, 4-fold, 5-fold or more, or any values in between 1-fold and five-fold. The change may be statistically significant with a p value of 0.1, 0.05, 0.001, or 0.0001.

The term "stable disease" refers to a diagnosis for the presence of a colon cancer, however the colon cancer has been treated and remains in a stable condition, i.e. one that that is not progressive, as determined by imaging data and/or best clinical judgment.

The term "progressive disease" refers to a diagnosis for the presence of a highly active state of a colon cancer, i.e. one has not been treated and is not stable or has been treated and has not responded to therapy, or has been treated and active disease remains, as determined by imaging data and/or best clinical judgment.

The term "neoplastic disease" refers to any abnormal growth of cells or tissues being either benign (non-cancerous) or malignant (cancerous). For example, the neoplastic disease can be a colon cancer.

The term "neoplastic tissue" refers to a mass of cells that grow abnormally.

The term "non-neoplastic tissue" refers to a mass of cells that grow normally.

The term "immunotherapy" can refer to activating immunotherapy or suppressing immunotherapy. As will be appreciated by those in the art, activating immunotherapy refers to the use of a therapeutic agent that induces, enhances, or promotes an immune response, including, e.g., a T cell response while suppressing immunotherapy refers to the use of a therapeutic agent that interferes with, suppresses, or inhibits an immune response, including, e.g., a T cell response. Activating immunotherapy may comprise the use of checkpoint inhibitors. Activating immunotherapy may comprise administering to a subject a therapeutic agent that activates a stimulatory checkpoint molecule. Stimulatory checkpoint molecules include, but are not limited to, CD27, CD28, CD40, CD122, CD137, OX40, GITR and ICOS. Therapeutic agents that activate a stimulatory checkpoint molecule include, but are not limited to, MEDI0562, TGN1412, CDX-1127, lipocalin.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody that binds to a target refers to an antibody that is capable of binding the target with sufficient affinity such that the antibody is useful as a diagnostic and/or therapeutic agent in targeting the target. In one embodiment, the extent of binding of an anti-target antibody to an unrelated, non-target protein is less than about 10% of the binding of the antibody to target as measured, e.g., by a radioimmunoassay (RIA) or biacore assay. In certain embodiments, an antibody that binds to a target has a dissociation constant (Kd) of <1 µM, <100 nM, <10 nM, <1 nM, <0.1 nM, <0.01 nM, or <0.001 nM (e.g. 108 M or less, e.g. from 108 M to 1013 M, e.g., from 109 M to 1013 M). In certain embodiments, an anti-target antibody binds to an epitope of a target that is conserved among different species.

A "blocking antibody" or an "antagonist antibody" is one that partially or fully blocks, inhibits, interferes, or neutralizes a normal biological activity of the antigen it binds. For example, an antagonist antibody may block signaling through an immune cell receptor (e.g., a T cell receptor) so as to restore a functional response by T cells (e.g., proliferation, cytokine production, target cell killing) from a dysfunctional state to antigen stimulation.

An "agonist antibody" or "activating antibody" is one that mimics, promotes, stimulates, or enhances a normal biological activity of the antigen it binds. Agonist antibodies can also enhance or initiate signaling by the antigen to which it binds. In some embodiments, agonist antibodies cause or activate signaling without the presence of the natural ligand. For example, an agonist antibody may increase memory T cell proliferation, increase cytokine production by memory T cells, inhibit regulatory T cell function, and/or inhibit regulatory T cell suppression of effector T cell function, such as effector T cell proliferation and/or cytokine production.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Administering chemotherapy to a subject can comprise administering a therapeutically effective dose of at least one chemotherapeutic agent. Chemotherapeutic agents include, but are not limited to, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abemaciclib, Abiraterone acetate, Abraxane, Accutane, Actinomycin-D, Adcetris, Ado-Trastuzumab Emtansine, Adriamycin, Adrucil, Afatinib, Afinitor, Agrylin, Ala-Cort, Aldesleukin, Alemtuzumab, Alecensa, Alectinib, Alimta, Alitretinoin, Alkaban-AQ, Alkeran, All-transretinoic Acid, Alpha Interferon, Altretamine, Alunbrig, Amethopterin, Amifostine, Aminoglutethimide, Anagrelide, Anandron, Anastrozole, Apalutamide, Arabinosylcytosine, Ara-C, Aranesp, Aredia, Arimidex, Aromasin, Arranon, Arsenic Trioxide, Arzerra, Asparaginase, Atezolizumab, Atra, Avastin, Avelumab, Axicabtagene Ciloleucel, Axitinib, Azacitidine, Bavencio, Bcg, Beleodaq, Belinostat, Bendamustine, Bendeka, Besponsa, Bevacizumab, Bexarotene, Bexxar, Bicalutamide, Bicnu, Blenoxane, Bleomycin, Blinatumomab, Blincyto, Bortezomib, Bosulif, Bosutinib, Brentuximab Vedotin, Brigatinib, Busulfan, Busulfex, C225, Cabazitaxel, Cabozantinib, Calcium Leucovorin, Campath, Camptosar, Camptothecin-11, Capecitabine, Caprelsa, Carac, Carboplatin, Carfilzomib, Carmustine, Carmustine Wafer, Casodex, CCI-779, Ccnu, Cddp, Ceenu, Ceritinib, Cerubidine, Cetuximab, Chlorambucil, Cisplatin, Citrovorum Factor, Cladribine, Clofarabine, Clolar, Cobimetinib, Cometriq, Cortisone, Cosmegen, Cotellic, Cpt-11, Crizotinib, Cyclophosphamide, Cyramza, Cytadren, Cytarabine, Cytarabine Liposomal, Cytosar-U, Cytoxan, Dabrafenib, Dacarbazine, Dacogen, Dactinomycin, Daratumumab, Darbepoetin Alfa, Darzalex, Dasatinib, Daunomycin, Daunorubicin, Daunorubicin Cytarabine (Liposomal), daunorubicin-hydrochloride, Daunorubicin Liposomal, DaunoXome, Decadron, Decitabine, Degarelix, Delta-Cortef, Deltasone, Denileukin Diftitox, Denosumab, DepoCyt, Dexamethasone, Dexamethasone Acetate, Dexamethasone Sodium Phosphate, Dexasone, Dexrazoxane, Dhad, Dic, Diodex, Docetaxel, Doxil, Doxorubicin, Doxorubicin Liposomal, Droxia, DTIC, Dtic-Dome, Duralone, Durvalumab, Eculizumab, Efudex, Ellence, Elotuzumab, Eloxatin, Elspar, Eltrombopag, Emcyt, Empliciti, Enasidenib, Enzalutamide, Epirubicin, Epoetin Alfa, Erbitux, Eribulin, Erivedge, Erleada, Erlotinib, Erwinia L-asparaginase, Estramustine, Ethyol, Etopophos, Etoposide, Etoposide Phosphate, Eulexin, Everolimus, Evista, Exemestane, Fareston, Farydak, Faslodex, Femara, Filgrastim, Firmagon, Floxuridine, Fludara, Fludarabine, Fluoroplex, Fluorouracil, Fluorouracil (cream), Fluoxymesterone, Flutamide, Folinic Acid, Folotyn, Fudr, Fulvestrant, G-Csf, Gazyva, Gefitinib, Gemcitabine, Gemtuzumab ozogamicin, Gemzar, Gilotrif, Gleevec, Gleostine, Gliadel Wafer, Gm-Csf, Goserelin, Granix, Granulocyte—Colony Stimulating Factor, Granulocyte Macrophage Colony Stimulating Factor, Halaven, Halotestin, Herceptin, Hexadrol, Hexalen, Hexamethylmelamine, Hmm, Hycamtin, Hydrea, Hydrocort Acetate, Hydrocortisone, Hydrocortisone Sodium Phosphate, Hydrocortisone Sodium Succinate, Hydrocortone Phosphate, Hydroxyurea, Ibrance, Ibritumomab, Ibritumomab Tiuxetan, Ibrutinib, Iclusig, Idamycin, Idarubicin, Idelalisib, Idhifa, Ifex, IFN-alpha, Ifosfamide, IL-11, IL-2, Imbruvica, Imatinib Mesylate, Imfinzi, Imidazole Carboxamide, Imlygic, Inlyta, Inotuzumab Ozogamicin, Interferon-Alfa, Interferon Alfa-2b (PEG Conjugate), Interleukin-2, Interleukin-11, Intron A (interferon alfa-2b), Ipilimumab, Iressa, Irinotecan, Irinotecan (Liposomal), Isotretinoin, Istodax, Ixabepilone, Ixazomib, Ixempra, Jakafi, Jevtana, Kadcyla, Keytruda, Kidrolase, Kisqali, Kymriah, Kyprolis, Lanacort, Lanreotide, Lapatinib, Lartruvo, L-Asparaginase, Lbrance, Lcr, Lenalidomide, Lenvatinib, Lenvima, Letrozole, Leucovorin, Leukeran, Leukine, Leuprolide, Leurocristine, Leustatin, Liposomal Ara-C, Liquid Pred, Lomustine, Lonsurf, L-PAM, L-Sarcolysin, Lupron, Lupron Depot, Lynparza, Marqibo, Matulane, Maxidex, Mechlorethamine, Mechlorethamine Hydrochloride, Medralone, Medrol, Megace, Megestrol, Megestrol Acetate, Mekinist, Mercaptopurine, Mesna, Mesnex, Methotrexate, Methotrexate Sodium, Methylprednisolone, Meticorten, Midostaurin, Mitomycin, Mitomycin-C, Mitoxantrone, M-Prednisol, MTC, MTX, Mustargen, Mustine, Mutamycin, Myleran, Mylocel, Mylotarg, Navelbine, Necitumumab, Nelarabine, Neosar, Neratinib, Nerlynx, Neulasta, Neumega, Neupogen, Nexavar, Nilandron, Nilotinib, Nilutamide, Ninlaro, Nipent, Niraparib, Nitrogen Mustard, Nivolumab, Nolvadex, Novantrone, Nplate, Obinutuzumab, Octreotide, Octreotide Acetate, Odomzo, Ofatumumab, Olaparib, Olaratumab, Omacetaxine, Oncospar, Oncovin, Onivyde, Ontak, Onxal, Opdivo, Oprelvekin, Oraprred, Orasone, Osimertinib, Otrexup, Oxaliplatin, Paclitaxel, Paclitaxel Protein-bound, Palbociclib, Pamidronate, Panitumumab, Panobinostat, Panretin, Paraplatin, Pazopanib, Pediapred, Peg Interferon, Pegaspargase, Pegfilgrastim, Peg-Intron, PEG-L-asparaginase, Pembrolizumab, Pemetrexed, Pentostatin, Perj eta, Pertuzumab, Phenylalanine Mustard, Platinol, Platinol-AQ, Pomalidomide, Pomalyst, Ponatinib, Portrazza, Pralatrexate, Prednisolone, Prednisone, Prelone, Procarbazine, Procrit, Proleukin, Prolia, Prolifeprospan 20 with Carmustine Implant, Promacta, Provenge, Purinethol, Radium 223 Dichloride, Raloxifene, Ramucirumab, Rasuvo, Regorafenib, Revlimid, Rheumatrex, Ribociclib, Rituxan, Rituxan Hycela, Rituximab, Rituximab Hyalurodinase, Roferon-A (Interferon Alfa-2a), Romidepsin, Romiplostim, Rubex, Rubidomycin Hydrochloride, Rubraca, Rucaparib, Ruxolitinib, Rydapt, Sandostatin, Sandostatin LAR, Sargramostim, Siltuximab, Sipuleucel-T, Soliris, Solu-Cortef, Solu-Medrol, Somatuline, Sonidegib, Sorafenib, Sprycel, Sti-571, Stivarga, Streptozocin, SU11248, Sunitinib, Sutent, Sylvant, Synribo, Tafinlar, Tagrisso, Talimogene Laherparepvec, Tamoxifen, Tarceva, Targretin, Tasigna, Taxol, Taxotere, Tecentriq, Temodar, Temozolomide, Temsirolimus, Teniposide, Tespa, Thalidomide, Thalomid, TheraCys, Thioguanine, Thioguanine Tabloid, Thiophosphoamide, Thioplex, Thiotepa, Tice, Ti sagenlecleucel, Toposar, Topotecan, Toremifene, Torisel, Tositumomab, Trabectedin, Trametinib, Trastuzumab, Treanda, Trelstar, Tretinoin, Trexall, Trifluridine/Tipiricil, Triptorelin pamoate, Trisenox, Tspa, T-VEC, Tykerb, Valrubicin, Valstar, Vandetanib, VCR, Vectibix, Velban, Velcade, Vemurafenib, Venclexta, Venetoclax, VePesid, Verzenio, Vesanoid, Viadur, Vidaza, Vinblastine, Vinblastine Sulfate, Vincasar Pfs, Vincristine, Vincristine Liposomal, Vinorelbine, Vinorelbine Tartrate, Vismodegib, Vlb, VM-26, Vorinostat, Votrient, VP-16, Vumon, Vyxeos, Xalkori Capsules, Xeloda, Xgeva, Xofigo, Xtandi, Yervoy, Yescarta, Yondelis, Zaltrap, Zanosar, Zarxio, Zejula, Zelboraf, Zevalin, Zinecard, Ziv-aflibercept, Zoladex, Zoledronic Acid, Zolinza, Zometa, Zydelig, Zykadia, Zytiga, or any combination thereof.

The terms "effective amount" and "therapeutically effective amount" of an agent or compound are used in the broadest sense to refer to a nontoxic but sufficient amount of an active agent or compound to provide the desired effect or benefit.

The term "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

The terms "cancer" and "cancerous" refer to or describe the physiological condition in mammals that is typically characterized by unregulated cell growth. Included in this definition are benign and malignant cancers. Examples of cancer include but are not limited to, carcinoma, lymphoma, blastoma, sarcoma, and leukemia. More particular examples of such cancers include adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer or cervical cancer.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

EXAMPLES

The disclosure is further illustrated by the following examples, which are not to be construed as limiting this disclosure in scope or spirit to the specific procedures herein described. It is to be understood that the examples are provided to illustrate certain aspects and that no limitation to the scope of the disclosure is intended thereby. It is to be further understood that resort may be had to various other aspects, embodiments, modifications, and equivalents thereof which may suggest themselves to those skilled in the art without departing from the spirit of the present disclosure and/or scope of the appended claims.

Example 1. Derivation of a 13-Marker Gene Panel

Figure 1B:
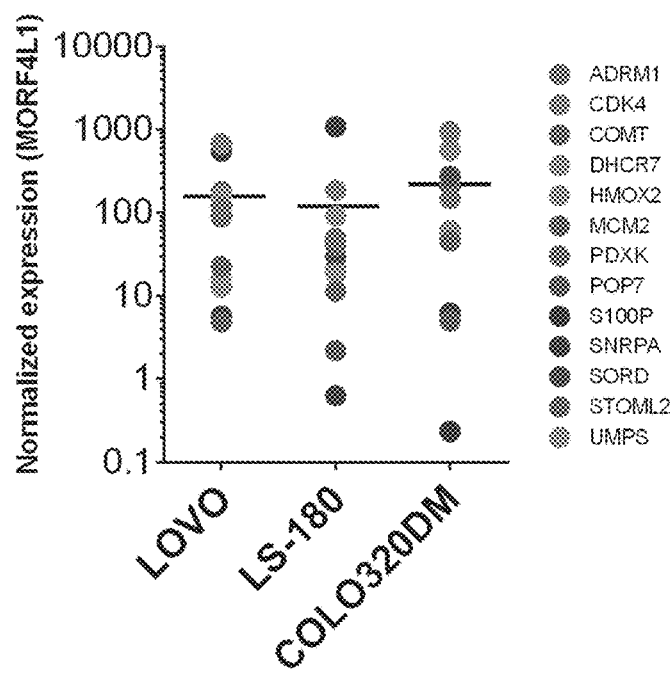

Raw probe intensities from n=24 colon cancer tumor tissue samples were compared to n=22 control colon mucosa to identify genes that best discriminated between disease using the transcriptional profile of E-MTAB-57. Gene co-expression networks were generated to identify temporal patterns of gene regulation associated with colon cancer. A total of 513 nodes with 53,786 links were identified. Differential expression analysis identified 103 genes were upregulated in tumor tissue compared to blood. To identify blood-specific colon cancer gene biomarkers, we evaluated expression of the 103 genes in peripheral blood transcriptomes (n=7). Thirty-three (32%) of the 103 genes were below the level of detection in blood identifying these as candidate genes. Evaluation of transcripts in a preliminary dataset of blood samples from colon cancer (n=20) and matched normal blood (n=20) identified thirteen genes and one house-keeping gene as markers of colon cancer (Table 2). These genes were demonstrated to be highly expressed in colon cancer tumor tissue compared to normal mucosa and in three different colon cancer cell lines, LOVO (metastatic, hyperdiploid, MSI unstable cell line), LS-180 (derived from a Duke's B, colorectal adenocarcinoma) and Colo 320DM (derived from a Duke's C, colorectal adenocarcinoma). These data demonstrate target transcripts are produced by neoplastically transformed colon mucosal cells (FIGS. 1A-1B).

An artificial intelligence model of colon cancer disease was built using normalized gene expression of these 13 markers in whole blood from Controls (n=120) and Colon Cancers (n=272) samples. The dataset was randomly split into training and testing partitions for model creation and validation respectively. Twelve algorithms were evaluated (XGB, RF, glmnet, cforest, CART, treebag, knn, nnet, SVM-radial, SVM-linear, NB and mlp). The top performing algorithm (XGB—"gradient boosting") best predicted the training data. In the test set, XGB produced probability scores that predicted the sample. Each probability score reflects the "certainty" of an algorithm that an unknown sample belongs to either "Control" or "Colon Cancer" class. For example, an unknown sample Si can have the following probability vector [Control=20%, Colon Cancer=80%]. This sample would be considered a colon cancer sample.

Example 2. Clinical Utility

The data (receiver operator cuver analysis and metrics) for the utility of the test to differentiate patients with colon cancer (n=136) from controls (n=60) in the training and test sets are included in FIGS. 2A-2B. The score exhibited an area under the curve (AUC) of 0.90 (training) and 0.86 (test set). The metrics are: sensitivity: 85.3-87.5% and specificity: 75-83.3%.

Figure 3A:
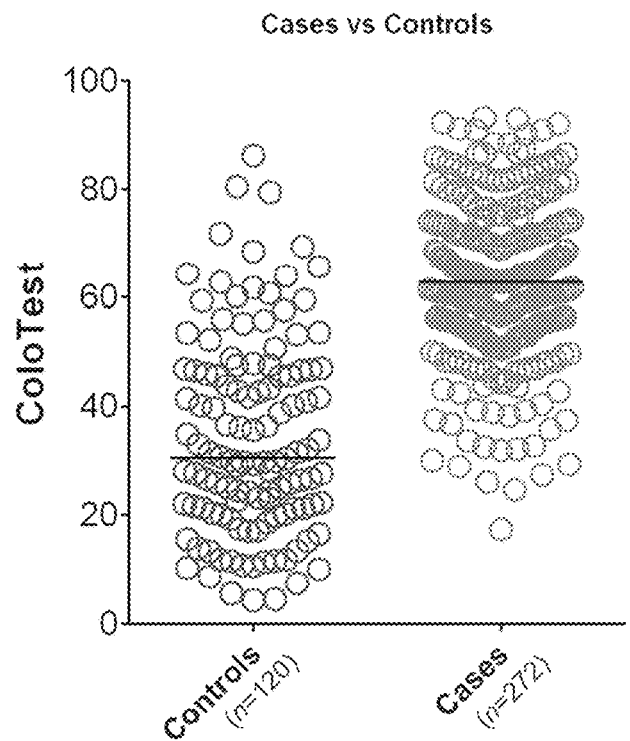
FIGS. 3A-3B are graphs showing that gene expression in the entire cohort (controls: n=120; colon cancer cases: n=272) identified levels were significantly (p<0.0001) elevated in cases (62.7±14%) versus controls (34.6±18%) (FIG. 3A). The AUROC was 0.88, p<0.0001 (FIG. 3B). Horizontal lines identify median expression of the normalized 13 gene signature (ColoTest).
Figure 3B:
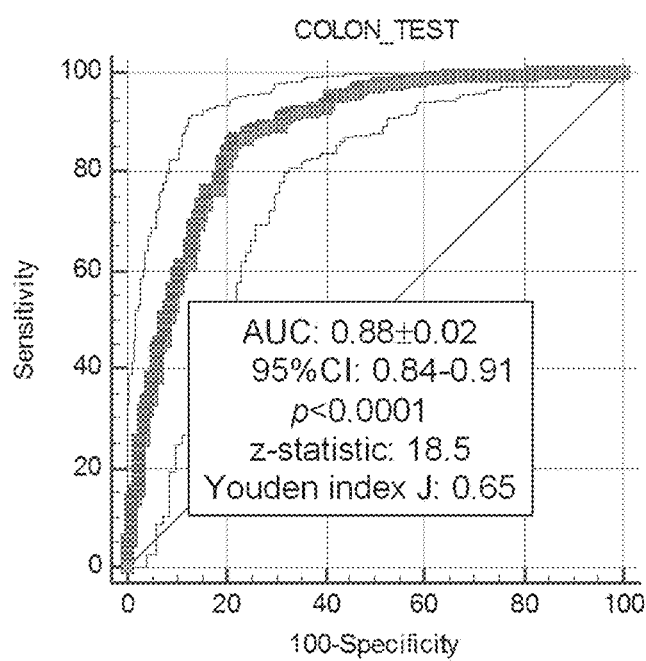

Overall, ColoTest scores were significantly elevated in cancers (63±1%) and controls (34±2%) (FIGS. 3A-3B). The overall accuracy (training and test cohort) is 84%, with an AUC: 0.88. The z-statistic for differentiating controls was 18.5.

Figure 4A:
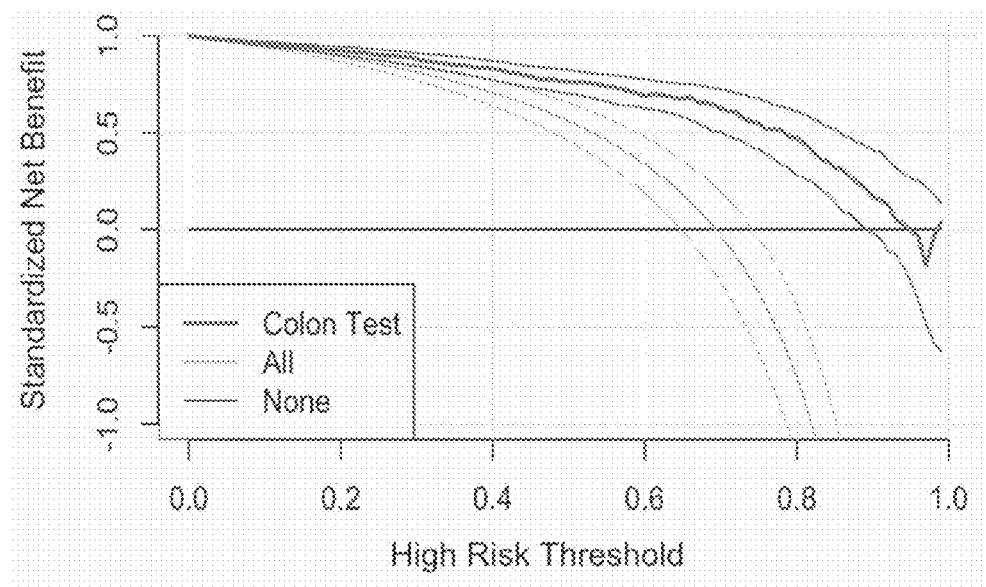
FIGS. 4A-4B are graphs showing decision curve analysis (FIG. 4A) and risk analysis (FIG. 4B) for the ColoTest. This exhibited >50% standardized predictive benefit up to a risk threshold of 80%. The probit risk assessment plot identified a ColoTest score >50% was 75% accurate for predicting colon cancer in a blood sample. This was increased to >80% at a ColoTest score >60%.
Figure 4B:
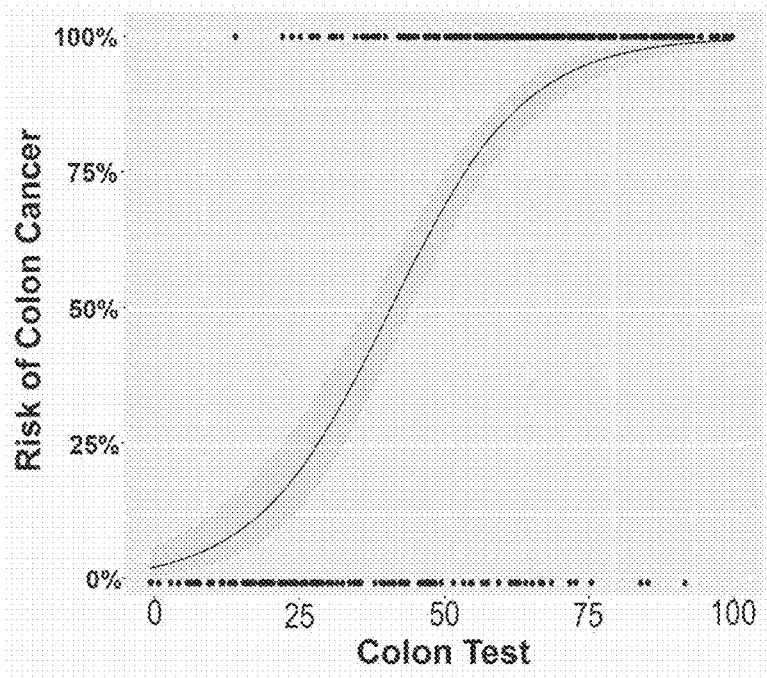

A decision curve analysis was used to quantify the clinical benefit of the diagnostic test (FIGS. 4A-4B). The ColoTest exhibited >50% standardized predictive benefit up to a risk threshold of 80%. The probit risk assessment plot identified a ColoTest score >50% was 75% accurate for predicting colon cancer in a blood sample. This was increased to >80% at a ColoTest score ≥60%. The tool can therefore accurately differentiate between controls and colon cancer disease.

Figure 5:
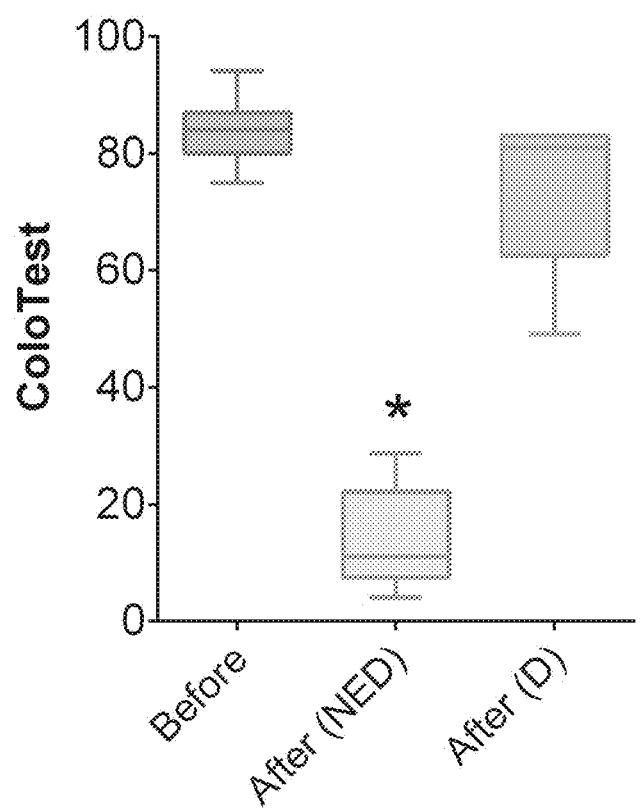
FIG. 5 is a graph showing the effect of surgery on the ColoTest. Levels prior to surgery are elevated (84±6%). In those with no evidence of disease (NED) levels were reduced by surgery to 14±9% (*p=0.0001). In those with disease (D) remaining after surgery, levels remained similar to pre-surgical values (74±4%).

Specific evaluation of a colon cancer cohort before and after surgery identified that complete removal of a tumor and no evidence of disease was associated with a significant decrease (p<0.0001) in the ColoTest (FIG. 5). Levels were not significantly different in those with evidence of residual disease.

Figure 6A:
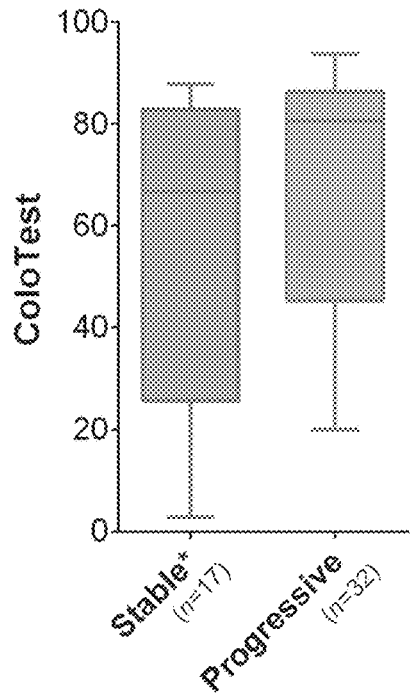
FIGS. 6A-6C are graphs showing ColoTest scores in stable and progressive disease. Test scores were not significantly different between those identified as stable and those with progressive disease at the time of assessment (FIG. 6A). Of the 17 with stable disease, 12 exhibited disease progression in the 3 month follow-up. Levels in those who truly had demonstrable stable disease were low (16±10%) (FIG. 6B). In those who did progress in the 3 months levels were not different to those that had progressive disease (73±16% vs. 68±25%). The AUROC for differentiating stable from progressing/progressive disease was 0.97, p<0.0001 (FIG. 6C).
Figure 6B:
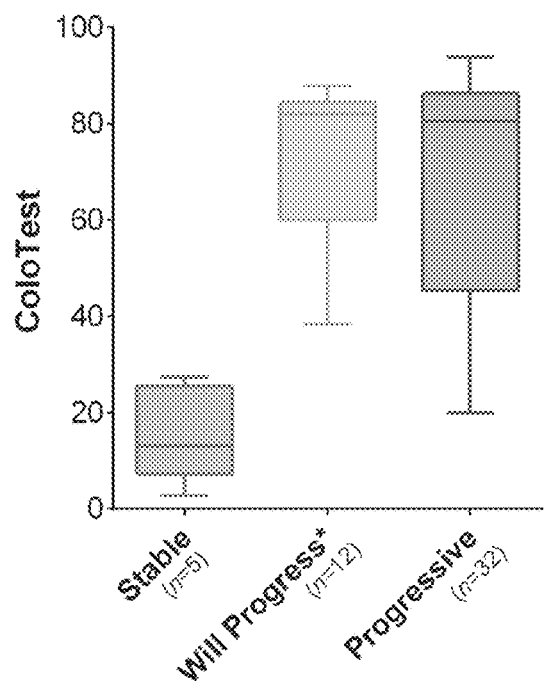
Figure 6C:
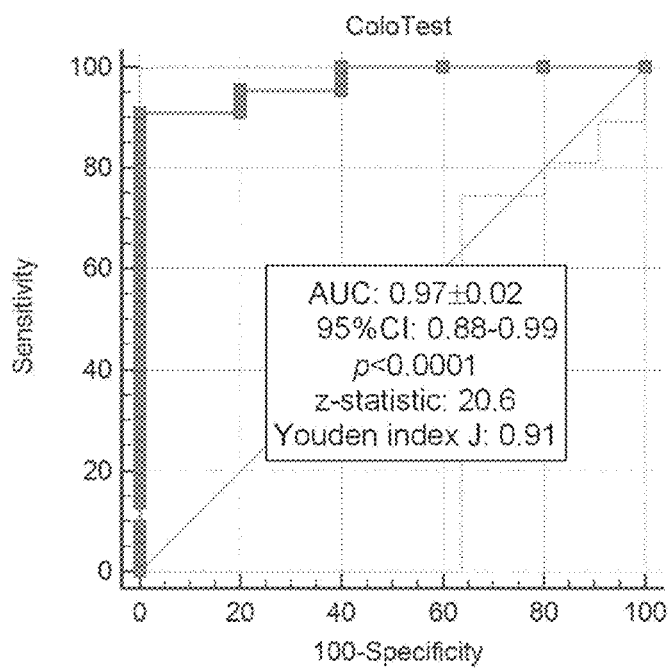
Figure 7:
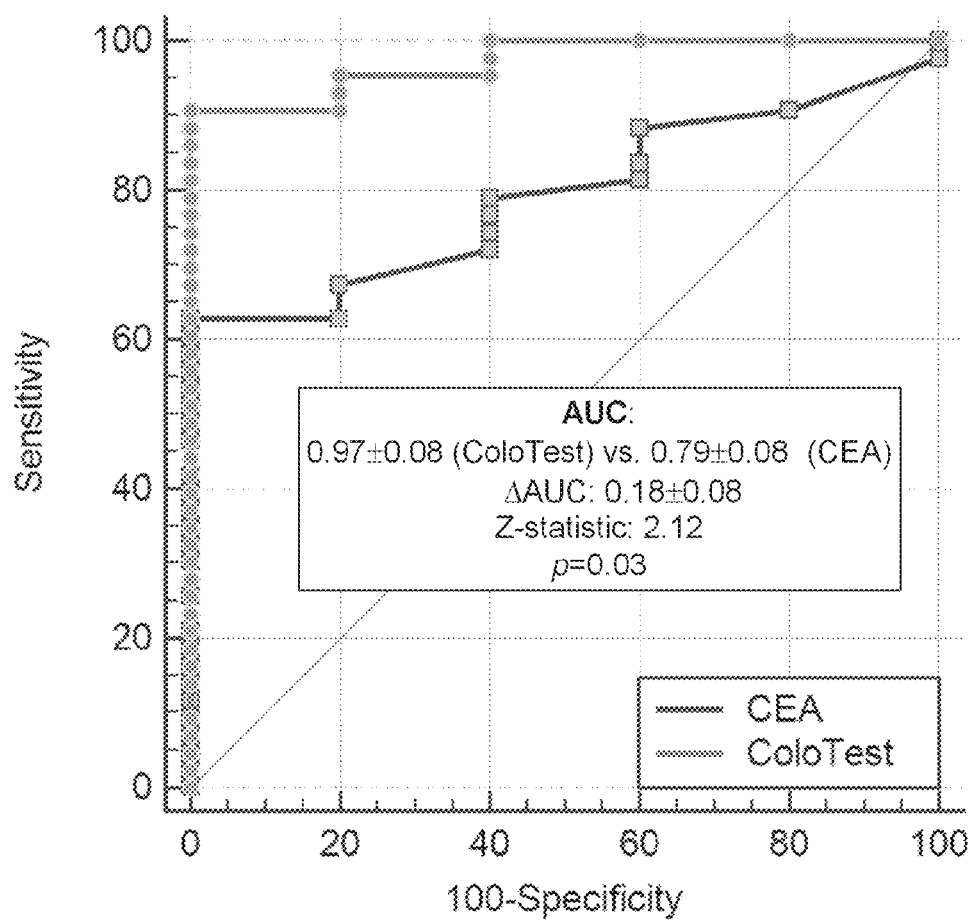
FIG. 7 is a graph showing comparison of AUROC between the ColoTest and CEA for differentiating stable from progressive disease. The ColoTest was significantly more sensitive than CEA (difference in AUC: 0.18, z-statistic: 2.1, p=0.03).

Examination of a separate colon cancer cohort by disease status (clinical evaluation at time of blood-draw) identified that the ColoTest was not significantly different between stable (n=17: 56±7%) and progressive disease (n=32: 68±4%) (FIGS. 6A-6C). However, 12 of the 17 patients progressed with 3 months of blood collection. Those that did progress exhibited elevated ColoTest scores at time of blood draw (n=12: 73±4%) that were not different to those with progressive disease at time of blood draw (n=32: 68±4%) (FIGS. 6A-6C). Levels in patients with stable disease were significantly lower (n=5: 16±4%, p<0.0001). A direct comparison between the ColoTest and CEA in these samples identified that the gene expression assay was significantly more sensitive (p<0.05) than CEA for predicting disease progression (FIG. 7). The ColoTest tool can therefore accurately predict progressive colon cancer disease.

Figure 8:
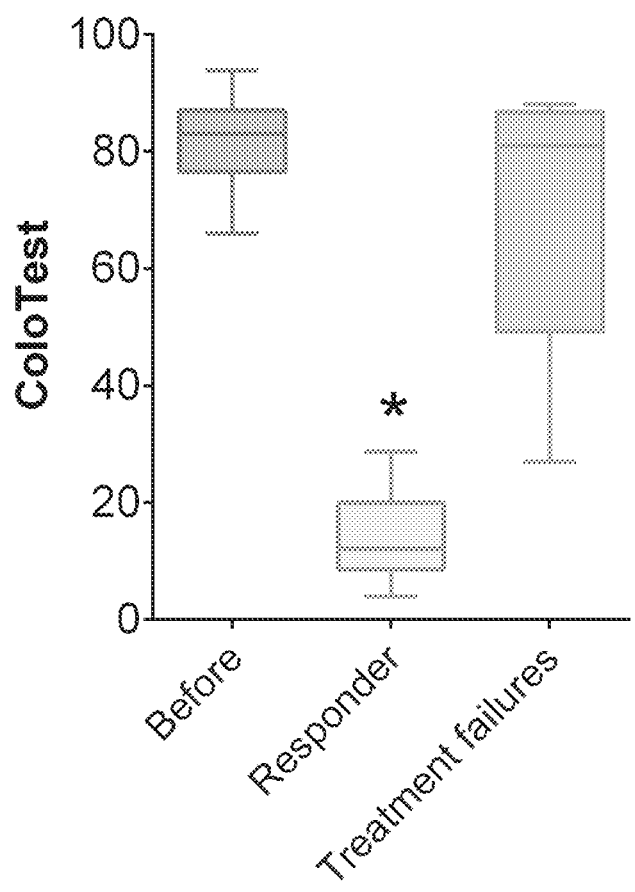
FIG. 8 is a graph showing the effect of treatment on the ColoTest. Levels prior to treatment are elevated (82±9%). In those who responded to therapy with disease stabilization, levels were reduced to 14±7% (*p<0.0001). In those that exhibited disease progression because of treatment failure, levels were elevated (69±21%).

ROC analysis identified the ColoTest had an AUC: 0.97 for differentiating stable from progressive disease. The z-statistic for differentiating controls was 20.6. Further evaluation of this cohort identified that patients who exhibited disease progression despite therapy exhibited higher scores than those responding to therapy (FIG. 8). Therapies included bevacizumab, chemotherapy and EGFR TKI inhibitors. The tool can therefore accurately identify treatment failure in colon cancer disease.

TABLE 2

| Colon Cancer Biomarker or Housekeeping Genes | | NCBI Chromosome | | | Amplicon | Exon | Assay |
|---|---|---|---|---|---|---|---|
| Symbol | Name | location | UniGene ID | RefSeq | length | Boundary | Location |
| ADRM1 | adhesion regulating molecule 1 | Chr.20: 62302056-62308862 | Hs.90107 | NM_007002.3 | 60 | 3-4 | 486 |
| CDK4 | cyclin dependent kinase 4 | Chr.12: 57747727-57752447 | Hs.95577 | NM_000075.3 | 65 | 5-6 | 928 |
| COMT | catechol-O-methyltransferase | Chr.22: 19941740-19969975 | Hs.370408 | NM_000754.3 | 118 | 5-6 | 864 |
| DHCR7 | 7-dehydrocholesterol reductase | Chr.11: 71434411-71448431 | Hs.503134 | NM_001163817.1 | 74 | 3-4 | 351 |
| HMOX2 | heme oxygenase 2 | Chr.16: 4474697-4510347 | Hs.284279 | NM_001127204.1 | 81 | 5-6 | 1002 |
| MCM2 | minichromosome maintenance complex component 2 | Chr.3: 127598357-127622436 | Hs.477481 | NM_004526.3 | 67 | 13-14 | 2374 |
| MORF4L1 (housekeeping gene) | mortality factor 4 like 1 | Chr.15: 78872781-78897739 | Hs.374503 | NM_001265603.1 | 62 | 1 | 116 |
| PDXK | pyridoxal (pyridoxine, vitamin B6) kinase | Chr.21: 43719097-43762307 | Hs.284491 | NM_003681.4 | 103 | 9-10 | 959 |
| POP7 | POP7 homolog, ribonuclease P/MRP subunit | Chr.7: 100706053-100707500 | Hs.416994 | NM_005837.2 | 136 | 2 | 828 |
| S100P | S100 calcium binding protein P | Chr.4: 6693839-6697170 | Hs.2962 | NM_005980.2 | 73 | 1-2 | 234 |
| SNRPA | small nuclear ribonucleoprotein polypeptide A | Chr.19: 40750854-40765392 | Hs.466775 | NM_004596.4 | 123 | 3-4 | 986 |
| SORD | sorbitol dehydrogenase | Chr.15: 45023104-45075089 | Hs.878 | NM_003104.5 | 72 | 4-5 | 601 |
| STOML2 | stomatin like 2 | Chr.9: 35099776-35103195 | Hs.3439 | NM_001287031.1 | 68 | 2-3 | 290 |
| UMPS | uridine monophosphate synthetase | Chr.3: 124730366-124749273 | Hs.2057 | NM_000373.3 | 85 | 3-4 | 1082 |

REFERENCES

1. Siegel R L, Miller K D, Jemal A. Cancer Statistics, 2017. CA Cancer J Clin. 2017; 67: 7-30. doi: 10.3322/caac.21387. Epub 2017 Jan. 5.
2. Ferlay J, Steliarova-Foucher E, Lortet-Tieulent J, Rosso S, Coebergh J W, Comber H, Forman D, Bray F. Cancer incidence and mortality patterns in Europe: estimates for 40 countries in 2012. Eur J Cancer. 2013; 49: 1374-403.
3. Fritzmann J, Morkel M, Besser D, Budczies J, Kosel F, Brembeck F H, Stein U, Fichtner I, Schlag P M, Birchmeier W. A colorectal cancer expression profile that includes transforming growth factor beta inhibitor BAMBI predicts metastatic potential. Gastroenterology. 2009; 137: 165-75.
4. Chen V W, Hsieh M C, Charlton M E, Ruiz B A, Karlitz J, Altekruse S F, Ries L A, Jessup J M. Analysis of stage and clinical/prognostic factors for colon and rectal cancer from SEER registries: AJCC and collaborative stage data collection system. Cancer. 2014; 120: 3793-806.
5. Heald R J, Lockhart-Mummery H E. The lesion of the second cancer of the large bowel. Br J Surg. 1972; 59: 16-9.
6. Mokhles S, Macbeth F, Farewell V, Fiorentino F, Williams N R, Younes R N, Takkenberg J J, Treasure T. Meta-analysis of colorectal cancer follow-up after potentially curative resection. Br J Surg. 2016; 103: 1259-68.
7. Thomas S N, Zhu F, Schnaar R L, Alves C S, Konstantopoulos K. Carcinoembryonic antigen and CD44 variant isoforms cooperate to mediate colon carcinoma cell adhesion to E- and L-selectin in shear flow. J Biol Chem. 2008; 283: 15647-55.
8. Amri R, Bordeianou L G, Sylla P, Berger D L. Preoperative carcinoembryonic antigen as an outcome predictor in colon cancer. J Surg Oncol. 2013; 108: 14-8.
9. Jansen N, Coy J F. Diagnostic use of epitope detection in monocytes blood test for early detection of colon cancer metastasis. Future Oncol. 2013; 9: 605-9.
10. Locker G Y, Hamilton S, Harris J, Jessup J M, Kemeny N, Macdonald J S, Somerfield M R, Hayes D F, Bast R C, Jr. ASCO 2006 update of recommendations for the use of tumor markers in gastrointestinal cancer. J Clin Oncol. 2006; 24: 5313-27.
11. Warren J D, Xiong W, Bunker A M, Vaughn C P, Furtado L V, Roberts W L, Fang J C, Samowitz W S, Heichman K A. Septin 9 methylated DNA is a sensitive and specific blood test for colorectal cancer. BMC Med. 2011; 9:133.: 10.1186/741-7015-9-133.
12. Mead R, Duku M, Bhandari P, Cree I A. Circulating tumour markers can define patients with normal colons, benign polyps, and cancers. Br J Cancer. 2011; 105: 239-45.
13. Molnar B, Floro L, Sipos F, Toth B, Sreter L, Tulassay Z. Elevation in peripheral blood circulating tumor cell number correlates with macroscopic progression in UICC stage IV colorectal cancer patients. Dis Markers. 2008; 24: 141-50. doi:
14. Mishaeli M, Klein B, Sadikov E, Bayer I, Koren R, Gal R, Rakowsky E, Levin I, Kfir B, Schachter J, Klein T. Initial TPS serum level as an indicator of relapse and survival in colorectal cancer. Anticancer Res. 1998; 18: 2101-5.

15. Piepoli A, Cotugno R, Merla G, Gentile A, Augello B, Quitadamo M, Merla A, Panza A, Carella M, Maglietta R, D'Addabbo A, Ancona N, Fusilli S, et al. Promoter methylation correlates with reduced NDRG2 expression in advanced colon tumour. BMC Med Genomics. 2009; 2:11.: 10.1186/755-8794-2-11.

EQUIVALENTS

While the present invention has been described in conjunction with the specific aspects set forth above, many alternatives, modifications and other variations thereof will be apparent to those of ordinary skill in the art. All such alternatives, modifications and variations are intended to fall within the spirit and scope of the present invention.

The invention claimed is:

1. A method of treating colon cancer in a subject comprising:
   determining the expression level of at least 14 biomarkers from a test sample from a subject by contacting the test sample with a plurality of agents specific to detect the expression of the at least 14 biomarkers, wherein the 14 biomarkers comprise ADRM1, CDK4, COMT, DHCR7, HMOX2, MCM2, PDXK, POP7, S100P, SNRPA, SORD, STOML2, UMPS, and a housekeeping gene, wherein the housekeeping gene is MORF4L1;
   normalizing the expression level of each of ADRM1, CDK4, COMT, DHCR7, HMOX2, MCM2, PDXK, POP7, S100P, SNRPA, SORD, STOML2, and UMPS to the expression level of the housekeeping gene, thereby obtaining a normalized expression level of each of ADRM1, CDK4, COMT, DHCR7, HMOX2, MCM2, PDXK, POP7, S100P, SNRPA, SORD, STOML2, and UMPS;
   inputting each normalized expression level into an algorithm to generate a score, wherein the algorithm is a product of a model of colon cancer disease derived using the XGB algorithm;
   comparing the score with a predetermined cutoff value;
   determining that the score is equal to or greater than the predetermined cutoff value, thereby identifying the subject as having colon cancer; and
   administering to the subject identified as having colon cancer a therapy, wherein the therapy comprises anti-cancer therapy, chemotherapy, targeted drug therapy, radiation therapy, immunotherapy or any combination thereof.

2. The method of claim 1, wherein the predetermined cutoff value is at least 50% on a scale of 0-100%.

3. The method of claim 1, wherein the predetermined cutoff value is at least 60% on a scale of 0-100%.

4. The method of claim 1, wherein the predetermined cutoff value has a sensitivity of identifying the subject as having colon cancer that is greater than 85%.

5. The method of claim 1, wherein the predetermined cutoff value has a specificity of identifying the subject as having colon cancer that is greater than 75%.

6. The method of claim 1, wherein at least one of the at least 14 biomarkers is RNA, cDNA or protein.

7. The method of claim 6, wherein when the biomarker is RNA, the RNA is reverse transcribed to produce cDNA, and the produced cDNA expression level is detected.

8. The method of claim 1, wherein the predetermined cutoff value is derived from a plurality of reference samples obtained from subjects not having or not diagnosed with a colon cancer.

9. The method of claim 1, wherein therapy comprises chemotherapy, wherein the chemotherapy comprises FOLFOX, FOLFIRI, a combination of 5-FU and leucovorin, capecitabine, irinotecan, CapeOx or any combination thereof.

10. The method of claim 1, wherein when the therapy comprises targeted drug therapy, wherein the targeted drug therapy comprises bevacizumab, cetuximab, panitumumab, regorafenib, a combination of trifluridine and tipiracil, an EGFR TKI inhibitor or any combination thereof.

11. The method of claim 1, wherein when the therapy comprises anti-cancer therapy, wherein the anticancer therapy comprises anti-colon cancer therapy.

12. The method of claim 1, wherein when the therapy comprises immunotherapy, wherein the immunotherapy comprises pembrolizumab, nivolumab or a combination of pembrolizumab and nivolumab.

* * * * *

SEQUENCE LISTING

```
Sequence total quantity: 31
SEQ ID NO: 1           moltype = DNA  length = 1496
FEATURE                Location/Qualifiers
source                 1..1496
                       mol_type = other DNA
                       organism = Homo sapiens
SEQUENCE: 1
gttagagccg gctgcgcggc ttacggggct caatcggcgg cgagagcggc aggcggggcg   60
ggccgaacgc gggtttccgg cggggccgg caggcgccga ggaggaagag cgagcccgga  120
cggcgcctct cgaacgagtg tgggcgcgag gcaggatgac gacctcaggc gcgctctttc  180
caagcctggt gccaggctct cggggcgcct ccaacaagta cttggtggag tttcgggcgg  240
gaaagatgtc cctgaagggg accaccgtga ctccggataa gcggaaaggg ctggtgtaca  300
ttcagcagac ggacgactcg cttattcact tctgctggaa ggacaggacg tccgggaacg  360
tggaagacga cttgatcatc ttccctgacg actgtgagtt caagcgggtg ccgcagtgcc  420
ccagcgggag ggtctacgtg ctgaagttca aggcagggtc caagcggctt ttcttctgga  480
tgcaggaacc caagacagac caggatgagg agcattgccg gaaagtcaac gagtatctga  540
acaaccccc gatgcctggg gcgctggggg ccagcggaag cagcggccac gaactctctg  600
cgctaggcgg tgagggtggc ctgcagagcc tgctgggaaa catgagccac agccagctca  660
tgcagctcat cggaccagcc ggcctcggag gactgggtgg gctgggggcc ctgactggac  720
ctggcctggc cagcttactg gggagcagtg ggcctccagg gagcagctcc tcctccagct  780
cccggagcca gtcggcagcg gtcaccccgt catccaccac ctcttccacc cgtgccaccc  840
cagccccttc tgctccagca gctgcctcag caactagccc gagcccgcg cccagttccg  900
ggaatggagc cagcacagca gccagcccga cccagcccat ccagctgagc gacctccaga  960
gcatcctggc cacgatgaac gtaccagccg ggccagcagg cggccagcaa gtggacctgg 1020
ccagtgtgct gacgccggag ataatggctc ccatcctcgc caacgcggat gtccaggagc 1080
gcctgcttcc ctacttgcca tctggggagt cgctgccgca gaccgcggat gagatccaga 1140
ataccctgac ctcgccccag ttccagcagg ccctgggcat gttcagcgca gccttggcct 1200
cggggcagct gggcccctc atgtgccagt tcggtctgcc tgcagaggct gtggaggccg 1260
ccaacaaggg cgatgtggaa gcgtttgcca aagccatgca gaacaacgcc aagcccgagc 1320
agaaagaggg cgacacgaag gacaagaagg acgaagagga ggacatgagc ctggactgag 1380
ccacgcgccg tcctccgagg aactgggcgc ttgcagtgcg ttgcacaccc tcacctccca 1440
cccactgatt attaataaag tcttttcttt tacctgccaa aaaaaaaaaa aaaaaa     1496

SEQ ID NO: 2           moltype = DNA  length = 2020
FEATURE                Location/Qualifiers
source                 1..2020
                       mol_type = other DNA
                       organism = Homo sapiens
SEQUENCE: 2
cacctcctgt ccgcccctca gcgcatgggt ggcggtcacg tgcccagaac gtccggcgtt   60
cgccccgccc tcccagtttc cgcgcgcctc tttggcagct ggtcacatgg tgagggtggg  120
ggtgaggggg cctctctagc ttgcggcctg tgtctatggt cgggccctct gcgtccagct  180
gctccggacc gagctcgggt gtatggggcc gtaggaacg gctccggggc cccgataacg  240
ggccgccccc acagcacccc gggctggcgt gagggtctcc cttgatctga gaatggctac  300
ctctcgatat gagccagtgg ctgaaattgg tgtcggtgcc tatgggacag tgtacaaggc  360
ccgtgatccc cacagtggcc actttgtggc cctcaagagt gtgagagtcc ccaatggagg  420
aggaggtgga ggaggccttc ccatcagcac agttcgtgag gtggctttac tgaggcgact  480
ggaggctttt gagcatccca atgttgtccg gctgatggac gtctgtgcca catcccgaaa  540
tgaccgggag atcaaggtaa ccctggtgtt tgagcatgta gaccaggacc taaggacata  600
tctggacaag gcacccccac caggcttgcc agccgaaacg atcaaggatc tgatgcgcca  660
gtttctaaga ggcctagatt tccttcatgc caattgcatc gttcaccgag atctgaagcc  720
agagaacatt ctggtgacaa gtggtggaac agtcaagctg gctgactttg gcctggccag  780
aatctacagc taccagatgg cacttacacc cgtggttgtt acactctggt accgagctcc  840
cgaagttctt ctgcagtcca catatgcaac acctgtggac atgtggagtg ttggctgtat  900
ctttgcagag atgtttcgtc gaaagcctct cttctgtgga aactctgaag ccgaccagtt  960
gggcaaaatc tttgacctga ttgggctgcc tccagaggat gactggcctc gagatgtatc 1020
cctgcccgt ggagcctttc ccccagagg gccccgccca gtgcagtcgg tggtacctga 1080
gatggaggag tcggagcac agctgctgct ggaaatgctg acttttaacc cacacaagcg 1140
aatctctgcc tttcgagctc tgcagcactc ttatctacat aaggatgaag gtaatccgga 1200
gtgagcaatg gagtggctgc catggaagga agaaaagctg ccatttccct tctgacact  1260
gagagggcaa tcttttgcct tatctctgag gctatgaggt gtcctcctcc atctttctac 1320
agagattact ttgctgcctt aatgacattc ccctcccacc tctccttttg aggcttctcc 1380
ttctccttcc catttctcta cactaagggg tatgttccct cttgtccctt tccctacctt 1440
tatatttggg gtccttttt atacaggaaa aacaaaacaa agaaataatg gtctttttt  1500
```

```
ttttttaat gtttcttcct ctgtttggct ttgccattgt gcgatttgga aaaaccactt   1560
ggaagaaggg actttcctgc aaaaccttaa agactggtta aattacaggg cctaggaagt   1620
cagtggagcc ccttgactga caaagcttag aaaggaactg aaattgcttc tttgaatatg   1680
gattttaggc ggggcgtggt ggctcacgcc tataatccca gcacgttggg aggccaacgc   1740
gggtggatca cctgaggtca ggagttcgag accagctgca ctaacatgtg gaaaccctgt   1800
ctctactaaa aatacaaaat tagtcaggcg tggtggtgca cacctgtaat cccagctact   1860
tgggagactg aggcaggagg atcgcttgaa cccgggaggc agaggttgcg gtgagccgag   1920
atcatgccat tgcactccag cctgggcaac agagcaagac tctgtgtcaa aaaaaaaaa   1980
agaatataga ttttttaaatg gcaaaaaaa aaaaaaaaa                          2020

SEQ ID NO: 3           moltype = DNA   length = 2304
FEATURE                Location/Qualifiers
source                 1..2304
                       mol_type = other DNA
                       organism = Homo sapiens
SEQUENCE: 3
cggcctgcgt ccgccaccgg aagcgccctc ctaatccccg cagcgccacc gccattgccg   60
ccatcgtcgt ggggcttctg gggcagctag ggctgcccgc cgcgctgcct gcgccggacc   120
ggggcgggtc cagtcccggg cgggccgtcg cgggagagaa ataacatctg ctttgctgcc   180
gagctcagag gagaccccag acccctcccg cagccagagg gctggagcct gctcagaggt   240
gctttgaaga tgccggaggc cccgcctctg ctgttggcag ctgtgttgct gggcctggtg   300
ctgctggtgg tgctgctgct gctttctgagg cactgggggt ggggcctgtg cctttatcggc   360
tggaacgagt tcatcctgca gcccatccac aacctgctca tgggtgacac caaggagcag   420
cgcatcctga ccacgtgct gcagcatgcg gagcccggga acgcacagag cgtgctggag   480
gccattgaca cctactgcga gcagaaggag tgggccatga acgtgggcga caagaaaggc   540
aagatcgtgg acgccgtgat tcaggacgac cagccctccg tgctgctgga gctggggggcc   600
tactgtggct actcagctgt gcgcatggcc cgcctgctgt caccaggggc gaggctcatc   660
accatcgaga tcaaccccga ctgtgccgcc atcacccagc ggatggtgga tttcgctggc   720
gtgaaggaca aggtcaccct tgtggttgga gcgtcccagg acatcatccc ccagctgaag   780
aagaagtatg atgtggacac actgacactg gtcttcctcg accactggaa ggaccggtac   840
ctgccggaca cgcttctctt ggaggaatgt ggcctgctgc ggaaggggac agtgctactg   900
gctgacaacg tgatctgccc aggtgcgcca gacttcctag cacacgtgcg cgggagcagc   960
tgctttgagt gcacacacta ccaatcgttc ctggaataca gggaggtggt ggacggcctg   1020
gagaaggcca tctacaaggg cccaggcagc gaagcagggc cctgactgcc ccccggcc   1080
ccctctcggg ctctctcacc cagcctggta ctgaaggtgc cagacgtgct cctgctgacc   1140
ttctgcggct ccgggctgtg tcctaaatgc aaagcacacc tcggccgagg cctgcgccct   1200
gacatgctaa cctctctgaa ctgcaacact ggattgttct ttttttaagac tcaatcatga   1260
ctttctttact aacactggct agctatatta tcttatatac taatatcatg ttttaaaaat   1320
ataaaataga aattaagaat ctaaatattt agatataact cgacttagta catccttctc   1380
aactgccatt ccctgctgc ccttgacttg gcaccaaac attcaaagct cccccttgacg   1440
gacgctaacg ctaagggcgg ggcccctagc tggctgggtt ctgggtggca cgcctggccc   1500
actggcctcc cagccacagt ggtgcagagg tcagccctcc tgcagctagg ccaggggcac   1560
ctgttagccc catgggggacg actgccggcc tgggaaacga agaggagtca gccagcattc   1620
acacctttct gaccaagcag gcgctgggga caggtggacc ccgcagcagc accagccctc   1680
ctgggcccca tgtggcacag agtggaagca tctccttccc tactcccac tgggccttgc   1740
ttacagaaga ggcaatggct cagaccagct cccgcatccc tgtagttgcc tccctggccc   1800
atgagtgagg atgcagtgct ggtttctgcc cacctacacc tagagctgtc cccatctcct   1860
ccaaggggtc agactgctag ccacctcaga ggctccaagg gcccagttcc caggcccagg   1920
acaggaatca accctgtgct agctgagttc acctgcaccg agaccagccc ctagccaaga   1980
ttctactcct gggctcaagg cctggctagc cccagccag cccactccta tggatagaca   2040
gaccagtgag cccaagtgga caagtttggg gccacccagg gaccagaaac agagcctctg   2100
caggacacag cagatgggca cctgggacca cctccaccca gggccctgcc ccagacgcgc   2160
agaggcccga cacaagggag aagccagcca cttgtgccag acctgagtgg cagaaagcaa   2220
aaagttcctt tgctgcttta atttttaaat ttcttacaa aaatttaggt gtttaccaat   2280
agtcttattt tggcttattt ttaa                                         2304

SEQ ID NO: 4           moltype = DNA   length = 2642
FEATURE                Location/Qualifiers
source                 1..2642
                       mol_type = other DNA
                       organism = Homo sapiens
SEQUENCE: 4
aatcgctgac atcatccggg gcggggcgcc cctgccctgc gggtgactcc gaccccctgc   60
tagagggtag gcgggcgtgga gcagcgcgcg caagcgaggc caggggaagg tgggcgcagg   120
acttagccg gttgagaagg atcaagcagg catttggagc acaggtgtct agaaactttt   180
aaggggccgg ttcaagaagg aaaagttccc ttctgctgtg aaactatttg gcaagaggct   240
ggagggccca atggctgcaa aatcgcaacc caacattccc aaagccaaga gtctagatgg   300
cgtcaccaat gacagaaccg catctcaagg gcagtgggc cgtgcctggg aggtggactg   360
gttttcactg gcgagcgtca tcttcctact gctgttcgcc cccttcatcg tctactactt   420
catcatggct tgtgaccagt acagctgcgc cctgactgcc cctgtggtgg acatcgtcac   480
cggacatgct cggctctcgg acatctgggc caagactcca cctataacga ggaaagccgc   540
ccagctctat accttgtggg tcaccttcca ggtgcttctg tacacgtctc tccctgactt   600
ctgccataag tttctacccg gctacgtagg aggcatccag gagggggccg tgactcctgc   660
aggggtgtg aacaagtatc agatcaatgg ctgcaagcc tgctcctca cgcacctgct   720
ctggtttgca aacgctcatc tcctgtcctg gttctcgccc accatcatct tcgacaactg   780
gatcccactg ctgtggtgcg ccaacatcct tggctatgcc gtctccacct tcgccatggt   840
caagggctac ttcttcccca ccagcgccag agactgcaaa ttcacaggca atttcttta   900
caactacatg atgggcatcg agtttaacccc tcggatcggg aagtggtttg acttcaagct   960
gttcttcaat gggcgcccg ggatcgtcgc ctggaccctc atcaacctgt cttcgcagc   1020
```

```
gaagcagcgg gagctccaca gccatgtgac caatgccatg gtcctggtca acgtcctgca   1080
ggccatctac gtgattgact tcttctggaa cgaaacctgg tacctgaaga ccattgacat   1140
ctgccatgac cacttcgggt ggtacctggg ctggggcgac tgtgtctggc tgccttatct   1200
ttacacgctg cagggtctgt acttggtgta ccacccgtg cagctgtcca ccccgcacgc    1260
cgtgggcgtc ctgctgctgg gcctgtgggg ctactacatc ttccgggtgg ccaaccacca   1320
gaaggacctg ttccgccgca cggatgggc ctgcctcatc tggggcagga agcccaaggt    1380
catcgagtgc tcctacacat ccgccgatgg gcagaggcac cacagcaagc tgctggtgtc   1440
gggcttctgg ggcgtggccc gccacttcaa ctacgtcggc gacctgatgg gcagcctggc   1500
ctactgcctg gcctgtggcg gcggccacct gctgccctac ttctacatca tctacatggc   1560
catcctgctg acccaccgct gcctccggga cgagcaccgc tgcgccagca gtacgaccgcg  1620
ggactgggag cgctacaccg ccgcagtgcc ttaccgcctg ctgcctggaa tcttctaagg   1680
gcacgcccta gggagaagcc ctgtggggct gtcaagagcg tgttctgcca ggtccatggg   1740
ggctggcatc ccagctccaa ctcgaggagc ctcagtttcc tcatctgtaa actggagaga   1800
gcccagcact tggcaggtgt ccagtaccta atcacgctct gttccttgct tttgccttca   1860
agggaattcc gagtgtccag cactgccgta ttgccagcag agacggattt tctctaatca   1920
gtgtccctgg ggcaggagga tgacccagtc acctttacta gtcctttgga gacaatttac   1980
ctgtattagg agcccaggcc acgctacact ctgcccacac tggtgagcag gaggtcttcc   2040
cacgcccgt cattaggctg catttactct tgctaaataa aagtgggagt ggggcgtgcg    2100
cgttatccat gtattgcctt tcagctctag atcccctcc cctgcctgct ctgcagtcgt    2160
gggtggggcc cgtgcgccgt ttctccttgg tagcgtgcac ggtgttgaac tgggacactg   2220
gggagaaagg ggctttcatg tcgtttcctt cctgctcctg ctgcacagct gccaggagtg   2280
ctctgcctgg agtctgcaga cctcagagag gtcccagcac gcgctgtgc ctttcaggtg    2340
taggcaggtg ggctctgctt cccgattccc tgtgagcgcc caccctccg aaagaatttt    2400
ctgcttgccc tatgactgtg cagactctgg ctcgagcaac ccggggaact tcaccctcag   2460
gggcctccca caccttctcc agcgaggagg tctcagtccc agcctcggga gggcacctcc   2520
ttttctgtgc tttcttccct gaggcattct tcctcatccc tagggtgttg tgtagaactc   2580
tttttaaact ctatgctccg agtagagttc atctttatat taaacttccc ctgttcaaat   2640
aa                                                                  2642

SEQ ID NO: 5         moltype = DNA  length = 1872
FEATURE              Location/Qualifiers
source               1..1872
                     mol_type = other DNA
                     organism = Homo sapiens
SEQUENCE: 5
catctctagg ccccgccccg cgctgcgtgc ccacgttgcg ccggcctcgc gccagtccgc     60
tgggctgcag ggactgcggc gcctgaggga gtcgctgacg ggcacgctga ctggaggctg    120
gcggacaggc gacagcgacc tgcggcagag tcttgctgcg acacccaggc tggagtgcaa    180
tggcgctatc tcggctcact gcaacctccg cttcccggat tcaagcgatt ctcctgcctc    240
agcctcccga gtaggtggga ctacaggacc agaggagcga gagcagcaag aaccacaccc    300
agcagcaatg tcagcggaag tggaaacctc agagggggta gacgagtcag aaaaaaagaa    360
ctctggggcc ctagaaaagg agaaccaaat gagaatggct gacctctcgg agctcctgaa    420
ggaagggacc aaggaagcac acgaccgggc agaaaacacc cagtttgtca aggacttctt    480
gaaaggcaac attaagaagg agctgtttaa gctggccacc acggcacttt acttcacata    540
ctcagccctc gaggaggaaa tggagcgcaa caaggaccat ccagcctttg ccccctttgta   600
cttccccatg gagctgcacc ggaaggaggc gctgaccaag gacatggagt atttcttttgg   660
tgaaaactgg gaggagcagg tgcagtgcc caaggctgcc cagaagtacg tggagcggat    720
ccactacata gggcagaacg agccggagct actggtggcc catgcataca cccgctacat    780
ggggatctc tcgggggcc aggtgctgaa gaaggtggcc cagcgagcac tgaaactccc    840
cagcacaggg gaagggaccc agttctacct gtttgagaat gtggacaatg cccagcagtt   900
caagcagctc taccgggcca ggatgaacgc cctggacctg aacatgaaga ccaaagagag    960
gatcgtggag gaggccaaca aggcttttga gtataacatg cagatattca atgaactgga   1020
ccaggccggc tccacactgg ccagagagac cttggaggat gggttccctg tacacgatgg   1080
gaaaggagac atgcgtaaat gccctttcta cgctgctgaa caagacaaag gtgccctgga   1140
gggcagcagc tgtcccttcc gaacagctat ggctgtgctg aggaagccca gcctccagtt   1200
catcctggcc gctggtgtgg ccctagctgc tggactcttg gcctggtact acatgtgaag   1260
cacccatcat gccacaccgg taccctcctc ccgactgacc actggcctac cccttttctcc  1320
agccctgact aaactaccac ctcaggtgac ttttttaaaa atgctgggtt taagaaaggc   1380
aaccaataaa agccagatgc tagagcctct gcctgacagc atcctctcta tgggccatat   1440
tcccgcactgg gcacaggccg tcaccctggg agcagtcagc acagtgcagc aagcctggcc   1500
cccgacccag ctctactcca ggcttccaca tttctgggcc ctaggctgct tccggtagtc   1560
cctgttttg cagtacatgg gtgactatct tccctgttgg aggtgagtgg cctgtaagtc    1620
caagctgtgc gaggggcct tgctggatgc tgctgtacaa cttctgggcc tctcttggac    1680
cctgggagtg aggtggggtg tgggtggaag cctcagaggc tttgggagct catccctctc   1740
acccagaatc cctctaaccc cttgggtgcg gtttgctcag ccccagctta tctcctcctc   1800
cgcgctgtgt aaatgctcca gcactcaata aagtgggctt tgcaagctaa aaaaaaaaaa   1860
aaaaaaaaaa aa                                                       1872

SEQ ID NO: 6         moltype = DNA  length = 3504
FEATURE              Location/Qualifiers
source               1..3504
                     mol_type = other DNA
                     organism = Homo sapiens
SEQUENCE: 6
atgacgtcgc gttccgtagg gctcttcccg ggctttggtg ggtcacgtga accactttc      60
gcgcgaaacc tggttgttgc tgtagtggcg gagaggatcg tggtactgct atggcggaat    120
catcggaatc cttcaccatg gcatccagcc cggcccagcg tcggcgaggc aatgatcctc    180
tcacctccag ccctggccga agctcccggc gtactgatgc cctcacctcc agccctggcc    240
gtgaccttcc accatttgag gatgagtccg aggggctcct aggcacagag gggccctgg    300
```

```
aggaagaaga ggatggagag gagctcattg gagatggcat ggaaagggac taccgcgcca 360
tcccagagct ggacgcctat gaggccgagg gactggctct ggatgatgag gacgtagagg 420
agctgacggc cagtcagagg gaggcagcag agcgggccat gcggcagcgt gaccgggagg 480
ctggccgggg cctgggccgc atgcgccgtg ggctcctgta tgacagcgat gaggaggacg 540
aggagcgcc tgcccgcaag cgccgccagg tggagcgggc cacggaggac ggcgaggagg 600
acgaggagat gatcgagagc atcgagaacc tggaggatct caaaggccac tctgtgcgcg 660
agtgggtgag catggcgggc cccggctgg agatccacca ccgcttcaag aacttcctgc 720
gcactcacgt cgacagccac ggccacaacg tcttcaagga gcgcatcagc gacatgtgca 780
aagagaaccg tgagagcctg gtggtgaact atgaggactt ggcagccagg gagcacgtgc 840
tggcctactt cctgcctgag gcaccggcgg agctgctgca gatctttgat gaggctgccc 900
tggaggtggt actggccatg taccccaagt acgaccgcat caccaaccac atccatgtcc 960
gcatctccca cctgcctctg gtggaggagc tgcgctcgct gaggcagctg catctgaacc 1020
agctgatccg caccagtggg gtggtgacca gctgcactgg cgtcctgccc cagctcagca 1080
tggtcaagta caactgcaac aagtgcaatt tcgtcctggg tccttctgc cagtcccaga 1140
accaggaggt gaaaccaggc tcctgtcctg agtgccagtc ggccggcccc tttgaggtca 1200
acatggagga gaccatctat cagaactacc agcgtatccg aatccaggag agtccaggca 1260
aagtggcggc tggccggctg ccccgctcca aggacgccat tctcctcgca gatctggtgg 1320
acagctgcaa gccaggagac gagatagagc tgactggcat ctatcacaac aactatgatg 1380
gctccctcaa cactgccaat ggcttccctg tctttgccac tgtcatccta gccaaccacg 1440
tggccaagaa ggacaacaag gttgctgtag gggaactgac cgatgaagat gtgaagatga 1500
tcactagcct ctccaaggat cagcagatcg agagaagat ctttgccagc attgctcctt 1560
ccatctatgg tcatgaagac atcaagagag gcctggctc ggccctgttc ggaggggagc 1620
ccaaaaccc aggtggcaag cacaaggtac gtggtgatat caacgtgctc ttgtgcggag 1680
accctggcac agcgaagtcg cagtttctca agtatattga gaaagtgtcc agccgagcca 1740
tcttcaccac tggccagggg gcgtcggctg tgggcctcac ggcgtatgtc cagcggcacc 1800
ctgtcagcag ggagtggacc ttggaggctg gggcctggt tctggctgac cgaggagtgt 1860
gtctcattga tgaatttgac aagatgaatg accaggacga aaccagcatc catgaggcca 1920
tggagcaaca gagcatctcc atctcgaagg ctggcatcgt cacctccctg caggctcgct 1980
gcacggtcat tgctgccgcc aaccccatag gagggcgcta cgaccctcg ctgactttct 2040
ctgagaacgt ggacctcaca gagcccatca tctcacgctt tgacatcctg tgtgtggtga 2100
gggacaccgt ggacccagtc caggacgaga tgctggcccg cttcgtggtg ggcagccacg 2160
tcagacacca ccccagcaac aaggaggagg aggggctggc caatggcagc gctgctgagc 2220
ccgccatgcc caacacgtat ggcgtggagc cctgccccca ggaggtcctg aagaagtaca 2280
tcatctacgc caaggagagg gtccacccga agctcaacca gatggaccag gacaaggtgg 2340
ccaagatgta cagtgacctg aggaaagaat ctatgcgac aggcagcatc cccattacgg 2400
tgcggcacat cgagtccatg atccgcatgg cggaggccca cgcgcgcatc catctgcggg 2460
actatgtgat cgaagacgac gtcaacatgg ccatccgcgt gatgctggag agcttcatag 2520
acacacagaa gttcagcgtc atgcgcagca tgcgcaaagac ttttgcccgc tacctttcat 2580
tccggcgtga caacaatgag ctgttgctct tcatactgaa gcagttagtg gcagagcagg 2640
tgacatatca gcgcaaccgc tttgggcgcc agcaggacac tattgaggtc cctgagaagg 2700
acttggtgga taaggctcgt cagatcaaca tccacaacct ctctgcattt tatgacagtg 2760
agctcttcag gatgaacaag ttcagccacg acctgaaaag gaaaatgatc ctgcagcagt 2820
tctgaggccc tatgccatcc ataaggattc cttgggattc tggtttgggg tggtcagtgc 2880
cctctgtgct ttatggacac aaaaccagag cacttgatga actcggggta ctagggtcag 2940
ggcttatagc aggatgtctg gctgcacctg gcatgactgt ttgtttctcc aagcctgctt 3000
tgtgcttctc acctttgggt gggatgcctt gccagtgtgt cttacttggt tgctgaacat 3060
cttgccacct ccgagtgctt tgtctccact cagtaccttg gatcagagct gctgagttca 3120
ggatgcctgc gtgtggttta ggtgttagcc ttcttacatg gatgtcagga gagctgctgc 3180
cctcttggcg tgagttgcgt attcaggctg cttttgctgc ctttggccag agagctggtt 3240
gaagatgttt gtaatcgttt tcagtctcct gcaggttct gtgcccctgt ggtggaagag 3300
ggcacgacag tgccagcgca gcgttctggg cctcctcagtc gcaggggtgg gatgtgagtg 3360
atgcggatta tccactcgcc acagttatca gctgccattg ctccctgtct gtttcccac 3420
tctcttattt gtgcattcgg tttggttct gtagttttaa ttttaataa agttgaataa 3480
aatataaaaa aaaaaaaaaa aaaa 3504
```

SEQ ID NO: 7        moltype = DNA  length = 7390
FEATURE              Location/Qualifiers
source               1..7390
                     mol_type = other DNA
                     organism = Homo sapiens
SEQUENCE: 7

```
cggaactcgc gggttcggag ccgcccgctg aggtcagaag gaggcgtctg cgctgatcgg 60
gtccgccgcg cgcagagcc agagtcgcag ccgaggggga ccggggccgg agcccgagcc 120
cgagccgagc cggagcccga gcgagcggcg gagaccgtgc ccccgcctcg gccccgcccc 180
gccgcggcca ggcccggcat ggaggaggag tgccgggtgc tctccataca gagccacgtc 240
atccgcggct acgtgggcaa ccgggcggcc acgttcccgc tgcaggtttt gggatttgag 300
attgacgcgg tgaactctgt ccagttttca aaccacacag gctatgccca ctggaagggc 360
caagtgctga attcagatga gctccaggag ttgtacgaag gctgaggct gaacaacatg 420
aataaatatg actacgtgct cacaggttat acgagggaca agtcgttcct ggccatgtgg 480
gtggacattg tgcaggagct gaagcagcag aaccccaggc tggtacgt gtgtgatcca 540
gtcttgggtg acaagtggga cggcgaaggc tcgatgtacg tcccgaagga cctccttccc 600
gtctacaaag aaaaagtggt gccgcttgca gacattatca cgcccaacca gtttgaggcc 660
gagttactga gtggccggaa gatccacagc caggaggaag ccttgcgggt gatggacatg 720
ctgcactcta tggccccga caccctggtc atcaccgact ccgatgcc ctccccgcag 780
ggcagcaact acctgattgt gctgggggagt cagaggagga ggaatccgc tggctccgtg 840
gtgatggaac gcatccggat ggacattcgc aaagtggacg ccgtctttgt gggcactggg 900
gacctgtttt ctgccatgct cctggcgtgg acacacaagc accccaataa cctcaaggtg 960
gcctgtgaga agaccgtgtc taccttgcac cacgttctgc agaggaccat ccagtgtgca 1020
aaagcccagg ccggggaagg agtgaggccc agccccatgc agctggagct gcggatggtg 1080
```

-continued

```
cagagcaaaa gggacatcga ggacccagag atcgtcgtcc aggccacggt gctgtgaggg  1140
ccccgccgct tgcccgtgac acgcagcgcg ttggtgtctc cgtgtttgtc cctgtgaaaa  1200
catgtaacgt ctgccttaga gccatgaccg aaacttgata ttttttttctt tcatgagtgt  1260
ccggcatctg ctggtcttca ttgtgaaacg tgccagtcgt gctttgtgaa aaataacaaa  1320
gtggtcacag aaatttgtga tctgaaaacc cggctccctt ccccacaagg ctcctgggcc  1380
tccgggaaga cgggcccctg tttgccatct cggggggtgtt ccctgtggga gggtgagtgg  1440
gtgaggccga gcctgctgcg tgtggagcct cgagtgggcc ctggctgcca ctaccgtaca  1500
gaggccgtgt cgcgctgggc tgggcctggg tggcctctgt ctttgcatct ctgagaagga  1560
gtcgggtggt aacggttggg gtcaggaaga attctgccaa gtatctttac tgtcattctg  1620
accatagcct ctttgttccc gcattcgaac ttttgttct tactttgctg ctcgtttagt  1680
ccctggggat ttcagatctt aggctgttgt ttcaccgtat gggagggttg atgtgagctt  1740
gcttggagac acacggtgca gcatcaggga ccttcccagg ccccagcaaa ttcaagtcgg  1800
tctgcagacc tctcagctac ccgcgggacc tcttgtaacc catcggcatc ttccaggaat  1860
ccgccgagtg acttgaggaa gatgctaacg cagtaaggtc tgtgctgggc caagagcagc  1920
tttgaagctc cagagaacca ccccgtcagg ttccttgtgg aagctcccct catccgtggt  1980
gcagcaggct gagcactgcg cgtttgccac gtgctgcccg tgacagcaca ttgagccaca  2040
gcatttgtag acaggacaga ggggtgcctg ccccctgccc ctgctggcac atttaaccct  2100
tgtccctga cctcagttct gtgcccccacc aaatgcccag gggcaagagg ccaccctgca  2160
agctgccaat cttccaaggt gggtgtgggg cacggtgggg gcgggcagct cccaggcccct  2220
tgggcaggct ggggtgacgg cagaggccac agcaccagct ctgacaagtc ctatcatcct  2280
ctgctcagca gtgacctccc tggccccact ttgcccagag tttggggtcc cccaggtat  2340
agctataggc ggcagtgcct gtccctggcc tgccttgatt tcagccacac ccctgcagcc  2400
ctgcatccca gctctgggct gtgcagaggt ttgtgtctcc agggaaccca cggctggaga  2460
gaaataggga gatgcaggaa gtgggggccc atggggcccc caagaagcgg actctccaag  2520
gggtaccccc accccgctac cttccccacg gacgggcccc tcctggagcc cataccctcc  2580
tgtgaggcca ttcagtgtc ttctagaaag actcgcttgc caggagtgcg ttctttgttg  2640
aaaaatgccc tgaagcgaaa agatgcaggt ttatatggaa ccccccaccc ctccccact  2700
ctcccactct gttcgttctg aatgtcttca cgagcgtgca tcaggcgcc tggctccccc  2760
acctcagcca gtgagtcaga cacggggttc gcagccatgt ttcctggctc cgaggacacg  2820
ggtggccga ccgttgcagc ccagagccaa tggtccctac agggcgccgc cacaccagca  2880
ggaaggagga tggctgtgtc cggagcctgg cggggaggcg gcctcccag tatgtgagtg  2940
cagggatctg ccagaaccac ctggccctct gtagggcgtt taactggaaa tacccctcact  3000
gccaagtgga gactggggcg tgtgccacat tgccagccac caggaaagct tttctttttc  3060
ttttttttt tttttaaac accaagagca cgtatagcat gggggaaaga acctaaatgt  3120
ctctctgtcc tgtgagctgg tgaaaaaccc agcatgagaa cgcagtgtca ggtgtgggac  3180
tccttctgcc cctgcagtgg gtgttacggg cggtgtgccc tggcgagcaa gctttgattc  3240
ttggttcttt gagctcgttt cagaggctga gtccccacat cagctttagt tcttggactt  3300
ccctgtatta agcaagaatt aggagaatgg ctgtccctgc aggcgcctcc cgtaaatcct  3360
gagctctctg gcgcaatctg aaacttctct tctgtttttct ttggctgtat cagccgaacc  3420
aggagaggcc tgggctgcga ctaaggagaa agaaatcggg ggtttctgag agcagatggt  3480
gccttttgtgg gtgcagggct tttgtggaaa ttgtcagcct ctacgggcag agtccggcat  3540
cccctcccca gactgcctgc tgtcaaacca cggagcagct ggagcctgcc ctgtccacgg  3600
cccgttccca cccgggcatg ttcgtctctc atgacttcgg cagaggcccc tggtggcctc  3660
cagtttcagt ttctcatcca ggaaggtaac cttgggcatt ggcagtgggt ttccctatgg  3720
cttggatcca gattagaatt gatctttgtt ttcactttcc atagttaata acatgcaaaa  3780
taatgagaag aatttatttt aaggtgacag ctatactggt ccaacatcgc ctgcttattg  3840
tcagggtaca gaagtttaat actttcttaa tccagttttt caaactttctc cctgtagacc  3900
gtaaggatga attccacaat aggatccttt ttaaaatcga ttttaaattg ttgcctagtc  3960
ctgccaaggt tattatgtgc atctgttatt tttccaatac atgtaaacag ttgcagcatg  4020
atgctttgtt taatgtcctg ttcttaagct cgttagagcc agtttgaaa cgtttggtct  4080
taccgtgaac ggaggctggc ttggcttagc cacgctgatg agtaagtgag ggatgtctcc  4140
atcttgagat caccaggcaa gagagttgcc tgcaccaggt aagaggccaa agcccctggg  4200
gtaacagtcc ccaccgctac ccgaggtaaa acaataaaag ctatgtggtt gagctcaggc  4260
ctctcgtgcc tggtgtcaga gaaggcagag cccacagtag gtgcacggtg caaggccctg  4320
ggagggcact ggcagggaa ggtgtatag atggccctca gattgcgggg ccccgagcag  4380
ctccccactc tgcccgtcca ccttcctgg ctccagcctc attctctctt tagtttaact  4440
atgcaaagag aggaggttga gagtgttctg gcagctggag ctcttttcct tgtccttcct  4500
gccctccgat ggggccacct gtgtcgggc agcagtgtcc atgtttatgg agatcagagg  4560
tgtccccact gtgtggctgg actgtactct gctgcccggg tagccaggag tctctccctc  4620
tctcccctgc cgccttcctg gtctcatggg cctccttcac acacccctcc ctgtggatcg  4680
cctgcctggg cccagagcag gggaactgga gttttgtgagt gagcagagca ggttatgtgc  4740
agacagggaa acgagaactt tggacctggc tttctgagtc caggtgagag ctgtgtggcc  4800
ccccgatgcc actctgcccg ccggagggat gtgcctgctg agccttttcc ttccacgccg  4860
cctctcactg ccaggccagc ggcttccgct gagactcgct ggagaggcgg ctcccgtctc  4920
cgtccaccga gcactcagat ggatgctgat caccagggcc gaggggggctc ccagaaggac  4980
cccaggccct ggggagggtg gctgtgggag gccaagtcca ctgcccggaa gtcttgtcag  5040
ccctaagcca gggaagcctg gagcgtgcc tgcgggtct gggtggacac cgtcccact  5100
ccggactccc agcacagggg aggatacctg agcctgtatg gccctgtagc cctgggcaga  5160
gctgggcctg tcgtgtgttc ctgcctggca ggtgcaggtg ggcatct gcaggtggga  5220
ggaggtggga atcttggatt tttttgtttttt ttttgttttt ttttttttga gatgaagtct  5280
cgctctgaca cccaggctgg cgtgcagtgg tgtgatctcg gctcactgca aactccgctt  5340
cctgggttca gtggttctc ctgccccagc ctccaagta gctgggatta caggcatgcg  5400
ccaccacgct cagctgattt ttgtatttttt agtagagatg gggtttcacc atgttggcca  5460
agctgtctc aaactcctga cctcaagtga tctgcccgcc cagagtgctgg  5520
gattacaggc atgagccagt gcacccggcg gaatcttgga atttttatag acagcacctc  5580
agtttctgac tccagccgca cacctcctgc ctctgccagc aggggttgcc gccagaccag  5640
agccagggcc aggtccctgc gtccatcccc ccggtaggga tggacgtgag ccatccttct  5700
aggggactttt tttcagtgtg cgactcgtct ctgttaggtg gtaggagcca gtttgtgtgg  5760
cctgtgccac gctccacagt gcgtggctgg gctctgtgtg tggcctgtgt cccctgtccc  5820
```

```
tgcaggaccc agcaggcatc gtggcgtgac agctgtgtcc aagccactgc ccgggcatcc     5880
catcacccac cagggtgcac ggtctctcct gctgggggct ttctgtcgca tgtgtgtctc     5940
ctgtcgactc tgcagtttgt tctcagagca gaatgtttcc tgttctcagt gcacaaagac    6000
actggttttc aatcggcgtc taaaaccacg ttcctgcctt tcattgcaac acggtgtgtt    6060
catttgttta aaacagttta atgagtaagt ttagatgact ggtcaatatc ttaaaaatgt    6120
atattagtaa gaagttcttc ctggaatttt tctttcgatt ctggcagaat aaacaggtgt    6180
ttttagtttt cccactgtct gagccaagca ggacccgtc ccagagcaag agatgtcccc     6240
ttccatctct gacccttgcc tgggacaagc tttgatgggg ggcccagct tcaaggctgt     6300
ggtgggaaca gcaccccaa atgccagcct ctccttttct cccatccacc agtatactgc     6360
ggggccattt ctggtctttg tccaacagga aacccatttc tggtgggata tgccttccag    6420
tgccacaggg ccactcaccc catgcatctc tgtcctgccc gtcagtgctg ggacggacag    6480
caagggcaag cccagtgtct ggcggatagg tgggtgggaa cagagagggg agaatgccgt    6540
cctaagcttc tgcttgggga tcccccacac gacctgggta ctgcctggga aacctgtcct    6600
aagtaaaact atggaccteg cctcgcccac cggcctgcga agccagcatc tccgtgaagg    6660
tggatggaag cgcctttgtc ctcattttga gctgcaagct gggtcagcgg ctctgaagcc    6720
ctcgagtgac tttctaaccc aagacccagc ccctggcagg aggagggtgg gtgcagggct    6780
ggtgggacaa aaagaggcct cagcaggcct ggaagaccct tccagtacat cccacagcgt    6840
gtcgagcagc tgggagaacc tgtgtcaagc tcgagccgtc ataggtcccc atgaggtgtc    6900
tgaagcccct tcttggtgat gggaggcaga ggtgctgacg ttctggagca tggacgtgag    6960
tcctcagctg gctccgcgtg ggccttgga gggtgccagg tgtgtggtga ccttctggat     7020
gcctttaact tcatggctgc gtcattcctg atttagaact ttaaccggag cttcatctag    7080
tgattgcaaa actggaccaa tgggaggacg gcggcgcaag ccgctccctc cgtggaatgg    7140
agctcagctc ttcggaggca tcaaagcacc tgtcgcctcc gtggtccccc tgctgaggga    7200
gtgcggcctc tgcaaggttc ggggtggct tcgtttgcct ggagtggccg gcctgcttg     7260
tgccatgtgg atgtttgtga gcctcggtcc tacagcactg tgtaggctgc atctgtttcg    7320
tgctggtcct gttgacttgt atgatatcca caaataaata ttttcatggc ggtcgtgttg    7380
aaaaaaaaaa                                                           7390

SEQ ID NO: 8            moltype = DNA  length = 949
FEATURE                 Location/Qualifiers
source                  1..949
                        mol_type = other DNA
                        organism = Homo sapiens
SEQUENCE: 8
ggaaggggcg gggcgaacgg aagccgggaa ggcgattcat agctcgcggg gtacgggcgc     60
gcgtgcgcac tccgcagccc gttcaggacc ccggcgcggg cagggcgccc acgagctggc    120
tggctgcttg cacccacatc cttctttctc tgggacctgg ggtcgcggtt acttgggctg    180
gccggcgaac ccttgagtgg cctggcgggg agcgggcctc gcgcgcctgg agggccctgt    240
ggaaccgaaga gaggcacaca gcatggcaga aaaccgacga cccccgcggtg ctgtggaggc   300
tgaactggat ccagtggaat acaccccttag gaaaaggctt cccagccgcc tgccccggag    360
acccaatgac atttatgtca acatgaagac ggacttaaag gcccagctgg cccgctgcca    420
gaagctgctg gacggagggg cccggggtca gaacgcgtgc tctgagatct acattcacgg    480
cttgggcctg gccatcaacc gcgccatcaa catcgccgtg cagtcgcagg cggtcagctt    540
cgggtccttg caggtggctg ccaataccte caccgtggag cttgttgatg agctggagcc    600
agagaccgac acacgggagc cactgactcg gatccgcaac aactcagcca tccacatccg    660
agtcttcagg gtcacaccca gtaattgaa aagcactcc tccacttatc ccctccgtga     720
tatggctctt cgcatgctga gtactggacc tcggaccaga gccatgtaag aaaaggcctg    780
ttccctggaa gcccaaagga ctctgccattg agggtggggg taattgtctc ttggtgggcc    840
cagttagtgg gccttcctga gtgtgtgtat gcggtctgta actattgcca tataaataaa    900
aaatcctgtt gcactagtgt cctgccatcc caaaaaaaaa aaaaaaaa                 949

SEQ ID NO: 9            moltype = DNA  length = 510
FEATURE                 Location/Qualifiers
source                  1..510
                        mol_type = other DNA
                        organism = Homo sapiens
SEQUENCE: 9
tgaggctgcc ttataaagca ccaagaggct gccagtggga catttttctcg gccctgccag     60
ccccaggag gaaggtgggt ctgaatctag caccatgacg gaactagaga cagccatggg    120
catgatcata gacgtctttt cccgatattc gggcagcgag ggcagcacgc agaccctgac    180
caaggggagg ctcaaggtgc tgatggaaa ggagctacca ggcttcctgc agagtggaaa    240
agacaaggat gccgtggata aattgctcaa ggacctggac gccaatggag atgcccaggt    300
ggacttcagt gagttcatcg tgttcgtggc tgcaatcacg tctgcctgtc acaagtactt    360
tgagaaggca ggactcaaat gatgccctgg agatgtcaca gattcctggc agagccatgg    420
tcccaggctt cccaaaagtg tttgttggca attattcccc taggctgagc ctgctcatgt    480
acctctgatt aataaatgct tatgaaatga                                     510

SEQ ID NO: 10           moltype = DNA  length = 1646
FEATURE                 Location/Qualifiers
source                  1..1646
                        mol_type = other DNA
                        organism = Homo sapiens
SEQUENCE: 10
ggcggggcca ggagagaaag ctttgtggtt tggtctcagg gaagtagcag gcgccggttg     60
agagaactac ggccctgtcg gaaggtaacc tccggtgcaa acgaccatcg gcggcaggcg    120
agcggtacgc ttggcgtccg ggccttcctg ggccgtctg aggaaacttg ctgctcgagg     180
ccaggctgcc taggacctgt ccctttttc tatactggct cccacatccg ggttttttct    240
ccgggacggc ccttcggatg cttgggcaa tgggaatcgc catttagggt gctccgccca    300
ccgggtcgcg tagagcatcc tggaagtcgt agtaaatctc tcgagagttc tctccgcacg    360
```

-continued

```
cggggctggag aagcgggtcc tacgcacgct ttgttgtcgc gctttgcctc cgtccttgcc    420
cctactcccg ccttacctga cttccttttc ggaggaagat ccttgagcag ccgacgttgg    480
gacaaaggat ttggagaaac ccagggctaa agtcacgttt ttcctccttt aagacttacc    540
tcaacacttc actccatggc agttcccgag acccgcccta accacactat ttatatcaac    600
aacctcaatg agaagatcaa gaaggatgaa ctaaaaaagt ccctgtacgc catcttctct    660
cagtttggcc agatcctgga tatcctggta tcacggagcc tgaagatgag gggccaggcc    720
tttgtcatct tcaaggaggt cagcagcgcc accaacgccc tgcgctccat gcagggtttc    780
cctttctatg acaaacctat gcgtatccag tatgccaaga ccgactcaga tatcattgcc    840
aagatgaaag gcaccttcgt ggagcgggac cgcaagcggg agaagaggaa gcccaagagc    900
caggagaccc cggccaccaa gaaggctgtg caaggcgggg agccaccccc cgtggtgggg    960
gctgtccagg ggcctgtccc gggcatgccg ccgatgactc aggcgccccg cattatgcac   1020
cacatgccgg ccagccgcc ctacatgccg cccctggta tgatccccc gccaggcctt     1080
gcacctggcc agatcccacc aggggccatg ccccgcagc agcttatgcc aggacagatg    1140
cccctgcccc agcctctttc tgagaatcca ccgaatcaca tcttgttcct caccaacctg   1200
ccagaggaga ccaacgagct catgctgtcc atgcttttca atcagttccc tggcttcaag   1260
gaggtccgtc tggtacccgg gcggcatgac atcgccttcg tggagtttga caatgaggta   1320
caggcagggg cagctcgcga tgccctgcag ggctttaaga tcacgcagaa caacgccatg   1380
aagatctcct ttgccaagaa gtagcacctt ttccccccat gcctgccccct tccccctgttc   1440
tggggccacc cctttccccc ttggctcagc ccctgaagg taagtcccc cttgggggcc      1500
ttcttggagc cgtgtgtgag tgagtggtcg ccacacagca ttgtacccag agtctgtccc   1560
cagacattgc acctggcgct gttaggccgg aattaaagtg gcttttttgag gtttggtttt   1620
tcacaatcaa aaaaaaaaaa aaaaaa                                         1646

SEQ ID NO: 11           moltype = DNA  length = 2813
FEATURE                 Location/Qualifiers
source                  1..2813
                        mol_type = other DNA
                        organism = Homo sapiens
SEQUENCE: 11
ctccacgcta gcgccgccca ggctggcaca aaggaggaag cctagtcccg cccctgcgtg     60
cggcgcttct cccaggcccc accttccatc cagtgccctg gaccctcggc tgggtagcgc    120
caccagagcg accaaacgtc ccgcgccttc caggccgcac tccagagcca aaagagctcc    180
atggcggcgg cggccaagcc caacaacctt tccctggtgg tgcacggacc ggggacttg     240
cgcctggaga actatcctat ccctgaacca ggcccaaatg aggtcttgct gaggatgcat    300
tctgtttgaa tctgtggctc agatgtccac tactggagt atggtcgaat tgggaatttt    360
attgtgaaaa agcccatggt gctgggacat gaagcttcgg gaacagtcga aaagtgggga   420
tcatcggtaa agcacctaaa accaggtgat cgtgttgcca tcgagcctgg tgctccccga    480
gaaaatgatg aattctgcaa gatgggccga tacaatctgt caccttccat cttcttctgt    540
gccacgcccc ccgatgacgg gaacctctgc cggttctata agcacaatgc agccttttgt    600
tacaagcttc ctgacaatgt caccttgag gaaggcgccc tgatcgagcc actttctgtg    660
gggatccatg cctgcaggag aggcggagtt accctgggac acaaggtcct tgtgtgtgga    720
gctgggccaa tcgggatggt cactttgctc gtggccaaag caatgggagc agctcaagta    780
gtggtgactg atctgtctgc tacccgattg tccaaagcca aggagattgg ggctgattta    840
gtcctccaga tctccaagga gagccctcag gaaatcgcca ggaaagtaga aggtcagctg    900
gggtgcaagc cggaagtcac catcgagtgc acggggcag aggcctccat ccaggcgggc    960
atctacgcca ctcgctctgg tgggaacctc gtgcttgtgg ggctgggctc tgagatgacc   1020
accgtaccccc tactgcatgc agccatccgg gaggtggata tcaagggcgt gtttcgatac   1080
tgcaacacgt ggccagtggc gatttcgatg cttgcgtcca agtctgtgaa tgtaaaaccc   1140
ctcgtcaccc ataggtttcc tctggagaaa gctctggagg cctttgaaac atttaaaaag   1200
ggattggggt tgaaaatcat gctcaagtgt gaccccagtg accagaatcc ctgatgttaa   1260
tgggctctgc cctcatcccc acagtcttgg gatctcaggg cacaatggct ggacatgggt   1320
gggctctgat gcagaacttt ctcttttgaa tgttaagaat aactaataca attcattgtg   1380
aacagaagtc cttaagcaga ggaattggtg tgccttaaag atacaatctg ggatagtttg   1440
gggggaacttg tagccagaat gccctgttca tgctgagcaa agttcagcaa gtagagcaga   1500
gtttggcagg caggtgccag gaactcccct tcttcctgga gtgccttcat tgaggaagga   1560
aatctggccc ttgggtttcc tggttccact gctactgacc cagagggaa tgagggctga    1620
gttatgaaaa gataacttca tgaagactta actggcccag aagctgattt tcatgaaaat   1680
ctgccactca gggtctggga tgaaggcttg tcagcacttc cagtttagaa cgcaatgttt   1740
ctagagacat attggctgtt tgttttgatg ataaaaggag aataagaaaa ggcatcactt   1800
tcctggatcc aggataattt ttaaaccaat caaatgaaaa aaacaaacaa acaaaaaagg   1860
aaatgtcatg tgaggttaaa ccagtttgca ttccctaat gtggaaaaag taagaggact    1920
actcagcact gtttgaagat tgcctcttct acagcttctg agaattgtgt tatttcactt    1980
gccaagtgaa ggacccctc cccaacatgc ccagcccac cctaagcat ggtcccttgt      2040
caccaggcaa ccaggaaact gctacttgtg gacctcacca gaccaggca gggtttggtt   2100
agctcacagg acttccccca ccccagaaga ttagcatccc atactagact catactcaac   2160
tcaactaggc tcatactcaa ttgatggtta ttagacaatt ccatttcttt ctggttatta   2220
taaacagaaa atctttcctc ttctcattac cagtaaaggc tcttggtatc tttctgttgg   2280
aatgatttct atgaacttgt cttatttaaa tggtgggttt ttttctggt aagatttaga    2340
cctaaatcgc atcatgccaa cttgtgactt tgagactatt catcaagaat gaggatatag   2400
tagccatgac atagcttgag ctatagcctt taattcctta ctttggctat gggtggaggg   2460
tgagtttgaa gaggttctga ttttcttgta acctgggaaa gccatgacct tgtgcccgat   2520
tctttcagat tgctttgggt aataaatatt ggtggtggta tctgactcat gctgctgttt   2580
atggtcctgt ttagtgggga atggactcag gttacccatt tcccagaggg aaggatccca   2640
ggattttttga aggttacata tttttctgtac caaatataat ttcattgaca tgaattatct   2700
ctaatcctca tgacaagcca catacacaat cattttgtag ataaagaaga tataaatgcc   2760
agaggagacc ttaagattgt cttacaacac aaccccttcag ttaacgagag agg          2813

SEQ ID NO: 12           moltype = DNA  length = 1296
FEATURE                 Location/Qualifiers
```

|  |  |  |
|---|---|---|
| source | 1..1296 | |
| | mol_type = other DNA | |
| | organism = Homo sapiens | |
| SEQUENCE: 12 | | |

```
tccggggag cggaactgca agaggaaagg ctcgggtagg cttctgggag cgaccgctcc    60
gctcgtctcg ttggttccgg aggtcgctgc ggcggtggga aatgctggcg cgcgcggcgc   120
ggggcactgg ggcccttttg ctgaggggct ctctactggc ttctggccgc gctccgcgcc   180
gcgcctcctc tggattgccc cgaaacaccg tggtactgtt cgtgccgcag caggaggcct   240
gggtggtgga gcgaatgggc cgattccacc ggatcctgga gcctggtttg aacatcctca   300
tccctgtgtt agaccggatc cgatatgtgc agagtctcaa ggaaattgtc atcaacgtgc   360
ctgagcagtc ggctgtgact ctcgacaatg taactctgca aatcgatgga gtcctttacc   420
tgcgcatcat ggacccttac aaggcaagct acggtgtgga ggaccctgag tatgccgtca   480
cccagctagc tcaaacaacc atgagatcag agctcggcaa actctctctg gacaaagtct   540
tccgggtgga ggcagagcgg cggaaacggg ccacagttct agagtctgag gggaccgag    600
agtcggccat caatgtggca gaagggaaga acaggcccaa gatcctggcc tccgaagcag   660
aaaaggctga acagataaat caggcagcag gagaggccag tgcagttctg gcgaaggcca   720
aggctaaagc tgaagctatt cgaatcctgg ctgcagctct gacacaacat aatggagatg   780
cagcagcttc actgactgtg gccgagcagt atgtcagcgc gttctccaaa ctggccaagg   840
actccaacac tatcctactg ccctccaacc ctggcgatgt caccagcatg gtggctcagg   900
ccatgggtgt atatggagcc ctcaccaaag ccccagtgcc agggactcca gactcactct   960
ccagtgggag cagcagagat gtccaggta cagatgcaag tcttgatgag gaacttgatc  1020
gagtcaagat gagttagtgg agctgggctt ggccagggag tctgggaaca aggaagcaga  1080
ttttcctgat tctggctcta gcttcccgc caagattttg gttttattt tttatttga    1140
actttagtcg tgtaataaac tcaccagtgg caaaccagaa actgtcctct ttgattgggg  1200
aatgaagttg ggaaagtcac tagcattttc cttggatcca gtcctgtcag catgatgcct  1260
ccatgaataa gagtgaactt cttgtaaagt gaaact                             1296
```

| SEQ ID NO: 13 | moltype = DNA length = 6738 |
|---|---|
| FEATURE | Location/Qualifiers |
| source | 1..6738 |
| | mol_type = other DNA |
| | organism = Homo sapiens |
| SEQUENCE: 13 | |

```
ctgcagacga ggcaggcgga agaggcggga cttcgcgggt gacgtcatcg gggcgccgga    60
ggcccggggc gcctgggaat ttgaagcaaa caggcagcgc gcgacaatgg cggtcgctcg   120
tgcagctttg gggccattgg tgacgggtct gtacgacgtg caggctttca agtttgggga   180
cttcgtgctg aagagcgggc tttcctcccc catctacatc gatctgcggg gcatcgtgtc   240
tcgaccgcgt cttctgagtc aggttgcaga tattttattc caaactgccc aaaatgcagg   300
catcagttt gacaccgtgt gtggagtgcc ttatacagct ttgccattgg ctacagttat   360
ctgttcaacc aatcaaattc caatgcttat tagaaggaaa gaaacaaagg attatgaac    420
taagcgtctt gtagaaggaa ctattaatcc aggagaaacc tgtttaatca ttgaagatgt   480
tgtcaccagt ggatctagtg ttttggaaac tgttgaggtt cttcagaagg agggcttgaa   540
ggtcactgat gccatagtgc tgttgacag agagcaggga gccaaggaca agttgcaggc   600
gcacgggatc cgcctccact cagtgtgtac attgtccaaa atgctggaga ttctcgagca   660
gcagaaaaaa gttgatgctg agacagttgg gagagtgaag aggtttattc aggagaatgt   720
ctttgtggca gcgaatcata tggttctccc ctttctata aaggaagcac ccaaagaact   780
cagcttcggt gcacgtgcag agctgcccag gatccaccca gttgcatcga agcttctcag   840
gcttatgcaa aagaaggaga ccaatctgtg tctatctgct gatgttcac tggccagaga    900
gctgttgcag ctagcagatg cttttaggacc tagtatctgc atgctgaaga ctcatgtaga   960
tattttgaat gatttactc tggatgtgat gaaggagttg ataactctgg caaaatgcca  1020
tgagttcttg atattgaag accggaagtt tgcagatata ggaaacacag tgaaaaagca  1080
gtatgaagga ggtatctttta aaatagcttc ctgggcagat ctagtaaatg ctcacgtggt  1140
gccaggctca ggagttgtga aaggcctgca agaagtgggc ctgccttttgc atcggggtg  1200
cctccttatt gcgaaatga gctccaccgg ctccctggcc actggggact acactagagc  1260
agcggttaga atggctgagg agcactctga atttgttgtt ggttttattt ctggctcccg  1320
agtaagcatg aaaccagaat tcttcacttt gactccagga gttcagttgg aagcaggagg  1380
agataatctt ggccaacagt acaatagccc acaagaagtt attggcaaac gaggttccga  1440
tatcatcatt gtaggtcgtg gcataatctc agcagctgat cgtctggaag cagcagagat  1500
gtacagaaaa gctgcttggg aagcgtattt gagtagactt ggtgttttag tgcttcagat  1560
acattttca gatacaatgt gaagacattg aagatatgtg gtcctcctga aagtcactgg  1620
ctggaaataa tccaattatt cctgcttgga ttcttccaca gggcctgtgt aagaatgggt  1680
tctggagttc tcatggtctt taggaaatat tgagtaattt gtaataccg cattgatact   1740
ataataagtt cattcttaag cttcttttt ttgagactgg tgtttgttag acagccacag  1800
tcctgtctgg gttagggtct tccacatttg aggatcctc ctatctctcc atgggactag  1860
actgctttgt tattctattt attttttaat tttttcgag acaggatctc actctgttgc  1920
ccaggatgga gtgcagtggt gagatcacgg ctcattgcag cctcgacctc ccaggtgatc  1980
ctcccacctc agcttccaga ttagctggtg ctataggcat gcaccaccac gtccatctaa  2040
attttcttat tatttgtaga gatgaggtct tgccatgtta cccggctgg tctcaactcc  2100
tgggctcaag cgatcctcct gcctcagtct ctcaaagtgc tgggattaca ggtgtgagcc  2160
actgtgccca gcctaattgc agtaagacaa aaattctagg gcaccaagag gctaaagtca  2220
gcacagcttt tcttgtgtcc tgtattctct gtctaatgtg ttgcccaaat aatacctaat  2280
tgttagccat tcccctccat ctctggccta aaagtgatag tccaggtatc cacatgggct  2340
ggttcccaga actgccattg ctcactctcc aaagaggga aggtgggaa ggggaaggtg   2400
actatagca agctcctgag ctagtatctg gctgttattt caacaaccgg agttgggtt   2460
tgggctcatt ttttccccta gccagcaatt atgaccagt agtaacacaa gtgcagcttt  2520
cctgtgactg acttcacaat taggaggtct aagattccat ttgggtattt gcttaaggat  2580
cccacataat tgtcccaacg gtcattagta gaggggaggt aagccttcat taataataaa  2640
gagaagccc acattcaagg tggtgtttga gcaggggcag ggtgagggct gtcccggtgc   2700
tcattgcacc agcacactca cattccttct catttggggc ccacctgcag gaagtggcac  2760
```

```
aggatcagcc atttccccac ccttgtcagc tgatggccca ctgttcttta atgactcaga    2820
ggaatgccta ggatttttt tttttttga gacagaatct cactgtcgcc caggctggag     2880
ttcagtggca cgatctcggc tcactgcaac ttctgcctct ctggttcaag cagttctcct    2940
gcctcagcct cccgagtagc tgggactaca agcctaggat ttttaactca ggttttatt    3000
atattccctc ctgaagtttt tacttcaaga gcttctgctc taaagtccaa tttgggcttc    3060
atgtccccag tgctgcatct ccagggaaat gctgtctgtg ggagagacca actctcaagg    3120
aagaagtggc cacagaagga gcaggaaggg agttggccct cagggctact ctggggaagc    3180
caaaagtcat gaaggggaga agaattttct gacaaaaact tgcaggaatc tcttaggtgt    3240
cttcagtgtt ggagtgatat gttgagaggc ctttggagtg atgtgctgag gtctcaggcg    3300
cccacctccc tggctgtcac ttccatgtgt cagtggttct cccactttag caggtatcag    3360
agtcacctgg agtcttgtca aaacaggtac cagcccacc cgcagcgttt ctgactctgg     3420
gtagctctgg gatgggcttg agaatttgc gtttccaaaa aggtcccagg tgatgctgcg    3480
gttgcctgcg cagggactgg actttgagaa ccacttcact ggttattcac atttctgcct    3540
ctgcagtgag acagccttga ggtctgcctc tgctaagag tcacatgctc ctgtccttta     3600
gaaatgtggg ctcctgccat ctccaggacg caggcactgt tcctgttgat gaaccctatt    3660
tcacaggacc cctgctaagg tgatttgagg ggaaatgaga ggaggctcaa ataatcaccc    3720
agcccctgcc acttactgaa agtgtaggtc cttgtgcccc acaccatcag agtttctgcg    3780
ttagcagatt tgtggtttgc ccagcagcct gggcgtgtga catttctaatg ggtgcctcaa    3840
gtgatctgtt tctgattttgt atttctattg tgaagagtca gcccagtact gcaggcctct    3900
tacctaagca gaatcccagt ctggcatcaa agctttagag gacaagttga ttcaggcaga    3960
gaagaacttg ggctatacaa gcgctgttct tcagcattga agtattttgg aggcattaga    4020
tagtttaacc cttctcagt caaggaatat ttacagaaca tgatctctgg gcattgtaac     4080
tcctggtctt agtggggaat atagggaccc catgtctcca tggggtgcac agaatgtctg    4140
tgagactgat ggagtggaga acgccatccc ccagcctctc cagctactcg aggcattctg    4200
tagaacataa gcccatagat tgtgtgtgtg tgtgtgtgtg tgtgtgtgtg tgtgtgtgtg    4260
tgcatgccgg cgcgtgcgca ctggaggaac ctaagaaact atttggtgca cttcctctta    4320
ttttagagct cccaaagtgt agctccagaa tcgtaaaggg atatgctcag tctcacagcc    4380
agcctgtgga tctcagtccc aacactcacc cttgtgctac tgagtcagct ctaagaaaat    4440
ctgccaaaag taggccgagg gctggttttt tgttttgttt tgtttgtttg atacagggtc    4500
ttcactctgt tgcccaggct ggagtatatc atggctcaat gcaaccttga cttgggctca    4560
agcgatccgc tcaagtagct ggaactactc tcaagtagct ctcaagagcc tctcgagtgg    4620
ctggaactac aggcgtgcac caccacagct ggttaatttt taaaattttt tgtagagacg    4680
gtggaggagg ttctcactgt gactcagtgt gtgcccgaca gcagagccca caccactcca    4740
gttgcagtgg ttgccatctg ggtcatcaga cctggctgtc aggggtgcag ccacaggaga    4800
gccaacagca gagggtgctg gccgctgagc tagctgctaa tgctggcctg ggtgcagttc    4860
tcatccaaag tacccggtgg gtgggagtca ctcagtacca gttccgagcc tgaacccaaa    4920
ctctcgtgtt tctgctcacc cctctctggc ttctgccacc acatgggaag aatatgcct      4980
ggttagccca tggcttctga agagcaagag aaagtagagc agagcctact ccagcctccc    5040
ccgtccaatg tatgaaagcc ccagctgatc tgtaagcctg gatgcgtgat aaatgcttag    5100
tagtgcatgc catggagttc cagggtggtt tattacacgg caatatctag ctaaatacat    5160
ttaacttgct gcagctctct ggatccagcc tggttaccag gaagacaaaa actgggctcc    5220
accaggaacc agtcttctgc cttcccaacc atcacctctg gctgcatcag cgatctctcc    5280
cagcgaaata gctgcttggt cttgtgtgaa tcctgtactt taacacagtg gaccaagtgt    5340
cagtcattga aaatgaccat gagtaaccct gtggactctc tgcagcttgg ttcctttgcc    5400
ccttaacagg tgggtatgaa tcgtgtcttc agtgccaggg ctgaatgaga aagggcattc    5460
cttttttgaag gaatctgata ctaaacacaa agcatgagaa aaatcaggac ttgttggagt    5520
tatatttta aaatatatat tttaacagtt atatatatat gatataatat ataatagtat    5580
atataaataa tactatattg cccaggctgg tctcgaactc cttagctcaa gtgatcctcc    5640
tgccttggct tcccaaagtg ctaggattac aggtgtgagc cactgctccc ggcctgttgg    5700
agttctttac atttatttta taatcaatgc tgtttttatta aatgcggatt ttattttgga    5760
ttacaggatg tagaatgcca tattttctct agatcatagg gcctttcaca tttgtaattt    5820
ggccttgtat gagttaccct gcaatccctt tgttttcccc ataacccttc caaaggaagg    5880
ccgcaataga aatacaaaga gaaacaaaat aattagaata ttttttaact tctaaagttc    5940
aaggttttgg cataagtctg gtttagaagc acatttgcct agccctttcc ttcccaccaa    6000
ggggaaagt cttcctctag acaagaggca gagggctcc cagatgcaga tcctggtgtg    6060
ggctctcacg tgctgctgct gaatcccagg gaaggagga ggaagggcag ttgacaccca     6120
aaataagggt ggggaactgt cagcagagga ggtctgtgtc atgttttca gcgctgggt    6180
tggggggagc ccaggagagc aggaagatcc agagatccct cgcccagct cggccatgtg    6240
tgtctgggac agagcctgag gtggcctgag cttcctgtgg ctccagagta acattataga    6300
gaagctgaat tctcctgttt ttctgaaaag ggcatggga ttagctgaga agcagacctg    6360
gtgggcctga gagtctcaat cgtcaggtaa ggacagtcag tgggaagtgg acgggccgca    6420
caaccaaggt tctcatgagg acaaccatgt cttcggggt gcccttgtgc acagacagct    6480
ccatagtcct gcctccaatg tcccaacact gcattgtctc cctgcactta gcagccctgc    6540
agggtgagac ttgggaggaa tcctgaaatg attgtattta acaagacatg ctgtcctgta    6600
ttacctggaa cctagcaatg ttgttttctg ccacaacttg aatagatact tgaagcagag    6660
atgatgttga gttaaaaaaa atatatacat aaaaatatgg ttctttttca acctgaatag    6720
atggcctaaa aattcaaa                                                 6738

SEQ ID NO: 14           moltype = DNA   length = 1779
FEATURE                 Location/Qualifiers
source                  1..1779
                        mol_type = other DNA
                        organism = Homo sapiens
SEQUENCE: 14
cggcgtgccc tggggcggcg cgggcgcagg ggcgcgtgcg cggcgggctg tcgttggctg     60
gagcagcggc tgcgcgggtc gcggtgctgt gaggtctgcg ggcgctggca aatccggccc    120
aggatgtaga gctggcagtg cctgacggcg cgtctgacgc ggagttgggt ggggtagaga    180
gtaggggcg gtagtcgggg gtggtgggag aaggaggagg cggcgaatca cttataaatg    240
gcgccgaagc aggacccgaa gcctaaattc caggaggttg ggatgaatgg gttccggaga    300
```

```
gcagagtact caaatacgtg gacaccaatt tgcagaaaca gcgagaactt caaaaagcca    360
atcaggagca gtatgcagag gggaagatga gaggggctgc cccaggaaag aagacatctg    420
gtctgcaaca gaaaaatgtt gaagtgaaaa cgaaaaagaa caaacagaaa acacctggaa    480
atggagatgt tggcagtacc agtgagaccc ctcagcctcc tcggaagaaa agggcccggg    540
tagatcctac tgttgaaaat gaggaaacat tcatgaacga agttgaagtt aaagtaaaga    600
ttcctgaaga gctaaaaccg tggcttgttg atgactggga cttaattacc aggcaaaaac    660
agctctttta tcttcctgcc aagaagaatg tggattccat tcttgaggat tatgcaaatt    720
acaagaaatc tcgtggaaac acagataata aggagtatgc ggttaatgaa gttgtggcag    780
ggataaaaga atacttcaac gtaatgttgg gtacccagct actctataaa tttgagagac    840
cacagtatgc tgaaattctt gcagatcatc ccgatgcacc catgtcccag gtgtatggag    900
cgccacatct cctgagatta tttgtacgaa ttggagcaat gttggcttat acacctctgg    960
atgagaagag ccttgcttta ttactcaatt atcttcacga tttcctaaag tacctggcaa   1020
agaattctgc aactttgttc agtgccagcg attatgaagt ggctcctcct gagtaccatc   1080
ggaaagctgt gtgagaggca ctctcactca cttatgtttg gatctccgta aacacattt    1140
tgttcttagt ctatctcttg tacaaacgat gtgctttgaa gatgttagtg tataacaatt   1200
gatgtttgtt ttctgtttga ttttaaacag agaaaaaata aaggggggta atagctcctt   1260
ttttcttctt tctttttttt tttcatttca aaattgctgc cagtgttttc aatgatggac   1320
aacagaggga tatgctgtag agtgttttat tgcctagttg acaaagctgc ttttgaatgc   1380
tggtggttct attcctttga cactacgcac ttttataata catgttaatg ctatatgaca   1440
aaatgctctg attcctagtg ccaaaggttc aattcagtgt atataactga acacactcat   1500
ccatttgtgc ttttgttttt ttttatggtg cttaaagtaa agagcccatc ctttgcaagt   1560
catccatgtt gttacttagg cattttatct tggctcaaat tgttgaagaa tggtggcttg   1620
tttcatggtt tttgtatttg tgtctaatgc acgttttaac atgatagacg caatgcattg   1680
tgtagctagt tttctggaaa agtcaatctt ttaggaattg ttttttcagat cttcaataaa   1740
ttttttcttt aaatttcaaa gaacaaaaaa aaaaaaaaa                           1779

SEQ ID NO: 15         moltype = DNA   length = 7827
FEATURE               Location/Qualifiers
source                1..7827
                      mol_type = other DNA
                      organism = Homo sapiens
SEQUENCE: 15
gtagtcttga cgtgagctag ctggcatggc ggcctgcatt gcagcggggc actgggctgc     60
aatgggccta ggccggagtt tccaagccgc caggactctg ctccccccgc cggcctctat    120
cgcctgcagg gtccacgcgg ggcctgtccg gcagcagagc actgggcctt ccgagcccgt    180
tgcgttccaa ccgccgccga aaccggtcat cgtggacaag caccgccccg tgaaccggaa    240
acgcaggttc ttgagtcctg aattcattcc tcgaagggga agaacagatc ctctgaaatt    300
tcaaatagaa agaaaagata tgttagaaag gagaaaagta ctcccacattc cagagttcta    360
tgttggaagt attcttcgtg ttactacagc tgacccatat gccagtggaa aaatcagcca    420
gtttctgggg atttgcattc agagatcagg aagaggactt ggagctactt tcatccttag    480
gaatgttatc gaaggacaag gtgtcgagat ttgctttgaa cttttataatc ctcgggtcca    540
ggagattcag gtggtcaaat tagagaaacg gctggatgat agcttgctat acttacgaga    600
tgccctttcct gaatatagca cttttgatgt gaatatgaac ccagtagtac aagagcctaa    660
ccaaaaagtt cctgttaatg agctgaaagt aaaaatgaag cctaagccct ggtctaaacg    720
ctgggaacgt ccaaattta atattaaagg aatcagatt gatctttgtt taactgaaca    780
gcaaatgaaa gaagctcaga gtggaatca gccatggctt gaatttgata tgatgaggga    840
atatgatact tcaaaaattg aagctgcaat atggaaggaa attgaagcgt cgaaaaggtc    900
ttgattctga gaatgaattt ggttagttgc agaagataca ttggctctaa gaggatatat    960
tttgagacca atttaatttc atttataaga acatagtaat taagtgaact aagcattcat   1020
tgttttatta atactttttt tctaaaataa aacttgtaca ccagtttatt actctaaaaa   1080
gagaattaca catgccaaat ggaccaatgt ccatttgctt attggaggca aagctacaat   1140
agaagtcaga gcatcaccag aatggtcttt aatgagcatg gaacctgagc aaagggaata   1200
ggtgggatga attttttttt taattgtgaa acaattcata agcacaatat gatttacaga   1260
ataataaaca ttcatgtacc cactatcagg ttaagaaata gaacatttat taatatgtag   1320
gaattgtaag aaataaaaca tttaataaga tctcagaaga ctccagtaaa tctgcaattg   1380
tatctctctc cttttttaaat gtaaatatca tcttgacttg ttaattattc ccttgcatttt   1440
cttttagttt actgccaaca catatattct tcaacaatat atttaattttt gaaaaacctg   1500
aaaaaaaaaa cctgttagca agtataaagg ggcagtatta ctattattgc atgaaggctt   1560
caagggaaac gttacagtct ttgggtcata gtctggcttc agcttcctct gagagtttac   1620
agaggccaat tttgagcaaa ttcatggcta aggttatgag tgagttctgc taaacagaag   1680
gctcaccaca aggtatctgg caggattata ctgggtagct ggatgttgca gaaatgtggt   1740
tagaggaagt aaactgtttt ttgatgctca cagcatgatg aatcaaactc tgtatcttag   1800
gattaggtta aaacaatacc tttggtatga tatgagtgtt gttgctgatc catgcagcat   1860
ggattggaaa gctggggtat aagcacacat gctaaagaaa aacatgtaat ttggtccata   1920
ctcacctgga tatactgttc ctcaggttaa aaaatacagt actatcctaa atcttgaagg   1980
caactctcag cctatccatt gagttacctt cagatctgcc ctctggttcc tagctgtctt   2040
gggactaact tctttcctgc gctcagctgt tttctggatt ccatgttttc cattttattg   2100
agtactaact tgttttgctg cagcacatcc tttggtagct tctagaggaa gtttgtgtag   2160
aggtaaaatt tttgagacct tgcatgtctc atgtttgatt gatactttat acgtttaggt   2220
aggaggtaat tttccttcag gactttaaaa atattgttgc tccatttttct ttgtttctat   2280
tgttgtattg agaaatccaa tgccattttg atttccccat cataaatttc atgatgatgt   2340
gtcttggtgt gggtctatat ttatccattg tattgggttt taggtgaacc cttcagata    2400
gtaactcatt tctgtcagtt ctgggaaaca cttagcattg gttgatgatt tattctctgc   2460
tgcttttgtc tcccaactat tatttggatg ttggatatcc agcactgggt atctattttc   2520
ttacctcct cccttgaccc cagtctctgt tttttagctc tttagctcaa tcttccaact    2580
ctttgctatt gtatttttaaa atcttaagac ccttcttga tttgtagaag ttcctttttct  2640
tacaaccaaa aagcctttat ctatggattt gttcacagat aaggggtatt caatatagtg   2700
tatttttttt tcatttaaaa ttgttgcgc atctatttcc tccaaatttc tttctgtatt   2760
tatttttgt tgtctatatt tcagacttttt ccaggatatc tgataatctt tggctgtctt   2820
```

```
cttatggttg aaagagggac taaaaagctt ggaaagcctt tgggttgtgg aaggggctg    2880
tctttaggat tatctgaatg ggcttttttg ggagtcccct cctccacatg aatattttgg  2940
ttttgtcaga ttccctagaa tagaggcttc caatctcctt cctggagggg tctgtccagg  3000
aaggagattg tctaggggtc tgtcagacag cagctttcag ctacttcctt gatctttttc  3060
actaatgatt atatagtcat ctaactactg tcaacaagta atagatatcc tatccttcac  3120
ttgtttagat tatttgctga gataacctct caaaagaacc tctcaaaata aaaggttaac  3180
aagagcctat atcttatatt tttcttctct ttatcttgtt agaagatagc tattaaaacc  3240
tgttcttttt ctgtcttgat aaacacactt caatcttggt agaatggtag atgggacagt  3300
atattttagg acctaaagct ctgcaaatgt atgatcagct tgtaagtaca ggtgctcaaa  3360
aacatgtaaa caatcatgct ttttactctg taggaatatc tttaaaattc ttgtgaattt  3420
ttccccagaa gtaaagcaaa tcttccccca gaaataaaat taaatgtgca taatctaaag  3480
cttttttttt ttattgtggt aggatatata tataaaacat aatttgccat tgtaaacatt  3540
ttaaatttac aagtcagagg cattaattac atcacaatgt tgtgaaatta ttactactat  3600
ttccaaaatt ttctcatcac cccaaactga aactctgtaa ctgttgagca ataacctcat  3660
tcctgtatct ctcccaaccc caggtaacct caaatctttc ttttttatctt tgagacaagg  3720
tctcattcta tcactcaggt aggagtgcag tggtgtgatc atagctcatt gcagcctcaa  3780
aatcctgggc tcaagcaatc ctccttgagt agctaagact ataggcacac attaactgcg  3840
cctggctgat tttgttttt tagagatgt ggtcttgcta tgtttcccat gctggtcttg     3900
agttcctggc ctcaagcagt ccttaagatt catccatgtt gtggcatgtg tcagaatttc  3960
atttgttttt atgactaaat aatattccat tgtatgtata tacattttgt tcatccatct  4020
tctgatgaac actgggatat gtctaccttt tggctattgt gaataatgct gcagtaaaca  4080
ttgacataac aagtatgtat ttgattgcct gttttctaagt tcttttgggt atacatcttg  4140
agtagaattg ctagataatg tcatgtttta tttctcttgt gatttcttct tcgatccct    4200
ggttgagtgt gttaatttct acatgtttat gaatttccca ctgtttttt gttattgatt   4260
tccaagttca ttccattgtg attagagaag atacttagta tgattttaat gttttgaga   4320
attggtgtt ggcctgatag atggctgtc ctggagaatg ttcctcatac acttgagcaa    4380
aatatttatc atgctattgt tgactgtagt tttctatatg tctcttaggt caaggtggtt   4440
tacaatgtgt taaggttctc ttttttttaaa aaaattttg cacagagtat cttttttctat 4500
gtgttccatg tatttgtgtc tttggagcta tagtctcttg tagacagcat atcactatct  4560
tgttttgttt tgttttttct gtccattctg ccaatttctg cctttgatt ggaaaattta   4620
atccatttgc atttaaagta attaaggaag gactttcttc taccatttaa cacttcttct  4680
atatgtcata tactttttttg gcccctcatt tcctctttat ggccttcttt tctgtttttt 4740
tgtagtgaac tagtctgatt ctcttccac tccccttttgt gtatatttgt tagatgtttt  4800
atttgtggtt gctatgggga ttatagttaa catcctacac ttaaaacaat ctaatttaaa  4860
ctgataccaa tttaccttca atagcataca aaatctctac tcctgtaaag ctctgcccct  4920
gccccctta tgttattgat ggcacaaatt gcctaataaa taatttatag ttatttgtat   4980
gagtttgtct tttaaatcat ttaggaaata aaaagtggag ttagaaaaca gtatgatagt  5040
aatactgact tttatatttg tcaatatatt tatcttaatt tggatcctta tttcattata  5100
tagatttgag ttactgtcta gtgcccttcc atttcggccc aaaggattcc cttatgcatt  5160
tcttgcaggg caagtctaat tgtaataaac tccctcagct tttgtttat ctgagaatgt   5220
cttgatttct ccccttatttt tgatggataa ttttgccaga tacatgaatt tttggtaaca 5280
gtattttct ttcagcactt taaatatgtc atcccactac cttctgactt catggtttct   5340
catgagatat tagatgttat aaaatttgag gattcctcat tcttgatgag tcagttctgt  5400
cttattgctt ttcggatttg ctcagctttt gtctttgac agtttgatta taacgcggct   5460
cagtgtgggg ctctgagttt atcccactta gagtttgttg agtttcttgg agtcatagat  5520
ttatgtcttt tatcaaattt tggacatatt tggctattat ttcttcaatt ttttttcactg 5580
cttctttctt ttccttctga aatattctta atgtatatgt tggtctgttt gatgctgtct  5640
caccagtttc ttaggctgtg ttctctttttg ttcctcagac ttgattattg cagttgccct  5700
tctttttatt tttttcaagt ttgttgattc ttctccctgt tcagatcaac tgttgaactc  5760
ctctagtgaa tttatttcag ttactgtact tttcagctcc aagatttatc tttggttcct  5820
ttttataacg tctgtgtcttt tattgatatt ctcattttgt tcatatgtct ctttcttcct 5880
ttagttcttt gtccatgttt tcctttagct ctttgggctt atttaagaca attgtttaaa  5940
gtctttgcat agtaagtcca atgtctgtgt tcttcaggg atggttttca ttattttgtt   6000
ttcaatgagc catactttcc tgtgtctttg tatgctgtct ttttgttgtt gaaaactgta  6060
tgtttgaaca tcataacgtg gtggccctga aaatcagata ttcccccctt cctgagagtt  6120
agtttttattt ttattattga agattgtagc agtctattgc tacatgtgca gtcatttcca  6180
aactattttt gcaaagactg tattccttct gtgtgtcatc actgcaagtct ctgttcctta 6240
gtttgtgttt aatagtttga catagatttc cttgaaagga gttaaaacta gcagaaaaat 6300
ctctctccca gtctttccag tcttttgtaga ttggttctgt gctgggcttt tccattaata  6360
cttagccagg cttgtactga gcctaacaat caggcccaaa agcgtagggt ctttgcagat  6420
cttgtctgag catgcttctt gctgtgtatg cacgtagttt tctaaatctc cctgtatgtg  6480
ctgttgaata ttcaatttc ccaaagaaac tcctttgcag cttttttctca cagaacatag  6540
atggtttttt ggatatcttg accatagtct ttcgacccag gtgtttgcgg ttgttagttc   6600
accttacact tttttcaagc attgcctact gcttacgatg agtgctctgt caatccttta  6660
agtagcccca gacaggctac cagagactta aacaagaatt tgtaagttct gctcagcttc  6720
ctctagaaat ggggatcagg gtccaagaca gaatgcagtt gctgatttca agactgctgc  6780
aacaccaggg agcttgtggg ggaagggcaa gcagaaatgt cacaaagctt tcttgccatt  6840
ttaaagttgc ctgttcttga ctcagcttt gcttcattgc tataaacttt ttactgtttt   6900
tcagagttct gataaaattg gctatgcctg ttcctgcttt aaaaaatata tatatttt    6960
ttagggattg gggtctcact atactgacca ggctggtctt gaacttctgg cctcaagcca  7020
tcctctcatt tcagcttccc aaaagtgctgc aattacacgc gtgaaccacc acacccagcc 7080
cctgcttgtt tttcaatgtg cctactccac catgttgctc aagtatgtat attttctaaa  7140
ctaccttgta gtgtgtgat gggaaataaa tccctgagcc ttttgaataa ctcagagaga   7200
tcaaaaactt agttttatcct attcgaagga ttagaaaaat gatatatctt tcactttttc 7260
agggataggc tcctcattag aaggctccta tgtgccgatg ctgtacaaga catttcattt  7320
ctcttaatgt ttacaacaag cttgttgcca aggctgatct tgaactcctg gcctcaaacg  7380
atcctcccag ctcagtctca caaagtgttg ggatgtctgg ccaactaatg actatcttaa  7440
ctcttgtgtt tcaatgtttta tgccttcttt tatcttgact gattgtatga ctatgtcttc  7500
tagaacaatg ttgaacagaa atggtgagag cagacatcct tgctttaata tttcaccatt  7560
```

```
atatatgatg ttaggtatag attttttctca cagatgcctt ttatcagatt gaggaattta   7620
tattcctact ttgccgaaag gttttttgtag tatgaggggg tgctgaattt tgtcaaacac   7680
tttttcggta ataattgaga tgattggttc tgcagtcatc gagatgtgga ttttctcctt   7740
tattctgttc gtgagtgatt acactggttg actaatgtta aaacaacctt actttccagg   7800
aataaaccct attatctttt ttataca                                        7827

SEQ ID NO: 16          moltype = DNA   length = 1821
FEATURE                Location/Qualifiers
source                 1..1821
                       mol_type = other DNA
                       organism = Homo sapiens
SEQUENCE: 16
tgcgggtacg gacagcgcat gagcttatgt tgagggcgga gcccagacca gcccttcgtc    60
ctatcctgcc cttccagcac ctctcagccg taacttaaac tacacttccc agaagcctcc   120
tcagccaggg acttccgttg tcgtcagcgg aagcggtgac agatcatccc aggccacaca   180
gaggccggct tggtcactat ggaggagata ggcatcttgg tggagaaggc tcaggatgag   240
atcccagcac tgtccgtgtc ccggcccag accggcctgt ccttcctggg ccctgagcct    300
gaggacctgg aggacctgta cagccgctac aaggaggagg tgaagcgaat ccaaagcatc   360
ccgctggtca tcggacaatt tctgaggct gtggatcaga atacagccat cgtgggctct    420
accacaggct ccaactatta tgtgcgcatc ctgagcacca tcgatcggga gctgctcaag   480
cccaacgcct cagtggccct ccacaagcac agcaatgcac tggtggacgt gctgcccccc   540
gaagccgaca gcagcatcat gatgctcacc tcagaccaga agcagatgt gatgtacgcg    600
gacatcggag gcatggacat ccagaagcag gaggtgcggg aggccgtgga gctcccgctc   660
acgcatttcg agctctacaa gcagatcggc atcgatcccc ccgaggcgt cctcatgtat    720
ggcccacctg gctgtgggaa gaccatgttg gcaaaggcgg tggcacatca cacaacagct   780
gcattcatcc gggtcgtggg ctcggagttt gtacagaagt atctgggtga gggccccgc    840
atggtccggg atgtgttccg cctgccaag gagaatgcac ctgccatcat cttcatagac    900
gagattgatg ccatcgccac caagagattc gatgctcaga caggggccga cagggaggtt   960
cagaggatcc tgctggagct gctgaatcag atggatggat ttgatcagaa tgtcaatgtc  1020
aaggtaatca tggccacaaa cagagcagac accctgactc cggccctgct acggccagga  1080
cggctggacc gtaaaattga atttccactt cctgaccgcc gccagaagag attgattttc  1140
tccactatca ctagcaagat gaacctctct gaggaggttg acttggaaga ctatgtggcc  1200
cggcagata agatttcagg agctgatatt aactccatct gtcaggagag tggaatgttg  1260
gctgtccgtg aaaaccgcta cattgtcctg gccaaggact tcgagaaagc atacaagact  1320
gtcatcaaga aggacgagca ggagcatgag ttttacaagt gaccctttcc ttccctccac  1380
cacaccactc aggggctggg gcttctctcg caccccagc acctctgtcc caaaacctca   1440
ttcccttttt tcttttaccca ggattggttt cttcaataaa tagataagat cgaatccatt  1500
taattcttc ttagaagttt aactcctttg gagaatgtgg gccttgaata ggatcctctg   1560
ggtccctctt aatctgcagg atgagcagac gaggtgcatg gcctgggttg cagcttgaga  1620
gaaccaaaat attcaaacca gatgacttcc aaaatgtggg gaaagggatg gaaatgaac   1680
ctgagatgga gtccttaatc acgggataaa gccctgtgca tctccctcat ttcctacagg  1740
taaaagacag taaagaaatt caggtcacag gccttgggag ttcataggaa ggagatgtcc  1800
agtgctgtcc agtagaactt t                                            1821

SEQ ID NO: 17          moltype = DNA   length = 5159
FEATURE                Location/Qualifiers
source                 1..5159
                       mol_type = other DNA
                       organism = Homo sapiens
SEQUENCE: 17
ggtcccggaa gtgcgccagt cgtaccttcg cggccgcaac tcgctcggcc gccgccatct    60
tgcgagctcg tcgtactgac cgagcgggga ggctgtcttg aggcggcacc gctcaccgac   120
accgaggcgg actggcagcc ctgagcgtcg cagtcatgcc ggccggaccc gtgcaggcgg   180
tgcccccgcc gccgccccgtg cccacggagc ccaaacagcc cacagaagaa gaagcatctt   240
caaaggagga ttctgcacct tctaagccag ttgtgggagt tatttaccct cctccagagg   300
tcagaaatat tgttgacaag actgccagct ttgtggccaa aaacgggcct gaatttgaag   360
ctaggatccg acagaacgag atcaacaacc ccaagttcaa ctttctgaac cccaatgacc   420
cttaccatgc ctactaccgc cacaaggtca gcgagttcaa ggaagggaag gctcaggagc   480
cgtccgccgc catcccaaag gtcatgcagc agcagcagca gaccacccag cagcagctgc   540
cccagaaggt ccaagcccaa gtaatccaag agaccatcgt gcccaaagag cctcctcctg   600
agtttgagtt cattgctgat cctccctcta tctcagcctt cgacttggat gtggtgaagc   660
tgacggctca gtttgtggcc aggaatgggc gccagtttct gacccagctg atgcagaaag   720
agcagcgcaa ctaccagtttt gacttttctcc gcccacagca cagcctcttc aactacttca   780
cgaagctagt ggaacagtac caaagatct tgattccaca caaaggtttta ttttcaaagc   840
tcaagaaaga ggctgaaaac ccccgagaag ttttggatca ggtgtgttac cgagtggaat   900
gggcaaatt ccaggaacgt gagaggaaga aggaagaaga ggagaaggag aaggagcggg   960
tggcctatgc tcagatcgac tggcatgatt ttgtggtggt ggaaacagtg gacttccaac  1020
ccaatgagca agggaacttc cctccccccca ccacgccaga ggagctgggg gcccgaatcc  1080
tcattcagga gcgctatgaa aagtttgggg agagtggaga agttgagatg gaggtcgagt  1140
ctgatgagga ggatgacaaa caggagaagg cggaggagcc tccttcccag ctggaccagg  1200
acacccaagt acaagatatg gatgagggtt cagatgatga agaagaagggg cagaaagtgc  1260
ccccacccca agagacaccc atgcctccac ctctgccccc aactccagac caagtcattg   1320
tccgcaagga ttatgatccc aaagccttcca agccctttgcc tccagccct gctccagatg  1380
agtatcttgt gtcccccatt actggggaga gatcccgcc cagcaaaatg caggaacaca   1440
tgcgcattgg acttcttgac cctcgctggc tggagcagcg ggatcgctcc atccgtgaga   1500
agcagagcga tgatgaggtg tacgcaccag tctctggatat tgagcagcc ttgaagcagt   1560
tggctgagcg gcgtactgac atcttcggtc tagaggaaac agcatggtt aagaagatcg  1620
gtgaggagga gatccagaag ccagaggaaa aggtgacctg gatgccgac tcaggcagca   1680
tggcccggac ccagcaggct gcccaggcca acatcacct ccaggagcag attgaggcca    1740
```

```
ttcacaaggc caaaggcctg gtgccagagg atgacactaa agagaagatt ggccccagca    1800
agcccaatga aatccctcaa cagccaccgc caccatcttc agccaccaac atccccagct    1860
cggctccacc catcacttca gtgccccgac cacccacaat gccacctcca gttcgtacta    1920
cagttgtctc cgcagtaccc gtcatgcccc ggccccccaat ggcatctgtg gtccggctgc    1980
ccccaggctc agtgatcgcc cccatgccgc ccatcatcca cgcgcccaga atcaacgtgg    2040
tgcccatgcc tccctcggcc cctcctatta tggcccccccg cccaccccccc atgattgtgc    2100
caacagcctt tgtgcctgct ccacctgtgg cacctgtccc agctccagcc ccaatgcccc    2160
ctgtgcatcc cccacctccc atggaagatg agcccacctc caaaaaactg aagacagagg    2220
acagcctcat gccagaggag gagttcctgc gcagaaacaa gggtccagtg tccatcaaag    2280
tccaggtgcc caacatgcag gataagacgg aatggaaact gaatgggcag gtgctggtct    2340
tcaccctccc actcacggac caggtctctg tcattaaggt gaagattcat gaagccacag    2400
gcatgcctgc agggaaacag aagctacagt atgagggtat cttcatcaaa gattccaact    2460
cactggctta ctacaaacat gccaatggcg cagtcatcca cctggccctc aaggagagag    2520
gcgggaggaa gaagtagaca agaggaacct gctgtcaagt ccctgccatt ttgcctctcc    2580
tgtctcccac cccctgcccc agacccagga gcccccctga ggctttgcct tgcctgcata    2640
tttgtttcgc tcttactcag tttgggaatt caaattgtcc tgcagaggtt cattcccctg    2700
acccttttccc cacattggta agagtagctg ggttttctaa gccactctct ggaatctctt    2760
tgtgttaggg tctcgatttg aggacattca ttctttcagc agcccattag caactgagag    2820
cccagggatg tcctacagga tagtttcata gtgacaggtg gcacttggct aatagaaat    2880
ggctgatatt gtcattaatc attttgtacc ttgacatggg ttgtctaata aaactcggac    2940
ccttcttgtg aaatcagtta aataagactt gtctcggtca cctgtgccct gtccagactc    3000
gaggcagtgg taacactgca cagtgctatg tggcttctct ttgaggattt ttgggttttg    3060
taactaaatt cttgctgccc tcatactttt tatgttattga aatcatattc gtattgcct    3120
tttaaaacat tgggatcctc caaggcctgc cccatgtat ttaacagtaa tacaggaagc    3180
atggcaggca ccatgcaaac caaggatgga tggtgcagtc cctgtgtcag tgggcggtgg    3240
tttcctgctg gcctggaatc actcatcacc tgattgattg gctctgtggt cctgggcagg    3300
tgcctcatag gtgtgtggat atgatgacgt ttcttttaaa tgtatgtatt taacaaatac    3360
ttaattgtat taaggtcatg taccaaggat ttgataaagt ttaaataatt tactctctac    3420
ttttatccat tttatccatt ttaactcatg taatcctcat gtgagtattc ctgtttaaca    3480
cttgagtaaa ctgaggcaca gagaacataa gttgcatgcc atagtcacac actgtgaaag    3540
tgaaaagaga atgtgtgcaa aacacgtcac agtcctggtt tctgagtaaa ggcaggctgt    3600
tatctttaga atcaagctat cacagggaga taggcaatgc tgtgggtgtt ggaggaaggt    3660
gagagcctgt tgctaacaat ttcctggttt taaagctaag gctgatttta ttgggaagat    3720
ctcacatgtg tgtggcccct gagagttccc agtgccttt atttgcagtc cttccatttg    3780
gacctcctag ctgccccatc aggtcatctc cagggctcag aggggtgaga ccatttccca    3840
aggtcacaga accagctctc tagtcaccac cctgcctctc cctctcaccc agagtcagta    3900
ccagttttat ggctttatta caaactgctg ggtccctccc attttcaact tgattgatgg    3960
gatgtcatcc cttatcctgt ctgacatttg cctctggcct ggttgctaga agtttgcccc    4020
aggggcaaga gttgaaattt ggcttcctga ggtgggcttt gtggtttgcg tccctaaagt    4080
gagcccacta ctggttgctt gtccatggcc aacaccagaa atcccctgag cactacctgg    4140
gtctcattcc aagaaggaag agggtcagga gacctgggga gtctcatatt ccaagttctt    4200
cttttctttct gggagcagtg ggcagttcat ggtgttaggg cactcacccc cacagactgg    4260
caaacccctgc aggacttccg tggctgaggc tgtgaccgga ggccaggaat gccgttggt    4320
ggattgtgag tgaatgggcc cttttgagctg ccctctagag agcaaatcca gtttcctgga    4380
gctcctgaat gaatatctgt actggctcgc tcagatgcag aagctccatt gaccatgagg    4440
ccttgtgaac atcagtggcc acaggcccag tgtgctgctt ggcactgcac tagtttagga    4500
cctgcagcat gtaggtagcg tcctagtgtt tataatacaa agctgctctg cacagctttt    4560
ctgattcttc ttgcaatctc ctgaggatta tctgccccat ttttaaaacg aggtggaata    4620
cccaaggtca tgtagccagt gagtgctctg gaaagccaaa gcagctcatc ccttcctggg    4680
gaccacactg ctctgctcca ccagaccaca ctatgaaata ggaataagtg ctcctgttgc    4740
aggactgctg ggaaaacagg tggtgtggga cttaagtcac cataattttg aagactttgca    4800
tgcagagggc tccaggaatt gtagacatta aggaatttca ctttcagttc tacccactac    4860
ttaagtactt gtcatgtact cttagaggag gccagtaatg atcagaacca ttttacttta    4920
aaattaataa tattgtatta gagaatatat taaatggtta tattgggtta tgttaggata    4980
tatacttgaa tggaaataca tgtactatta gcaatcatat ttcatttatc cctgtaatta    5040
gacaagaaag cataatatag ctctactcat gggtacacat accagtgtat aagattttta    5100
gaagtttact ttttaaaaat aaaagcaaaa tgtaagatct taaaaaaaaa aaaaaaaaa    5159
```

SEQ ID NO: 18          moltype = DNA    length = 5416  
FEATURE                Location/Qualifiers  
source                 1..5416  
                       mol_type = other DNA  
                       organism = Homo sapiens  
SEQUENCE: 18

```
agtgggccgc catgttgtcg gagtgaaagg taaggggggag cgagagcgcc agagagaaa     60
gatcggggg ctgaaatcca tcttcatcct accgctccgc ccgtgttggt ggaatgagcg    120
ttgcatgtgt cttgaagaga aaagcagtgc tttggcagga ctctttcagc ccccacctga    180
aacatcaccc tcaagaacca gctaatccca acatgcctgt tgttttgaca tctgaaacag    240
ggtcgcaagc gcagccacaa ccagctgcaa atcaggctct tgcagctgag actcactcca    300
gccctgtccc aggatctata ggagttgcag gccgttccca ggacgacgct atggtggact    360
acttctttca gaggcagcat ggtgagcagc ttgggggagg aggaagtgga ggaggcggct    420
ataataatag caaacatcga tggcctactg gggataacat tcatgcagaa catcaggtgc    480
gttccatgga tgaactgaat catgattttc aagcacttgc tctggaggga agagcgatgg    540
gagagcagct cttgccaggt aaaaagttttt gggaaacaga tgaatccagc aaagatggac    600
caaaaggaat attcctgggt gatcaatggc gagacagttg ctggggaaca tcagatcatt    660
cagtttccca gccaatcatg gtgcagagaa gacctggtca gagttccat gtgaacagtg    720
aggtcaattc tgtactgtcc ccacgatcgg agagtggggg actaggcgtt agcatggtgg    780
agtatgtgtt gagctcatcc ccgggcgatt cctgtctaag aaaaggagga tttggcccaa    840
gggatgcaga cagtgatgaa aacgacaaag gtgaaaagaa gaacaagggt acgtttgatg    900
```

```
gagataagct aggagatttg aaggaggagg gtgatgtgat ggacaagacc aatggtttac    960
cagtgcagaa tgggattgat gcagacgtca aagattttag ccgtacccct ggtaattgcc   1020
agaactctgc taatgaagtg gatcttctgg gtccaaacca gaatggttct gagggcttag   1080
cccagctgac cagcaccaat ggtgccaagc ctgtggagga tttctccaac atggagtccc   1140
agagtgtccc cttggacccc atggaacatg tgggcatgga gcctcttcag tttgattatt   1200
caggcacgca ggtacctgtg gactcagcag cagcaactgt gggacttttt gactacaatt   1260
ctcaacaaca gctgttccaa agacctaatg cgcttgctgt ccagcagttg acagctgctc   1320
agcagcagca gtatgcactg gcagctgctc atcagccgca catcggttta gctcccgctg   1380
cgtttgtccc caatccatac atcatcagcg ctgctccccc agggacggac ccctacacag   1440
ctggattggc tgcagcagcg acactaggcc cagctgtggt ccctcaccag tattatggag   1500
ttactccctg gggagtctac cctgccagtc ttttccagca gcaagctgcc gctgccgctg   1560
cagcaactaa ttcagctaat caacagacca ccccacaggc tcagcaagga cagcagcagg   1620
ttctccgtgg aggagccagc caacgtcctt tgacccccaa aaccagcaag cagggacagc   1680
aaacggatcc ccttgtggca gctgcgcag tgaattctgc ccttgcattt ggacaaggtc    1740
tggcagcagg catgccaggt tatccggtgt tggctcctgc tgcttactat gaccaaactg   1800
gtgcccttgt agtgaatgca ggcgcgagaa atggtcttgg agctcctgtt cgacttgtag   1860
ctcctgcccc agtcatcatt agttcctcag ctgcacaagc agctgttgca gcagccgcag   1920
cttcagcaaa tggagcagct ggtggtcttg ctggaacaac aaatggacca tttcgccctt   1980
taggaacaca gcagcctcag ccccagcccc agcagcagcc caataacaac ctggcatcca   2040
gttctttcta cggcaacaac tctctgaaca gcaattcaca gagcagctcc ctcttctccc   2100
agggctctgc ccagcctgcc aacacatcct gggattcgg aagtagcagt tctctcggcg    2160
ccacctgggg atccgcctt ggaggggttg gaacagcagt tgcaaactcc aacactggca   2220
gtggctcccg ccgtgactcc ctgactggca gcagtgacct ttataagagg acatcgagca   2280
gcttgacccc cattggacac agtttttata acggccttag cttttcctcc tctcctggac   2340
ccgtgggcat gcctctccct agtcagggac caggacattc acagacacca cctccttccc   2400
tctcttcaca tggatcctct tcaagcttaa acctgggagg actcacgaat ggcagtggaa   2460
gatacatctc tgctgctcca ggcgctgaag ccaagtaccc cagtgcaagc agcgcctcca   2520
gcctcttcag cccgagcagc actcttttct cttcctctcg tttgcgatat ggaatgtctg   2580
atgtcatgcc ttctggcagg agcaggcttt tggaagattt cgaaacaac cggtacccca    2640
atttacaact gcgggagatt gctgagcata taatggaatt ttccaagac cagcatgggt    2700
ccagattcat tcagctgaaa ctggagcgtg ccacaccagc tgagcgccag cttgtcttca   2760
atgaaatcct ccaggctgcc taccaactca tggtggatgt gtttggtaat tacgtcattc   2820
agaagttctt tgaatttggc agtcttgaac agaagctggc tttggcagaa cggattcgag   2880
gccacgtcct gtcattggca ctacatgt atggctgccg tgttatccag aaagctcttg    2940
agtttattcc ttcagaccag caggtaatta atgagatggt tcgggaacta gatggccatg   3000
tcttgaagtg tgtgaaagat cagaatggca atcacgtggt tcagaaatgc attgaatgtg   3060
tacagcccca gtctttgcaa tttatcatcg atgcgtttaa gggacaggta tttgccttat   3120
ccacacatcc ttatggctgc cgagtgattc agagaatcct ggagcactgt ctccctgacc   3180
agcactccc tattttagag gagcttcacc agcacacaag gcagcttgta caggatcaat   3240
atggaaatta tgtaatccaa catgtactgg agcacggtcg tcctgaggat aaaagcaaaa   3300
ttgtagcaga aatccgaggc aatgtacttg tattgagtca gcacaaattt gcaagcaatg   3360
ttgtggagaa gtgtgttact cacgcctcac gtacggagcg cgctgtgctc atcgatgagg   3420
tgtgcaccat gaacgacgt ccccacagtg ccttatacac catgatgaag gaccagtatg    3480
ccaactacgt ggtccagaag atgattgacg tggcggagcc aggccagcgg aagatcgtca   3540
tgcataagat ccggccccac atcgcaactc ttcgtaagta cacctatggc aagcacattc   3600
tggccaagct ggagaagtac tacatgaaga acggtgttga cttagggccc atctgtggcc   3660
cccctaatgg tatcatctga ggcagtgtca cccgctgttc cctcattccc gctgacctca   3720
ctggcccact ggcaaatcca accagcaacc agaaatgttc tagtgtagag tctgagacgg   3780
gcaagtggtt gctccaggat tactccctcc tccaaaaaag gaatcaaatc cacgagtgga   3840
aaagcctttg taaatttaat tttattacac ataacatgta ctatttttt taattgacta    3900
attgcctgc tgttttactg gtgtataga tacttgtaca taggtaacca atgtacatgg    3960
gaggccacat atttttgttca ctgttgtatc tatatttcac atgtggaaac tttcagggtg   4020
gttggtttaa caaaaaaaaa aagctttaaa aaaaaagaa aaaaaggaaa aggttttag     4080
ctcatttgcc tggccggcaa gttttgcaaa tagctcttcc ccacctcctc attttagtaa   4140
aaaacaaaca aaacaaaaa aacctgagaa gtttgaattg tagttaaatg accccaaact    4200
ggcatttaac actgtttata aaaatatat atatatatat atatatatat aatgaaaaag    4260
gtttcagagt tgctaaagct tcagttttgtg acattaagtt tatgaaattc taaaaaatgc   4320
cttttttgga gactatatta tgctgaagaa ggctgttcgt gaggaggaga tgcgagcacc   4380
cagaacgtct tttgaggctg gcgggtgtg attgtttact gcctactgga ttttttttcta   4440
ttaacattga aaggtaaaat ctgattattt agcatgaagaa aaaaaaatcc aactctgctt   4500
ttggtcttgc ttctataaat atatagtgta tacttggtgt agactttgca tatatacaaa   4560
tttgtagtat tttcttgttt tgatgtctaa tctgtatcta taatgtaccc tagtagtcga   4620
acatactttt gattgtacaa ttgtacatt gtatacctgt aatgtaaatg tggagaagtt    4680
tgaatcaaca taaacacgtt tttggtaag aaaagagaat tagccagccc tgtgcattca    4740
gtgtatattc tcaccttta tggtcgtagc atatagtgt gtatattgta aattgtaatt    4800
tcaaccagaa gtaaattttt tcttttgaa ggataaaatg ttcttatac agcctagtta    4860
atgtttaaaa agaaaaaaat agcttggttt tatttgtcat ctagtctcaa gtatagcgag   4920
attcttttcta aatgttattc aagattgagt tctcactagt gttttttttaa tcctaaaaaa   4980
gtaatgtttt gattttgtga cagtcaaaag gacgtgcaaa agtctagcct tgcccgagct   5040
ttccttacaa tcagagccc tctcaccttg taaagtgtga atcgccttc cctttttgtac    5100
agaagatgaa ctgtattttg cattttgtct acttgtaagt gaatgtaaca tactgtcaat   5160
tttccttgtt tgaatataga attgtaacac tacacggtgt acatttccag agccttgtgt   5220
atatttccaa tgaactttt tgcaagcaca cttgtaacca tatgtgtata attaacaaac    5280
ctgtgatgc ttatgcctgg gcaactattt tttgtaactc ttgtgtagat tgtctctaaa    5340
caatgtgtga tctttatttt gaaaaataca gaactttgga atctgaaaaa aaaaaaaaaa   5400
aaaaaaaaaa aaaaaa                                                   5416

SEQ ID NO: 19         moltype = DNA  length = 1940
FEATURE               Location/Qualifiers
```

```
source                  1..1940
                        mol_type = other DNA
                        organism = Homo sapiens
SEQUENCE: 19
gagtgagcgg cgcggggcca atcagcgtgc gccgttccga aagttgcctt ttatggctcg    60
agcggccgcg gcggcgccct ataaaaccca gcggcgcgac gcgccaccac cgccagacc    120
gcgtccgccc cgcgagcaca gagcctcgcc tttgccgatc cgccgcccgt ccacacccgc   180
cgccagctca ccatggatga tgatatcgcc gcgctcgtcg tcgacaacgg ctccggcatg   240
tgcaaggccg gcttcgcggg cgacgatgcc ccccggggcg tcttcccctc catcgtgggg   300
cgccccaggc accagggcgt gatggtgggc atggtgcaga aggattccta tgtgggcgac   360
gaggcccaga gcaagagagg catcctcacc ctgaagtacc ccatcgagca cggcatcgtc   420
accaactggg acgacatgga gaaaatctgg caccacacct tctacaatga gctgcgtgtg   480
gctcccgagg agcaccccgt gctgctgacc gaggcccccc tgaacccaa ggccaaccgc    540
gagaagatga cccagatcat gttttgagacc ttcaacaccc cagccatgta cgttgctatc   600
caggctgtgc tatccctgta cgcctctggc cgtaccactg gcatcgtgat ggactccggt   660
gacggggtca cccacactgt gcccatctac gagggggtatg ccctccccca tgccatcctg   720
cgtctggacc tggctggccg ggacctgact gactacctca tgaagatcct caccgagcgc   780
ggctacagct tcaccaccac ggccgagcgg gaaatcgtgc gtgacattaa ggagaagctg   840
tgctacgtcg ccctggactt cgagcaagag atgccacgg ctgcttccag ctcctccctg    900
gagaagagct acgagctgcc tgacggccag gtcatcacca ttggcaatga gcggttccgc   960
tgccctgagg cactcttcca gccttccttc ctgggcatgg agtcctgtgg catccacgaa  1020
actaccttca actccatcat gaagtgtgac gtggacatcc gcaaagacct gtacgccaac  1080
acagtgctgt ctggcggcac caccatgtac cctggcattg ccgacaggat gcagaaggag  1140
atcactgccc tggcacccag cacaatgaag atcaagatca ttgctcctcc tgagcgcaag  1200
tactccgtgt ggatcggcgg ctccatcctg gcctcgctgt ccaccttcca gcagatgtgg  1260
atcagcaagc aggagtatga cgagtccggc ccctccatcg tccaccgcaa atgcttctag  1320
gcggactatg acttagttgc gttacaccct tccttgacaa aacctaactt gcgcagaaaa  1380
caagatgaga ttggcatggc tttatttgtt ttttttgttt tgttttggtt ttttttttt   1440
ttttggcttg actcaggatt taaaaactgg aacggtgaag gtgacagcag tcggttggag  1500
cgagcatccc ccaaagttca caatgtggcc gaggacttg attgcacatt gttgttttt    1560
taatagtcat tccaaatatg agatgcgttg ttacaggaag tcccttgcca tcctaaaagc  1620
cacccccactt ctctctaagg agaatggccc agtcctctcc caagtccaca caggggaggt  1680
gatagccattg ctttcgtgta aattatgtaa tgcaaaattt ttttaatctt cgccttaata  1740
ctttttattt ttgttttatt tgaatgatg agccttcgtg ccccccttc cccttttt     1800
gtccccccaac ttgagactgta tgaaggcttt tggtctccct gggagtgggt ggaggcagcc  1860
agggcttacc tgtacactga cttgagacca gttgaataaa agtgcacacc ttaaaaatga  1920
ggaaaaaaaa aaaaaaaaaa                                             1940

SEQ ID NO: 20           moltype = DNA  length = 1309
FEATURE                 Location/Qualifiers
source                  1..1309
                        mol_type = other DNA
                        organism = Homo sapiens
SEQUENCE: 20
gctctctgct cctcctgttc gacagtcagc cgcatcttct tttgcgtcgc cagccgagcc    60
acatcgctca gacaccatgg ggaaggtgaa ggtcggagtc aacggatttg gtcgtattgg   120
gcgcctggtc accagggctg cttttaactc tggtaaagtg gatattgttg ccatcaatga   180
ccccttcatt gacctcaact acatggttta catgttccaa tatgattcca cccatggcaa   240
attccatggc accgtcaagg ctgagaacgg gaagcttgtc atcaatggaa atcccatcac   300
catcttccag gagcgagatc cctccaaaat caagtggggc gatgctggcg ctgagtacgt   360
cgtggagtcc actggcgtct tcaccaccat ggagaaggct ggggctcatt tgcagggggc   420
agccaaaagg gtcatcatct ctgcccctc tgctgatgcc cccatgttcg tcatgggtgt    480
gaaccatgag aagtatgaca cagcctcaa gatcatcagc aatgcctcct gcaccaccaa   540
ctgcttagca cccctggcca aggtcatcca tgacaacttt ggtatcgtgg aaggactcat   600
gaccacagtc catgccatca ctgccaccca gaagactgtg gatggccct ccgggaaact    660
gtggcgtgat ggccgcgggg ctctccagaa catcatccct gcctctactg gcgctgccaa   720
ggctgtgggc aagtcatcc tgagctgaa cgggaagctc actggcatgg ccttccgtgt    780
ccccactgcc aacgtgtcag tggtggacct gacctgccgt ctagaaaaac tgccaaaata   840
tgatgacatc aagaaggtgg tgaagcaggc gtcggagggc cccctcaagg gcatcctggg   900
ctacactgag caccaggtgg tctcctctga cttcaacagc gacacccact cctccaccctt   960
tgacgctggg gctggcattg ccctcaacga ccactttgtc aagctcattt cctggtatga  1020
caacgaattt ggctacagca acaggggtgt ggacctcatg gcccacatgg cctccaagga  1080
gtaagacccc tggaccacca gccccagcaa gagcacaaga ggaagagaga ccctcact    1140
gctggggagt ccctgccaca ctcagtcccc caccacactg aattcccct cctcacagtt   1200
gccatgtaga ccccttgaag aggggagggg cctagggagc cgcaccttgt catgtaccat  1260
caataaagta ccctgtgctc aaccagttaa aaaaaaaaaa aaaaaaaa              1309

SEQ ID NO: 21           moltype = DNA  length = 2321
FEATURE                 Location/Qualifiers
source                  1..2321
                        mol_type = other DNA
                        organism = Homo sapiens
SEQUENCE: 21
gtcctcaacc aagatggcgc ggatggcttc aggcgcatca cgacaccggc gcgtcacgcg    60
acccgcccta cggcaccctc ccgcgcttt cttagcgccg cagacggtgg ccgagcgggg   120
gaccgggaag catggcccgg gggtcggcgg ttgcctgggc ggcgctcggg ccgttgttgt   180
ggggctgcgc gctgggctg cagggcggga tgctgtaccc ccaggagagc ccgtcgcggg   240
agtgcaagga gctggacggc ctctggagct tccgcgcgca cttctctgac aaccgacgcc   300
ggggcttcga ggagcagtgg taccggcggc cgctgtggga gtcaggcccc accgtggaca  360
```

```
tgccagttcc ctccagcttc aatgacatca gccaggactg gcgtctgcgg cattttgtcg    420
gctgggtgtg gtacgaacgg gaggtgatcc tgccggagcg atggacccag gacctgcgca    480
caagagtggt gctgaggatt ggcagtgccc attcctatgc catcgtgtgg gtgaatgggg    540
tcgacacgct agagcatgag gggggctacc tcccctcga ggccgacatc agcaacctgg     600
tccaggtggg gcccctgccc tcccggctcc gaatcactat cgccatcaac aacacactca    660
cccccaccac cctgccacca gggaccatcc aatacctgac tgacacctcc aagtatccca    720
agggttactt tgtccagaac acatattttg acttttcaa ctacgctgga ctgcagcggt     780
ctgtacttct gtacacgaca cccaccacct acatcgatga catcaccgtc accaccagcg    840
tggagcaaga cagtgggctg gtgaattacc agatctctgt cagggcagt aacctgttca     900
agttggaagt gcgtcttttg gatgcagaaa acaaagtcgt ggcgaatggg actgggaccc    960
agggccaact taaggtgcca ggtgtcagcc tctggtggcc gtacctgatg cacgaacgcc   1020
ctgcctatct gtattcattg gaggtgcagc tgactgcaca gacgtcactg gggcctgtgt   1080
ctgacttcta cacactccct gtggggatcc gcactgtggc tgtcaccaag agccagttcc   1140
tcatcaatgg gaaacctttc tatttccacg gtgtcaacaa gcatgaggat gcggacatcc   1200
gagggaaggg cttcgactgg ccgctgctgg tgaaggactt caacctgctt cgctggcttg   1260
gtgccaacgc tttccgtacc agccactacc cctatgcaga ggaagtgatg cagatgtgtg   1320
accgctatgc gattgtggtc atcgatgagt gtcccggcgt gggcctggcg ctgccgcagt   1380
tcttcaacaa cgtttctctg catcaccaca tgcaggtgat gaagaagtg gtgcgtaggg    1440
acaagaacca ccccgcgtc gtgatgtggt ctgtggccaa cgagcctgcg tcccacctag     1500
aatctgctgg ctactacttg aagatggtga tcgctcacac caaatccttg gacccctccc   1560
ggcctgtgac ctttgtgagc aactctaact atgcagcaga caaggggct ccgtatgtgg    1620
atgtgatctg tttgaacagc tactactctt ggtatcacca ctacgggcac ctggagttga   1680
ttcagctgca gctggccacc cagtttgaga actggtataa gaagtatcag aagcccatta   1740
ttcagagcga gtatggagca gaaacgattg cagggtttca ccaggatcca cctctgatgt   1800
tcactgaaga gtaccagaaa agtctgctag agcagtacca tctgggtctg gatcaaaaac   1860
gcagaaaata cgtggttgga gagctcattt ggaattttgc cgatttcatg actgaacagt   1920
caccgacgag agtgctgggg aataaaaagg ggatcttcac tcggcagaga caaccaaaaa   1980
gtgcagcgtt cctttgcga gagagatact ggaagattgc caatgaaacc aggtatcccc    2040
actcagtagc caagtcacaa tgtttggaaa acagcctgtt tacttgagca agactgatac   2100
cacctgcgtg tccttcctc cccgagtcag ggcgacttcc acagcagcag aacaagtgcc    2160
tcctggactg ttcacggcag accgaacgt ttctggcctg ggttttgtgg tcatctattc    2220
tagcagggaa cactaaaggt ggaaataaaa gattttctat tatggaaata aagagttggc   2280
atgaaagtgg ctactgaaaa aaaaaaaaaa aaaaaaaaa a                        2321

SEQ ID NO: 22         moltype = DNA  length = 1229
FEATURE               Location/Qualifiers
source                1..1229
                      mol_type = other DNA
                      organism = Homo sapiens
SEQUENCE: 22
gtctgacggg cgatggcgca gccaatagac aggagcgcta tccgcggttt ctgattggct     60
actttgttcg cattataaaa ggcacgcgcg ggcgcgaggc ccttctctcg ccaggcgtcc    120
tcgtggaagt gacatcgtct ttaaaccctg cgtggcaatc cctgacgcac cgccgtgatg    180
cccagggaag acagggcgac ctggaagtcc aactacttcc ttaagatcat ccaactattg    240
gatgattatc cgaaatgttt cattgtggga gcagacaatg tgggctccaa gcagatgcag    300
cagatccgca tgtcccttcg cgggaaggct gtggtgctga tgggcaagaa caccatgatg    360
cgcaaggcca tccgagggca cctggaaaaa aacccagtc gtgagaaact gctgcctcat     420
atccggggga atgtgggctt tgtgttcacc aaggaggacc tcactgagat cagggacatg    480
ttgctggcca ataaggtgcc agctgctgcc cgtgctggtg ccattgcccc atgtgaagtc    540
actgtgccaa cccagaacac tggtctcggg cccgagaaga cctccttttt ccaggcttta    600
ggtatcacca ctaaaatctc caggggcacc attgaaatct tagtgatgt gcagctgatc    660
aagactggag acaaagtggg agccagcgaa gccacgctgc tgaacatgct caacatctcc    720
cccttctcct tgggctggt catccagcag gtgttcgaca atggcagcat ctacaaccct    780
gaagtgcttg atatcacaga ggaaactctg cattctcgct tcctggaggg tgtccgcaat    840
gttgccagtg tctgtctgca gattgcctac ccaactgttg catcagtacc ccattctatc    900
atcaacgggt acaaacgagt cctggccttg tctgtggaga cggattacac cttcccactt    960
gctgaaaagg tcaaggcctt cttggctgat ccatctgcct ttgtggctgc tgcccctgtg   1020
gctgctgcca ccacagctgc tcctgctgct gctgcagccc agctaaggt tgaagccaag    1080
gaaagtcgg aggagtcgga cgaggatatg ggatttggtc tctttgacta atcaccaaaa    1140
agcaaccaac ttagccagtt ttatttgcaa aacaaggaaa taaggctta cttcttaaa     1200
aagtaaaaaa aaaaaaaaaa aaaaaaaa                                       1229

SEQ ID NO: 23         moltype = DNA  length = 5234
FEATURE               Location/Qualifiers
source                1..5234
                      mol_type = other DNA
                      organism = Homo sapiens
SEQUENCE: 23
agagcgtcgg gatatcgggt ggcggctcgg gacggaggac gcgctagtgt gagtgcgggc     60
ttctagaact acaccgaccc tcgtgtcctc ccttcatcct gcggggctgg ctggagcggc    120
cgctccggtg ctgtccagca gccataggga gccgcacggg gagcgggaaa gcggtcgcgg    180
ccccaggcgg ggcggccggg atggagcggg gccgcgagcc tgtggggaag gggctgtggc    240
ggcgcctcga gcggctgcag gttcttctgt gtggcagttc agaatgatgg atcaagctag    300
atcagcattc tctaacttgt ttggtggaga accattgtca tatacccggt tcagcctggc    360
tcggcaagta gatggcgata acagtcatgt ggagatgaaa cttgctgtag atgaagaaga    420
aaatgctgac aataacacaa aggccaatgt cacaaaacca aaaaggtgta gtggaagtat    480
ctgctatggg actattgctg tgatcgtctt tttcttgatt ggatttatga ttggctactt    540
gggctattgt aaaggggtag aaccaaaaac tgagtgtgag agactggcag gaaccgagtc    600
tccagtgagg gaggagccag gagaggactt ccctgcagca cgtcgcttat attgggatga    660
```

```
cctgaagaga aagttgtcgg agaaactgga cagcacagac ttcaccggca ccatcaagct    720
gctgaatgaa aattcatatg tccctcgtga ggctggatct caaaaagatg aaaatcttgc    780
gttgtatgtt gaaaatcaat ttcgtgaatt taaactcagc aaagtctggc gtgatcaaca    840
ttttgttaag attcaggtca aagacagcgc tcaaaactcg gtgatcatag ttgataagaa    900
cggtagactt gtttacctgg tggagaatcc tgggggttat gtggcgtata gtaaggctgc    960
aacagttact ggtaaactgg tccatgctaa ttttggtact aaaaaagatt ttgaggattt   1020
atacactcct gtgaatggat ctatagtgat tgtcagagca gggaaaatca cctttgcaga   1080
aaaggttgca aatgctgaaa gcttaaatgc aattggtgtg ttgatataca tggaccagac   1140
taaatttccc attgttaacg cagaactttc attctttgga catgctcatc tggggacagg   1200
tgacccttac acacctggat tcccttcctt caatcacact cagtttccac catctcggtc   1260
atcaggattg cctaatatac ctgtccagac aatccagac gctgctgcag aaaagctgtt   1320
tgggaatatg aaggagact gtccctctga ctggaaaaca gactctacat gtaggatggt   1380
aacctcagaa agcaagaatg tgaagctcac tgtgagcaac gtgctgaaag agataaaaat   1440
tcttaacatc tttggagtta ttaaaggctt tgtagaacca gatcactatg ttgtagttgg   1500
ggcccagaga gatgcatggg gccctggagc tgcaaaatcc ggtgtaggca cagctctcct   1560
attgaaactt gcccagatgt tctcagatat ggtcttaaaa gatgggtttc agcccagcag   1620
aagcattatc tttgccagtt ggagtgctgg agactttgga tcggttggtg ccactgaatg   1680
gctagaggga tacctttcgt ccctgcattt aaaggctttc acttatatta atctggataa   1740
agcggttctt ggtaccagca acttcaaggt ttctgccagc ccactgttgt atacgcttat   1800
tgagaaaaca atgcaaaatg tgaagcatcc ggttactggg caatttctat atcaggacag   1860
caactgggcc agcaaagttg agaaactcac tttagacaat gctgctttcc cttttccttg   1920
atattctgga atcccagcag ttttctttctg tttttgcgag gacacagatt atccttattt   1980
gggtaccacc atggacacct ataaggaact gattgagagg attcctgagt tgaacaaagt   2040
ggcacgagca gctgcagagg tcgctggtca gttcgtgatt aaactaaccc atgatgttga   2100
attgaacctg gactatgaga ggtacaacag ccaactgctt tcatttgtga gggatctgaa   2160
ccaatacaga gcagactaa aggaaatggg cctgagttta cagtggctgt attctgctcg   2220
tggagacttc ttccgtgcta cttccagact aacaacagat ttcgggaatg ctgagaaaac   2280
agacagattt gtcatgaaga aactcaatga tcgtgtcatg agagtggagt atcacttcct   2340
ctctccctac gtatctccaa aagagtctcc tttccgacat gtcttctggg gctccggctc   2400
tcacacgctg ccagctttac tggagaactt gaaactgcgt aaacaaaata acggtgctta   2460
taatgaaacg ctgttcagaa accagttggc tctagtact tggactattc agggagctgc   2520
aaatgccctc tctggtgacg tttgggacat tgacaatgag ttttaaatgt gatcccata   2580
gcttccatga aacagcagg gtagtctggt ttctagactt gtgctgatcg tgctaaattt   2640
tcagtagggc tacaaaacct gatgttaaaa ttccatccca tcatcttggt actactagat   2700
gtcttaggc agcagctttt aatacagggt agataacctg tacttcaagt taaagtgaat   2760
aaccacttaa aaaatgtcca tgatggaata ttccccatc tctagaattt taagtgcttt   2820
gtaatgggaa ctgcctcttt cctgttgttg ttaatgaaaa tgtcagaaac cagttatgtg   2880
aatgatctct ctgaatccta agggctggtc tctgctgaag gttgtaagtg gtcgcttact   2940
ttgagtgatc ctccaacttc atttgatgct aaatatggaa taccaggttg aaagaccttc   3000
tccaaatgag atctaagcct ttccataagg aatgtagctg gtttcctcat tcctgaaaga   3060
aacagttaac tttcagaaga gatgggcttg ttttctgtgcc aatgaggtct gaaatggagg   3120
tccttctgct ggataaaatg aggttcaact gttgattgca ggaataaggc cttaatatgt   3180
taacctcagt gtcatttatg aaaagagggg accagaagcc aaagacttag tatattttct   3240
tttcctctgt ccttccccc ataagcctcc atttagttct ttgttatttt tgtttcttcc   3300
aaagcacatt gaaagagaac cagtttcagg tgtttagttg cagactcagt ttgtcagact   3360
ttaaagaata atatgctgcc aaattttggc caaagtgtta atcttagggg agagcttct   3420
gtccttttgg cactgagata tttattgttt atttatcagt gacagagttc actataaatg   3480
gtgtttttttt aatagaatat aattatcgga agcagtgcct tccataatta tgacagttat   3540
actgtcggtt tttttttaaat aaaagcagca tctgctaata aaaccaaaca gatactggaa   3600
gttttgcatt tatggtcaac acttaagggt tttagaaaac agccgtcagc caaatgtaat   3660
tgaataaagt tgaagctaag atttagagat gaattaaatt taattagggg ttgctaagaa   3720
gcgagcactg accagataag aatgctggtt ttcctaaatg cagtgaattg tgaccaagtt   3780
ataaatcaat gtcacttaaa ggctgtggta gtactcctgc aaaattttat agctcagttt   3840
atccaaggtc taactctaat tcccattttg caaaatttcc agtacctttg tcacaatcct   3900
aacacattat cgggagcagt gtcttccata atgtataaaa aacaaggtag tttttaccta   3960
ccacagtgtc tgtatcggag acagtgatct ccatatgtta cactaagggt gtaagtaatt   4020
atcgggaaca gtgtttccca taattttctt catgcaatga catcttcaaa gcttgaagat   4080
cgttagtatc taacatgtat cccaactcct ataattccct atctttagt tttagttgca   4140
gaaacatttt gtggtcatta agcattgggt gggtaaattc aaccactgta aaatgaaatt   4200
actacaaaat ttgaaattta gcttggggttt ttgttaccttt tatggtttct ccaggtcctc   4260
tacttaatga gatagtagca tacatttata atgtttgcta ttgacaagtc atttttaactt   4320
tatcacatta tttgcatgtt acctcctata aacttagtgc ggacaagttt taatccagaa   4380
ttgacctttt gacttaaagc agagggactt tgtatagaag gtttggggc tgtggggaag   4440
gagagtcccc tgaaggtctg acacgtctgc ctacccattc gtggtgatca attaaatgta   4500
ggtatgaata agttcgaagc tccgtgagtg aaccatcatt ataaacgtga tgatcagctg   4560
tttgtcatag ggcagttgga aacggcctcc tagggaaag ttcatagggt ctcttcaggt   4620
tcttagtgtc acttacctag atttacagcc tcacttgaat gtgtcactac tcacagtctc   4680
tttaatcttc agttttatct ttaatctcct ctttatctt ggactacagt ttagcgtagc   4740
taagtgaaaa ggtcatagct gagattcctg gttcgggtgt tacgcacacg tacttaaatg   4800
aaagcatgtg gcatgttcat cgtataacac aatatgaata cagggcatgc attttgcagc   4860
agtgagtctc ttcagaaaac ccttttctac agttagggtt gagttacttc ctatcaagcc   4920
agtacgtgct aacaggctca atattcctga tgaaatatc agactagtga caagctcctg   4980
gtcttgagat gtcttctcgt taaggagatg ggcctttgtg aggtaaagga taaatgaat   5040
gagttcgtgc atgattcact attctagaac ttgcatgacc tttactgtgt tagctctttg   5100
aatgttcttg aaattttaga ctttctttgt aaacaaatga tatgtcctta tcattgtata   5160
aaagctgtta tgtgcaacag tgtgggagatt ccttgtctga tttaataaaa tacttaaaca   5220
ctgaaaaaaa aaaa                                                      5234

SEQ ID NO: 24      moltype = DNA   length = 1869
```

| FEATURE | Location/Qualifiers |
|---|---|
| source | 1..1869 |
| | mol_type = other DNA |
| | organism = Homo sapiens |

SEQUENCE: 24

```
tacctggttg atcctgccag tagcatatgc ttgtctcaaa gattaagcca tgcatgtcta   60
agtacgcacg gccggtacag tgaaactgcg aatggctcat taaatcagtt atggttcctt  120
tggtcgctcg ctcctctccc acttggataa ctgtggtaat tctagagcta atacatgccg  180
acgggcgctg accccttcg cggggggat gcgtgcattt atcagatcaa aaccaaccg  240
gtcagcccct ctccggcccc ggccggggg cgggcgacgg cggctttggt gactctagat  300
aacctcgggc cgatcgcacg ccccccgtgg cggcgacgac ccattcgaac gtctgccta  360
tcaactttcg atggtagtcg ccgtgcctac catggtgacc acgggtgacg gggaatcagg  420
gttcgattcc ggagagggag cctgagaaac ggctaccaca tccaaggaag gcagcaggcg  480
cgcaaaattac ccactcccga cccggggagg tagtgacgaa aaataacaat acaggactct  540
ttcgaggccc tgtaattgga atgagtccac tttaaatcct ttaacgagga tccattggag  600
ggcaagtctg gtgccagcag ccgcggtaat tccagctcca atagcgtata ttaaagttgc  660
tgcagttaaa aagctcgtag ttggatcttg ggagcgggcg ggcggtccgc cgcgaggcga  720
gccaccgccc gtccccgccc cttgcctctc ggcgccccct cgatgctctt agctgagtgt  780
cccgcgggc ccgaagcgtt tactttgaaa aaattagagt gttcaaagca ggcccgagcc  840
gcctggatac cgcagctagg aataatggaa taggaccgcg gttctatttt gttggttttc  900
ggaactgagg ccatgattaa gagggacggc cgggggcatt cgtattgcgc cgctagaggt  960
gaaattcttg gaccggcgca agacgaccca gagcgaaagc atttgccaag aatgtttca  1020
ttaatcaaga acgaaagtcg gaggttcgaa gacgatcaga taccgtcgta gttccgacca 1080
taaacgatgc cgaccggcga tgcggcgcg ttattcccat gacccgccgg gcagcttccg 1140
ggaaaccaaa gtctttgggt tccggggga gtatggttgc aaagctgaaa cttaaaggaa 1200
ttgacggaag ggcaccacca ggagtggagc ctgcggctta atttgactca acacgggaaa 1260
cctcacccgg cccggacacg gacaggattg acagattgat agctctttct cgattccgtg 1320
ggtggtggtg catggccgtt cttagttggt ggagcgattt gtctggttaa ttccgataac 1380
gaacgagact ctggcatgct aactagttac gcgacccccg agcggtcggc gtccccaac  1440
ttcttagagg gacaagtggc gttcagccac ccgagattga gcaataacag gtctgtgatg 1500
cccttagatg tccggggctg cacgcgcgct acactgactg gctcagcgtg tgcctaccct 1560
acgccggcag gcgcgggtaa cccgttgaac cccattcgtg atgggatcg gggattgcaa 1620
ttattcccca tgaacgagga attcccagta agtgcgggtc ataagcttgc gttgattaag 1680
tccctgccct ttgtacacac cgcccgtcgc tactaccgat tggatggttt agtgaggccc 1740
tcggatcggc cccgccgggg tcggcccacg gccctggcgg agcgctgaga agacggtcga 1800
acttgactat ctagaggaag taaagtcgt aacaaggttt ccgtaggtga acctgcgaa  1860
ggatcatta                                                        1869
```

| SEQ ID NO: 25 | moltype = DNA length = 2288 |
|---|---|
| FEATURE | Location/Qualifiers |
| source | 1..2288 |
| | mol_type = other DNA |
| | organism = Homo sapiens |

SEQUENCE: 25

```
ggggccgaac gtggtataaa aggggcggga ggccaggctc gtgccgtttt gcagacgcca   60
ccgccgagga aaaccgtgta ctattagcca tggtcaaccc caccgtgttc ttcgacattg  120
ccgtcgacgg cgagcccttg ggccgcgtct cctttgagct gtttgcagac aaggtcccaa  180
agacagcaga aaattttcgt gctctgagca ctggagagaa aggatttggt tataaggggt  240
cctgctttca cagaattatt ccagggttta tgtgtcaggg tggtgacttc acacgccata  300
atggcactgg tggcaagtcc atctatgggg agaaatttga agatgagaac ttcatcctaa  360
agcataccgg tcctggcatc ttgtccatgg caaatgctgg acccaacaca aatggttcaa  420
agttttttcat ctgcactgcc aagactgagt ggttggatgg caagcatgtg gtgtttggca  480
aagtgaaaga aggcatgaat attgtggagg ccatggagcg cttggggtcc aggaatggca  540
agaccagcaa gaagatcacc attgctgact gtggacaact cgaataagtt tgacttgtgt  600
tttatcttaa ccaccagatc attccttctg tagctacagga gagcacccct ccacccatt  660
tgctcgcagt atcctagaat ctttgtgctc tcgctgcagt tcccctttggg ttccatgttt  720
tccttgttcc ctcccatgcc tagctggatt gcagagttaa gttatgatt atgaaataaa  780
aactaaataa caattgtcct cgtttgagtt aagagtgttg atgtaggctt tattttaagc  840
agtaatgggt tacttctgaa acatcacttg tttgcttaat tctacacagt acttagtt   900
tttttacttt ccagtcccag gaagtgtcaa tgtttgttga gtggaatatt gaaaatgtag  960
gcagcaactg ggcatggtgg ctcactgtct gtaatgtatt acctgaggca gaagaccacc 1020
tgagggtagg agtcaagatc agcctgggca acatagtgag acgctgtctc tacaaaaaat 1080
aattagcctg gcctggtggt gcatgcctag tcctagctga tctggaggct gacgtgggag 1140
gattgcttga gcctagagtg agctattatc atgccactga acagcctggg tgttcacaga 1200
tcttgtgtct caaaggtagg cagaggcagg aaaagcaagg agccagaatt aagaggttgg 1260
gtcagtctgc agtgagttca tgcatttaga ggtgttcttc aagatgacta atgtcaaaaa 1320
ttgagacatc tgttgcggtt tttttttttt ttttttcccc tggaatgcag tggcgtgatc 1380
tcagctcact gcaccctccg cctcctgggt tcaagtgatt ctagtgcctc agcctcctga 1440
gtagctggga taatgggcgt gtgccaccat gcccagctaa tttttgtatt tttagtatag 1500
atggggtttc atcattttga ccaggctggt ctcaaactct tgacctcagc tgatgcgcct 1560
gccttggcct cccaaactgc tgagattaca gatgtgagcc accgcaccct acctcatttt 1620
ctgtaacaaa gctaagcttg aacactgttg atgttcttga gggaagcata ttgggcttta 1680
ggctgtaggt caagttttata catcttaatt atggtggaat tcctatgtag agtctaaaaa 1740
gccaggtact tggtgctaca gtcagtctcc ctgcagaggg ttaaggcgca gactacctgc 1800
agtgaggagg tactgcttgt agcatataga gcctctccct agctttggtt atggaggctt 1860
tgaggttttg caaacctgac caatttaagc cataagatct ggtcaaaggg ataccttcc  1920
cactaaggac ttggtttctc aggaaattat atgtacagtg cttgctggca gttagatgtc 1980
aggacaatct aagctgagaa aaccccttct ctgcccacct taacagacct ctagggtct  2040
taacccagca atcaagtttg cctatcctag aggtggcgga tttgatcatt tggtgtggtg 2100
```

```
ggcaatttttt gttttactgt ctggttcctt ctgcgtgaat taccaccacc accacttgtg   2160
catctcagtc ttgtgtgttg tctggttacg tattccctgg gtgataccat tcaatgtctt   2220
aatgtacttg tggctcagac ctgagtgcaa ggtggaaata aacatcaaac atcttttcat   2280
tatcccta                                                            2288
```

| SEQ ID NO: 26 | moltype = DNA length = 2439 |
|---|---|
| FEATURE | Location/Qualifiers |
| source | 1..2439 |
|  | mol_type = other DNA |
|  | organism = Homo sapiens |

SEQUENCE: 26
```
gagagcagcg gccgggaagg ggcggtgcgg gaggcggggt gtggggcggt agtgtgggcc    60
ctgttcctgc ccgcgcggtg ttccgcattc tgcaagcctc cggagcgcac gtcggcagtc   120
ggctccctcg ttgaccgaat caccgacctc tctcccagc tgtatttcca aaatgtcgct   180
ttctaacaag ctgacgctgg acaagctgga cgttaaaggg aagcgggtcg ttatgagagt   240
cgacttcaat gttcctatga agaacaacca gataacaaac aaccagagga ttaaggctgc   300
tgtcccaagc atcaaattct gcttggacaa tggagccaag tcggtagtcc ttatgagcca   360
cctaggccgg cctgatggtg tgcccatgcc tgacaagtac tccttagagc cagttgctgt   420
agaactcaaa tctctgctgg gcaaggatgt tctgttcttg aaggactgtg taggcccaga   480
agtggagaaa gcctgtgcca acccagctgc tgggtctgtc atcctgctgg agaacctccg   540
ctttcatgtg gaggaagaag ggaagggaaa agatgcttct gggaacaagg ttaaagccga   600
gccagccaaa ataaagcttt tccgagcttc acttcccaag ctaggggatg tctatgtcaa   660
tgatgctttt ggcactgctc acagagccca cagctccatg gtaggagtca atctgccaca   720
gaaggctggt gggttttga tgaagaagga gctgaactac tttgcaaagg ccttggagag   780
cccagagcga cccttcctgg ccatcctggg cggagctaaa gttgcagaca gatccagct   840
catcaataat atgctgacaa aagtcaatga gatgattatt ggtggtgaa tggctttac   900
cttccttaag gtgctcaaca acatggagat tggcacttct ctgtttgatg aagagggagc   960
caagattgtc aaagacctaa tgtccaaagc tgaagaagaat ggtgtgaaga ttaccttgcc  1020
tgttgacttt gtcactgctg acaagttga tgagaatgcc aagactggcc aagccactgt  1080
ggcttctggc atacctgctg gctggatggg ctttggactgt ggtcctgaaa gcagcaagaa  1140
gtatgctgag gctgtcactc gggctaagca gattgtgtgg aatggtcctg tgggggtatt  1200
tgaatgggaa gcttttgccc ggggaaccaa agctctcatg gatgaggtgg tgaaagccac  1260
ttctaggggc tgcatcacca tcataggtgg tggagacact gccacttgct gtgccaaatg  1320
gaacacggag gataaagtca gccatgtgag cactgggggt ggtgccagtt tggagctcct  1380
ggaaggtaaa gtccttcctg gggtggatgc tctcagcaat atttagtact ttcctgcctt  1440
ttagttcctg tgcacagccc ctaagtcaac ttagcatttt ctgcatctcc acttggcatt  1500
agctaaaacc ttccatgtca agattcagct agtggccaag agatgcagtg ccaggaaccc  1560
ttaaacagtt gcacagcatc tcagctcatc ttcactgcac cctggatttg catacattct  1620
tcaagatccc atttgaattt tttagtgact aaaccattgt gcattctaga gtgcatatat  1680
ttatattttg cctgttaaaa agaaagtgag cagtgttagc ttagttctct tttgatgtag  1740
gttattatga ttagctttgt cactgtttca ctactcagca tggaaacaag atgaaattcc  1800
atttgtaggt agtgagacaa aattgatgat ccattagta aacaataaaa gtgtccattg  1860
aaaccgtgat ttttttttt tcctgtcat actttgttag gaggggtgag aatagaatct  1920
tgaggaacgg atcagatgtc tatattgctg aatgcaagaa gtggggcagc agcagtggag  1980
agatgggaca attagataaa tgtccattct ttatcagggg cctactttat ggcagacatt  2040
gtgctagtgc ttttattcta acttttattt ttatcagtta cacatgatca taatttaaaa  2100
agtcaaggct tataacaaaa aagcccccagc ccattcctcc cattcaagat tcccactccc  2160
cagaggtgac cactttcaac tcttgagttt ttcaggtata tacctccatg tttctaagta  2220
atatgcttat attgttcact tcttttttttt ttattttta aagaaatcta tttcatacca  2280
tggaggaagg ctctgttcca catatatttc cacttcttca ttctctcggt atagttttgt  2340
cacaattata gattagatca aaagtctaca taactaatac agctgagcta tgtagtatgc  2400
tatgattaaa tttacttatg taaaaaaaaa aaaaaaaaa                         2439
```

| SEQ ID NO: 27 | moltype = DNA length = 1196 |
|---|---|
| FEATURE | Location/Qualifiers |
| source | 1..1196 |
|  | mol_type = other DNA |
|  | organism = Homo sapiens |

SEQUENCE: 27
```
cacttctgcc gccctgttt caagggataa gaaaccctgc gacaaaacct cctcctttc      60
caagcggctg ccgaagatgg cggaggtgca ggtcctggtg cttgatggtc gaggccatct   120
cctgggccgc ctggcggcca tcgtggctaa acaggtactg ctgggccgga aggtggtggt   180
cgtacgctgt gaaggcatca acatttctgg caatttctac agaaacaagt tgaagtacct   240
ggcttcctc cgcaagcgga tgaacaccaa cccttcccga ggccctacc acttccggga   300
ccccagccgc atcttctggc ggaccgtgcg aggtatgctg ccccacaaaa ccaagcgagg   360
ccaggccgct ctggacgtc tcaaggtgtt tgacggcatc ccaccgccct acgacaagaa   420
aaagcggatg gtggttcctg ctgccctcaa ggtcgtgcgt ctgaagccta caagaaagtt   480
tgcctatctg gggcgcctgg ctcacgaggt tggctggaag taccaggcag tgacagccac   540
cctggaggag aagaggaaag aaaagccaa gatccactac cggaagagaa aacagctcat   600
gaggctacgg aaacaggccg agaagaacgt ggagaagaaa attgacaaat acacagaggt   660
cctcaagacc cacggactcc tggtctgagc ccaataaaga ctgttaattc ctcatgcgtt   720
gcctgccctt cctccattgt tgccctgaa tgtacggac ccaggggcag cagcagtcca   780
ggtgccacag gcagccctgg acataggaa gctgggagca aggaaagggt cttagtcact   840
gcctcccgaa gttgcttgaa agcactcgga ggtgtcattt atctatgacc   900
aataggaaga gcaaccagtt actatgagtg aaagggagcc agaagactga ttggagggcc   960
ctatcttgtg agtgggcat ctgttggact ttccacctgg tcatatactc tgcagctgtt  1020
agaatgtgca agcacttggg gacagcatga gcttgctgtt gtacacaggg tatttctaga  1080
agcagaaata gactgggaag atgcacaacc aagggggttac aggcatcgcc catgctcctc  1140
acctgtattt tgtaatcaga aataaattgc ttttaaagaa aaaaaaaaa aaaaaa        1196
```

```
SEQ ID NO: 28          moltype = DNA   length = 987
FEATURE                Location/Qualifiers
source                 1..987
                       mol_type = other DNA
                       organism = Homo sapiens
SEQUENCE: 28
aatataagtg gaggcgtcgc gctggcgggc attcctgaag ctgacagcat tcgggccgag    60
atgtctcgct ccgtggcctt agctgtgctc gcgctactct ctctttctgg cctggaggct   120
atccagcgta ctccaaagat tcaggtttac tcacgtcatc cagcagagaa tggaaagtca   180
aatttcctga attgctatgt gtctgggttt catccatccg acattgaagt tgacttactg   240
aagaatggaa agagaattga aaaagtggag cattcagact tgtctttcag caaggactgg   300
tctttctatc tcttgtacta cactgaattc acccccactg aaaaagatga gtatgcctgc   360
cgtgtgaacc atgtgacttt gtcacagccc aagatagtta agtgggatcg agacatgtaa   420
gcagcatcat ggaggtttga agatgccgca tttggattgg atgaattcca aattctgctt   480
gcttgctttt taatattgat atgcttatac acttacactt tatgcacaaa atgtagggtt   540
ataataatgt taacatggac atgatcttct ttataattct actttgagtg ctgtctccat   600
gtttgatgta tctgagcagg ttgctccaca ggtagctcta ggagggctgg caacttagag   660
gtggggagca gagaattctc ttatccaaca tcaacatctt ggtcagattt gaactcttca   720
atctcttgca ctcaaagctt gttaagatag ttaagcgtgc ataagttaac ttccaattta   780
catactctgc ttagaatttg ggggaaaatt tagaaatata attgacagga ttattggaaa   840
tttgttataa tgaatgaaac attttgtcat ataagtatca tatttacttc ttatacatttt  900
gataaagtaa ggcatggttg tggttaatct ggtttatttt tgttccacaa gttaaataaa   960
tcataaaact tgatgtgtta tctctta                                       987

SEQ ID NO: 29          moltype = DNA   length = 3003
FEATURE                Location/Qualifiers
source                 1..3003
                       mol_type = other DNA
                       organism = Homo sapiens
SEQUENCE: 29
ctttctcctt cccttcttc cgggctcccg tccggctca tcaccggcc tgtggcccac      60
tcccaccgcc agctggaacc ctggggacta cgacgtccct caaaccttgc ttctaggaga   120
taaaagaac atccagtcat ggataaaaat gagctggtc agaaggccaa actggccgag     180
caggctgagc gatatgatga catggcagcc tgcatgaagt ctgtaactga gcaaggagct   240
gaattatcca atgaggagag gaatcttctc tcagttgctt ataaaaatgt tgtaggagcc   300
cgtaggtcat cttggagggt cgtctcaagt attgaacaaa agacggaagg tgctgagaaa   360
aaacagcaga tggctcgaga atacagagag aaaattgaga cggagctaag agatatctgc   420
aatgatgtac tgtctctttt ggaaaagttc ttgatcccca tagcttcaca agcagaggac   480
aaagtcttct atttgaaaat gaaaggagat tactaccgtt acttggctga ggttgccgct   540
ggtgatgaca agaagggat tgtcgatcag tcacaacaag cataccaaga agcttttgaa   600
atcagcaaaa aggaaatgca accaacacat cctatcgac tgggtctggc ccttaacttc   660
tctgtgttct attatgagat tctgaactcc ccagagaag cctgctctct tgcaaagaca   720
gcttttgatg aagccattgc tgaacttgat acattaagtg aagagtcata caaagacagc   780
acgctaataa tgcaattact gagagacaac ttgacattgt ggacatcgga tacccaagga   840
gacgaagctg aagcaggaga aggaggggaa aattaaccgg ccttccaact tttgtctgcc   900
tcattctaaa atttacacag tagaccattt gtcatccata ctgtcccaca aatagttttt   960
tgtttacgat ttatgacagg tttatgttac ttctatttga atttctatat ttcccatgtg  1020
gtttttatgt ttaatattag gggagtagag ccagttaaca tttagggagt tatctgtttt  1080
catcttgagg tggccaatat ggggatgtgg aattttata caagttataa gtgtttggca   1140
tagtactttt ggtacattgt ggcttcaaaa gggccagtgt aaaactgctt ccatgtctaa  1200
gcaaagaaaa ctgcctacat actggtttgt cctggcgggg aataaaaggg atcattggtt  1260
ccagtcacag gtgtagtaat tgtgggtact ttaaggtttg gagcacttac aaggctgtgg  1320
tagaatcata ccccatggat accacatatt aaaccatgta tatctgtgga atactcaatg  1380
tgtacacctt tgactacagc tgcagaagtg ttccttttga caaagtttgg acccatttta  1440
ctctggataa gggcagaaac ggttcacatt ccattatttg taaagttacc tgctgttagc  1500
tttcattatt tttgctacac tcattttatt tgtatttaaa tgtttaggc aacctaagaa    1560
caaatgtaaa agtaaagatg caggaaaaat gaattgcttg gtattcatta cttcatgtat  1620
atcaagcaca gcagtaaaac aaaaacccat gtatttaact tttttttagg attttttgctt 1680
ttgtgatttt tttttttttg atacttgcct aacatgcatg tgctgtaaaa atagttaaca  1740
gggaaataac ttgagatgat ggctagcttt gtttaatgtc ttatgaaatt tcatgaaca    1800
atccaagcat aattgttaag aacacgtgta ttaaattcat gtaagtggaa taaaagtttt  1860
atgaatggac ttttcaacta ctttctctac agcttttcat gtaaattagt cttggttctg  1920
aaacttcctct aaaggaaatt gtacattttt tgaaatttat tccttattcc ctcttggca   1980
ctaatgggct cttaccaagt ttaaacacaa aatttatcat aacaaaaata ctactaatat  2040
aactactgtt tccatgtccc atgatcccct ctcttcctcc ccaccctgaa aaaaatgagt  2100
tcctattttt tctgggagag gggggattg attagaaaaa aatgtagtgt gttccattta   2160
aaattttggc atatggcatt ttctaactta ggaagccaca atgttcttgg cccatcatga  2220
cattgggtag cattaactgt aagttttgtg cttccaaatc acttttttgt ttttaagaat  2280
ttcttgatac tcttatagcc tgccttcaat tttgatcctt tattctttct atttgtcagg  2340
tgcacaagat taccttcctg ttttagcctt ctgtcttgtc accaaccatt cttacttggt  2400
ggccatgtac ttggaaaaag gccgcatgat ctttctggct ccactcagtg tctaaggcac  2460
cctgcttcct ttgcttgcat cccacagact atttccctca tcctatttac tgcagcaaat  2520
ctctccttag tcttgatgac tgtgtttatc tcccttaaa accctaccta tcctgaatgg   2580
tctgtcattg tctgccttta aaatccttcc tcttttcttcc tcctctattc tctaaataat  2640
gatgggcta agttatacccc aaagctcact ttacaaaata ttttcctcagt actttgcaga  2700
aaacaccaaa caaaaatgcc attttaaaaa aggtgtattt tttctttag aatgtaagct   2760
cctcaagagc agggacaatg ttttctgtat gttctattgt gcctagtaca ctgtaaatgc  2820
tcaataaata ttgatgatgg gaggcagtga gtcttgatga taagggtgag aaactgaaat  2880
```

```
cccaaacact gttttgttgc ttgttttatt atgacctcag attaaattgg gaaatattgg   2940
cccttttgaa taattgtccc aaatattaca ttcaaataaa agtgcaatgg agaaaaaaaa   3000
aaa                                                                3003

SEQ ID NO: 30          moltype = DNA   length = 2803
FEATURE                Location/Qualifiers
source                 1..2803
                       mol_type = other DNA
                       organism = Homo sapiens
SEQUENCE: 30
actgcagccc cgctcgactc cggcgtggtg cgcaggcgcg gtatcccccc tcccccgcca     60
gctcgacccc ggtgtggtgc gcaggcgcag tctgcgcagg gactggcggg actgcgcggc    120
ggcaacagca gacatgtcgg gggtccgggg cctgtcgcgg ctgctgagcg ctcggcgcct    180
ggcgctggcc aaggcgtggc caacagtgtt gcaaacagga acccgaggtt ttcacttcac    240
tgttgatggg aacaagaggg catctgctaa agtttcagat tccatttctg ctcagtatcc    300
agtagtggat catgaatttg atgcagtggt ggtaggcgct ggaggggcag gcttgcgagc    360
tgcatttggc ctttctgagg cagggtttaa tacagcatgt gttaccaagc tgtttcctac    420
caggtcacac actgttgcag cacagggagg aatcaatgct gctctgggga acatggagga    480
ggacaactgg aggtggcatt tctacgacac cgtgaagggc tccgactggc tgggggacca    540
ggatgccatc cactacatga cggagcaggc ccccgccgcc gtggtcgagc tagaaaatta    600
tggcatgccg tttagcagaa ctgaagatgg gaagatttat cagcgtgcat ttggtggaca    660
gagcctcaag tttggaaagg gcgggcaggc ccatccggtgc tgctgtgtgg ctgatcggac    720
tggccactcg ctattgcaca ccttatatgg aaggtctctg cgatatgata ccagctattt    780
tgtggagtat tttgccttgg atctcctgat ggagaatggg gagtgccgtg gtgtcatcgc    840
actgtgcata gaggacgggt ccatccatcg cataagagca agaacactg ttgttgccac     900
aggaggctac gggcgcacct acttcagctg cacgtctcgc cacaccagca ctggcgacgg    960
cacggccatg atcaccaggg caggccttcc ttgccaggac ctagagtttg ttcagttcca   1020
ccctacaggc atatatggtg ctggttgtct cattacggaa ggatgtcgtg gagagggagg   1080
cattctcatt aacagtcaag gcgaaaggtt tatggagcga tacgcccctg tcgcgaagga   1140
cctgcgcgtct agagatgtgg tgtctcggtc catgactctg gagatccgag aaggaagagg   1200
ctgtggccct gagaaagatc acgtctacct gcagctgcac cacctacctc cagagcagct   1260
ggccacgcgc ctgcctggca tttcagagac agccatgatc ttcgctgcg tggacgtcac    1320
gaaggagccg atccctgtcc tccccaccgt gcattataac atgggcggca ttcccaccaa   1380
ctacaagggg caggtcctga ggcacgtgaa tggccaggat cagattgtgc ccggcctgta   1440
cgtcgtggg gaggccgcct gtgcctcggt acatggtgcc aaccgcctcg gggcaaactc    1500
gctcttggac ctggttgtct ttggtcgggc atgtgccctg agcatcgaag agtcatgcag   1560
gcctggagat aaagtccctc caattaaacc aaacgctggg gaagaatctg tcatgaatct   1620
tgacaaattg agatttgctg atggaagcat aagaacatcg gaactgcgac tcagcatgca   1680
gaagtcaatg caaaatcatg ctgccgtgtt ccgtgtggga agcgtgttgc aagaaggttg   1740
tgggaaaatc agcaagctct atggagacct aaagcacctg aagacgttcg accgggaat    1800
ggtctgaac acggacctgg tggagaccct ggagctgcag aacctgatgc tgtgtgcgct   1860
gcagaccatc tacggagcag aggcacgaa ggagtcacgg ggcgcatg ccaggaaga      1920
ctacaaggtg cggattgatg agtacgatta ctccaagccc atccagggc aacagaagaa   1980
gcccttttgag gagcactgga ggaagcacac cctgtcctat gtggacgttg gcactggaa    2040
ggtcactctg gaatatagac ccgtgatcga caaaactttg aacgaggctg actgtgccac   2100
cgtccccgcca gccattcgct cctactgatg agacaagatg tggtgatgac agaatcagct   2160
tttgtaatta tgtataatag ctcatgcatg tgtccatgtc ataactgtct tcatacgctt   2220
ctgcactctg gggaagaagg agtacattga agggagattg gcacctagtg gctgggagct   2280
tgccaggaac ccagtggcca gggagcgtgg cacttacctt tgtcccttgc ttcattcttg   2340
tgagatgata aaactgggca cagctcttaa ataaatata aatgaacaaa ctttcttta     2400
tttccaaatc catttgaaat attttactgt tgtgacttta gtcatatttg ttgacctaaa   2460
aatcaaatgt aatctttgta ttgtgttaca tcaaaatcca gatattttgt atagtttctt   2520
ttttctttt tcttttcttt tttttttga cacaggatcg gtgcagtagt acaatcacag      2580
ctcactgcag cctcaaactc ctgggcagct caggtgatct tcctgactca gccttctgag   2640
tagttgggc tacaggtgtg caccaccatg cccagctcat ttattttgta attgtaggga   2700
cagggtctca ctgtgttgcc taggctggtc tcaagtgatc ctccctcctt ggcctcccaa   2760
ggtgctggaa ttataggtgt gaacaaacca aaaaaaaaaa aaa                    2803

SEQ ID NO: 31          moltype = DNA   length = 1435
FEATURE                Location/Qualifiers
source                 1..1435
                       mol_type = other DNA
                       organism = Homo sapiens
SEQUENCE: 31
ggcggggcct gcttctcctc agcttcaggc ggctgcgacg agccctcagg cgaacctctc     60
ggctttcccg cgcggcgccg cctcttgctg cgcctccgcc tcctcctctg ctccgccacc    120
ggcttcctcc tcctgagcag tcagcccgcg cgccggccgg ctccgttatg cgacccgca    180
gccctggcgt cgtgattagt gatgatgaac caggttatga ccttgattta ttttgcatac    240
ctaatcatta tgctgaggat ttggaaaggg tgtttattcc tcatgactta attatggaa     300
ggactgaacg tcttgctcga gatgtgatga aggagatggg aggccatcac attgtagccc    360
tctgtgtgct caagggggc tataaattct ttgctgaccct gctggattac atcaaagcac    420
tgaatagaaa tagtgataga tccattccta tgactgtaga tttatcaga ctgaagagct     480
attgtaatga ccagtcaaca ggggacataa agtaattgg tggagatgat ctctcaactt    540
taactgaaa gaattgcttg attgtggaag atataattga cactggcaaa acaatgcaga    600
ctttgctttc cttggtcagg cagtataatc caaagatggt caaggtcgca agcttgctgg    660
tgaaaggac cccacgaagt gttggatata agccagactt tgttggattt gaaattccag    720
acaagtttgt tgtaggatat gcccttgact ataatgaata cttcagggat ttgaatcatg   780
tttgtgtcat tagtgaaact ggaaaagcaa aatacaaagc ctaagatgag agttcaagtt    840
gagtttggaa acatctggag tcctattgac atcgccagta aaattatcaa tgttctagtt   900
```

```
ctgtggccat ctgcttagta gagctttttg catgtatctt ctaagaattt tatctgtttt   960
gtactttaga aatgtcagtt gctgcattcc taaactgttt atttgcacta tgagcctata  1020
gactatcagt tccctttggg cggattgttg tttaacttgt aaatgaaaaa attctcttaa  1080
accacagcac tattgagtga aacattgaac tcatatctgt aagaaataaa gagaagatat  1140
attagttttt taattggtat tttaattttt atatatgcag gaaagaatag aagtgattga  1200
atattgttaa ttataccacc gtgtgttaga aaagtaagaa gcagtcaatt ttcacatcaa  1260
agacagcatc taagaagttt tgttctgtcc tggaattatt ttagtagtgt ttcagtaatg  1320
ttgactgtat tttccaactt gttcaaatta ttaccagtga atctttgtca gcagttccct  1380
tttaaatgca aatcaataaa ttcccaaaaa tttaaaaaaa aaaaaaaaaa aaaaa       1435
```